US011970708B2

(12) United States Patent
Kim et al.

(10) Patent No.: US 11,970,708 B2
(45) Date of Patent: Apr. 30, 2024

(54) GENE THERAPY VECTOR WITH MINIMIZING RECOMBINATION, RECOMBINANT RETROVIRUS COMPRISING THE VECTOR, AND PHARMACEUTICAL COMPOSITION FOR PREVENTING OR TREATING CANCER COMPRISING THE RECOMBINANT RETROVIRUS

(71) Applicant: ARTICURE INC., Daejeon (KR)

(72) Inventors: Yeon-Soo Kim, Daejeon (KR); Moonkyung Kang, Daejeon (KR); Soojin Kim, Daejeon (KR)

(73) Assignee: Articure Inc., Yuseong-gu (KR)

(*) Notice: Subject to any disclaimer, the term of this patent is extended or adjusted under 35 U.S.C. 154(b) by 0 days.

(21) Appl. No.: 18/185,656

(22) Filed: Mar. 17, 2023

(65) Prior Publication Data

US 2023/0265458 A1 Aug. 24, 2023

Related U.S. Application Data

(63) Continuation-in-part of application No. PCT/KR2021/012776, filed on Sep. 17, 2021.

(30) Foreign Application Priority Data

Sep. 18, 2020 (KR) ........................ 10-2020-0120797
Sep. 7, 2021 (KR) ........................ 10-2021-0118834

(51) Int. Cl.

| | |
|---|---|
| ***C12N 15/86*** | (2006.01) |
| ***A61K 31/513*** | (2006.01) |
| ***A61K 31/522*** | (2006.01) |
| ***A61K 35/76*** | (2015.01) |
| ***A61K 48/00*** | (2006.01) |
| ***A61P 35/00*** | (2006.01) |
| ***C07K 14/535*** | (2006.01) |
| ***C07K 14/705*** | (2006.01) |
| ***C12N 9/12*** | (2006.01) |
| ***C12N 9/78*** | (2006.01) |

(52) U.S. Cl.

CPC ............ *C12N 15/86* (2013.01); *A61K 31/513* (2013.01); *A61K 31/522* (2013.01); *A61K 35/76* (2013.01); *A61K 48/005* (2013.01); *A61P 35/00* (2018.01); *C07K 14/535* (2013.01); *C07K 14/70596* (2013.01); *C12N 9/1211* (2013.01); *C12N 9/78* (2013.01); *C12Y 305/04001* (2013.01)

(58) Field of Classification Search

None

See application file for complete search history.

(56) References Cited

U.S. PATENT DOCUMENTS 10,039,841 B2 * 8/2018 Kim ........................ C12N 9/78

FOREIGN PATENT DOCUMENTS

| | | | |
|---|---|---|---|
| KR | 1020020040452 A | 5/2002 | |
| KR | 100423022 B1 | 3/2004 | |
| KR | 101381064 B1 | 4/2014 | |
| KR | 1020180011979 A | 2/2018 | |
| KR | 1020180060520 A | 6/2018 | |
| WO | WO-2017207979 A1 * | 12/2017 | ............. A61P 35/00 |

OTHER PUBLICATIONS

Dorsch-Hasler (1985) "A long and complex enhancer activates transcription of the gene coding for the highly abundant immediate early mRNA in a murine cytomegalovirus", Proceedings of the National Academy of Science, USA, 83(24): 8325-29. (Year: 1985).*

English Abstract and Machine Translation for Korean Publication No. 1020020040452 A, published May 30, 2002, 11 pages.

English Abstract and Machine Translation for Korean Publication No. 1020180011979 A, published Feb. 5, 2018, 18 pages.

English Abstract and Machine Translation for Korean Publication No. 1020180060520 A, published Jun. 7, 2018, 18 pages.

English Abstract and Machine Translation for Korean Patent No. 100423022 B1, published Mar. 12, 2004, 11 pages.

English Abstract and Machine Translation for Korean Patent No. 101381064 B1, published Apr. 25, 2014, 23 pages.

Bi et al., "In Vitro Evidence That Metabolic Cooperation Is Responsible for the Bystander Effect Observed with HSV tk Retroviral Gene Therapy," Human Gene Therapy, vol. 4, 1993, pp. 725-731.

Trask et al., "Phase I Study of Adenoviral Delivery of the HSV-tk Gene and Ganciclovir Administration in Patients with Recurrent Malignant Brain Tumors," Molecular Therapy, vol. 1, No. 2, Feb. 2000, pp. 195-203.

Lafemina et al., "Differences in Cell Type-specific Blocks to Immediate Early Gene Expression and DNA Replication of Human, Simian and Murine Cytomegalovirus," J. Gen. Virol., vol. 69, 1988, pp. 355-374.

(Continued)

*Primary Examiner* — Robert M Kelly

(74) *Attorney, Agent, or Firm* — Fredrikson & Byron, P.A.

(57) ABSTRACT

Disclosed is a gene therapy vector in which the occurrence of recombination is minimized. In order to minimize the occurrence of recombination, which is a major problem in the production and infection of a retroviral vector virus that continuously expresses a therapeutic gene during virus replication, a cleaved MCMV promoter was prepared by cutting the MCMV promoter on the basis of a repeat sequence, and the cleaved MCMV promoter was introduced to prepare a vector. It was confirmed that the vector having the cleaved MCMV promoter incorporated therein does not cause recombinations even after being incubated multiple times, and shows a continuous expression of the therapeutic protein, and in cells transfected with the virus containing the vector, cell death effectively occurs when a prodrug is administered thereto. Accordingly, the vector with minimized recombination occurrence of the present invention can be advantageously used for the treatment of cancer.

13 Claims, 22 Drawing Sheets

Specification includes a Sequence Listing.

(56) References Cited

OTHER PUBLICATIONS

Aiba-Masago et al., "Murine Cytomegalovirus Immediate-Early Promoter Directs Astrocyte-Specific Expression in Transgenic Mice," American Journal of Pathology, vol. 154, No. 3, Mar. 1999, pp. 735-743.
Kim et al., "TAR-Independent Transactivation of the Murine Cytomegalovirus Major Immediate-Early Promoter by the Tat Protein," Journal of Virology, vol. 67, No. 1, Jan. 1993, pp. 239-248.
Kim, "Requirement of the Human Immunodeficiency Virus Type 1 ENV Gene Sequence for TAR-Independent Trans Activation by TAT from the Major Immediate-Early Promoter of Murine Cytomegalovirus," Biochemical and Biophysical Research Communications, vol. 203, No. 2, Sep. 15, 1994, pp. 1152-1159.
Young et al., "Viral gene therapy strategies: from basic science to clinical application," Journal of Pathology, vol. 208, 2006, pp. 299-318.
Lotze et al., "Viruses as gene delivery vectors: Application to gene function, target validation, and assay development," Cancer Gene Therapy, vol. 9, 2002, pp. 692-699.
Logg et al., "Genomic Stability of Murine Leukemia Viruses Containing Insertions at the Env-3' Untranslated Region Boundary," Journal of Virology, vol. 75, No. 15, Aug. 2001, pp. 6989-6998.
Gottesman, "Cancer gene therapy: an awkward adolescence," Cancer Gene Therapy, vol. 10, 2003, pp. 501-508.
NCBI, GenBank Accession No. BC006338.2, *Homo sapiens* CD19 molecule, mRNA (cDNA clone MGC: 12802 Image:4054919), complete cds, Jul. 15, 2006.
International Patent Application No. PCT/KR2021/012776, International Preliminary Report on Patentability dated Jan. 9, 2023, 3 pages.
International Patent Application No. PCT/KR2021/012776, International Search Report dated Dec. 24, 2021, 8 pages (including 4 pages English translation).

* cited by examiner

FIG. 6

AACAGGAAAGTTCCATTGGAGCCAAGTACATTGAGTCAATA *GGGACTTTCCAATGGGTTTTGCCCAGTACA* TAAGGTCAA TGGGAGGTAAGCCAA *TGGGTTTTTCC* CATTACTGGCACGTATACTGAGTCATTA *GGGACTTTCCAATGGGTTTTGCCCAGT ACA* TAAGGTCAATAGGGGTGAATC AACAGGAAA GTCCCATTGGAGCCAAGTACACTGAGTCAATAGGGACTTTCCATTGGG TTTTGCCCAGTACAAAAGGTCAATAGGGGGTGAGTCAA *TGGGTTTTTCC* CATTATTGGCACGTACATAAGGTCAATAGGGGT GAGTCATTGGGTTTTTCCAGCCAATTTAATTAAAACGCCAT GTACTTTCCCA CCATTGACGTCAATGGGCTATTGAAACTAATG CAACGTGACCTTTAAACG GTACTTTCCCA TAGCTGATTAATGGGAAAGTACCGTTCTCGAGCCAATACACGTCAATGGGAAGB TGAAAGGGCAGCCAAAACGTAACACCGCCCCGGTTTTCCCTGGAAATTCCATATTGGCACGCATTCTATTGGCTGAGCTGCG TTCACGTGGGTATAAGAGGCGCGACCAGCGTCGGTACCGTCGCAGTCTTCGGTCTGACCACCGTAGAACGCAGA (SEQ.ID.NO:3)

FIG. 7

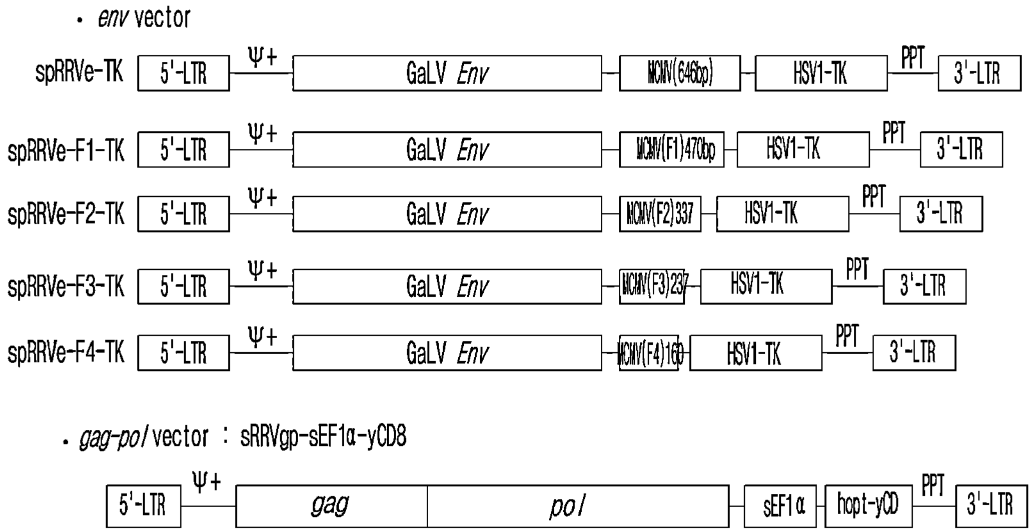

SEQUENCE LISTING

```
Sequence total quantity: 84
SEQ ID NO: 1            moltype = DNA  length = 21
FEATURE                 Location/Qualifiers
misc_feature            1..21
                        note = GaLV 1624F
source                  1..21
                        mol_type = other DNA
                        organism = synthetic construct
SEQUENCE: 1
gactcagtca gcaagttaga g                                            21

SEQ ID NO: 2            moltype = DNA  length = 27
FEATURE                 Location/Qualifiers
misc_feature            1..27
                        note = MFGSacIR
source                  1..27
                        mol_type = other DNA
                        organism = synthetic construct
SEQUENCE: 2
caatcggagg actggcgccc cgagtga                                      27

SEQ ID NO: 3            moltype = DNA  length = 646
FEATURE                 Location/Qualifiers
misc_feature            1..646
                        note = MCMV promoter
source                  1..646
                        mol_type = other DNA
```

-continued

```
                         organism = synthetic construct
SEQUENCE: 3
aacaggaaag ttccattgga gccaagtaca ttgagtcaat agggactttc caatgggttt  60
tgcccagtac ataaggtcaa tgggaggtaa gccaatgggt ttttcccatt actggcacgt  120
atactgagtc attagggact ttccaatggg ttttgcccag tacataaggt caataggggt  180
gaatcaacag gaaagtccca ttggagccaa gtacactgag tcaataggga ctttccattg  240
ggttttgccc agtacaaaag gtcaataggg ggtgagtcaa tgggtttttc ccattattgg  300
cacgtacata aggtcaatag gggtgagtca ttgggttttt ccagccaatt taattaaaac  360
gccatgtact ttcccaccat tgacgtcaat gggctattga aactaatgca acgtgacctt  420
taaacggtac tttcccatag ctgattaatg ggaaagtacc gttctcgagc caatacacgt  480
caatgggaag tgaaagggca gccaaaacgt aacaccgccc cggttttccc tggaaattcc  540
atattggcac gcattctatt ggctgagctg cgttcacgtg ggtataagag gcgcgaccag  600
cgtcggtacc gtcgcagtct tcggtctgac caccgtagaa cgcaga                646

SEQ ID NO: 4             moltype = DNA  length = 470
FEATURE                  Location/Qualifiers
misc_feature             1..470
                         note = MCMV F1 promoter
source                   1..470
                         mol_type = other DNA
                         organism = synthetic construct
SEQUENCE: 4
gggtgaatca acaggaaagt cccattggag ccaagtacac tgagtcaata gggactttcc  60
attgggtttt gcccagtaca aaaggtcaat agggggtgag tcaatgggtt tttcccatta  120
ttggcacgta cataaggtca ataggggtga gtcattgggt ttttccagcc aatttaatta  180
aaacgccatg tactttccca ccattgacgt caatgggcta ttgaaactaa tgcaacgtga  240
cctttaaacg gtactttccc atagctgatt aatgggaaag taccgttctc gagccaatac  300
acgtcaatgg gaagtgaaag ggcagccaaa acgtaacacc gccccggttt tccctggaaa  360
ttccatattg gcacgcattc tattggctga gctgcgttca cgtgggtata agaggcgcga  420
ccagcgtcgg taccgtcgca gtcttcggtc tgaccaccgt agaacgcaga            470

SEQ ID NO: 5             moltype = DNA  length = 337
FEATURE                  Location/Qualifiers
misc_feature             1..337
                         note = MCMV F2 promoter
source                   1..337
                         mol_type = other DNA
                         organism = synthetic construct
SEQUENCE: 5
aaggtcaata ggggtgagtc attgggtttt tccagccaat ttaattaaaa cgccatgtac  60
tttcccacca ttgacgtcaa tgggctattg aaactaatgc aacgtgacct ttaaacggta  120
ctttcccata gctgattaat gggaaagtac cgttctcgag ccaatacacg tcaatgggaa  180
gtgaaagggc agccaaaacg taacaccgcc ccggttttcc ctggaaattc catattggca  240
cgcattctat tggctgagct gcgttcacgt gggtataaga ggcgcgacca gcgtcggtac  300
cgtcgcagtc ttcggtctga ccaccgtaga acgcaga                          337

SEQ ID NO: 6             moltype = DNA  length = 237
FEATURE                  Location/Qualifiers
misc_feature             1..237
                         note = MCMV F3 promoter
source                   1..237
                         mol_type = other DNA
                         organism = synthetic construct
SEQUENCE: 6
aacgtgacct ttaaacggta ctttcccata gctgattaat gggaaagtac cgttctcgag  60
ccaatacacg tcaatgggaa gtgaaagggc agccaaaacg taacaccgcc ccggttttcc  120
ctggaaattc catattggca cgcattctat tggctgagct gcgttcacgt gggtataaga  180
ggcgcgacca gcgtcggtac cgtcgcagtc ttcggtctga ccaccgtaga acgcaga    237

SEQ ID NO: 7             moltype = DNA  length = 161
FEATURE                  Location/Qualifiers
misc_feature             1..161
                         note = MCMV F4 promoter
source                   1..161
                         mol_type = other DNA
                         organism = synthetic construct
SEQUENCE: 7
ggaagtgaaa gggcagccaa aacgtaacac cgccccggtt ttccctggaa attccatatt  60
ggcacgcatt ctattggctg agctgcgttc acgtgggtat aagaggcgcg accagcgtcg  120
gtaccgtcgc agtcttcggt ctgaccaccg tagaacgcag a                     161

SEQ ID NO: 8             moltype = DNA  length = 33
FEATURE                  Location/Qualifiers
misc_feature             1..33
                         note = MCMV F1-PmeI
source                   1..33
                         mol_type = other DNA
                         organism = synthetic construct
SEQUENCE: 8
```

-continued

```
cggtttaaac gggtgaatca acaggaaagt ccc                                33

SEQ ID NO: 9           moltype = DNA  length = 32
FEATURE                Location/Qualifiers
misc_feature           1..32
                       note = MCMV F2-PmeI
source                 1..32
                       mol_type = other DNA
                       organism = synthetic construct
SEQUENCE: 9
cggtttaaac aaggtcaata ggggtgagtc at                                 32

SEQ ID NO: 10          moltype = DNA  length = 32
FEATURE                Location/Qualifiers
misc_feature           1..32
                       note = MCMV F3-PmeI
source                 1..32
                       mol_type = other DNA
                       organism = synthetic construct
SEQUENCE: 10
cggtttaaac aacgtgacct ttaaacggta ct                                 32

SEQ ID NO: 11          moltype = DNA  length = 31
FEATURE                Location/Qualifiers
misc_feature           1..31
                       note = MCMV F4-PmeI
source                 1..31
                       mol_type = other DNA
                       organism = synthetic construct
SEQUENCE: 11
cggtttaaac ggaagtgaaa gggcagccaa a                                  31

SEQ ID NO: 12          moltype = DNA  length = 34
FEATURE                Location/Qualifiers
misc_feature           1..34
                       note = MCMV-R-NotI
source                 1..34
                       mol_type = other DNA
                       organism = synthetic construct
SEQUENCE: 12
cggcggccgc tctgcgttct acggtggtca gacc                               34

SEQ ID NO: 13          moltype = DNA  length = 32
FEATURE                Location/Qualifiers
misc_feature           1..32
                       note = MCMV R-BamHI
source                 1..32
                       mol_type = other DNA
                       organism = synthetic construct
SEQUENCE: 13
cgggatcctc tgcgttctac ggtggtcaga cc                                 32

SEQ ID NO: 14          moltype = DNA  length = 21
FEATURE                Location/Qualifiers
misc_feature           1..21
                       note = GaLV 1932F
source                 1..21
                       mol_type = other DNA
                       organism = synthetic construct
SEQUENCE: 14
gttgctcatc ctcgggccat g                                             21

SEQ ID NO: 15          moltype = DNA  length = 20
FEATURE                Location/Qualifiers
misc_feature           1..20
                       note = Am1801F
source                 1..20
                       mol_type = other DNA
                       organism = synthetic construct
SEQUENCE: 15
atcattgacc ctggcccttc                                               20

SEQ ID NO: 16          moltype = DNA  length = 21
FEATURE                Location/Qualifiers
misc_feature           1..21
                       note = pol7130F
source                 1..21
                       mol_type = other DNA
                       organism = synthetic construct
```

-continued

```
SEQUENCE: 16
cggcccggca ctcattggga g                                           21

SEQ ID NO: 17          moltype = DNA  length = 19
FEATURE                Location/Qualifiers
misc_feature           1..19
                       note = MuLV4194F
source                 1..19
                       mol_type = other DNA
                       organism = synthetic construct
SEQUENCE: 17
agcaagctat tggccactg                                              19

SEQ ID NO: 18          moltype = DNA  length = 212
FEATURE                Location/Qualifiers
misc_feature           1..212
                       note = sEF1alpha promoter
source                 1..212
                       mol_type = other DNA
                       organism = synthetic construct
SEQUENCE: 18
gggcagagcg cacatcgccc acagtccccg agaagttggg gggaggggtc ggcaattgat  60
ccggtgccta gagaaggtgg cgcggggtaa actgggaaag tgatgtcgtg tactggctcc  120
gcctttttcc cgagggtggg ggagaaccgt atataagtgc agtagtcgcc gtgaacgttc  180
tttttcgcaa cgggtttgcc gccagaacac ag                               212

SEQ ID NO: 19          moltype = DNA  length = 2058
FEATURE                Location/Qualifiers
misc_feature           1..2058
                       note = GaLV env
source                 1..2058
                       mol_type = other DNA
                       organism = synthetic construct
SEQUENCE: 19
atggtattgc tgcctgggtc catgcttctc acctcaaacc tgcaccacct tcggcaccag  60
atgagtcctg ggagctggaa aagactgatc atcctcttaa gctgcgtatt cggcggcggc  120
gggacgagtc tgcaaaataa gaacccccac cagcccatga ccctcacttg gcaggtactg  180
tcccaaactg gagacgttgt ctgggataca aaggcagtcc agcccccttg gacttggtgg  240
cccacactta aacctgatgt atgtgccttg gcggctagtc ttgagtcctg ggatatcccg  300
ggaaccgatg tctcgtcctc taaacgagtc agacctccgg actcagacta tactgccgct  360
tataagcaaa tcacctgggg agccataggg tgcagctacc ctcgggctag gactagaatg  420
gcaagctcta ccttctacgt atgtccccgg gatggccgga ccctttcaga agctagaagg  480
tgcggggggc tagaatccct atactgtaaa gaatgggatt gtgagaccac ggggaccggt  540
tattggctat ctaaatcctc aaaagacctc ataactgtaa aatgggacca aaatagcgaa  600
tggactcaaa aatttcaaca gtgtcaccag accggctggt gtaacccccct taaaatagat  660
ttcacagaca aaggaaaatt atccaaggac tggataacgg gaaaaacctg gggattaaga  720
ttctatgtgt ctggacatcc aggcgtacag ttcaccattc gcttaaaaat caccaacatg  780
ccagctgtgg cagtaggtcc tgacctcgtc cttgtggaac aaggacctcc tagaacgtcc  840
ctcgctctcc cacctcctct tcccccaagg gaagcgccac cgccatctct ccccgactct  900
aactccacag ccctggcgac tagtgcacaa actcccacgg tgagaaaaac aattgttacc  960
ctaaacactc cgcctcccac cacaggcgac agactttttg atcttgtgca gggggccttc  1020
ctaaccttaa atgctaccaa cccaggggcc actgagtctt gctggctttg tttggccatg  1080
ggcccccctt attatgaagc aatagcctca tcaggagagg tcgcctactc caccgacctt  1140
gaccggtgcc gctgggggac ccaaggaaag ctcaccctca ctgaggtctc aggacacggg  1200
ttgtgcatag gaaaggtgcc ctttacccat cagcatctct gcaatcagac cctatccatc  1260
aattcctccg gagaccatca gtatctgctc ccctccaacc atagctggtg ggcttgcagc  1320
actggcctca ccccttgcct ctccacctca gtttttaatc agactagaga tttctgtatc  1380
caggtccagc tgattcctcg catctattac tatcctgaag aagttttgtt acaggcctat  1440
gacaattctc accccaggac taaaagagag gctgtctcac ttaccctagc tgttttactg  1500
gggttgggaa tcacggcggg aataggtact ggttcaactg ccttaattaa aggacctata  1560
gacctccagc aaggcctgac aagcctccag atcgccatag atgctgacct ccgggccctc  1620
caagactcag tcagcaagtt agaggactca ctgacttccc tgtccgaggt agtgctccaa  1680
aataggagag gccttgactt gctgtttcta aaagaaggtg gcctctgtgc ggccctaaag  1740
gaagagtgct gtttttacat agaccactca ggtgcagtac gggactccat gaaaaaactc  1800
aaagaaaaac tggataaaag acagttagag cgccagaaaa gccaaaactg gtatgaagga  1860
tggttcaata actccccttg gttcactacc ctgctatcaa ccatcgctgg gcccctatta  1920
ctcctccttc tgttgctcat cctcgggcca tgcatcatca ataagttagt tcaattcatc  1980
aatgatagga taagtgcagt taaaattctg gtccttagac aaaaatatca ggccctagag  2040
aacgaaggta acctttaa                                               2058

SEQ ID NO: 20          moltype = DNA  length = 1965
FEATURE                Location/Qualifiers
misc_feature           1..1965
                       note = MuLV env
source                 1..1965
                       mol_type = other DNA
                       organism = synthetic construct
SEQUENCE: 20
atggcgcgtt caacgctctc aaaacccccct caagataaga ttaacccgtg gaagccctta  60
```

-continued

```
atagtcatgg gagtcctgtt aggagtaggg atggcagaga gcccccatca ggtctttaat  120
gtaacctgga gagtcaccaa cctgatgact gggcgtaccg ccaatgccac ctccctcctg  180
ggaactgtac aagatgcctt cccaaaatta tattttgatc tatgtgatct ggtcggagag  240
gagtgggacc cttcagacca ggaaccgtat gtcgggtatg gctgcaagta ccccgcaggg  300
agacagcgga cccggacttt tgacttttac gtgtgccctg ggcataccgt aaagtcgggg  360
tgtgggggac caggagaggg ctactgtggt aaatgggggt gtgaaaccac cggacaggct  420
tactggaagc ccacatcatc gtgggaccta atctccctta agcgcggtaa cacccccctgg  480
gacacgggat gctctaaagt tgcctgtggc ccctgctacg acctctccaa agtatccaat  540
tccttccaag gggctactcg agggggcaga tgcaaccctc tagtcctaga attcactgat  600
gcaggaaaaa aggctaactg ggacgggccc aaatcgtggg gactgagact gtaccggaca  660
ggaacagatc ctattaccat gttctccctg acccggcagg tccttaatgt gggaccccga  720
gtccccatag ggcccaaccc agtattaccc gaccaaagac tcccttcctc accaatagag  780
attgtaccgg ctccacagcc acctagcccc ctcaatacca gttacccccc ttccactacc  840
agtacaccct caacctcccc tacaagtcca agtgtcccac agccaccccc aggaactgga  900
gatagactac tagctctagt caaaggagcc tatcaggcgc ttaacctcac caatcccgac  960
aagacccaag aatgttggct gtgcttagtg tcgggacctc cttattacga aggagtagcg  1020
gtcgtgggca cttataccaa tcattccacc gctccggcca actgtacggc cacttcccaa  1080
cataagctta ccctatctga agtgacagga cagggcctat gcatgggggc agtacctaaa  1140
actcaccagg ccttatgtaa caccacccaa agcgccggct caggatccta ctaccttgca  1200
gcacccgccg gaacaatgtg ggcttgcagc actggattga ctccctgctt gtccaccacg  1260
gtgctcaatc taaccacaga ttattgtgta ttagttgaac tctggcccag agtaatttac  1320
cactcccccg attatatgta tggtcagctt gaacagcgta ccaaatataa aagagagcca  1380
gtatcattga ccctggccct tctactagga ggattaacca tgggagggat tgcagctgga  1440
atagggacgg ggaccactgc cttaattaaa acccagcagt ttgagcagct tcatgccgct  1500
atccagacag acctcaacga agtcgaaaag tcaattacca acctagaaaa gtcactgacc  1560
tcgttgtctg aagtagtcct acagaaccgc agaggcctag atttgctatt cctaaaggag  1620
ggaggtctct gcgcagccct aaaagaagaa tgttgttttt atgcagacca cacggggcta  1680
gtgagagaca gcatggccaa attaagagaa aggcttaatc agagacaaaa actatttgag  1740
acaggccaag gatggttcga agggctgttt aatagatccc cctggtttac caccttaatc  1800
tccaccatca tgggacctct aatagtactc ttactgatct tactctttgg accttgcatt  1860
ctcaatcgat tagtccaatt tgttaaagac aggatatcag tggtccaggc tctagttttg  1920
actcaacaat atcaccagct gaagcctata gagtacgagc catag                 1965
```

```
SEQ ID NO: 21          moltype = DNA  length = 1131
FEATURE                Location/Qualifiers
misc_feature           1..1131
                       note = Thymidine kinase encoding sequence
source                 1..1131
                       mol_type = other DNA
                       organism = synthetic construct
SEQUENCE: 21
atggcttcgt accccctgcca tcaacacgcg tctgcgttcg accaggctgc gcgttctcgc  60
ggccatagca accgacgtac ggcgttgcgc cctcgccggc agcaagaagc cacggaagtc  120
cgcctggagc agaaaatgcc cacgctactg cgggtttata tagacggtcc tcacgggatg  180
gggaaaacca ccaccacgca actgctggtg gccctgggtt cgcgcgacga tatcgtctac  240
gtacccgagc cgatgactta ctggcaggtg ctgggggctt ccgagacaat cgcgaacatc  300
tacaccacac aacaccgcct cgaccagggt gagatatcgg ccggggacgc ggcggtggta  360
atgacaagcg cccagataac aatgggcatg ccttatgccg tgaccgacgc cgttctggct  420
cctcatatcg gggggggaggc tgggagctca catgccccgc ccccggccct caccctcatc  480
ttcgaccgcc atcccatcgc cgccctcctg tgctacccgg ccgcgcgata ccttatgggc  540
agcatgacct cccaggccgt gctggcgttc gtggccctca tcccgccgac cttgcccggc  600
acaaacatcg tgttgggggc ccttccggag gacagacaca tcgaccgcct ggccaaacgc  660
cagcgccccg gcgagcggct tgacctggct atgctggccg cgattcgccg cgtttacggg  720
ctgcttgcca atacggtgcg gtatctgcag ggcggcgggt cgtggcggga ggattgggga  780
cagctttcgg ggacggccgt gccgccccag ggtgccgagc cccagagcaa cgcgggccca  840
cgaccccata tcggggacac gttatttacc ctgtttcggg cccccgagtt gctggccccc  900
aacggcgacc tgtacaacgt gtttgcctgg gccttggacg tcttggccaa acgcctccgt  960
cccatgcacg tctttatcct ggattacgac caatcgcccg ccggctgccg ggacgccctg  1020
ctgcaactta cctccgggat ggtccagacc cacgtcacca cccccggctc cataccgacg  1080
atctgcgacc tggcgcgcac gtttgcccgg gagatggggg aggctaactg a         1131

SEQ ID NO: 22          moltype = DNA  length = 477
FEATURE                Location/Qualifiers
misc_feature           1..477
                       note = Human-codon optimized yeast cytosine deaminase
                        encoding sequence
source                 1..477
                       mol_type = other DNA
                       organism = synthetic construct
SEQUENCE: 22
atggttactg ggggaatggc atctaagtgg gatcagaaag gtatggacat cgcttatgaa  60
gaggctgctc tcggctacaa agagggtgga gtgcctatcg gagggtgcct gatcaacaac  120
aaggacggca gtgtgctggg gaggggccac aatatgaggt tccaaaaagg ctccgccact  180
ctccacgggg aaattagtac cctcgagaat tgcggacgat tggaagggaa ggtgtacaag  240
gatacaacac tgtacaccac cctgtcaccc tgtgatatgt gcacaggcgc cattatcatg  300
tacggaatcc ctagatgtgt cgtgggggag aatgtaaact tcaaaagtaa gggggagaaa  360
tatctccaga cccgggggca cgaagtcgtc gttgtggacg atgaacggtg taagaagatc  420
atgaagcagt ttatcgatga gaggccccag gactggttcg aagacatcgg ggaataa     477
```

-continued

```
SEQ ID NO: 23          moltype = DNA  length = 1617
FEATURE                Location/Qualifiers
misc_feature           1..1617
                       note = MuLV gag
source                 1..1617
                       mol_type = other DNA
                       organism = synthetic construct
SEQUENCE: 23
atgggccaga ctgttaccac tcccttaagt ttgaccttag gtcactggaa agatgtcgag  60
cggatcgctc acaaccagtc ggtagatgtc aagaagagac gttgggttac cttctgctct  120
gcagaatggc caacctttaa cgtcggatgg ccgcgagacg gcacctttaa ccgagacctc  180
atcacccagg ttaagatcaa ggtcttttca cctggcccgc atggacaccc agaccaggtc  240
ccctacatcg tgacctggga agccttggct tttgaccccc ctccctgggt caagcccttt  300
gtacacccta agcctccgcc tcctcttcct ccatccgccc cgtctctccc ccttgaacct  360
cctcgttcga ccccgcctcg atcctccctt tatccagccc tcactccttc tctaggcgcc  420
aaacctaaac ctcaagttct ttctgacagt gggggccgc tcatcgacct acttacagaa  480
gacccccgc cttataggga cccaagacca cccccttccg acagggacgg aaatggtgga  540
gaagcgaccc ctgcgggaga ggcaccggac ccctccccaa tggcatctcg cctacgtggg  600
agacgggagc cccctgtggc cgactccact acctcgcagg cattcccccct ccgcgcagga  660
ggaaacggac agcttcaata ctggccgttc tcctcttctg acctttacaa ctggaaaaat  720
aataaccctt ctttttctga agatccaggt aaactgacag ctctgatcga gtctgttctc  780
atcacccatc agcccacctg ggacgactgt cagcagctgt tggggactct gctgaccgga  840
gaagaaaaac aacgggtgct cttagaggct agaaaggcgg tgcggggcga tgatgggcgc  900
cccactcaac tgcccaatga agtcgatgcc gcttttcccc tcgagcgccc agactgggat  960
tacaccaccc aggcaggtag gaaccaccta gtccactatc gccagttgct cctagcgggt  1020
ctccaaaacg cgggcagaag ccccaccaat ttggccaagg taaaaggaat aacacaaggg  1080
cccaatgagt ctccctcggc cttcctagag agacttaagg aagcctatcg caggtacact  1140
ccttatgacc ctgaggaccc agggcaagaa actaatgtgt ctatgtcttt catttggcag  1200
tctgccccag acattgggag aaagttagag aggttagaag atttaaaaaa caagacgctt  1260
ggagatttgg ttagagaggc agaaaagatc tttaataaac gagaaacccc ggaagaaaga  1320
gaggaacgta tcaggagaga aacagaggaa aaagaagaac gccgtaggac agaggatgag  1380
cagaaagaga aagaaagaga tcgtaggaga catagagaga tgagcaagct attggccact  1440
gtcgttagtg gacagaaaca ggatagacag ggaggagaac gaaggaggtc ccaactcgat  1500
cgcgaccagt gtgcctactg caaagaaaag gggcactggg ctaaagattg tcccaagaaa  1560
ccacgaggac ctcggggacc aagaccccag acctccctcc tgaccctaga tgactag     1617

SEQ ID NO: 24          moltype = DNA  length = 3635
FEATURE                Location/Qualifiers
misc_feature           1..3635
                       note = MuLV pol
source                 1..3635
                       mol_type = other DNA
                       organism = synthetic construct
SEQUENCE: 24
ggaggtcagg gtcaggagcc ccccctgaa cccaggataa ccctcaaagt cgggggcaa  60
cccgtcacct tcctggtaga tactggggcc caacactccg tgctgaccca aaatcctgga  120
cccctaagtg ataagtctgc ctgggtccaa ggggctactg gaggaaagcg gtatcgctgg  180
accacggatc gcaaagtaca tctagctacc ggtaaggtca cccactcttt cctccatgta  240
ccagactgtc cctatcctct gttaggaaga gatttgctga ctaaactaaa agcccaaatc  300
cactttgagg gatcaggagc tcaggttatg ggaccaatgg ggcagcccct gcaagtgttg  360
accctaaata tagaagatga gcatcggcta catgagacct caaaagagcc agatgtttct  420
ctagggtcca catggctgtc tgattttcct caggcctggg cggaaaccgg gggcatggga  480
ctggcagttc gccaagctcc tctgatcata cctctgaaag caacctctac ccccgtgtcc  540
ataaaacaat accccatgtc acaagaagcc agactgggga tcaagcccca catacagaga  600
ctgttggacc agggaatact ggtaccctgc cagtccccct ggaacacgcc cctgctaccc  660
gttaagaaac cagggactaa tgattatagg cctgtccagg atctgagaga agtcaacaag  720
cgggtggaag acatccaccc caccgtgccc aacccttaca acctcttgag cgggctccca  780
ccgtcccacc agtggtacac tgtgcttgat ttaaaggatg cctttttctg cctgagactc  840
caccccacca gtcagcctct cttcgccttt gagtggagag atccagagat gggaatctca  900
ggacaattga cctggaccag actcccacag ggtttcaaaa acagtcccac cctgtttgat  960
gaggcactgc acagagacct agcagacttc cggatccagc acccagactt gatcctgcta  1020
cagtacgtgg atgacttact gctggccgcc acttctgagc tagactgcca acaaggtact  1080
cgggccctgt tacaaaccct agggaacctc gggtatcggg cctcggccaa gaaagcccaa  1140
atttgccaga aacaggtcaa gtatctgggg tatcttctaa aagagggtca gagatggctg  1200
actgaggcca gaaaagagac tgtgatgggg cagcctactc cgaagacccc tcgacaacta  1260
agggagttcc tagggacggc aggcttctgt cgcctctgga tccctgggtt tgcagaaatg  1320
gcagcccccct tgtaccctct caccaaaacg gggactctgt ttaattgggg cccagaccaa  1380
caaaaggcct atcaagaaat caagcaagct cttctaactg ccccagccct ggggttgcca  1440
gatttgacta agccctttga actctttgtc gacgagaagc agggctacgc caaaggtgtc  1500
ctaacgcaaa aactgggacc ttggcgtcgg ccggtggcct acctgtccaa aaagctagac  1560
ccagtagcag ctgggtggcc cccttgccta cggatggtag cagccattgc cgtactgaca  1620
aaggatgcag gcaagctaac catgggacag ccactagtca ttctggcccc ccatgcagta  1680
gaggcactag tcaaacaacc ccccgaccgc tggctttcca acgcccggat gactcactat  1740
caggccttgc ttttggacac ggaccgggtc cagttcggac cggtggtagc cctgaacccg  1800
gctacgctgc tcccactgcc tgaggaaggg ctgcaacaca actgccttga tatcctggcc  1860
gaagcccacg gaacccgacc cgacctaacg gaccagccgc tcccagacgc cgaccacacc  1920
tggtacacgg atggaagcag tctcttacaa gagggacagc gtaaggcggg agctgcggtg  1980
accaccgaga ccgaggtaat ctgggctaaa gccctgccag ccgggacatc cgctcagcgg  2040
gctgaactga tagcactcac ccaggcccta aagatggcag aaggtaagaa gctaaatgtt  2100
```

```
tatactgata gccgttatgc ttttgctact gcccatatcc atggagaaat atacagaagg  2160
cgtgggttgc tcacatcaga aggcaaagag atcaaaaata aagacgagat cttggcccta  2220
ctaaaagccc tctttctgcc caaaagactt agcataatcc attgtccagg acatcaaaag  2280
ggacacagcg ccgaggctag aggcaaccgg atggctgacc aagcggcccg aaaggcagcc  2340
atcacagaga ctccagacac ctctaccctc ctcatagaaa attcatcacc ctacacctca  2400
gaacattttc attacacagt gactgatata aaggacctaa ccaagttggg ggccatttat  2460
gataaaacaa agaagtattg ggtctaccaa ggaaaacctg tgatgcctga ccagtttact  2520
tttgaattat tagactttct tcatcagctg actcacctca gcttctcaaa aatgaaggct  2580
ctcctagaga gaagccacag tccctactac atgctgaacc gggatcgaac actcaaaaat  2640
atcactgaga cctgcaaagc ttgtgcacaa gtcaacgcca gcaagtctgc cgttaaacag  2700
ggaactaggg tccgcgggca tcggcccggc actcattggg agatcgattt caccgagata  2760
aagcccggat tgtatggcta taaatatctt ctagttttta tagatacctt ttctggctgg  2820
atagaagcct tcccaaccaa gaaagaaacc gccaaggtcg taaccaagaa gctactagag  2880
gagatcttcc ccaggttcgg catgcctcag gtattgggaa ctgacaatgg gcctgccttc  2940
gtctccaagg tgagtcagac agtggccgat ctgttgggga ttgattggaa attacattgt  3000
gcatacagac cccaaagctc aggccaggta gaaagaatga atagaaccat caaggagact  3060
ttaactaaat taacgcttgc aactggctct agagactggg tgctcctact ccccttagcc  3120
ctgtaccgag cccgcaacac gccgggcccc catggcctca ccccatatga gatcttatat  3180
ggggcacccc cgccccttgt aaacttccct gaccctgaca tgacaagagt tactaacagc  3240
ccctctctcc aagctcactt acaggctctc tacttagtcc agcacgaagt ctggagacct  3300
ctggcggcag cctaccaaga acaactggac cgaccggtgg tacctcaccc ttaccgagtc  3360
ggcgacacag tgtgggtccg ccgacaccag actaagaacc tagaacctcg ctggaaagga  3420
ccttacacag tcctgctgac cacccccacc gccctcaaag tagacggcat cgcagcttgg  3480
atacacgccg cccacgtgaa ggctgccgac cccgggggtg gaccatcctc tagactgaca  3540
tggcgcgttc aacgctctca aaacccctta aaaataaggt taacccgcga ggccccctaa  3600
tccccttaat tcttctgatg ctcagagggg tcagt                           3635
```

```
SEQ ID NO: 25          moltype = DNA  length = 9694
FEATURE                Location/Qualifiers
misc_feature           1..9694
                       note = spRRVe-yCD env vector
source                 1..9694
                       mol_type = other DNA
                       organism = synthetic construct
SEQUENCE: 25
aacgccattt tgcaaggcat ggaaaaatac ataactgaga atagaaaagt tcagatcaag  60
gtcaggaaca gatggaacag ctgaatatgg gccaaacagg atatctgtgg taagcagttc  120
ctgccccggc tcagggccaa gaacagatgg aacagctgaa tatgggccaa acaggatatc  180
tgtggtaagc agttcctgcc ccggctcagg gccaagaaca gatggtcccc agatgcggtc  240
cagccctcag cagtttctag agaaccatca gatgtttcca gggtgcccca aggacctgaa  300
atgaccctgt gccttatttg aactaaccaa tcagttcgct tctcgcttct gttcgcgcgc  360
ttatgctccc cgagctcaat aaaagagccc acaacccctc actcggggcg ccagtcctcc  420
gattgactga gtcgcccggg tacccgtgta tccaataaac cctcttgcag ttgcatccga  480
cttgtggtct cgctgttcct tgggagggtc tcctctgagt gattgactac ccgtcagcgg  540
gggtctttca tttgggggct cgtccgggat cgggagaccc ctgcccaggg accaccgacc  600
caccaccggg aggtaagctg gccagcaact tatctgtgtc tgtccgattg tctagtgtct  660
atgactgatt ttatgcgcct gcgtcggtac tagttagcta actagctctg tatctggcgg  720
acccgtggtg gaactgacga gttcggaaca cccggccgca accctgggag acgtcccagg  780
gacttcgggg gccgtttttg tggcccgacc tgagtcctaa aatcccgatc gtttaggact  840
ctttggtgca ccccccttag aggagggata tgtggttctg gtaggagacg agaacctaaa  900
acagttcccg cctccgtctg aatttttgct ttcggtttgg gaccgaagcc gcgccgcgcg  960
tcttgtctgc tgcagcatcg ttctgtgttg tctctgtctg actgtgtttc tgtatttgtc  1020
tgaaaatatg ggcccgggct agcctgttac cactccctta agtttgacct taggtcactg  1080
gaaagatgtc gagcggatcg ctcacaacca gtcggtagat gtcaagaaga gacgttgggt  1140
taccttctgc tctgcagaat ggccaacctt taacgtcgga tggccgcgag acggcacctt  1200
taaccgagac ctcactaccc aggttaagat caaggtcttt tcacctggcc cgcatggaca  1260
cccagaccag gtggggtaca tcgtgacctg ggaagccttg gcttttgacc cccctccctg  1320
ggtcaagccc tttgtacacc ctaagcctcc gcctcctctt cctccatccg ccccgtctct  1380
ccccccttgaa cctcctcgtt cgaccccgcc tcgatcctcc ctttatccag ccctcactcc  1440
ttctctaggc gcccccatat ggccatatga gatcttatat ggggcacccc cgccccttgt  1500
aaacttccct gaccctgaca tgacaagagt tactaacagc ccctctctcc aagctcactt  1560
acaggctctc tacttagtcc agcacgaagt ctggagacct ctggcggcag cctaccaaga  1620
acaactggac cgaccggtgg tacctcaccc ttaccgagtc ggcgacacag tgtgggtccg  1680
ccgacaccag actaagaacc tagaacctcg ctggaaagga ccttacacag tcctgctgac  1740
cacccccacc gccctcaaag tagacggcat cgcagcttgg atacacgccg cccacaattc  1800
gatcatacct ggtgttgctg actaccccga ccgcggtaaa agtcgatggt attgctgcct  1860
gggtccatgc ttctcacctc aaacctgcac caccttcggc accagatgag tcctgggagc  1920
tggaaaagac tgatcatcct cttaagctgc gtattcggcg gcggcgggac gagtctgcaa  1980
aataagaacc cccaccagcc catgaccctc acttggcagg tactgtccca aactggagac  2040
gttgtctggg atacaaaggc agtccagccc ccttggactt ggtggcccac acttaaacct  2100
gatgtatgtg ccttggcggc tagtcttgag tcctgggata tcccgggaac cgatgtctcg  2160
tcctctaaac gagtcagacc tccggactca gactatactg ccgcttataa gcaaatcacc  2220
tggggagcca tagggtgcag ctaccctcgg gctaggacta gaatggcaag ctctaccttc  2280
tacgtatgtc cccgggatgg ccggaccctt tcagaagcta gaaggtgcgg ggggctagaa  2340
tccctatact gtaaagaatg ggattgtgag accacgggga ccggttattg gctatctaaa  2400
tcctcaaaag acctcataac tgtaaaatgg gaccaaaata gcgaatggac tcaaaaattt  2460
caacagtgtc accagaccgg ctggtgtaac cccccttaaaa tagatttcac agacaaagga  2520
aaattatcca aggactggat aacgggaaaa acctggggat taagattcta tgtgtctgga  2580
catccaggcg tacagttcac cattcgctta aaaatcacca acatgccagc tgtggcagta  2640
```

-continued ggtcctgacc tcgtccttgt ggaacaagga cctcctagaa cgtccctcgc tctcccacct 2700
cctcttcccc caagggaagc gccaccgcca tctctccccg actctaactc cacagccctg 2760
gcgactagtg cacaaactcc cacggtgaga aaaacaattg ttaccctaaa cactccgcct 2820
cccaccacag gcgacagact ttttgatctt gtgcaggggg ccttcctaac cttaaatgct 2880
accaacccag gggccactga gtcttgctgg ctttgtttgg ccatgggccc cccttattat 2940
gaagcaatag cctcatcagg agaggtcgcc tactccaccg accttgaccg gtgccgctgg 3000
gggacccaag gaaagctcac cctcactgag gtctcaggac acgggttgtg cataggaaag 3060
gtgcccttta cccatcagca tctctgcaat cagaccctat ccatcaattc ctccggagac 3120
catcagtatc tgctcccctc caaccatagc tggtgggctt gcagcactgg cctcacccct 3180
tgcctctcca cctcagtttt taatcagact agagatttct gtatccaggt ccagctgatt 3240
cctcgcatct attactatcc tgaagaagtt ttgttacagg cctatgacaa ttctcacccc 3300
aggactaaaa gagaggctgt ctcacttacc ctagctgttt tactggggtt gggaatcacg 3360
gcgggaatag gtactggttc aactgcctta attaaaggac ctatagacct ccagcaaggc 3420
ctgacaagcc tccagatcgc catagatgct gacctccggg ccctccaaga ctcagtcagc 3480
aagttagagg actcactgac ttccctgtcc gaggtagtgc tccaaaatag gagaggcctt 3540
gacttgctgt ttctaaaaga aggtggcctc tgtgcggccc taaaggaaga gtgctgtttt 3600
tacatagacc actcaggtgc agtacgggac tccatgaaaa aactcaaaga aaaactggat 3660
aaaagacagt tagagcgcca gaaaagccaa aactggtatg aaggatggtt caataactcc 3720
ccttggttca ctaccctgct atcaaccatc gctgggcccc tattactcct ccttctgttg 3780
ctcatcctcg ggccatgcat catcaataag ttagttcaat tcatcaatga taggataagt 3840
gcagttaaaa ttctggtcct tagacaaaaa tatcaggccc tagagaacga aggtaacctt 3900
taattttgct ctaagattag agctattcac aagagaaatg gggaatcact agtgaattaa 3960
accgataagc gttttttttca ataacaggaa agtcccattg gagccaagta cattgagtca 4020
atagggactt tccaatgggt tttgcccagt acataaggtc aatgggaggt aagccaatgg 4080
gtttttccca ttactggcac gtatactgag tcattaggga ctttccaatg ggttttgccc 4140
agtacataag gtcaataggg gtgaatcaac aggaaagtcc cattggagcc aagtacactg 4200
agtcaatagg gactttccat tgggttttgc ccagtacaaa aggtcaatag ggggtgagtc 4260
aatgggtttt tcccattatt ggcacgtaca taaggtcaat aggggtgagt cattgggttt 4320
ttccagccaa tttaattaaa acgccatgta ctttcccacc attgacgtca atgggctatt 4380
gaaactaatg caacgtgacc tttaaacggt actttcccat agctgattaa tgggaaagta 4440
ccgttctcga gccaatacac gtcaatggga agtgaaaggg cagccaaaac gtaacaccgc 4500
cccggttttc cctggaaatt ccatattggc acgcattcta ttggctgagc tgcgttctac 4560
gtgggtataa gaggcgcgac cagcgtcggt accgtcgcag tcttcggtct gaccaccgta 4620
gaacgcagaa ctctagaact agtcgggatc cgcgttaaca tttgcggccg ctttagttta 4680
gcttatggtg acaggggggaa tggcaagcaa gtgggatcag aagggtatgg acattgccta 4740
tgaggaggcg gccttaggtt acaaagaggg tggtgttcct attggcggat gtcttatcaa 4800
taacaaagac ggaagtgttc tcggtcgtgg tcacaacatg agatttcaaa agggatccgc 4860
cacactacat ggtgagatct ccactttgga aaactgtggg agattagagg gcaaagtgta 4920
caaagatacc actttgtata cgacgctgtc tccatgcgac atgtgtacag gtgccatcat 4980
catgtatggt attccacgct gtgttgtcgg tgagaacgtt aatttcaaaa gtaagggcga 5040
gaaatattta caaactagag gtcacgaggt tgttgttgtt gacgatgaga ggtgtaaaaa 5100
gatcatgaaa caatttatcg atgaaagacc tcaggattgg tttgaagata ttggtgagta 5160
gctcgaaaac gcgtcgaccc atcgatggta ccagatccgg attagtccaa tttgttaaag 5220
acaggatatc agtggtccag gctctagttt tgactcaaca atatcaccag ctgaagccta 5280
tagagtacga gccatagata aaataaaaga ttttatttag tctccagaaa aaggggggaa 5340
tgaaagaccc cacctgtagg tttggcaagc tagcttaagt aacgccattt tgcaaggcat 5400
ggaaaaatac ataactgaga atagagaagt tcagatcaag gtcaggaaca gatggaacag 5460
ctgaatatgg gccaaacagg atatctgtgg taagcagttc ctgccccggc tcagggccaa 5520
gaacagatgg aacagctgaa tatgggccaa acaggatatc tgtggtaagc agttcctgcc 5580
ccggctcagg gccaagaaca gatggtcccc agatgcggtc cagccctcag cagtttctag 5640
agaaccatca gatgtttcca gggtgcccca aggacctgaa atgaccctgt gccttatttg 5700
aactaaccaa tcagttcgct tctcgcttct gttcgcgcgc ttctgctccc cgagctcaat 5760
aaaagagccc acaacccctc actcggggcg ccagtcctcc gattgactga gtcgcccggg 5820
tacccgtgta tccaataaac cctcttgcag ttgcatccga cttgtggtct cgctgttcct 5880
tgggagggtc tcctctgagt gattgactac ccgtcagcgg gggtctttca cacatgcagc 5940
atgtatcaaa attaatttgg tttttttttct taagtattta cattaaatgg ccatagtact 6000
taaagttaca ttggcttcct tgaaataaac atggagtatt cagaatgtgt cataaatatt 6060
tctaatttta agatagtatc tccattggct ttctactttt tcttttattt tttttgtcc 6120
tctgtcttcc atttgttgtt gttgttgttt gtttgtttgt ttgttggttg gttggttaat 6180
tttttttttaa agatcctaca ctatagttca agctagacta ttagctactc tgtaacccag 6240
ggtgaccttg aagtcatggg tagcctgctg ttttagcctt cccacatcta agattacagg 6300
tatgagctat catttttggt atatgattga ttgattgatt gatgtgtgtg tgtgtgattg 6360
tgtttgtgtg tgtgactgtg aaaatgtgtg tatgggtgtg tgtgaatgtg tgtatgtatg 6420
tgtgtgtgtg agtgtgtgtg tgtgtgtgtg catgtgtgtg tgtgtgactg tgtctatgtg 6480
tatgactgtg tgtgtgtgtg tgtgtgtgtg tgtgtgtgtg tgtgtgtgtg tgttgtgaaa 6540
aaatattcta tggtagtgag agccaacgct ccggctcagg tgtcaggttg gtttttgaga 6600
cagagtcttt cacttagctt ggaattcact ggccgtcgtt ttacaacgtc gtgactggga 6660
aaaccctggc gttacccaac ttaatcgcct tgcagcacat ccccctttcg ccagctggcg 6720
taatagcgaa gaggcccgca ccgatcgccc ttcccaacag ttgcgcagcc tgaatggcga 6780
atggcgcctg atgcggtatt ttctccttac gcatctgtgc ggtatttcac accgcatatg 6840
gtgcactctc agtacaatct gctctgatgc cgcatagtta agccagcccc gacacccgcc 6900
aacacccgct gacgcgccct gacgggcttg tctgctcccg gcatccgctt acagacaagc 6960
tgtgaccgtc tccgggagct gcatgtgtca gaggttttca ccgtcatcac cgaaacgcgc 7020
gagacgaaag ggcctcgtga tacgcctatt tttataggtt aatgtcatga taataatggt 7080
ttcttagacg tcaggtggca cttttcgggg aaatgtgcgc ggaaccccta tttgtttatt 7140
tttctaaata cattcaaata tgtatccgct catgagacaa taaccctgat aaatgcttca 7200
ataatattga aaaaggaaga gtatgagtat tcaacatttc cgtgtcgccc ttattccctt 7260
ttttgcggca ttttgccttc ctgtttttgc tcacccagaa acgctggtga aagtaaaaga 7320
tgctgaagat cagttgggtg cacgagtggg ttacatcgaa ctggatctca acagcggtaa 7380

-continued

```
gatccttgag agttttcgcc ccgaagaacg ttttccaatg atgagcactt ttaaagttct  7440
gctatgtggc gcggtattat cccgtattga cgccgggcaa gagcaactcg gtcgccgcat  7500
acactattct cagaatgact tggttgagta ctcaccagtc acagaaaagc atcttacgga  7560
tggcatgaca gtaagagaat tatgcagtgc tgccataacc atgagtgata acactgcggc  7620
caacttactt ctgacaacga tcggaggacc gaaggagcta accgcttttt tgcacaacat  7680
gggggatcat gtaactcgcc ttgatcgttg ggaaccggag ctgaatgaag ccataccaaa  7740
cgacgagcgt gacaccacga tgcctgtagc aatggcaaca acgttgcgca aactattaac  7800
tggcgaacta cttactctag cttcccggca acaattaata gactggatgg aggcggataa  7860
agttgcagga ccacttctgc gctcggccct tccggctggc tggtttattg ctgataaatc  7920
tggagccggt gagcgtgggt ctcgcggtat cattgcagca ctggggccag atggtaagcc  7980
ctcccgtatc gtagttatct acacgacggg gagtcaggca actatggatg aacgaaatag  8040
acagatcgct gagataggtg cctcactgat taagcattgg taactgtcag accaagttta  8100
ctcatatata ctttagattg atttaaaact tcatttttaa tttaaaagga tctaggtgaa  8160
gatccttttt gataatctca tgaccaaaat cccttaacgt gagttttcgt tccactgagc  8220
gtcagacccc gtagaaaaga tcaaaggatc ttcttgagat cctttttttc tgcgcgtaat  8280
ctgctgcttg caaacaaaaa aaccaccgct accagcggtg gtttgtttgc cggatcaaga  8340
gctaccaact ctttttccga aggtaactgg cttcagcaga gcgcagatac caaatactgt  8400
tcttctagtg tagccgtagt taggccacca cttcaagaac tctgtagcac cgcctacata  8460
cctcgctctg ctaatcctgt taccagtggc tgctgccagt ggcgataagt cgtgtcttac  8520
cgggttggac tcaagacgat agttaccgga taaggcgcag cggtcgggct gaacgggggg  8580
ttcgtgcaca cagcccagct tggagcgaac gacctacacc gaactgagat acctacagcg  8640
tgagctatga gaaagcgcca cgcttcccga agggagaaag gcggacaggt atccggtaag  8700
cggcagggtc ggaacaggag agcgcacgag ggagcttcca gggggaaacg cctggtatct  8760
ttatagtcct gtcgggtttc gccacctctg acttgagcgt cgatttttgt gatgctcgtc  8820
aggggggcgg agcctatgga aaaacgccag caacgcggcc tttttacggt tcctggcctt  8880
ttgctggcct tttgctcaca tgttctttcc tgcgttatcc cctgattctg tggataaccg  8940
tattaccgcc tttgagtgag ctgataccgc tcgccgcagc cgaacgaccg agcgcagcga  9000
gtcagtgagc gaggaagcgg aagagcgccc aatacgcaaa ccgcctctcc ccgcgcgttg  9060
gccgattcat taatgcagct ggcacgacag gtttcccgac tggaaagcgg gcagtgagcg  9120
caacgcaatt aatgtgagtt agctcactca ttaggcaccc caggctttac actttatgct  9180
tccggctcgt atgttgtgtg gaattgtgag cggataacaa tttcacacag gaaacagcta  9240
tgaccatgat tacgccaagc tttgctccta ggagtttcct aatacttccc aaactcaaat  9300
atataaagca tttgacttgt tctatgccct agggggcggg gggaagctaa gccagctttt  9360
tttaacattt aaaatgttaa ttccatttta aatgcacaga tgtttttatt tcataagggt  9420
ttcaatgtgc atgaatgctg caatattcct gttaccaaag ctagtataaa taaaaataga  9480
taaacgtgga aattacttag agtttctgtc attaacgttt ccttcctcag ttgacaacat  9540
aaatgcgctg ctgagcaagc cagtttgcat ctgtcaggat caatttccca ttatgccagt  9600
catattaatt actagtcaat tagttgattt ttatttttga catatacatg tgaatgaaag  9660
accccacctg taggtttggc aagctagctt aagt                             9694
```

```
SEQ ID NO: 26          moltype = DNA  length = 11162
FEATURE                Location/Qualifiers
misc_feature           1..11162
                       note = sRRVgp-TK:gag-pol vector
source                 1..11162
                       mol_type = other DNA
                       organism = synthetic construct
SEQUENCE: 26
catgtgagca aaaggccagc aaaaggccag gaaccgtaaa aaggccgcgt tgctggcgtt  60
tttccatagg ctccgccccc ctgacgagca tcacaaaaat cgacgctcaa gtcagaggtg  120
gcgaaacccg acaggactat aaagatacca ggcgtttccc cctggaagct ccctcgtgcg  180
ctctcctgtt ccgaccctgc cgcttaccgg atacctgtcc gcctttctcc cttcgggaag  240
cgtggcgctt tctcatagct cacgctgtag gtatctcagt tcggtgtagg tcgttcgctc  300
caagctgggc tgtgtgcacg aaccccccgt tcagcccgac cgctgcgcct tatccggtaa  360
ctatcgtctt gagtccaacc cggtaagaca cgacttatcg ccactggcag cagccactgg  420
taacaggatt agcagagcga ggtatgtagg cggtgctaca gagttcttga agtggtggcc  480
taactacggc tacactagaa ggacagtatt tggtatctgc gctctgctga agccagttac  540
cttcggaaaa agagttggta gctcttgatc cggcaaacaa accaccgctg gtagcggtgg  600
tttttttgtt tgcaagcagc agattacgcg cagaaaaaaa ggatctcaag aagatccttt  660
gatcttttct acggggtctg acgctcagtg gaacgaaaac tcacgttaag ggattttggt  720
catgagatta tcaaaaagga tcttcaccta gatcctttta aattaaaaat gaagttttaa  780
atcaatctaa agtatatatg agtaacctga tcaggactct tcctttttcat gaacaataaa  840
actgtctgct tacataaaca gtaatacaag gggtgttatg agccatattc aacgggaaac  900
gtcttgctct aggccgcgat taaattccaa catggatgct gatttatatg ggtataaatg  960
ggctcgcgat aatgtcgggc aatcaggtgc gacaatctat cgattgtatg ggaagcccga  1020
tgcgccagag ttgtttctga aacatggcaa aggtagcgtt gccaatgatg ttacagatga  1080
gatggtcaga ctaaactggc tgacggaatt tatgcctctt ccgaccatca agcattttat  1140
ccgtactcct gatgatgcat ggttactcac cactgcgatc cccgggaaaa cagcattcca  1200
ggtattagaa gaatatcctg attcaggtga aaatattgtt gatgcgctgg cagtgttcct  1260
gcgccggttg cattcgattc ctgtttgtaa ttgtcctttt aacagcgatc gcgtatttcg  1320
tctcgctcag gcgcaatcac gaatgaataa cggtttggtt gatgcgagtg attttgatga  1380
cgagcgtaat ggctggcctg ttgaacaagt ctggaaagaa atgcataaac ttttgccatt  1440
ctcaccggat tcagtcgtca ctcatggtga tttctcactt gataacctta tttttgacga  1500
ggggaaatta ataggttgta ttgatgttgg acgagtcgga atcgcagacc gataccagga  1560
tcttgccatc ctatggaact gcctcggtga gttttctcct tcattacaga aacggctttt  1620
tcaaaaatat ggtattgata atcctgatat gaataaattg cagtttcatt tgatgctcga  1680
tgagtttttc taagaatttg tgaatgaaag accccacctg taggtttggc aagctagctt  1740
aagtaacgcc attttgcaag gcatggaaaa atacataact gagaatagaa aagttcagat  1800
caaggtcagg aacagatgga acagctgaat atgggccaaa caggatatct gtggtaagca  1860
```

-continued gttcctgccc cggctcaggg ccaagaacag atggaacagc tgaatatggg ccaaacagga 1920
tatctgtggt aagcagttcc tgccccggct cagggccaag aacagatggt ccccagatgc 1980
ggtccagccc tcagcagttt ctagagaacc atcagatgtt tccagggtgc cccaaggacc 2040
tgaaatgacc ctgtgcctta tttgaactaa ccaatcagtt cgcttctcgc ttctgttcgc 2100
gcgcttatgc tccccgagct caataaaaga gcccacaacc cctcactcgg ggcgccagtc 2160
ctccgattga ctgagtcgcc cgggtacccg tgtatccaat aaaccctctt gcagttgcat 2220
ccgacttgtg gtctcgctgt tccttgggag ggtctcctct gagtgattga ctacccgtca 2280
gcgggggtct ttcatttggg ggctcgtccg ggatcgggag acccctgccc agggaccacc 2340
gacccaccac cgggaggtaa gctggccagc aacttatctg tgtctgtccg attgtctagt 2400
gtctatgact gattttatgc gcctgcgtcg gtactagtta gctaactagc tctgtatctg 2460
gcggacccgt ggtggaactg acgagttcgg aacacccggc cgcaaccctg ggagacgtcc 2520
cagggacttc gggggccgtt tttgtggccc gacctgagtc caaaaatccc gatcgttttg 2580
gactctttgg tgcacccccc ttagaggagg gatatgtggt tctggtagga gacgagaacc 2640
taaaacagtt cccgcctccg tctgaatttt tgctttcggt ttgggaccga agccgcgccg 2700
cgcgtcttgt ctgctgcagc atcgttctgt gttgtctctg tctgactgtg tttctgtatt 2760
tgtctgagaa tatgggccag actgttacca ctcccttaag tttgacctta ggtcactgga 2820
aagatgtcga gcggatcgct cacaaccagt cggtagatgt caagaagaga cgttgggtta 2880
ccttctgctc tgcagaatgg ccaaccttta acgtcggatg gccgcgagac ggcaccttta 2940
accgagacct catcacccag gttaagatca aggtcttttc acctggcccg catggacacc 3000
cagaccaggt cccctacatc gtgacctggg aagccttggc ttttgacccc cctccctggg 3060
tcaagccctt tgtacaccct aagcctccgc ctcctcttcc tccatccgcc ccgtctctcc 3120
cccttgaacc tcctcgttcg accccgcctc gatcctccct ttatccagcc ctcactcctt 3180
ctctaggcgc caaacctaaa cctcaagttc tttctgacag tggggggccg ctcatcgacc 3240
tacttacaga agaccccccg ccttataggg acccaagacc acccccttcc gacagggacg 3300
gaaatggtgg agaagcgacc cctgcgggag aggcaccgga cccctcccca atggcatctc 3360
gcctacgtgg gagacgggag ccccctgtgg ccgactccac tacctcgcag gcattccccc 3420
tccgcgcagg aggaaacgga cagcttcaat actggccgtt ctcctcttct gacctttaca 3480
actggaaaaa taataaccct tctttttctg aagatccagg taaactgaca gctctgatcg 3540
agtctgttct catcacccat cagcccacct gggacgactg tcagcagctg ttggggactc 3600
tgctgaccgg agaagaaaaa caacgggtgc tcttagaggc tagaaaggcg gtgcggggcg 3660
atgatgggcg ccccactcaa ctgcccaatg aagtcgatgc cgcttttccc ctcgagcgcc 3720
cagactggga ttacaccacc caggcaggta ggaaccacct agtccactat cgccagttgc 3780
tcctagcggg tctccaaaac gcgggcagaa gccccaccaa tttggccaag gtaaaaggaa 3840
taacacaagg gcccaatgag tctccctcgg ccttcctaga gagacttaag gaagcctatc 3900
gcaggtacac tccttatgac cctgaggacc cagggcaaga aactaatgtg tctatgtctt 3960
tcatttggca gtctgcccca gacattggga gaaagttaga gaggttagaa gatttaaaaa 4020
acaagacgct tggagatttg gttagagagg cagaaaagat ctttaataaa cgagaaaccc 4080
cggaagaaag agaggaacgt atcaggagag aaacagagga aaaagaagaa cgccgtagga 4140
cagaggatga gcagaaagag aaagaaagag atcgtaggag acatagagag atgagcaagc 4200
tattggccac tgtcgttagt ggacagaaac aggatagaca gggaggagaa cgaaggaggt 4260
cccaactcga tcgcgaccag tgtgcctact gcaaagaaaa ggggcactgg gctaaagatt 4320
gtcccaagaa accacgagga cctcggggac caagacccca gacctccctc ctgaccctag 4380
atgactaggg aggtcagggt caggagcccc cccctgaacc caggataacc ctcaaagtcg 4440
gggggcaacc cgtcaccttc ctggtagata ctggggccca acactccgtg ctgacccaaa 4500
atcctggacc cctaagtgat aagtctgcct gggtccaagg ggctactgga ggaaagcggt 4560
atcgctggac cacggatcgc aaagtacatc tagctaccgg taaggtcacc cactctttcc 4620
tccatgtacc agactgtccc tatcctctgt taggaagaga tttgctgact aaactaaaag 4680
cccaaatcca ctttgaggga tcaggagctc aggttatggg accaatgggg cagcccctgc 4740
aagtgttgac cctaaatata gaagatgagc atcggctaca tgagacctca aaagagccag 4800
atgtttctct agggtccaca tggctgtctg attttcctca ggcctgggcg gaaaccgggg 4860
gcatgggact ggcagttcgc caagctcctc tgatcatacc tctgaaagca acctctaccc 4920
ccgtgtccat aaaacaatac cccatgtcac aagaagccag actggggatc aagccccaca 4980
tacagagact gttggaccag ggaatactgg taccctgcca gtcccccctgg aacacgcccc 5040
tgctacccgt taagaaacca gggactaatg attataggcc tgtccaggat ctgagagaag 5100
tcaacaagcg ggtggaagac atccacccca ccgtgcccaa cccttacaac ctcttgagcg 5160
ggctcccacc gtcccaccag tggtacactg tgcttgattt aaaggatgcc tttttctgcc 5220
tgagactcca ccccaccagt cagcctctct tcgcctttga gtggagagat ccagagatgg 5280
gaatctcagg acaattgacc tggaccagac tcccacaggg tttcaaaaac agtcccaccc 5340
tgtttgatga ggcactgcac agagacctag cagacttccg gatccagcac ccagacttga 5400
tcctgctaca gtacgtggat gacttactgc tggccgccac ttctgagcta gactgccaac 5460
aaggtactcg ggccctgtta caaaccctag ggaacctcgg gtatcgggcc tcggccaaga 5520
aagcccaaat ttgccagaaa caggtcaagt atctggggta tcttctaaaa gagggtcaga 5580
gatggctgac tgaggccaga aaagagactg tgatggggca gcctactccg aagaccccctc 5640
gacaactaag ggagttccta gggacggcag gcttctgtcg cctctggatc cctgggtttg 5700
cagaaatggc agccccccttg taccctctca ccaaaacggg gactctgttt aattggggcc 5760
cagaccaaca aaaggcctat caagaaatca agcaagctct tctaactgcc ccagccctgg 5820
ggttgccaga tttgactaag ccctttgaac tctttgtcga cgagaagcag ggctacgcca 5880
aaggtgtcct aacgcaaaaa ctgggacctt ggcgtcggcc ggtggcctac ctgtccaaaa 5940
agctagaccc agtagcagct gggtggcccc cttgcctacg gatggtagca gccattgccg 6000
tactgacaaa ggatgcaggc aagctaacca tgggacagcc actagtcatt ctggcccccc 6060
atgcagtaga ggcactagtc aaacaacccc ccgaccgctg gctttccaac gcccggatga 6120
ctcactatca ggccttgctt ttggacacgg accgggtcca gttcggaccg gtggtagccc 6180
tgaacccggc tacgctgctc ccactgcctg aggaagggct gcaacacaac tgccttgata 6240
tcctggccga agcccacgga acccgacccg acctaacgga ccagccgctc ccagacgccg 6300
accacacctg gtacacggat ggaagcagtc tcttacaaga gggacagcgt aaggcgggag 6360
ctgcggtgac caccgagacc gaggtaatct gggctaaagc cctgccagcc gggacatccg 6420
ctcagcgggc tgaactgata gcactcaccc aggccctaaa gatggcagaa ggtaagaagc 6480
taaatgttta tactgatagc cgttatgctt ttgctactgc ccatatccat ggagaaatat 6540
acagaaggcg tgggttgctc acatcagaag gcaaagagat caaaaataaa gacgagatct 6600

-continued

```
tggccctact aaaagccctc tttctgccca aaagacttag cataatccat tgtccaggac  6660
atcaaaaggg acacagcgcc gaggctagag gcaaccggat ggctgaccaa gcggcccgaa  6720
aggcagccat cacagagact ccagacacct ctaccctcct catagaaaat tcatcaccct  6780
acacctcaga acattttcat tacacagtga ctgatataaa ggacctaacc aagttggggg  6840
ccatttatga taaaacaaag aagtattggg tctaccaagg aaaacctgtg atgcctgacc  6900
agtttacttt tgaattatta gactttcttc atcagctgac tcacctcagc ttctcaaaaa  6960
tgaaggctct cctagagaga agccacagtc cctactacat gctgaaccgg gatcgaacac  7020
tcaaaaatat cactgagacc tgcaaagctt gtgcacaagt caacgccagc aagtctgccg  7080
ttaaacaggg aactagggtc cgcgggcatc ggcccggcac tcattgggag atcgatttca  7140
ccgagataaa gcccggattg tatggctata aatatcttct agtttttata gatacctttt  7200
ctggctggat agaagccttc ccaaccaaga aagaaaccgc caaggtcgta accaagaagc  7260
tactagagga gatcttcccc aggttcggca tgcctcaggt attgggaact gacaatgggc  7320
ctgccttcgt ctccaaggtg agtcagacag tggccgatct gttggggatt gattggaaat  7380
tacattgtgc atacagaccc caaagctcag gccaggtaga aagaatgaat agaaccatca  7440
aggagacttt aactaaatta acgcttgcaa ctggctctag agactgggtg ctcctactcc  7500
ccttagccct gtaccgagcc cgcaacacgc cgggcccccca tggcctcacc ccatatgaga  7560
tcttatatgg ggcacccccg ccccttgtaa acttccctga ccctgacatg acaagagtta  7620
ctaacagccc ctctctccaa gctcacttac aggctctcta cttagtccag cacgaagtct  7680
ggagacctct ggcggcagcc taccaagaac aactggaccg accggtggta cctcaccctt  7740
accgagtcgg cgacacagtg tgggtccgcc gacaccagac taagaaccta gaacctcgct  7800
ggaaaggacc ttacacagtc ctgctgacca cccccaccgc cctcaaagta gacggcatcg  7860
cagcttggat acacgccgcc cacgtgaagg ctgccgaccc cgggggtgga ccatcctcta  7920
gactgacatg gcgcgttcaa cgctctcaaa accccttaaa aataaggtta acccgcgagg  7980
ccccctaatc cccttaattc ttctgatgct cagaggggtc agtaaacgaa ttcaacagga  8040
aagttccatt ggagccaagt acattgagtc aatagggact ttccaatggg ttttgcccag  8100
tacataaggt caatgggagg taagccaatg ggtttttccc attactggca cgtatactga  8160
gtcattaggg actttccaat gggttttgcc cagtacataa ggtcaatagg ggtgaatcaa  8220
caggaaagtc ccattggagc caagtacact gagtcaatag ggactttcca ttgggttttg  8280
cccagtacaa aaggtcaata gggggtgagt caatgggttt ttcccattat tggcacgtac  8340
ataaggtcaa taggggtgag tcattgggtt tttccagcca atttaattaa aacgccatgt  8400
actttcccac cattgacgtc aatgggctat tgaaactaat gcaacgtgac ctttaaacgg  8460
tactttccca tagctgatta atgggaaagt accgttctcg agccaataca cgtcaatggg  8520
aagtgaaagg gcagccaaaa cgtaacaccg ccccggtttt ccctggaaat tccatattgg  8580
cacgcattct attggctgag ctgcgttcta cgtgggtata agaggcgcga ccagcgtcgg  8640
taccgtcgca gtcttcggtc tgaccaccgt agaacgcaga gtttgatccg cgttaacatt  8700
tgcggccgct ttagtttcat ggcttcgtac ccctgccatc aacacgcgtc tgcgttcgac  8760
caggctgcgc gttctcgcgg ccatagcaac cgacgtacgg cgttgcgccc tcgccggcag  8820
caagaagcca cggaagtccg cctggagcag aaaatgccca cgctactgcg ggtttatata  8880
gacggtcctc acgggatggg gaaaaccacc accacgcaac tgctggtggc cctgggttcg  8940
cgcgacgata tcgtctacgt acccgagccg atgacttact ggcaggtgct gggggcttcc  9000
gagacaatcg cgaacatcta caccacacaa caccgcctcg accagggtga gatatcggcc  9060
ggggacgcgg cggtggtaat gacaagcgcc cagataacaa tgggcatgcc ttatgccgtg  9120
accgacgccg ttctggctcc tcatatcggg ggggaggctg ggagctcaca tgccccgccc  9180
ccggccctca ccctcatctt cgaccgccat cccatcgccg ccctcctgtg ctacccggcc  9240
gcgcgatacc ttatgggcag catgaccccc caggccgtgc tggcgttcgt ggccctcatc  9300
ccgccgacct tgcccggcac aaacatcgtg ttgggggccc ttccggagga cagacacatc  9360
gaccgcctgg ccaaacgcca gcgccccggc gagcggcttg acctggctat gctggccgcg  9420
attcgccgcg tttacgggct gcttgccaat acggtgcggt atctgcaggg cggcgggtcg  9480
tggcgggagg attggggaca gctttcgggg acggccgtgc cgccccaggg tgccgagccc  9540
cagagcaacg cgggcccacg accccatatc ggggacacgt tatttaccct gtttcgggcc  9600
cccgagttgc tggcccccaa cggcgacctg tacaacgtgt ttgcctgggc cttggacgtc  9660
ttggccaaac gcctccgtcc catgcacgtc tttatcctgg attacgacca atcgcccgcc  9720
ggctgccggg acgccctgct gcaacttacc tccgggatgg tccagaccca cgtcaccacc  9780
cccggctcca taccgacgat ctgcgacctg gcgcgcacgt ttgcccggga gatgggggag  9840
gctaactgaa acacggaagg ggtaccgaat tcctcgaaaa cgcgtcgaaa acgaattcat  9900
aaaataaaag attttatttt gtctccagaa aaaggggggga atgaaagacc ccacctgtag  9960
gtttggcaag ctagcttaag taacgccatt ttgcaaggca tggaaaaata cataactgag  10020
aatagagaag ttcagatcaa ggtcaggaac agatggaaca gctgaatatg ggccaaacag  10080
gatagctgtg gtaagcagtt cctgccccgg ctcagggcca agaacagatg gaacagctga  10140
atatgggcca aacaggatat ctgtggtaag cagttcctgc cccggctcag ggccaagaac  10200
agatggtccc cagatgcggt ccagccctca gcagtttcta gagaaccatc agatgtttcc  10260
agggtgcccc aaggacctga aatgaccctg tgccttattt gaactaacca atcagttcgc  10320
ttctcgcttc tgttcgcgcg cttctgctcc ccgagctcaa taaaagagcc cacaacccct  10380
cactcggggc gccagtcctc cgattgactg agtcgcccgg gtacccgtgt atccaataaa  10440
ccctcttgca gttgcatccg acttgtggtc tcgctgttcc ttgggagggt ctcctctgag  10500
tgattgacta cccgtcagcg ggggtctttc attgttactt aaagttacat tggcttcctt  10560
gaaataaaca tggagtattc agaatgtgtc ataaatattt ctaattttaa gatagtatct  10620
ccattggctt tctacttttt cttttatttt tttttgtcct ctgtcttcca tttgttgttg  10680
ttgttgtttg tttgttttgtt tgttggttgg ttggttaatt ttttttttaaa gatcctacac  10740
tatagttcaa gctagactat tagctactct gtaacccagg gtgaccttga agtcatgggt  10800
agcctgctgt tttagccttc ccacatctaa gattacaggt atgagctatc atttttggta  10860
tattgattga ttgattgatt gatgtgtgtg tgtgtgattg tgtttgtgtg tgtgactgtg  10920
aaaatgtgtg tatgggtgtg tgtgaatgtg tgtatgtatg tgtgtgtgtg agtgtgtgtg  10980
tgtgtgtgtg catgtgtgtg tgtgtgactg tgtctatgtg tatgactgtg tgtgtgtgtg  11040
tgtgtgtgtg tgtgtgtgtg tgtgtgtgtg tgttgtgaaa aaatattcta tggtagtgag  11100
agccaacgct ccggctcagg tgtcaggttg gtttttgaga cagagtcttt cacttagctt  11160
gg                                                                 11162
```

SEQ ID NO: 27 moltype = DNA length = 10383

-continued

```
FEATURE                  Location/Qualifiers
misc_feature             1..10383
                         note = spRRVe-TK vector
source                   1..10383
                         mol_type = other DNA
                         organism = synthetic construct
SEQUENCE: 27
aacgccattt tgcaaggcat ggaaaaatac ataactgaga atagaaaagt tcagatcaag  60
gtcaggaaca gatggaacag ctgaatatgg gccaaacagg atatctgtgg taagcagttc  120
ctgccccggc tcagggccaa gaacagatgg aacagctgaa tatgggccaa acaggatatc  180
tgtggtaagc agttcctgcc ccggctcagg gccaagaaca gatggtcccc agatgcggtc  240
cagccctcag cagtttctag agaaccatca gatgtttcca gggtgcccca aggacctgaa  300
atgaccctgt gccttatttg aactaaccaa tcagttcgct tctcgcttct gttcgcgcgc  360
ttatgctccc cgagctcaat aaaagagccc acaacccctc actcggggcg ccagtcctcc  420
gattgactga gtcgcccggg tacccgtgta tccaataaac cctcttgcag ttgcatccga  480
cttgtggtct cgctgttcct tgggagggtc tcctctgagt gattgactac ccgtcagcgg  540
gggtctttca tttgggggct cgtccgggat cgggagaccc ctgcccaggg accaccgacc  600
caccaccggg aggtaagctg gccagcaact tatctgtgtc tgtccgattg tctagtgtct  660
atgactgatt ttatgcgcct gcgtcggtac tagttagcta actagctctg tatctggcgg  720
acccgtggtg gaactgacga gttcggaaca cccggccgca accctgggag acgtcccagg  780
gacttcgggg gccgtttttg tggcccgacc tgagtcctaa aatcccgatc gtttaggact  840
ctttggtgca cccccettag aggagggata tgtggttctg gtaggagacg agaacctaaa  900
acagttcccg cctccgtctg aatttttgct ttcggtttgg gaccgaagcc gcgccgcgcg  960
tcttgtctgc tgcagcatcg ttctgtgttg tctctgtctg actgtgtttc tgtatttgtc  1020
tgaaaatatg ggcccgggct agcctgttac cactccctta agtttgacct taggtcactg  1080
gaaagatgtc gagcggatcg ctcacaacca gtcggtagat gtcaagaaga gacgttgggt  1140
taccttctgc tctgcagaat ggccaacctt taacgtcgga tggccgcgag acggcacctt  1200
taaccgagac ctcactaccc aggttaagat caaggtcttt tcacctggcc cgcatggaca  1260
cccagaccag gtggggtaca tcgtgacctg ggaagccttg gcttttgacc cccctccctg  1320
ggtcaagccc tttgtacacc ctaagcctcc gcctcctctt cctccatccg ccccgtctct  1380
ccccccttgaa cctcctcgtt cgaccccgcc tcgatcctcc ctttatccag ccctcactcc  1440
ttctctaggc gcccccatat ggccatatga gatcttatat ggggcacccc cgccccttgt  1500
aaacttccct gaccctgaca tgacaagagt tactaacagc ccctctctcc aagctcactt  1560
acaggctctc tacttagtcc agcacgaagt ctggagacct ctggcggcag cctaccaaga  1620
acaactggac cgaccggtgg tacctcaccc ttaccgagtc ggcgacacag tgtgggtccg  1680
ccgacaccag actaagaacc tagaacctcg ctggaaagga ccttacacag tcctgctgac  1740
cacccccacc gccctcaaag tagacggcat cgcagcttgg atacacgccg cccacaattc  1800
gatcatacct ggtgttgctg actaccccga ccgcggtaaa agtcgatggt attgctgcct  1860
gggtccatgc ttctcacctc aaacctgcac caccttcggc accagatgag tcctgggagc  1920
tggaaaagac tgatcatcct cttaagctgc gtattcggcg gcggcgggac gagtctgcaa  1980
aataagaacc cccaccagcc catgaccctc acttggcagg tactgtccca aactggagac  2040
gttgtctggg atacaaaggc agtccagccc ccttggactt ggtggcccac acttaaacct  2100
gatgtatgtg ccttggcggc tagtcttgag tcctgggata tcccgggaac cgatgtctcg  2160
tcctctaaac gagtcagacc tccggactca gactatactg ccgcttataa gcaaatcacc  2220
tggggagcca tagggtgcag ctaccctcgg gctaggacta gaatggcaag ctctaccttc  2280
tacgtatgtc cccgggatgg ccggaccctt tcagaagcta gaaggtgcgg ggggctagaa  2340
tccctatact gtaaagaatg ggattgtgag accacgggga ccggttattg gctatctaaa  2400
tcctcaaaag acctcataac tgtaaaatgg gaccaaaata gcgaatggac tcaaaaattt  2460
caacagtgtc accagaccgg ctggtgtaac cccccttaaaa tagatttcac agacaaagga  2520
aaattatcca aggactggat aacgggaaaa acctggggat taagattcta tgtgtctgga  2580
catccaggcg tacagttcac cattcgctta aaaatcacca acatgccagc tgtggcagta  2640
ggtcctgacc tcgtccttgt ggaacaagga cctcctagaa cgtccctcgc tctcccacct  2700
cctcttcccc caagggaagc gccaccgcca tctctccccg actctaactc cacagccctg  2760
gcgactagtg cacaaactcc cacggtgaga aaaacaattg ttaccctaaa cactccgcct  2820
cccaccacag gcgacagact tttgatcttt gtgcaggggg ccttcctaac cttaaatgct  2880
accaacccag ggccactga gtcttgctgg ctttgtttgg ccatgggccc cccttattat  2940
gaagcaatag cctcatcagg agaggtcgcc tactccaccg accttgaccg gtgccgctgg  3000
gggacccaag gaaagctcac cctcactgag gtctcaggac acgggttgtg cataggaaag  3060
gtgcccttta cccatcagca tctctgcaat cagaccctat ccatcaattc ctccggagac  3120
catcagtatc tgctcccctc caaccatagc tggtgggctt gcagcactgg cctcacccct  3180
tgcctctcca cctcagtttt taatcagact agagatttct gtatccaggt ccagctgatt  3240
cctcgcatct attactatcc tgaagaagtt ttgttacagg cctatgacaa ttctcacccc  3300
aggactaaaa gagaggctgt ctcacttacc ctagctgttt tactggggtt gggaatcacg  3360
gcgggaatag gtactggttc aactgcctta attaaaggac ctatagacct ccagcaaggc  3420
ctgacaagcc tccagatcgc catagatgct gacctccggg ccctccaaga ctcagtcagc  3480
aagttagagg actcactgac ttccctgtcc gaggtagtgc tccaaaatag gagaggcctt  3540
gacttgctgt ttctaaaaga aggtggcctc tgtgcggccc taaaggaaga gtgctgtttt  3600
tacatagacc actcaggtgc agtacgggac tccatgaaaa aactcaaaga aaaactggat  3660
aaaagacagt tagagcgcca gaaaagccaa aactggtatg aaggatggtt caataactcc  3720
ccttggttca ctaccctgct atcaaccatc gctgggcccc tattactcct ccttctgttg  3780
ctcatcctcg ggccatgcat catcaataag ttagttcaat tcatcaatga taggataagt  3840
gcagttaaaa ttctggtcct tagacaaaaa tatcaggccc tagagaacga aggtaacctt  3900
taattttgct ctaagattag agctattcac aagagaaatg gggaatcact agtgaattaa  3960
accgataagc gttttttttca ataacaggaa agtcccattg gagccaagta cattgagtca  4020
atagggactt tccaatgggt tttgcccagt acataaggtc aatgggaggt aagccaatgg  4080
gtttttccca ttactggcac gtatactgag tcattaggga ctttccaatg ggttttgccc  4140
agtacataag gtcaataggg gtgaatcaac aggaaagtcc cattggagcc aagtacactg  4200
agtcaatagg gactttccat tgggttttgc ccagtacaaa aggtcaatag ggggtgagtc  4260
aatgggtttt tcccattatt ggcacgtaca taaggtcaat aggggtgagt cattgggttt  4320
```

-continued

```
ttccagccaa tttaattaaa acgccatgta ctttcccacc attgacgtca atgggctatt  4380
gaaactaatg caacgtgacc tttaaacggt actttcccat agctgattaa tgggaaagta  4440
ccgttctcga gccaatacac gtcaatgggg aagtgaaagg gcagccaaac gtaacacgcc  4500
ccggtttccc ctggaaattc atattggcac gcattctatt ggctgagctg cgttctacgt  4560
gggtataaga ggcgcgacca gcgtcggtac cgtcgcagtc ttcggtctga ccaccgtaga  4620
acgcagaact ctagaactag tggatccgcg ttaacatttg cggccgcttt agtttcatgg  4680
cttcgtaccc ctgccatcaa cacgcgtctg cgttcgacca ggctgcgcgt tctcgcggcc  4740
atagcaaccg acgtacggcg ttgcgccctc gccggcagca agaagccacg gaagtccgcc  4800
tggagcagaa aatgcccacg ctactgcggg tttatataga cggtcctcac gggatgggga  4860
aaaccaccac cacgcaactg ctggtggccc tgggttcgcg cgacgatatc gtctacgtac  4920
ccgagccgat gacttactgg caggtgctgg gggcttccga gacaatcgcg aacatctaca  4980
ccacacaaca ccgcctcgac cagggtgaga tatcggccgg ggacgcggcg gtggtaatga  5040
caagcgccca gataacaatg ggcatgcctt atgccgtgac cgacgccgtt ctggctcctc  5100
atatcggggg ggaggctggg agctcacatg ccccgccccc ggccctcacc ctcatcttcg  5160
accgccatcc catcgccgcc ctcctgtgct acccggccgc gcgatacctt atgggcagca  5220
tgaccccca ggccgtgctg gcgttcgtgg ccctcatccc gccgaccttg cccggcacaa  5280
acatcgtgtt gggggccctt ccggaggaca gacacatcga ccgcctggcc aaacgccagc  5340
gccccggcga gcggcttgac ctggctatgc tggccgcgat tcgccgcgtt tacgggctgc  5400
ttgccattta cgggctgctt gccaatacgg tgcggtatct gcagggcggc gggtcgtggc  5460
gggaggattg gggacagctt tcggggacgg ccgtgccgcc ccagggtgcc gagccccaga  5520
gcaacgcggg cccacgaccc catatcgggg acacgttatt taccctgttt cgggcccccg  5580
agttgctggc ccccaacggc gacctgtaca acgtgtttgc ctgggccttg gacgtcttgg  5640
ccaaacgcct ccgtcccatg cacgtcttta tcctggatta cgaccaatcg cccgccggct  5700
gccgggacgc cctgctgcaa cttacctccg ggatggtcca gacccacgtc accacccccg  5760
gctccatacc gacgatctgc gacctggcgc gcacgtttgc ccgggagatg gggaggcta  5820
actgaaacac ggaaggggta ccgaattcct cgaaaacgcg tcgacccatc gatggtacca  5880
gatccggatt agtccaattt gttaaagaca ggatatcagt ggtccaggct ctagttttga  5940
ctcaacaata tcaccagctg aagcctatag agtacgagcc atagataaaa taaaagattt  6000
tatttagtct ccagaaaaag gggggaatga aagaccccac ctgtaggttt ggcaagctag  6060
cttaagtaac gccattttgc aaggcatgga aaaatacata actgagaata ganaagttca  6120
gatcaaggtc aggaacagat ggaacagctg aatatgggcc aaacaggata tctgtggtaa  6180
gcagttcctg ccccggctca gggccaagaa cagatggaac agctgaatat gggccaaaca  6240
ggatatctgt ggtaagcagt tcctgccccg gctcagggcc aagaacagat ggtccccaga  6300
tgcggtccag ccctcagcag tttctagaga accatcagat gtttccaggg tgccccaagg  6360
acctgaaatg accctgtgcc ttatttgaac taaccaatca gttcgcttct cgcttctgtt  6420
cgcgcgcttc tgctccccga gctcaataaa agagcccaca acccctcact cggggcgcca  6480
gtcctccgat tgactgagtc gcccgggtac ccgtgtatcc aataaaccct cttgcagttg  6540
catccgactt gtggtctcgc tgttccttgg gagggtctcc tctgagtgat tgactacccg  6600
tcagcggggg tctttcacac atgcagcatg tatcaaaatt aatttggttt tttttcttaa  6660
gtatttacat taaatggcca tagtacttaa agttacattg gcttccttga aataaacatg  6720
gagtattcag aatgtgtcat aaatatttct aattttaaga tagtatctcc attggctttc  6780
tacttttct tttattttt tttgtcctct gtcttccatt tgttgttgtt gttgtttgtt  6840
tgtttgtttg ttggttggtt ggttaatttt tttttaaaga tcctacacta tagttcaagc  6900
tagactatta gctactctgt aacccagggt gaccttgaag tcatgggtag cctgctgttt  6960
tagccttccc acatctaaga ttacaggtat gagctatcat ttttggtata tgattgattg  7020
attgattgat gtgtgtgtgt gtgattgtgt ttgtgtgtgt gactgtgaaa atgtgtgtat  7080
gggtgtgtgt gaatgtgtgt atgtatgtgt gtgtgtgagt gtgtgtgtgt gtgtgtgcat  7140
gtgtgtgtgt gtgactgtgt ctatgtgtat gactgtgtgt gtgtgtgtgt gtgtgtgtgt  7200
gtgtgtgtgt gtgtgtgtgt tgtgaaaaaa tattctatgg tagtgagagc caacgctccg  7260
gctcaggtgt caggttggtt tttgagacag agtctttcac ttagcttgga attccractg  7320
gccgtcgttt tacaacgtcg tgactgggaa aaccctggcg ttacccaact taatcgcctt  7380
gcagcacatc ccccttcgc cagctggcgt aatagcgaag aggcccgcac cgatcgccct  7440
tcccaacagt tgcgcagcct gaatggcgaa tggcgcctga tgcggtattt tctccttacg  7500
catctgtgcg gtatttcaca ccgcatatgg tgcactctca gtacaatctg ctctgatgcc  7560
gcatagttaa gccagccccg acacccgcca acacccgctg acgcgccctg acgggcttgt  7620
ctgctcccgg catccgctta cagacaagct gtgaccgtct ccgggagctg catgtgtcag  7680
aggttttcac cgtcatcacc gaaacgcgcg agacgaaagg gcctcgtgat acgcctattt  7740
ttataggtta atgtcatgat aataatggtt tcttagacgt caggtggcac ttttcgggga  7800
aatgtgcgcg gaacccctat ttgtttattt ttctaaatac attcaaatat gtatccgctc  7860
atgagacaat aaccctgata aatgcttcaa taatattgaa aaaggaagag tatgagtatt  7920
caacatttcc gtgtcgccct tattcccttt tttgcggcat tttgccttcc tgtttttgct  7980
cacccagaaa cgctggtgaa agtaaaagat gctgaagatc agttgggtgc acgagtgggt  8040
tacatcgaac tggatctcaa cagcggtaag atccttgaga gttttcgccc cgaagaacgt  8100
tttccaatga tgagcacttt taaagttctg ctatgtggcg cggtattatc ccgtattgac  8160
gccgggcaag agcaactcgg tcgccgcata cactattctc agaatgactt ggttgagtac  8220
tcaccagtca cagaaaagca tcttacggat ggcatgacag taagagaatt atgcagtgct  8280
gccataacca tgagtgataa cactgcggcc aacttacttc tgacaacgat cggaggaccg  8340
aaggagctaa ccgctttttt gcacaacatg ggggatcatg taactcgcct tgatcgttgg  8400
gaaccggagc tgaatgaagc cataccaaac gacgagcgtg acaccacgat gcctgtagca  8460
atggcaacaa cgttgcgcaa actattaact ggcgaactac ttactctagc ttcccggcaa  8520
caattaatag actggatgga ggcggataaa gttgcaggac cacttctgcg ctcggccctt  8580
ccggctggct ggtttattgc tgataaatct ggagccggtg agcgtgggtc tcgcggtatc  8640
attgcagcac tggggccaga tggtaagccc tcccgtatcg tagttatcta cacgacgggg  8700
agtcaggcaa ctatggatga acgaaataga cagatcgctg agataggtgc ctcactgatt  8760
aagcattggt aactgtcaga ccaagtttac tcatatatac tttagattga tttaaaactt  8820
catttttaat ttaaaaggat ctaggtgaag atcctttttg ataatctcat gaccaaaatc  8880
ccttaacgtg agttttcgtt ccactgagcg tcagaccccg tagaaaagat caaaggatct  8940
tcttgagatc cttttttct gcgcgtaatc tgctgcttgc aaacaaaaaa accaccgcta  9000
ccagcggtgg tttgtttgcc ggatcaagag ctaccaactc tttttccgaa ggtaactggc  9060
```

-continued

```
ttcagcagag cgcagatacc aaatactgtt cttctagtgt agccgtagtt aggccaccac  9120
ttcaagaact ctgtagcacc gcctacatac ctcgctctgc taatcctgtt accagtggct  9180
gctgccagtg gcgataagtc gtgtcttacc gggttggact caagacgata gttaccggat  9240
aaggcgcagc ggtcgggctg aacggggggt tcgtgcacac agcccagctt ggagcgaacg  9300
acctacaccg aactgagata cctacagcgt gagctatgag aaagcgccac gcttcccgaa  9360
gggagaaagg cggacaggta tccggtaagc ggcagggtcg gaacaggaga gcgcacgagg  9420
gagcttccag ggggaaacgc ctggtatctt tatagtcctg tcgggtttcg ccacctctga  9480
cttgagcgtc gatttttgtg atgctcgtca ggggggcgga gcctatggaa aaacgccagc  9540
aacgcggcct ttttacggtt cctggccttt tgctggcctt ttgctcacat gttctttcct  9600
gcgttatccc ctgattctgt ggataaccgt attaccgcct ttgagtgagc tgataccgct  9660
cgccgcagcc gaacgaccga gcgcagcgag tcagtgagcg aggaagcgga agagcgccca  9720
atacgcaaac cgcctctccc cgcgcgttgg ccgattcatt aatgcagctg gcacgacagg  9780
tttcccgact ggaaagcggg cagtgagcgc aacgcaatta atgtgagtta gctcactcat  9840
taggcacccc aggctttaca ctttatgctt ccggctcgta tgttgtgtgg aattgtgagc  9900
ggataacaat ttcacacagg aaacagctat gaccatgatt acgccaagct ttgctcctag  9960
gagtttccta atacttccca aactcaaata tataaagcat ttgacttgtt ctatgcccta  10020
gggggcgggg ggaagctaag ccagcttttt ttaacattta aaatgttaat tccattttaa  10080
atgcacagat gtttttattt cataagggtt tcaatgtgca tgaatgctgc aatattcctg  10140
ttaccaaagc tagtataaat aaaaatagat aaacgtggaa attacttaga gtttctgtca  10200
ttaacgtttc cttcctcagt tgacaacata aatgcgctgc tgagcaagcc agtttgcatc  10260
tgtcaggatc aatttcccat tatgccagtc atattaatta ctagtcaatt agttgatttt  10320
tatttttgac atatacatgt gaatgaaaga ccccacctgt aggtttggca agctagctta  10380
agt                                                                10383

SEQ ID NO: 28          moltype = DNA  length = 9993
FEATURE                Location/Qualifiers
misc_feature           1..9993
                       note = spRRVe-F1-TK vector
source                 1..9993
                       mol_type = other DNA
                       organism = synthetic construct
SEQUENCE: 28
aacgccattt tgcaaggcat ggaaaaatac ataactgaga atagaaaagt tcagatcaag  60
gtcaggaaca gatggaacag ctgaatatgg gccaaacagg atatctgtgg taagcagttc  120
ctgccccggc tcagggccaa gaacagatgg aacagctgaa tatgggccaa acaggatatc  180
tgtggtaagc agttcctgcc ccggctcagg gccaagaaca gatggtcccc agatgcggtc  240
cagccctcag cagtttctag agaaccatca gatgtttcca gggtgcccca aggacctgaa  300
atgaccctgt gccttatttg aactaaccaa tcagttcgct tctcgcttct gttcgcgcgc  360
ttatgctccc cgagctcaat aaaagagccc acaacccctc actcggggcg ccagtcctcc  420
gattgactga gtcgcccggg tacccgtgta tccaataaac cctcttgcag ttgcatccga  480
cttgtggtct cgctgttcct tgggagggtc tcctctgagt gattgactac ccgtcagcgg  540
gggtctttca tttgggggct cgtccgggat cgggagaccc ctgcccaggg accaccgacc  600
caccaccggg aggtaagctg gccagcaact tatctgtgtc tgtccgattg tctagtgtct  660
atgactgatt ttatgcgcct gcgtcggtac tagttagcta actagctctg tatctggcgg  720
acccgtggtg gaactgacga gttcggaaca cccggccgca accctgggag acgtcccagg  780
gacttcgggg gccgtttttg tggcccgacc tgagtcctaa aatcccgatc gtttaggact  840
ctttggtgca ccccccttag aggagggata tgtggttctg gtaggagacg agaacctaaa  900
acagttcccg cctccgtctg aatttttgct ttcggtttgg gaccgaagcc gcgccgcgcg  960
tcttgtctgc tgcagcatcg ttctgtgttg tctctgtctg actgtgtttc tgtatttgtc  1020
tgaaaatatg ggcccgggct agcctgttac cactccctta agtttgacct taggtcactg  1080
gaaagatgtc gagcggatcg ctcacaacca gtcggtagat gtcaagaaga gacgttgggt  1140
taccttctgc tctgcagaat ggccaacctt taacgtcgga tggccgcgag acggcacctt  1200
taaccgagac ctcactaccc aggttaagat caaggtcttt tcacctggcc cgcatggaca  1260
cccagaccag gtggggtaca tcgtgacctg ggaagccttg gcttttgacc cccctccctg  1320
ggtcaagccc tttgtacacc ctaagcctcc gcctcctctt cctccatccg ccccgtctct  1380
ccccccttgaa cctcctcgtt cgaccccgcc tcgatcctcc ctttatccag ccctcactcc  1440
ttctctaggc gcccccatat ggccatatga gatcttatat ggggcacccc cgccccttgt  1500
aaacttccct gaccctgaca tgacaagagt tactaacagc ccctctctcc aagctcactt  1560
acaggctctc tacttagtcc agcacgaagt ctggagacct ctggcggcag cctaccaaga  1620
acaactggac cgaccggtgg tacctcaccc ttaccgagtc ggcgacacag tgtgggtccg  1680
ccgacaccag actaagaacc tagaacctcg ctggaaagga ccttacacag tcctgctgac  1740
cacccccacc gccctcaaag tagacggcat cgcagcttgg atacacgccg cccacaattc  1800
gatcatacct ggtgttgctg actaccccga ccgcggtaaa agtcgatggt attgctgcct  1860
gggtccatgc ttctcacctc aaacctgcac caccttcggc accagatgag tcctgggagc  1920
tggaaaagac tgatcatcct cttaagctgc gtattcggcg gcggcgggac gagtctgcaa  1980
aataagaacc cccaccagcc catgacccctc acttggcagg tactgtccca aactggagac  2040
gttgtctggg atacaaaggc agtccagccc ccttggactt ggtggcccac acttaaacct  2100
gatgtatgtg ccttggcggc tagtcttgag tcctgggata tcccgggaac cgatgtctcg  2160
tcctctaaac gagtcagacc tccggactca gactatactg ccgcttataa gcaaatcacc  2220
tggggagcca tagggtgcag ctaccctcgg gctaggacta gaatggcaag ctctaccttc  2280
tacgtatgtc cccgggatgg ccggaccctt tcagaagcta gaaggtgcgg ggggctagaa  2340
tccctatact gtaaagaatg ggattgtgag accacgggga ccggttattg gctatctaaa  2400
tcctcaaaag acctcataac tgtaaaatgg gaccaaaata gcgaatggac tcaaaaattt  2460
caacagtgtc accagaccgg ctggtgtaac cccccttaaaa tagatttcac agacaaagga  2520
aaattatcca aggactggat aacgggaaaa acctggggat taagattcta tgtgtctgga  2580
catccaggcg tacagttcac cattcgctta aaaatcacca acatgccagc tgtggcagta  2640
ggtcctgacc tcgtccttgt ggaacaagga cctcctagaa cgtccctcgc tctcccacct  2700
cctcttcccc caagggaagc gccaccgcca tctctccccg actctaactc cacagccctg  2760
gcgactagtg cacaaactcc cacggtgaga aaaacaattg ttaccctaaa cactccgcct  2820
```

-continued

```
cccaccacag gcgacagact tttgatcttt gtgcaggggg ccttcctaac cttaaatgct  2880
accaacccag gggccactga gtcttgctgg ctttgtttgg ccatgggccc cccttattat  2940
gaagcaatag cctcatcagg agaggtcgcc tactccaccg accttgaccg gtgccgctgg  3000
gggacccaag gaaagctcac cctcactgag gtctcaggac acgggttgtg cataggaaag  3060
gtgcccttta cccatcagca tctctgcaat cagaccctat ccatcaattc ctccggagac  3120
catcagtatc tgctcccctc caaccatagc tggtgggctt gcagcactgg cctcacccct  3180
tgcctctcca cctcagtttt taatcagact agagatttct gtatccaggt ccagctgatt  3240
cctcgcatct attactatcc tgaagaagtt ttgttacagg cctatgacaa ttctcacccc  3300
aggactaaaa gagaggctgt ctcacttacc ctagctgttt tactggggtt gggaatcacg  3360
gcgggaatag gtactggttc aactgcctta attaaaggac ctatagacct ccagcaaggc  3420
ctgacaagcc tccagatcgc catagatgct gacctccggg ccctccaaga ctcagtcagc  3480
aagttagagg actcactgac ttccctgtcc gaggtagtgc tccaaaatag gagaggcctt  3540
gacttgctgt ttctaaaaga aggtggcctc tgtgcggccc taaaggaaga gtgctgtttt  3600
tacatagacc actcaggtgc agtacgggac tccatgaaaa aactcaaaga aaaactggat  3660
aaaagacagt tagagcgcca gaaaagccaa aactggtatg aaggatggtt caataactcc  3720
ccttggttca ctaccctgct atcaaccatc gctgggcccc tattactcct ccttctgttg  3780
ctcatcctcg ggccatgcat catcaataag ttagttcaat tcatcaatga taggataagt  3840
gcagttaaaa ttctggtcct tagacaaaaa tatcaggccc tagagaacga aggtaacctt  3900
taacacgtga aggctgccga ccccgggggt ggaccatcct ctagactgtg ctcgacgttt  3960
aaacgggtga atcaacagga aagtcccatt ggagccaagt acactgagtc aatagggact  4020
ttccattggg ttttgcccag tacaaaaggt caataggggg tgagtcaatg ggtttttccc  4080
attattggca cgtacataag gtcaataggg gtgagtcatt gggtttttcc agccaattta  4140
attaaaacgc catgtacttt cccaccattg acgtcaatgg gctattgaaa ctaatgcaac  4200
gtgaccttta aacggtactt tcccatagct gattaatggg aaagtaccgt tctcgagcca  4260
atacacgtca atgggaagtg aaagggcagc caaaacgtaa caccgccccg gttttccctg  4320
gaaattccat attggcacgc attctattgg ctgagctgcg ttcacgtggg tataagaggc  4380
gcgaccagcg tcggtaccgt cgcagtcttc ggtctgacca ccgtagaacg cagaacgcgt  4440
atggcttcgt accccctgcca tcaacacgcg tctgcgttcg accaggctgc gcgttctcgc  4500
ggccatagca accgacgtac ggcgttgcgc cctcgccggc agcaagaagc cacggaagtc  4560
cgcctggagc agaaaatgcc cacgctactg cgggtttata tagacggtcc tcacgggatg  4620
gggaaaacca ccaccacgca actgctggtg gccctgggtt cgcgcgacga tatcgtctac  4680
gtacccgagc cgatgactta ctggcaggtg ctgggggctt ccgagacaat cgcgaacatc  4740
tacaccacac aacaccgcct cgaccagggt gagatatcgg ccggggacgc ggcggtggta  4800
atgacaagcg cccagataac aatgggcatg ccttatgccg tgaccgacgc cgttctggct  4860
cctcatatcg gggggggaggc tgggagctca catgccccgc ccccggccct caccctcatc  4920
ttcgaccgcc atcccatcgc cgccctcctg tgctacccgg ccgcgcgata ccttatgggc  4980
agcatgaccc cccaggccgt gctggcgttc gtggccctca tcccgccgac cttgcccggc  5040
acaaacatcg tgttgggggc ccttccggag gacagacaca tcgaccgcct ggccaaacgc  5100
cagcgccccg gcgagcggct tgacctggct atgctggccg cgattcgccg cgtttacggg  5160
ctgcttgcca atacggtgcg gtatctgcag ggcggcgggt cgtggcggga ggattgggga  5220
cagctttcgg ggacggccgt gccgccccag ggtgccgagc cccagagcaa cgcgggccca  5280
cgacccccata tcggggacac gttatttacc ctgtttcggg cccccgagtt gctggccccc  5340
aacggcgacc tgtacaacgt gtttgcctgg gccttggacg tcttggccaa acgcctccgt  5400
cccatgcacg tctttatcct ggattacgac caatcgcccg ccggctgccg ggacgccctg  5460
ctgcaactta cctccgggat ggtccagacc cacgtcacca cccccggctc cataccgacg  5520
atctgcgacc tggcgcgcac gtttgcccgg gagatggggg aggctaactg agtcgacatc  5580
gatggtacca gatccgataa aataaaaggt tttatttagt ctcctgaaaa agggggggaat  5640
gaaagacccc acctgtaggt ttggcaagct agcttaagta acgccatttt gcaaggcatg  5700
gaaaaataca taactgagaa tagagaagtt cagatcaagg tcaggaacag atggaacagc  5760
tgaatatggg ccaaacagga tatctgtggt aagcagttcc tgccccggct cagggccaag  5820
aacagatgga acagctgaat atgggccaaa caggatatct gtggtaagca gttcctgccc  5880
cggctcaggg ccaagaacag atggtcccca gatgcggtcc agccctcagc agtttctaga  5940
gaaccatcag atgtttccag ggtgccccaa ggacctgaaa tgaccctgtg ccttatttga  6000
actaaccaat cagttcgctt ctcgcttctg ttcgcgcgct tctgctcccc gagctcaata  6060
aaagagccca caacccctca ctcggggcgc cagtcctccg attgactgag tcgcccgggt  6120
acccgtgtat ccaataaacc ctcttgcagt tgcatccgac ttgtggtctc gctgttcctt  6180
gggagggtct cctctgagtg attgactacc cgtcagcggg ggtctttcac acatgcagca  6240
tgtatcaaaa ttaatttggt tttttttctt aagtatttac attaaatggc catagtactt  6300
aaagttacat tggcttcctt gaaataaaca tggagtattc agaatgtgtc ataaatattt  6360
ctaattttaa gatagtatct ccattggctt tctacttttt cttttatttt tttttgtcct  6420
ctgtcttcca tttgttgttg ttgttgtttg tttgtttgtt tgttggttgg ttggttaatt  6480
tttttttaaa gatcctacac tatagttcaa gctagactat tagctactct gtaacccagg  6540
gtgaccttga agtcatgggt agcctgctgt tttagccttc ccacatctaa gattacaggt  6600
atgagctatc atttttggta tatgattgat tgattgattg atgtgtgtgt gtgtgattgt  6660
gtttgtgtgt gtgactgtga aaatgtgtgt atgggtgtgt gtgaatgtgt gtatgtatgt  6720
gtgtgtgtga gtgtgtgtgt gtgtgtgtgc atgtgtgtgt gtgtgactgt gtctatgtgt  6780
atgactgtgt gtgtgtgtgt gtgtgtgtgt gtgtgtgtgt gtgtgtgtgt gttgtgaaaa  6840
aatattctat ggtagtgaga gccaacgctc cggctcaggt gtcaggttgg tttttgagac  6900
agagtctttc acttagcttg gaattcactg gccgtcgttt tacaacgtcg tgactgggaa  6960
aaccctggcg ttacccaact taatcgcctt gcagcacatc cccctttcgc cagctggcgt  7020
aatagcgaag aggcccgcac cgatcgccct tcccaacagt tgcgcagcct gaatggcgaa  7080
tggcgcctga tgcggtattt tctccttacg catctgtgcg gtatttcaca ccgcatatgg  7140
tgcactctca gtacaatctg ctctgatgcc gcatagttaa gccagccccg acacccgcca  7200
acacccgctg acgcgccctg acgggcttgt ctgctcccgg catccgctta cagacaagct  7260
gtgaccgtct ccgggagctg catgtgtcag aggttttcac cgtcatcacc gaaacgcgcg  7320
agacgaaagg gcctcgtgat acgcctattt ttataggtta atgtcatgat aataatggtt  7380
tcttagacgt caggtggcac ttttcgggga aatgtgcgcg gaacccctat ttgtttattt  7440
ttctaaatac attcaaatat gtatccgctc atgagacaat aaccctgata aatgcttcaa  7500
taatattgaa aaaggaagag tatgagtatt caacatttcc gtgtcgccct tattcccttt  7560
```

-continued

```
tttgcggcat tttgccttcc tgtttttgct cacccagaaa cgctggtgaa agtaaaagat  7620
gctgaagatc agttgggtgc acgagtgggt tacatcgaac tggatctcaa cagcggtaag  7680
atccttgaga gttttcgccc cgaagaacgt tttccaatga tgagcacttt taaagttctg  7740
ctatgtggcg cggtattatc ccgtattgac gccgggcaag agcaactcgg tcgccgcata  7800
cactattctc agaatgactt ggttgagtac tcaccagtca cagaaaagca tcttacggat  7860
ggcatgacag taagagaatt atgcagtgct gccataacca tgagtgataa cactgcggcc  7920
aacttacttc tgacaacgat cggaggaccg aaggagctaa ccgctttttt gcacaacatg  7980
ggggatcatg taactcgcct tgatcgttgg gaaccggagc tgaatgaagc cataccaaac  8040
gacgagcgtg acaccacgat gcctgtagca atggcaacaa cgttgcgcaa actattaact  8100
ggcgaactac ttactctagc ttcccggcaa caattaatag actggatgga ggcggataaa  8160
gttgcaggac cacttctgcg ctcggccctt ccggctggct ggtttattgc tgataaatct  8220
ggagccggtg agcgtgggtc tcgcggtatc attgcagcac tggggccaga tggtaagccc  8280
tcccgtatcg tagttatcta cacgacgggg agtcaggcaa ctatggatga acgaaataga  8340
cagatcgctg agataggtgc ctcactgatt aagcattggt aactgtcaga ccaagtttac  8400
tcatatatac tttagattga tttaaaactt catttttaat ttaaaaggat ctaggtgaag  8460
atcctttttg ataatctcat gaccaaaatc ccttaacgtg agttttcgtt ccactgagcg  8520
tcagaccccg tagaaaagat caaaggatct tcttgagatc cttttttct gcgcgtaatc  8580
tgctgcttgc aaacaaaaaa accaccgcta ccagcggtgg tttgtttgcc ggatcaagag  8640
ctaccaactc tttttccgaa ggtaactggc ttcagcagag cgcagatacc aaatactgtt  8700
cttctagtgt agccgtagtt aggccaccac ttcaagaact ctgtagcacc gcctacatac  8760
ctcgctctgc taatcctgtt accagtggct gctgccagtg gcgataagtc gtgtcttacc  8820
gggttggact caagacgata gttaccggat aaggcgcagc ggtcgggctg aacggggggt  8880
tcgtgcacac agcccagctt ggagcgaacg acctacaccg aactgagata cctacagcgt  8940
gagctatgag aaagcgccac gcttcccgaa gggagaaagg cggacaggta tccggtaagc  9000
ggcagggtcg gaacaggaga gcgcacgagg gagcttccag ggggaaacgc ctggtatctt  9060
tatagtcctg tcgggtttcg ccacctctga cttgagcgtc gatttttgtg atgctcgtca  9120
ggggggcgga gcctatggaa aaacgccagc aacgcggcct ttttacggtt cctggccttt  9180
tgctggcctt ttgctcacat gttctttcct gcgttatccc ctgattctgt ggataaccgt  9240
attaccgcct ttgagtgagc tgataccgct cgccgcagcc gaacgaccga gcgcagcgag  9300
tcagtgagcg aggaagcgga agagcgccca atacgcaaac cgcctctccc cgcgcgttgg  9360
ccgattcatt aatgcagctg gcacgacagg tttcccgact ggaaagcggg cagtgagcgc  9420
aacgcaatta atgtgagtta gctcactcat taggcacccc aggctttaca ctttatgctt  9480
ccggctcgta tgttgtgtgg aattgtgagc ggataacaat ttcacacagg aaacagctat  9540
gaccatgatt acgccaagct ttgctcctag gagtttccta atacttccca aactcaaata  9600
tataaagcat ttgacttgtt ctatgcccta gggggcgggg ggaagctaag ccagcttttt  9660
ttaacattta aaatgttaat tccattttaa atgcacagat gtttttattt cataagggtt  9720
tcaatgtgca tgaatgctgc aatattcctg ttaccaaagc tagtataaat aaaaatagat  9780
aaacgtggaa attacttaga gtttctgtca ttaacgtttc cttcctcagt tgacaacata  9840
aatgcgctgc tgagcaagcc agtttgcatc tgtcaggatc aatttcccat tatgccagtc  9900
atattaatta ctagtcaatt agttgatttt tatttttgac atatacatgt gaatgaaaga  9960
ccccacctgt aggtttggca agctagctta agt                                9993

SEQ ID NO: 29          moltype = DNA  length = 9860
FEATURE                Location/Qualifiers
misc_feature           1..9860
                       note = spRRVe-F2-TK vector
source                 1..9860
                       mol_type = other DNA
                       organism = synthetic construct
SEQUENCE: 29
aacgccattt tgcaaggcat ggaaaaatac ataactgaga atagaaaagt tcagatcaag  60
gtcaggaaca gatggaacag ctgaatatgg gccaaacagg atatctgtgg taagcagttc  120
ctgccccggc tcagggccaa gaacagatgg aacagctgaa tatgggccaa acaggatatc  180
tgtggtaagc agttcctgcc ccggctcagg gccaagaaca gatggtcccc agatgcggtc  240
cagccctcag cagtttctag agaaccatca gatgtttcca gggtgcccca aggacctgaa  300
atgaccctgt gccttatttg aactaaccaa tcagttcgct tctcgcttct gttcgcgcgc  360
ttatgctccc cgagctcaat aaaagagccc acaacccctc actcggggcg ccagtcctcc  420
gattgactga gtcgcccggg tacccgtgta tccaataaac cctcttgcag ttgcatccga  480
cttgtggtct cgctgttcct tgggagggtc tcctctgagt gattgactac ccgtcagcgg  540
gggtctttca tttgggggct cgtccgggat cgggagaccc ctgcccaggg accaccgacc  600
caccaccggg aggtaagctg gccagcaact tatctgtgtc tgtccgattg tctagtgtct  660
atgactgatt ttatgcgcct gcgtcggtac tagttagcta actagctctg tatctggcgg  720
acccgtggtg gaactgacga gttcggaaca cccggccgca accctgggag acgtcccagg  780
gacttcgggg gccgtttttg tggcccgacc tgagtcctaa aatcccgatc gtttaggact  840
ctttggtgca cccccctag aggagggata tgtggttctg gtaggagacg agaacctaaa  900
acagttcccg cctccgtctg aatttttgct ttcggtttgg gaccgaagcc gcgccgcgcg  960
tcttgtctgc tgcagcatcg ttctgtgttg tctctgtctg actgtgtttc tgtatttgtc  1020
tgaaaatatg ggcccgggct agcctgttac cactccctta agtttgacct taggtcactg  1080
gaaagatgtc gagcggatcg ctcacaacca gtcggtagat gtcaagaaga gacgttgggt  1140
taccttctgc tctgcagaat ggccaacctt taacgtcgga tggccgcgag acggcacctt  1200
taaccgagac ctcactaccc aggttaagat caaggtcttt tcacctggcc cgcatggaca  1260
cccagaccag gtggggtaca tcgtgacctg ggaagccttg gcttttgacc cccctccctg  1320
ggtcaagccc tttgtacacc ctaagcctcc gcctcctctt cctccatccg ccccgtctct  1380
ccccttgaa cctcctcgtt cgaccccgcc tcgatcctcc ctttatccag ccctcactcc  1440
ttctctaggc gcccccatat ggccatatga gatcttatat ggggcacccc cgcccttgt  1500
aaacttccct gaccctgaca tgacaagagt tactaacagc ccctctctcc aagctcactt  1560
acaggctctc tacttagtcc agcacgaagt ctggagacct ctggcggcag cctaccaaga  1620
acaactggac cgaccggtgg tacctcaccc ttaccgagtc ggcgacacag tgtgggtccg  1680
ccgacaccag actaagaacc tagaacctcg ctggaaagga ccttacacag tcctgctgac  1740
```

-continued

```
caccccacc gccctcaaag tagacggcat cgcagcttgg atacacgccg cccacaattc  1800
gatcatacct ggtgttgctg actaccccga ccgcggtaaa agtcgatggt attgctgcct  1860
gggtccatgc ttctcacctc aaacctgcac caccttcggc accagatgag tcctgggagc  1920
tggaaaagac tgatcatcct cttaagctgc gtattcggcg gcggcgggac gagtctgcaa  1980
aataagaacc cccaccagcc catgaccctc acttggcagg tactgtccca aactggagac  2040
gttgtctggg atacaaaggc agtccagccc ccttggactt ggtggcccac acttaaacct  2100
gatgtatgtg ccttggcggc tagtcttgag tcctgggata tcccgggaac cgatgtctcg  2160
tcctctaaac gagtcagacc tccggactca gactatactg ccgcttataa gcaaatcacc  2220
tggggagcca tagggtgcag ctaccctcgg gctaggacta gaatggcaag ctctaccttc  2280
tacgtatgtc cccgggatgg ccggaccctt tcagaagcta gaaggtgcgg ggggctagaa  2340
tccctatact gtaaagaatg ggattgtgag accacgggga ccggttattg gctatctaaa  2400
tcctcaaaag acctcataac tgtaaaatgg gaccaaaata gcgaatggac tcaaaaattt  2460
caacagtgtc accagaccgg ctggtgtaac cccccttaaaa tagatttcac agacaaagga  2520
aaattatcca aggactggat aacgggaaaa acctggggat taagattcta tgtgtctgga  2580
catccaggcg tacagttcac cattcgctta aaaatcacca acatgccagc tgtggcagta  2640
ggtcctgacc tcgtccttgt ggaacaagga cctcctagaa cgtccctcgc tctcccacct  2700
cctcttcccc caagggaagc gccaccgcca tctctccccg actctaactc cacagccctg  2760
gcgactagtg cacaaactcc cacggtgaga aaaacaattg ttaccctaaa cactccgcct  2820
cccaccacag gcgacagact ttttgatctt gtgcaggggg ccttcctaac cttaaatgct  2880
accaacccag gggccactga gtcttgctgg ctttgtttgg ccatgggccc cccttattat  2940
gaagcaatag cctcatcagg agaggtcgcc tactccaccg accttgaccg gtgccgctgg  3000
gggacccaag gaaagctcac cctcactgag gtctcaggac acgggttgtg cataggaaag  3060
gtgcccttta cccatcagca tctctgcaat cagaccctat ccatcaattc ctccggagac  3120
catcagtatc tgctcccctc caaccatagc tggtgggctt gcagcactgg cctcacccct  3180
tgcctctcca cctcagtttt taatcagact agagatttct gtatccaggt ccagctgatt  3240
cctcgcatct attactatcc tgaagaagtt ttgttacagg cctatgacaa ttctcacccc  3300
aggactaaaa gagaggctgt ctcacttacc ctagctgttt tactggggtt gggaatcacg  3360
gcgggaatag gtactggttc aactgcctta attaaaggac ctatagacct ccagcaaggc  3420
ctgacaagcc tccagatcgc catagatgct gacctccggg ccctccaaga ctcagtcagc  3480
aagttagagg actcactgac ttccctgtcc gaggtagtgc tccaaaatag gagaggcctt  3540
gacttgctgt ttctaaaaga aggtggcctc tgtgcggccc taaaggaaga gtgctgtttt  3600
tacatagacc actcaggtgc agtacgggac tccatgaaaa aactcaaaga aaaactggat  3660
aaaagacagt tagagcgcca gaaaagccaa aactggtatg aaggatggtt caataactcc  3720
ccttggttca ctaccctgct atcaaccatc gctgggcccc tattactcct ccttctgttg  3780
ctcatcctcg ggccatgcat catcaataag ttagttcaat tcatcaatga taggataagt  3840
gcagttaaaa ttctggtcct tagacaaaaa tatcaggccc tagagaacga aggtaacctt  3900
taacacgtga aggctgccga ccccgggggt ggaccatcct ctagactgtg ctcgacgttt  3960
aaacaaggtc aataggggtg agtcattggg tttttccagc caatttaatt aaaacgccat  4020
gtactttccc accattgacg tcaatgggct attgaaacta atgcaacgtg acctttaaac  4080
ggtactttcc catagctgat taatgggaaa gtaccgttct cgagccaata cacgtcaatg  4140
ggaagtgaaa gggcagccaa aacgtaacac cgccccggtt ttccctggaa attccatatt  4200
ggcacgcatt ctattggctg agctgcgttc acgtgggtat aagaggcgcg accagcgtcg  4260
gtaccgtcgc agtcttcggt ctgaccaccg tagaacgcag aacgcgtatg gcttcgtacc  4320
cctgccatca acacgcgtct gcgttcgacc aggctgcgcg ttctcgcggc catagcaacc  4380
gacgtacggc gttgcgccct cgccggcagc aagaagccac ggaagtccgc ctggagcaga  4440
aaatgcccac gctactgcgg gtttatatag acggtcctca cgggatgggg aaaaccacca  4500
ccacgcaact gctggtggcc ctgggttcgc gcgacgatat cgtctacgta cccgagccga  4560
tgacttactg gcaggtgctg gggggcttccg agacaatcgc gaacatctac accacacaac  4620
accgcctcga ccagggtgag atatcggccg gggacgcggc ggtggtaatg acaagcgccc  4680
agataacaat gggcatgcct tatgccgtga ccgacgccgt tctggctcct catatcgggg  4740
gggaggctgg gagctcacat gccccgcccc cggccctcac cctcatcttc gaccgccatc  4800
ccatcgccgc cctcctgtgc tacccggccg cgcgatacct tatgggcagc atgacccccc  4860
aggccgtgct ggcgttcgtg gccctcatcc cgccgacctt gcccggcaca aacatcgtgt  4920
tgggggccct tccggaggac agacacatcg accgcctggc caaacgccag cgccccggcg  4980
agcggcttga cctggctatg ctggccgcga ttcgccgcgt ttacgggctg cttgccaata  5040
cggtgcggta tctgcagggc ggcgggtcgt ggcgggagga ttggggacag ctttcgggga  5100
cggccgtgcc gccccagggt gccgagcccc agagcaacgc gggcccacga ccccatatcg  5160
gggacacgtt atttaccctg tttcgggccc ccgagttgct ggcccccaac ggcgacctgt  5220
acaacgtgtt tgcctgggcc ttggacgtct tggccaaacg cctccgtccc atgcacgtct  5280
ttatcctgga ttacgaccaa tcgcccgccg gctgccggga cgccctgctg caacttacct  5340
ccgggatggt ccagacccac gtcaccaccc ccggctccat accgacgatc tgcgacctgg  5400
cgcgcacgtt tgcccgggag atgggggagg ctaactgagt cgacatcgat ggtaccagat  5460
ccgataaaat aaaaggtttt atttagtctc ctgaaaaagg ggggaatgaa agaccccacc  5520
tgtaggtttg gcaagctagc ttaagtaacg ccattttgca aggcatggaa aaatacataa  5580
ctgagaatag agaagttcag atcaaggtca ggaacagatg gaacagctga atatgggcca  5640
aacaggatat ctgtggtaag cagttcctgc cccggctcag ggccaagaac agatggaaca  5700
gctgaatatg ggccaaacag gatatctgtg gtaagcagtt cctgccccgg ctcagggcca  5760
agaacagatg gtccccagat gcggtccagc cctcagcagt ttctagagaa ccatcagatg  5820
tttccagggt gccccaagga cctgaaatga ccctgtgcct tatttgaact aaccaatcag  5880
ttcgcttctc gcttctgttc gcgcgcttct gctccccgag ctcaataaaa gagcccacaa  5940
cccctcactc ggggcgccag tcctccgatt gactgagtcg cccgggtacc cgtgtatcca  6000
ataaaccctc ttgcagttgc atccgacttg tggtctcgct gttccttggg agggtctcct  6060
ctgagtgatt gactacccgt cagcgggggt ctttcacaca tgcagcatgt atcaaaatta  6120
atttggtttt ttttcttaag tatttacatt aaatggccat agtacttaaa gttacattgg  6180
cttccttgaa ataaacatgg agtattcaga atgtgtcata aatatttcta attttaagat  6240
agtatctcca ttggctttct actttttctt ttattttttt ttgtcctctg tcttccattt  6300
gttgttgttg ttgtttgttt gtttgtttgt tggttggttg gttaattttt ttttaaagat  6360
cctacactat agttcaagct agactattag ctactctgta acccagggtg accttgaagt  6420
catgggtagc ctgctgtttt agccttccca catctaagat tacaggtatg agctatcatt  6480
```

```
tttggtatat gattgattga ttgattgatg tgtgtgtgtg tgattgtgtt tgtgtgtgtg  6540
actgtgaaaa tgtgtgtatg ggtgtgtgtg aatgtgtgta tgtatgtgtg tgtgtgagtg  6600
tgtgtgtgtg tgtgtgcatg tgtgtgtgtg tgactgtgtc tatgtgtatg actgtgtgtg  6660
tgtgtgtgtg tgtgtgtgtg tgtgtgtgtg tgtgtgtgtt gtgaaaaaat attctatggt  6720
agtgagagcc aacgctccgg ctcaggtgtc aggttggttt ttgagacaga gtctttcact  6780
tagcttggaa ttcactggcc gtcgttttac aacgtcgtga ctgggaaaac cctggcgtta  6840
cccaacttaa tcgccttgca gcacatcccc ctttcgccag ctggcgtaat agcgaagagg  6900
cccgcaccga tcgcccttcc caacagttgc gcagcctgaa tggcgaatgg cgcctgatgc  6960
ggtattttct ccttacgcat ctgtgcggta tttcacaccg catatggtgc actctcagta  7020
caatctgctc tgatgccgca tagttaagcc agccccgaca cccgccaaca cccgctgacg  7080
cgccctgacg ggcttgtctg ctcccggcat ccgcttacag acaagctgtg accgtctccg  7140
ggagctgcat gtgtcagagg ttttcaccgt catcaccgaa acgcgcgaga cgaaagggcc  7200
tcgtgatacg cctattttta taggttaatg tcatgataat aatggtttct tagacgtcag  7260
gtggcacttt tcggggaaat gtgcgcggaa cccctatttg tttatttttc taaatacatt  7320
caaatatgta tccgctcatg agacaataac cctgataaat gcttcaataa tattgaaaaa  7380
ggaagagtat gagtattcaa catttccgtg tcgcccttat tccctttttt gcggcatttt  7440
gccttcctgt ttttgctcac ccagaaacgc tggtgaaagt aaaagatgct gaagatcagt  7500
tgggtgcacg agtgggttac atcgaactgg atctcaacag cggtaagatc cttgagagtt  7560
ttcgccccga agaacgtttt ccaatgatga gcacttttaa agttctgcta tgtggcgcgg  7620
tattatcccg tattgacgcc gggcaagagc aactcggtcg ccgcatacac tattctcaga  7680
atgacttggt tgagtactca ccagtcacag aaaagcatct tacggatggc atgacagtaa  7740
gagaattatg cagtgctgcc ataaccatga gtgataacac tgcggccaac ttacttctga  7800
caacgatcgg aggaccgaag gagctaaccg cttttttgca caacatgggg gatcatgtaa  7860
ctcgccttga tcgttgggaa ccggagctga atgaagccat accaaacgac gagcgtgaca  7920
ccacgatgcc tgtagcaatg gcaacaacgt tgcgcaaact attaactggc gaactactta  7980
ctctagcttc ccggcaacaa ttaatagact ggatggaggc ggataaagtt gcaggaccac  8040
ttctgcgctc ggcccttccg gctggctggt ttattgctga taaatctgga gccggtgagc  8100
gtgggtctcg cggtatcatt gcagcactgg ggccagatgg taagccctcc cgtatcgtag  8160
ttatctacac gacggggagt caggcaacta tggatgaacg aaatagacag atcgctgaga  8220
taggtgcctc actgattaag cattggtaac tgtcagacca agtttactca tatatacttt  8280
agattgattt aaaacttcat ttttaattta aaaggatcta ggtgaagatc ctttttgata  8340
atctcatgac caaaatccct taacgtgagt tttcgttcca ctgagcgtca gaccccgtag  8400
aaaagatcaa aggatcttct tgagatcctt tttttctgcg cgtaatctgc tgcttgcaaa  8460
caaaaaaacc accgctacca gcggtggttt gtttgccgga tcaagagcta ccaactcttt  8520
ttccgaaggt aactggcttc agcagagcgc agataccaaa tactgttctt ctagtgtagc  8580
cgtagttagg ccaccacttc aagaactctg tagcaccgcc tacatacctc gctctgctaa  8640
tcctgttacc agtggctgct gccagtggcg ataagtcgtg tcttaccggg ttggactcaa  8700
gacgatagtt accggataag gcgcagcggt cgggctgaac ggggggttcg tgcacacagc  8760
ccagcttgga gcgaacgacc tacaccgaac tgagatacct acagcgtgag ctatgagaaa  8820
gcgccacgct tcccgaaggg agaaaggcgg acaggtatcc ggtaagcggc agggtcggaa  8880
caggagagcg cacgagggag cttccagggg gaaacgcctg gtatctttat agtcctgtcg  8940
ggtttcgcca cctctgactt gagcgtcgat ttttgtgatg ctcgtcaggg gggcggagcc  9000
tatggaaaaa cgccagcaac gcggcctttt tacggttcct ggccttttgc tggccttttg  9060
ctcacatgtt ctttcctgcg ttatcccctg attctgtgga taaccgtatt accgcctttg  9120
agtgagctga taccgctcgc cgcagccgaa cgaccgagcg cagcgagtca gtgagcgagg  9180
aagcggaaga gcgcccaata cgcaaaccgc ctctccccgc gcgttggccg attcattaat  9240
gcagctggca cgacaggttt cccgactgga aagcgggcag tgagcgcaac gcaattaatg  9300
tgagttagct cactcattag gcaccccagg ctttacactt tatgcttccg gctcgtatgt  9360
tgtgtggaat tgtgagcgga taacaatttc acacaggaaa cagctatgac catgattacg  9420
ccaagctttg ctcctaggag tttcctaata cttcccaaac tcaaatatat aaagcatttg  9480
acttgttcta tgccctaggg ggcgggggga agctaagcca gcttttttta acatttaaaa  9540
tgttaattcc attttaaatg cacagatgtt tttatttcat aagggtttca atgtgcatga  9600
atgctgcaat attcctgtta ccaaagctag tataaataaa aatagataaa cgtggaaatt  9660
acttagagtt tctgtcatta acgtttcctt cctcagttga caacataaat gcgctgctga  9720
gcaagccagt ttgcatctgt caggatcaat ttcccattat gccagtcata ttaattacta  9780
gtcaattagt tgatttttat ttttgacata tacatgtgaa tgaaagaccc cacctgtagg  9840
tttggcaagc tagcttaagt                                              9860
```

```
SEQ ID NO: 30          moltype = DNA  length = 9760
FEATURE                Location/Qualifiers
misc_feature           1..9760
                       note = spRRVe-F3-TK vector
source                 1..9760
                       mol_type = other DNA
                       organism = synthetic construct
SEQUENCE: 30
aacgccattt tgcaaggcat ggaaaaatac ataactgaga atagaaaagt tcagatcaag  60
gtcaggaaca gatggaacag ctgaatatgg gccaaacagg atatctgtgg taagcagttc  120
ctgccccggc tcagggccaa gaacagatgg aacagctgaa tatgggccaa acaggatatc  180
tgtggtaagc agttcctgcc ccggctcagg gccaagaaca gatggtcccc agatgcggtc  240
cagccctcag cagtttctag agaaccatca gatgtttcca gggtgcccca aggacctgaa  300
atgaccctgt gccttatttg aactaaccaa tcagttcgct tctcgcttct gttcgcgcgc  360
ttatgctccc cgagctcaat aaaagagccc acaacccctc actcggggcg ccagtcctcc  420
gattgactga gtcgcccggg tacccgtgta tccaataaac cctcttgcag ttgcatccga  480
cttgtggtct cgctgttcct tgggagggtc tcctctgagt gattgactac ccgtcagcgg  540
gggtctttca tttgggggct cgtccgggat cgggagaccc ctgcccaggg accaccgacc  600
caccaccggg aggtaagctg gccagcaact tatctgtgtc tgtccgattg tctagtgtct  660
atgactgatt ttatgcgcct gcgtcggtac tagttagcta actagctctg tatctggcgg  720
acccgtggtg gaactgacga gttcggaaca cccggccgca accctgggag acgtcccagg  780
```

-continued

```
gacttcgggg gccgttttg tggcccgacc tgagtcctaa aatcccgatc gtttaggact  840
ctttggtgca cccccttag aggagggata tgtggttctg gtaggagacg agaacctaaa  900
acagttcccg cctccgtctg aatttttgct ttcggtttgg gaccgaagcc gcgccgcgcg  960
tcttgtctgc tgcagcatcg ttctgtgttg tctctgtctg actgtgtttc tgtatttgtc  1020
tgaaaatatg ggcccgggct agcctgttac cactccctta agtttgacct taggtcactg  1080
gaaagatgtc gagcggatcg ctcacaacca gtcggtagat gtcaagaaga gacgttgggt  1140
taccttctgc tctgcagaat ggccaacctt taacgtcgga tggccgcgag acggcacctt  1200
taaccgagac ctcactaccc aggttaagat caaggtcttt tcacctggcc cgcatggaca  1260
cccagaccag gtggggtaca tcgtgacctg ggaagccttg gcttttgacc cccctccctg  1320
ggtcaagccc tttgtacacc ctaagcctcc gcctcctctt cctccatccg ccccgtctct  1380
ccccttgaa cctcctcgtt cgaccccgcc tcgatcctcc ctttatccag ccctcactcc  1440
ttctctaggc gcccccatat ggccatatga gatcttatat ggggcacccc cgccccttgt  1500
aaacttccct gaccctgaca tgacaagagt tactaacagc ccctctctcc aagctcactt  1560
acaggctctc tacttagtcc agcacgaagt ctggagacct ctggcggcag cctaccaaga  1620
acaactggac cgaccggtgg tacctcaccc ttaccgagtc ggcgacacag tgtgggtccg  1680
ccgacaccag actaagaacc tagaacctcg ctggaaagga ccttacacag tcctgctgac  1740
cacccccacc gccctcaaag tagacggcat cgcagcttgg atacacgccg cccacaattc  1800
gatcatacct ggtgttgctg actaccccga ccgcggtaaa agtcgatggt attgctgcct  1860
gggtccatgc ttctcacctc aaacctgcac caccttcggc accagatgag tcctgggagc  1920
tggaaaagac tgatcatcct cttaagctgc gtattcggcg gcggcgggac gagtctgcaa  1980
aataagaacc cccaccagcc catgaccctc acttggcagg tactgtccca aactggagac  2040
gttgtctggg atacaaaggc agtccagccc ccttggactt ggtggcccac acttaaacct  2100
gatgtatgtg ccttggcggc tagtcttgag tcctgggata tcccgggaac cgatgtctcg  2160
tcctctaaac gagtcagacc tccggactca gactatactg ccgcttataa gcaaatcacc  2220
tggggagcca tagggtgcag ctaccctcgg gctaggacta gaatggcaag ctctaccttc  2280
tacgtatgtc cccgggatgg ccggaccctt tcagaagcta gaaggtgcgg ggggctagaa  2340
tccctatact gtaaagaatg ggattgtgag accacgggga ccggttattg gctatctaaa  2400
tcctcaaaag acctcataac tgtaaaatgg gaccaaaata gcgaatggac tcaaaaattt  2460
caacagtgtc accagaccgg ctggtgtaac ccccttaaaa tagatttcac agacaaagga  2520
aaattatcca aggactggat aacgggaaaa acctggggat taagattcta tgtgtctgga  2580
catccaggcg tacagttcac cattcgctta aaaatcacca acatgccagc tgtggcagta  2640
ggtcctgacc tcgtccttgt ggaacaagga cctcctagaa cgtccctcgc tctcccacct  2700
cctcttcccc caagggaagc gccaccgcca tctctccccg actctaactc cacagccctg  2760
gcgactagtg cacaaactcc cacggtgaga aaaacaattg ttaccctaaa cactccgcct  2820
cccaccacag gcgacagact tttgatcttt gtgcaggggg ccttcctaac cttaaatgct  2880
accaacccag gggccactga gtcttgctgg ctttgtttgg ccatgggccc cccttattat  2940
gaagcaatag cctcatcagg agaggtcgcc tactccaccg accttgaccg gtgccgctgg  3000
gggacccaag gaaagctcac cctcactgag gtctcaggac acgggttgtg cataggaaag  3060
gtgcccttta cccatcagca tctctgcaat cagaccctat ccatcaattc ctccggagac  3120
catcagtatc tgctcccctc caaccatagc tggtgggctt gcagcactgg cctcacccct  3180
tgcctctcca cctcagtttt taatcagact agagatttct gtatccaggt ccagctgatt  3240
cctcgcatct attactatcc tgaagaagtt ttgttacagg cctatgacaa ttctcacccc  3300
aggactaaaa gagaggctgt ctcacttacc ctagctgttt tactggggtt gggaatcacg  3360
gcgggaatag gtactggttc aactgcctta attaaaggac ctatagacct ccagcaaggc  3420
ctgacaagcc tccagatcgc catagatgct gacctccggg ccctccaaga ctcagtcagc  3480
aagttagagg actcactgac ttccctgtcc gaggtagtgc tccaaaatag gagaggcctt  3540
gacttgctgt ttctaaaaga aggtggcctc tgtgcggccc taaaggaaga gtgctgtttt  3600
tacatagacc actcaggtgc agtacgggac tccatgaaaa aactcaaaga aaaactggat  3660
aaaagacagt tagagcgcca gaaaagccaa aactggtatg aaggatggtt caataactcc  3720
ccttggttca ctaccctgct atcaaccatc gctgggcccc tattactcct ccttctgttg  3780
ctcatcctcg ggccatgcat catcaataag ttagttcaat tcatcaatga taggataagt  3840
gcagttaaaa ttctggtcct tagacaaaaa tatcaggccc tagagaacga aggtaacctt  3900
taacacgtga aggctgccga ccccggggt ggaccatcct ctagactgtg ctcgacgttt  3960
aaacaacgtg acctttaaac ggtactttcc catagctgat taatgggaaa gtaccgttct  4020
cgagccaata cacgtcaatg ggaagtgaaa gggcagccaa aacgtaacac cgccccggtt  4080
ttccctggaa attccatatt ggcacgcatt ctattggctg agctgcgttc acgtgggtat  4140
aagaggcgcg accagcgtcg gtaccgtcgc agtcttcggt ctgaccaccg tagaacgcag  4200
aacgcgtatg gcttcgtacc cctgccatca acacgcgtct gcgttcgacc aggctgcgcg  4260
ttctcgcggc catagcaacc gacgtacggc gttgcgccct cgccggcagc aagaagccac  4320
ggaagtccgc ctggagcaga aaatgcccac gctactgcgg gtttatatag acggtcctca  4380
cgggatgggg aaaaccacca ccacgcaact gctggtggcc ctgggttcgc gcgacgatat  4440
cgtctacgta cccgagccga tgacttactg gcaggtgctg gggcttccg agacaatcgc  4500
gaacatctac accacacaac accgcctcga ccagggtgag atatcggccg gggacgcggc  4560
ggtggtaatg acaagcgccc agataacaat gggcatgcct tatgccgtga ccgacgccgt  4620
tctggctcct catatcgggg gggaggctgg gagctcacat gccccgcccc cggccctcac  4680
cctcatcttc gaccgccatc ccatcgccgc cctcctgtgc tacccggccg cgcgatacct  4740
tatgggcagc atgaccccc aggccgtgct ggcgttcgtg gccctcatcc cgccgacctt  4800
gcccggcaca aacatcgtgt tgggggccct tccggaggac agacacatcg accgcctggc  4860
caaacgccag cgccccggcg agcggcttga cctggctatg ctggccgcga ttcgccgcgt  4920
ttacgggctg cttgccaata cggtgcggta tctgcagggc ggcgggtcgt ggcgggagga  4980
ttggggacag ctttcgggga cggccgtgcc gccccagggt gccgagcccc agagcaacgc  5040
gggcccacga ccccatatcg gggacacgtt atttaccctg tttcgggccc ccgagttgct  5100
ggcccccaac ggcgacctgt acaacgtgtt tgcctgggcc ttggacgtct tggccaaacg  5160
cctccgtccc atgcacgtct ttatcctgga ttacgaccaa tcgcccgccg gctgccggga  5220
cgccctgctg caacttacct ccgggatggt ccagacccac gtcaccaccc ccggctccat  5280
accgacgatc tgcgacctgg cgcgcacgtt tgcccgggag atgggggagg ctaactgagt  5340
cgacatcgat ggtaccagat ccgataaaat aaaaggtttt atttagtctc ctgaaaaagg  5400
ggggaatgaa agaccccacc tgtaggtttg gcaagctagc ttaagtaacg ccattttgca  5460
aggcatggaa aaatacataa ctgagaatag agaagttcag atcaaggtca ggaacagatg  5520
```

```
gaacagctga atatgggcca aacaggatat ctgtggtaag cagttcctgc cccggctcag  5580
ggccaagaac agatggaaca gctgaatatg ggccaaacag gatatctgtg gtaagcagtt  5640
cctgccccgg ctcagggcca agaacagatg gtccccagat gcggtccagc cctcagcagt  5700
ttctagagaa ccatcagatg tttccagggt gccccaagga cctgaaatga ccctgtgcct  5760
tatttgaact aaccaatcag ttcgcttctc gcttctgttc gcgcgcttct gctccccgag  5820
ctcaataaaa gagcccacaa cccctcactc ggggcgccag tcctccgatt gactgagtcg  5880
cccgggtacc cgtgtatcca ataaaccctc ttgcagttgc atccgacttg tggtctcgct  5940
gttccttggg agggtctcct ctgagtgatt gactacccgt cagcgggggt ctttcacaca  6000
tgcagcatgt atcaaaatta atttggtttt ttttcttaag tatttacatt aaatggccat  6060
agtacttaaa gttacattgg cttccttgaa ataaacatgg agtattcaga atgtgtcata  6120
aatatttcta attttaagat agtatctcca ttggctttct acttttttctt ttattttttt  6180
ttgtcctctg tcttccattt gttgttgttg ttgtttgttt gtttgtttgt tggttggttg  6240
gttaattttt ttttaaagat cctacactat agttcaagct agactattag ctactctgta  6300
acccagggtg accttgaagt catgggtagc ctgctgtttt agccttccca catctaagat  6360
tacaggtatg agctatcatt tttggtatat gattgattga ttgattgatg tgtgtgtgtg  6420
tgattgtgtt tgtgtgtgtg actgtgaaaa tgtgtgtatg ggtgtgtgtg aatgtgtgta  6480
tgtatgtgtg tgtgtgagtg tgtgtgtgtg tgtgtgcatg tgtgtgtgtg tgactgtgtc  6540
tatgtgtatg actgtgtgtg tgtgtgtgtg tgtgtgtgtg tgtgtgtgtg tgtgtgtgtt  6600
gtgaaaaaat attctatggt agtgagagcc aacgctccgg ctcaggtgtc aggttggttt  6660
ttgagacaga gtctttcact tagcttggaa ttcactggcc gtcgttttac aacgtcgtga  6720
ctgggaaaac cctggcgtta cccaacttaa tcgccttgca gcacatcccc ctttcgccag  6780
ctggcgtaat agcgaagagg cccgcaccga tcgcccttcc caacagttgc gcagcctgaa  6840
tggcgaatgg cgcctgatgc ggtattttct ccttacgcat ctgtgcggta tttcacaccg  6900
catatggtgc actctcagta caatctgctc tgatgccgca tagttaagcc agccccgaca  6960
cccgccaaca cccgctgacg cgccctgacg ggcttgtctg ctcccggcat ccgcttacag  7020
acaagctgtg accgtctccg ggagctgcat gtgtcagagg ttttcaccgt catcaccgaa  7080
acgcgcgaga cgaaagggcc tcgtgatacg cctattttta taggttaatg tcatgataat  7140
aatggtttct tagacgtcag gtggcacttt tcggggaaat gtgcgcggaa cccctatttg  7200
tttatttttc taaatacatt caaatatgta tccgctcatg agacaataac cctgataaat  7260
gcttcaataa tattgaaaaa ggaagagtat gagtattcaa catttccgtg tcgcccttat  7320
tccctttttt gcggcatttt gccttcctgt ttttgctcac ccagaaacgc tggtgaaagt  7380
aaaagatgct gaagatcagt tgggtgcacg agtgggttac atcgaactgg atctcaacag  7440
cggtaagatc cttgagagtt ttcgccccga agaacgtttt ccaatgatga gcacttttaa  7500
agttctgcta tgtggcgcgg tattatcccg tattgacgcc gggcaagagc aactcggtcg  7560
ccgcatacac tattctcaga atgacttggt tgagtactca ccagtcacag aaaagcatct  7620
tacggatggc atgacagtaa gagaattatg cagtgctgcc ataaccatga gtgataacac  7680
tgcggccaac ttacttctga caacgatcgg aggaccgaag gagctaaccg cttttttgca  7740
caacatgggg gatcatgtaa ctcgccttga tcgttgggaa ccggagctga atgaagccat  7800
accaaacgac gagcgtgaca ccacgatgcc tgtagcaatg gcaacaacgt tgcgcaaact  7860
attaactggc gaactactta ctctagcttc ccggcaacaa ttaatagact ggatggaggc  7920
ggataaagtt gcaggaccac ttctgcgctc ggcccttccg gctggctggt ttattgctga  7980
taaatctgga gccggtgagc gtgggtctcg cggtatcatt gcagcactgg ggccagatgg  8040
taagccctcc cgtatcgtag ttatctacac gacggggagt caggcaacta tggatgaacg  8100
aaatagacag atcgctgaga taggtgcctc actgattaag cattggtaac tgtcagacca  8160
agtttactca tatatacttt agattgattt aaaacttcat ttttaattta aaaggatcta  8220
ggtgaagatc ctttttgata atctcatgac caaaatccct taacgtgagt tttcgttcca  8280
ctgagcgtca gaccccgtag aaaagatcaa aggatcttct tgagatcctt tttttctgcg  8340
cgtaatctgc tgcttgcaaa caaaaaaacc accgctacca gcggtggttt gtttgccgga  8400
tcaagagcta ccaactcttt ttccgaaggt aactggcttc agcagagcgc agataccaaa  8460
tactgttctt ctagtgtagc cgtagttagg ccaccacttc aagaactctg tagcaccgcc  8520
tacatacctc gctctgctaa tcctgttacc agtggctgct gccagtggcg ataagtcgtg  8580
tcttaccggg ttggactcaa gacgatagtt accggataag gcgcagcggt cgggctgaac  8640
ggggggttcg tgcacacagc ccagcttgga gcgaacgacc tacaccgaac tgagatacct  8700
acagcgtgag ctatgagaaa gcgccacgct tcccgaaggg agaaaggcgg acaggtatcc  8760
ggtaagcggc agggtcggaa caggagagcg cacgagggag cttccagggg gaaacgcctg  8820
gtatctttat agtcctgtcg ggtttcgcca cctctgactt gagcgtcgat ttttgtgatg  8880
ctcgtcaggg gggcggagcc tatggaaaaa cgccagcaac gcggcctttt tacggttcct  8940
ggccttttgc tggccttttg ctcacatgtt ctttcctgcg ttatcccctg attctgtgga  9000
taaccgtatt accgcctttg agtgagctga taccgctcgc cgcagccgaa cgaccgagcg  9060
cagcgagtca gtgagcgagg aagcggaaga gcgcccaata cgcaaaccgc ctctccccgc  9120
gcgttggccg attcattaat gcagctggca cgacaggttt cccgactgga aagcgggcag  9180
tgagcgcaac gcaattaatg tgagttagct cactcattag gcaccccagg ctttacactt  9240
tatgcttccg gctcgtatgt tgtgtggaat tgtgagcgga taacaatttc acacaggaaa  9300
cagctatgac catgattacg ccaagctttg ctcctaggag tttcctaata cttcccaaac  9360
tcaaatatat aaagcatttg acttgttcta tgccctaggg ggcgggggga agctaagcca  9420
gcttttttta acatttaaaa tgttaattcc attttaaatg cacagatgtt tttatttcat  9480
aagggtttca atgtgcatga atgctgcaat attcctgtta ccaaagctag tataaataaa  9540
aatagataaa cgtggaaatt acttagagtt tctgtcatta acgtttcctt cctcagttga  9600
caacataaat gcgctgctga gcaagccagt ttgcatctgt caggatcaat ttcccattat  9660
gccagtcata ttaattacta gtcaattagt tgatttttat ttttgacata tacatgtgaa  9720
tgaaagaccc cacctgtagg tttggcaagc tagcttaagt                        9760
```

```
SEQ ID NO: 31          moltype = DNA  length = 9685
FEATURE                Location/Qualifiers
misc_feature           1..9685
                       note = spRRVe-F4-TK vector
source                 1..9685
                       mol_type = other DNA
                       organism = synthetic construct
```

-continued

```
SEQUENCE: 31
aacgccattt tgcaaggcat ggaaaaatac ataactgaga atagaaaagt tcagatcaag  60
gtcaggaaca gatggaacag ctgaatatgg gccaaacagg atatctgtgg taagcagttc  120
ctgccccggc tcagggccaa gaacagatgg aacagctgaa tatgggccaa acaggatatc  180
tgtggtaagc agttcctgcc ccggctcagg gccaagaaca gatggtcccc agatgcggtc  240
cagccctcag cagtttctag agaaccatca gatgtttcca gggtgcccca aggacctgaa  300
atgaccctgt gccttatttg aactaaccaa tcagttcgct tctcgcttct gttcgcgcgc  360
ttatgctccc cgagctcaat aaaagagccc acaacccctc actcggggcg ccagtcctcc  420
gattgactga gtcgcccggg tacccgtgta tccaataaac cctcttgcag ttgcatccga  480
cttgtggtct cgctgttcct tgggagggtc tcctctgagt gattgactac ccgtcagcgg  540
gggtctttca tttgggggct cgtccgggat cgggagaccc ctgcccaggg accaccgacc  600
caccaccggg aggtaagctg gccagcaact tatctgtgtc tgtccgattg tctagtgtct  660
atgactgatt ttatgcgcct gcgtcggtac tagttagcta actagctctg tatctggcgg  720
acccgtggtg gaactgacga gttcggaaca cccggccgca accctgggag acgtcccagg  780
gacttcgggg gccgtttttg tggcccgacc tgagtcctaa aatcccgatc gtttaggact  840
ctttggtgca cccccccttag aggagggata tgtggttctg gtaggagacg agaacctaaa  900
acagttcccg cctccgtctg aatttttgct ttcggtttgg gaccgaagcc gcgccgcgcg  960
tcttgtctgc tgcagcatcg ttctgtgttg tctctgtctg actgtgtttc tgtatttgtc  1020
tgaaaatatg ggcccgggct agcctgttac cactccctta agtttgacct taggtcactg  1080
gaaagatgtc gagcggatcg ctcacaacca gtcggtagat gtcaagaaga gacgttgggt  1140
taccttctgc tctgcagaat ggccaacctt taacgtcgga tggccgcgag acggcacctt  1200
taaccgagac ctcactaccc aggttaagat caaggtcttt tcacctggcc cgcatggaca  1260
cccagaccag gtggggtaca tcgtgacctg ggaagccttg gcttttgacc cccctccctg  1320
ggtcaagccc tttgtacacc ctaagcctcc gcctcctctt cctccatccg ccccgtctct  1380
ccccccttgaa cctcctcgtt cgaccccgcc tcgatcctcc ctttatccag ccctcactcc  1440
ttctctaggc gcccccatat ggccatatga gatcttatat ggggcacccc cgccccttgt  1500
aaacttccct gaccctgaca tgacaagagt tactaacagc ccctctctcc aagctcactt  1560
acaggctctc tacttagtcc agcacgaagt ctggagacct ctggcggcag cctaccaaga  1620
acaactggac cgaccggtgg tacctcaccc ttaccgagtc ggcgacacag tgtgggtccg  1680
ccgacaccag actaagaacc tagaacctcg ctggaaagga ccttacacag tcctgctgac  1740
cacccccacc gccctcaaag tagacggcat cgcagcttgg atacacgccg cccacaattc  1800
gatcatacct ggtgttgctg actaccccga ccgcggtaaa agtcgatggt attgctgcct  1860
gggtccatgc ttctcacctc aaacctgcac caccttcggc accagatgag tcctgggagc  1920
tggaaaagac tgatcatcct cttaagctgc gtattcggcg gcggcgggac gagtctgcaa  1980
aataagaacc cccaccagcc catgaccctc acttggcagg tactgtccca aactggagac  2040
gttgtctggg atacaaaggc agtccagccc ccttggactt ggtggcccac acttaaacct  2100
gatgtatgtg ccttggcggc tagtcttgag tcctgggata tcccgggaac cgatgtctcg  2160
tcctctaaac gagtcagacc tccggactca gactatactg ccgcttataa gcaaatcacc  2220
tggggagcca tagggtgcag ctaccctcgg gctaggacta gaatggcaag ctctaccttc  2280
tacgtatgtc cccgggatgg ccggaccctt tcagaagcta gaaggtgcgg ggggctagaa  2340
tccctatact gtaaagaatg ggattgtgag accacgggga ccggttattg gctatctaaa  2400
tcctcaaaag acctcataac tgtaaaatgg gaccaaaata gcgaatggac tcaaaaattt  2460
caacagtgtc accagaccgg ctggtgtaac cccccttaaaa tagatttcac agacaaagga  2520
aaattatcca aggactggat aacgggaaaa acctggggat taagattcta tgtgtctgga  2580
catccaggcg tacagttcac cattcgctta aaaatcacca acatgccagc tgtggcagta  2640
ggtcctgacc tcgtccttgt ggaacaagga cctcctagaa cgtccctcgc tctcccacct  2700
cctcttcccc caagggaagc gccaccgcca tctctccccg actctaactc cacagccctg  2760
gcgactagtg cacaaactcc cacggtgaga aaaacaattg ttaccctaaa cactccgcct  2820
cccaccacag gcgacagact tttgatcttg gtgcaggggg ccttcctaac cttaaatgct  2880
accaacccag gggccactga gtcttgctgg ctttgtttgg ccatgggccc cccttattat  2940
gaagcaatag cctcatcagg agaggtcgcc tactccaccg accttgaccg gtgccgctgg  3000
gggacccaag gaaagctcac cctcactgag gtctcaggac acgggttgtg cataggaaag  3060
gtgcccttta cccatcagca tctctgcaat cagaccctat ccatcaattc ctccggagac  3120
catcagtatc tgctcccctc caaccatagc tggtgggctt gcagcactgg cctcacccct  3180
tgcctctcca cctcagtttt taatcagact agagatttct gtatccaggt ccagctgatt  3240
cctcgcatct attactatcc tgaagaagtt ttgttacagg cctatgacaa ttctcacccc  3300
aggactaaaa gagaggctgt ctcacttacc ctagctgttt tactggggtt gggaatcacg  3360
gcgggaatag gtactggttc aactgcctta attaaaggac ctatagacct ccagcaaggc  3420
ctgacaagcc tccagatcgc catagatgct gacctccggg ccctccaaga ctcagtcagc  3480
aagttagagg actcactgac ttccctgtcc gaggtagtgc tccaaaatag gagaggcctt  3540
gacttgctgt ttctaaaaga aggtggcctc tgtgcggccc taaaggaaga gtgctgtttt  3600
tacatagacc actcaggtgc agtacgggac tccatgaaaa aactcaaaga aaaactggat  3660
aaaagacagt tagagcgcca gaaaagccaa aactggtatg aaggatggtt caataactcc  3720
ccttggttca ctaccctgct atcaaccatc gctgggcccc tattactcct ccttctgttg  3780
ctcatcctcg ggccatgcat catcaataag ttagttcaat tcatcaatga taggataagt  3840
gcagttaaaa ttctggtcct tagacaaaaa tatcaggccc tagagaacga aggtaacctt  3900
taacacgtga aggctgccga ccccgggggt ggaccatcct ctagactgtg ctcgacgttt  3960
aaacggaagt gaaagggcag ccaaaacgta acaccgcccc ggttttccct ggaaattcca  4020
tattggcacg cattctattg gctgagctgc gttcacgtgg gtataagagg cgcgaccagc  4080
gtcggtaccg tcgcagtctt cggtctgacc accgtagaac gcagaggatc ctatggcttc  4140
gtacccctgc catcaacacg cgtctgcgtt cgaccaggct gcgcgttctc gcggccatag  4200
caaccgacgt acggcgttgc gccctcgccg gcagcaagaa gccacggaag tccgcctgga  4260
gcagaaaatg cccacgctac tgcgggttta tatagacggt cctcacggga tggggaaaac  4320
caccaccacg caactgctgg tggccctggg ttcgcgcgac gatatcgtct acgtacccga  4380
gccgatgact tactggcagg tgctgggggc ttccgagaca atcgcgaaca tctacaccac  4440
acaacaccgc ctcgaccagg gtgagatatc ggccggggac gcggcggtgg taatgacaag  4500
cgcccagata acaatgggca tgccttatgc cgtgaccgac gccgttctgg ctcctcatat  4560
cggggggggag gctgggagct cacatgcccc gcccccggcc ctcaccctca tcttcgaccg  4620
ccatcccatc gccgccctcc tgtgctaccc ggccgcgcga taccttatgg gcagcatgac  4680
```

-continued

```
cccccaggcc gtgctggcgt tcgtggccct catcccgccg accttgcccg gcacaaacat  4740
cgtgttgggg gcccttccgg aggacagaca catcgaccgc ctggccaaac gccagcgccc  4800
cggcgagcgg cttgacctgg ctatgctggc cgcgattcgc cgcgtttacg ggctgcttgc  4860
caatacggtg cggtatctgc agggcggcgg gtcgtggcgg gaggattggg gacagctttc  4920
ggggacggcc gtgccgcccc agggtgccga gccccagagc aacgcgggcc cacgacccca  4980
tatcggggac acgttattta ccctgtttcg ggcccccgag ttgctggccc ccaacggcga  5040
cctgtacaac gtgtttgcct gggccttgga cgtcttggcc aaacgcctcc gtcccatgca  5100
cgtctttatc ctggattacg accaatcgcc cgccggctgc cgggacgccc tgctgcaact  5160
tacctccggg atggtccaga cccacgtcac caccccggc tccataccga cgatctgcga  5220
cctggcgcgc acgtttgccc gggagatggg ggaggctaac tgagtcgaca tcgatggtac  5280
cagatccgat aaaataaaag gttttattta gtctcctgaa aaagggggga atgaaagacc  5340
ccacctgtag gtttggcaag ctagcttaag taacgccatt ttgcaaggca tggaaaaata  5400
cataactgag aatagagaag ttcagatcaa ggtcaggaac agatggaaca gctgaatatg  5460
ggccaaacag gatatctgtg gtaagcagtt cctgccccgg ctcagggcca agaacagatg  5520
gaacagctga atatgggcca aacaggatat ctgtggtaag cagttcctgc cccggctcag  5580
ggccaagaac agatggtccc cagatgcggt ccagccctca gcagtttcta gagaaccatc  5640
agatgtttcc agggtgcccc aaggacctga aatgaccctg tgccttattt gaactaacca  5700
atcagttcgc ttctcgcttc tgttcgcgcg cttctgctcc ccgagctcaa taaaagagcc  5760
cacaacccct cactcggggc gccagtcctc cgattgactg agtcgcccgg gtacccgtgt  5820
atccaataaa ccctcttgca gttgcatccg acttgtggtc tcgctgttcc ttgggagggt  5880
ctcctctgag tgattgacta cccgtcagcg ggggtctttc acacatgcag catgtatcaa  5940
aattaatttg gttttttttc ttaagtattt acattaaatg gccatagtac ttaaagttac  6000
attggcttcc ttgaaataaa catggagtat tcagaatgtg tcataaatat ttctaatttt  6060
aagatagtat ctccattggc tttctacttt ttcttttatt tttttttgtc ctctgtcttc  6120
catttgttgt tgttgttgtt tgtttgtttg tttgttggtt ggttggttaa ttttttttta  6180
aagatcctac actatagttc aagctagact attagctact ctgtaaccca gggtgacctt  6240
gaagtcatgg gtagcctgct gttttagcct tcccacatct aagattacag gtatgagcta  6300
tcatttttgg tatatgattg attgattgat tgatgtgtgt gtgtgtgatt gtgtttgtgt  6360
gtgtgactgt gaaaatgtgt gtatgggtgt gtgtgaatgt gtgtatgtat gtgtgtgtgt  6420
gagtgtgtgt gtgtgtgtgt gcatgtgtgt gtgtgtgact gtgtctatgt gtatgactgt  6480
gtgtgtgtgt gtgtgtgtgt gtgtgtgtgt gtgtgtgtgt gtgttgtgaa aaaatattct  6540
atggtagtga gagccaacgc tccggctcag gtgtcaggtt ggtttttgag acagagtctt  6600
tcacttagct tggaattcac tggccgtcgt tttacaacgt cgtgactggg aaaaccctgg  6660
cgttacccaa cttaatcgcc ttgcagcaca tccccctttc gccagctggc gtaatagcga  6720
agaggcccgc accgatcgcc cttcccaaca gttgcgcagc ctgaatggcg aatggcgcct  6780
gatgcggtat tttctcctta cgcatctgtg cggtatttca caccgcatat ggtgcactct  6840
cagtacaatc tgctctgatg ccgcatagtt aagccagccc cgacacccgc caacacccgc  6900
tgacgcgccc tgacgggctt gtctgctccc ggcatccgct tacagacaag ctgtgaccgt  6960
ctccgggagc tgcatgtgtc agaggttttc accgtcatca ccgaaacgcg cgagacgaaa  7020
gggcctcgtg atacgcctat ttttataggt taatgtcatg ataataatgg tttcttagac  7080
gtcaggtggc acttttcggg gaaatgtgcg cggaacccct atttgtttat ttttctaaat  7140
acattcaaat atgtatccgc tcatgagaca ataaccctga taaatgcttc aataatattg  7200
aaaaaggaag agtatgagta ttcaacattt ccgtgtcgcc cttattccct tttttgcggc  7260
attttgcctt cctgtttttg ctcacccaga aacgctggtg aaagtaaaag atgctgaaga  7320
tcagttgggt gcacgagtgg gttacatcga actggatctc aacagcggta agatccttga  7380
gagttttcgc cccgaagaac gttttccaat gatgagcact tttaaagttc tgctatgtgg  7440
cgcggtatta tcccgtattg acgccgggca agagcaactc ggtcgccgca tacactattc  7500
tcagaatgac ttggttgagt actcaccagt cacagaaaag catcttacgg atggcatgac  7560
agtaagagaa ttatgcagtg ctgccataac catgagtgat aacactgcgg ccaacttact  7620
tctgacaacg atcggaggac cgaaggagct aaccgctttt ttgcacaaca tgggggatca  7680
tgtaactcgc cttgatcgtt gggaaccgga gctgaatgaa gccataccaa acgacgagcg  7740
tgacaccacg atgcctgtag caatggcaac aacgttgcgc aaactattaa ctggcgaact  7800
acttactcta gcttcccggc aacaattaat agactggatg gaggcggata aagttgcagg  7860
accacttctg cgctcggccc ttccggctgg ctggtttatt gctgataaat ctggagccgg  7920
tgagcgtggg tctcgcggta tcattgcagc actggggcca gatggtaagc cctcccgtat  7980
cgtagttatc tacacgacgg ggagtcaggc aactatggat gaacgaaata gacagatcgc  8040
tgagataggt gcctcactga ttaagcattg gtaactgtca gaccaagttt actcatatat  8100
actttagatt gatttaaaac ttcattttta atttaaaagg atctaggtga agatcctttt  8160
tgataatctc atgaccaaaa tcccttaacg tgagttttcg ttccactgag cgtcagaccc  8220
cgtagaaaag atcaaaggat cttcttgaga tccttttttt ctgcgcgtaa tctgctgctt  8280
gcaaacaaaa aaaccaccgc taccagcggt ggtttgtttg ccggatcaag agctaccaac  8340
tctttttccg aaggtaactg gcttcagcag agcgcagata ccaaatactg ttcttctagt  8400
gtagccgtag ttaggccacc acttcaagaa ctctgtagca ccgcctacat acctcgctct  8460
gctaatcctg ttaccagtgg ctgctgccag tggcgataag tcgtgtctta ccgggttgga  8520
ctcaagacga tagttaccgg ataaggcgca gcggtcgggc tgaacggggg gttcgtgcac  8580
acagcccagc ttggagcgaa cgacctacac cgaactgaga tacctacagc gtgagctatg  8640
agaaagcgcc acgcttcccg aagggagaaa ggcggacagg tatccggtaa gcggcagggt  8700
cggaacagga gagcgcacga gggagcttcc agggggaaac gcctggtatc tttatagtcc  8760
tgtcgggttt cgccacctct gacttgagcg tcgatttttg tgatgctcgt caggggggcg  8820
gagcctatgg aaaaacgcca gcaacgcggc ctttttacgg ttcctggcct tttgctggcc  8880
ttttgctcac atgttctttc ctgcgttatc ccctgattct gtggataacc gtattaccgc  8940
ctttgagtga gctgataccg ctcgccgcag ccgaacgacc gagcgcagcg agtcagtgag  9000
cgaggaagcg gaagagcgcc caatacgcaa accgcctctc cccgcgcgtt ggccgattca  9060
ttaatgcagc tggcacgaca ggtttcccga ctggaaagcg ggcagtgagc gcaacgcaat  9120
taatgtgagt tagctcactc attaggcacc ccaggcttta cactttatgc ttccggctcg  9180
tatgttgtgt ggaattgtga gcggataaca atttcacaca ggaaacagct atgaccatga  9240
ttacgccaag ctttgctcct aggagtttcc taatacttcc caaactcaaa tatataaagc  9300
atttgacttg ttctatgccc tagggggcgg ggggaagcta agccagcttt ttttaacatt  9360
taaaatgtta attccatttt aaatgcacag atgtttttat ttcataaggg tttcaatgtg  9420
```

-continued

```
catgaatgct gcaatattcc tgttaccaaa gctagtataa ataaaaatag ataaacgtgg  9480
aaattactta gagtttctgt cattaacgtt tccttcctca gttgacaaca taaatgcgct  9540
gctgagcaag ccagtttgca tctgtcagga tcaatttccc attatgccag tcatattaat  9600
tactagtcaa ttagttgatt tttatttttg acatatacat gtgaatgaaa gaccccacct  9660
gtaggtttgg caagctagct taagt                                        9685
```

```
SEQ ID NO: 32          moltype = DNA  length = 10008
FEATURE                Location/Qualifiers
misc_feature           1..10008
                       note = sRRVgp-sEF1a-hopt-yCD
source                 1..10008
                       mol_type = other DNA
                       organism = synthetic construct
SEQUENCE: 32
catgtgagca aaaggccagc aaaaggccag gaaccgtaaa aaggccgcgt tgctggcgtt  60
tttccatagg ctccgccccc ctgacgagca tcacaaaaat cgacgctcaa gtcagaggtg  120
gcgaaacccg acaggactat aaagatacca ggcgtttccc cctggaagct ccctcgtgcg  180
ctctcctgtt ccgaccctgc cgcttaccgg atacctgtcc gcctttctcc cttcgggaag  240
cgtggcgctt tctcatagct cacgctgtag gtatctcagt tcggtgtagg tcgttcgctc  300
caagctgggc tgtgtgcacg aaccccccgt tcagcccgac cgctgcgcct tatccggtaa  360
ctatcgtctt gagtccaacc cggtaagaca cgacttatcg ccactggcag cagccactgg  420
taacaggatt agcagagcga ggtatgtagg cggtgctaca gagttcttga agtggtggcc  480
taactacggc tacactagaa ggacagtatt tggtatctgc gctctgctga agccagttac  540
cttcggaaaa agagttggta gctcttgatc cggcaaacaa accaccgctg gtagcggtgg  600
tttttttgtt tgcaagcagc agattacgcg cagaaaaaaa ggatctcaag aagatccttt  660
gatcttttct acggggtctg acgctcagtg gaacgaaaac tcacgttaag ggattttggt  720
catgagatta tcaaaaagga tcttcaccta gatcctttta aattaaaaat gaagttttaa  780
atcaatctaa agtatatatg agtaacctga tcaggactct tccttttcat gaacaataaa  840
actgtctgct tacataaaca gtaatacaag ggtgttatg agccatattc aacgggaaac  900
gtcttgctct aggccgcgat taaattccaa catggatgct gatttatatg ggtataaatg  960
ggctcgcgat aatgtcgggc aatcaggtgc gacaatctat cgattgtatg ggaagcccga  1020
tgcgccagag ttgtttctga aacatggcaa aggtagcgtt gccaatgatg ttacagatga  1080
gatggtcaga ctaaactggc tgacggaatt tatgcctctt ccgaccatca agcattttat  1140
ccgtactcct gatgatgcat ggttactcac cactgcgatc cccgggaaaa cagcattcca  1200
ggtattagaa gaatatcctg attcaggtga aaatattgtt gatgcgctgg cagtgttcct  1260
gcgccggttg cattcgattc ctgtttgtaa ttgtcctttt aacagcgatc gcgtatttcg  1320
tctcgctcag gcgcaatcac gaatgaataa cggtttggtt gatgcgagtg attttgatga  1380
cgagcgtaat ggctggcctg ttgaacaagt ctggaaagaa atgcataaac ttttgccatt  1440
ctcaccggat tcagtcgtca ctcatggtga tttctcactt gataacctta tttttgacga  1500
ggggaaatta ataggttgta ttgatgttgg acgagtcgga atcgcagacc gataccagga  1560
tcttgccatc ctatggaact gcctcggtga gttttctcct tcattacaga aacggctttt  1620
tcaaaaatat ggtattgata atcctgatat gaataaattg cagtttcatt tgatgctcga  1680
tgagtttttc taagaatttg tgaatgaaag accccacctg taggtttggc aagctagctt  1740
aagtaacgcc attttgcaag gcatggaaaa atacataact gagaatagaa aagttcagat  1800
caaggtcagg aacagatgga acagctgaat atgggccaaa caggatatct gtggtaagca  1860
gttcctgccc cggctcaggg ccaagaacag atggaacagc tgaatatggg ccaaacagga  1920
tatctgtggt aagcagttcc tgccccggct cagggccaag aacagatggt ccccagatgc  1980
ggtccagccc tcagcagttt ctagagaacc atcagatgtt tccagggtgc cccaaggacc  2040
tgaaatgacc ctgtgcctta tttgaactaa ccaatcagtt cgcttctcgc ttctgttcgc  2100
gcgcttatgc tccccgagct caataaaaga gcccacaacc cctcactcgg ggcgccagtc  2160
ctccgattga ctgagtcgcc cgggtacccg tgtatccaat aaaccctctt gcagttgcat  2220
ccgacttgtg gtctcgctgt tccttgggag ggtctcctct gagtgattga ctacccgtca  2280
gcgggggtct ttcatttggg ggctcgtccg ggatcgggag acccctgccc agggaccacc  2340
gacccaccac cgggaggtaa gctggccagc aacttatctg tgtctgtccg attgtctagt  2400
gtctatgact gattttatgc gcctgcgtcg gtactagtta gctaactagc tctgtatctg  2460
gcggacccgt ggtggaactg acgagttcgg aacacccggc cgcaaccctg ggagacgtcc  2520
cagggacttc gggggccgtt tttgtggccc gacctgagtc caaaaatccc gatcgttttg  2580
gactctttgg tgcacccccc ttagaggagg gatatgtggt tctggtagga gacgagaacc  2640
taaaacagtt cccgcctccg tctgaatttt tgctttcggt ttgggaccga agccgcgccg  2700
cgcgtcttgt ctgctgcagc atcgttctgt gttgtctctg tctgactgtg tttctgtatt  2760
tgtctgagaa tatgggccag actgttacca ctcccttaag tttgacctta ggtcactgga  2820
aagatgtcga gcggatcgct cacaaccagt cggtagatgt caagaagaga cgttgggtta  2880
ccttctgctc tgcagaatgg ccaaccttta acgtcggatg gccgcgagac ggcaccttta  2940
accgagacct catcacccag gttaagatca aggtcttttc acctggcccg catggacacc  3000
cagaccaggt ccccctacatc gtgacctggg aagccttggc ttttgacccc cctccctggg  3060
tcaagccctt tgtacaccct aagcctccgc ctcctcttcc tccatccgcc ccgtctctcc  3120
cccttgaacc tcctcgttcg accccgcctc gatcctccct ttatccagcc ctcactcctt  3180
ctctaggcgc caaacctaaa cctcaagttc tttctgacag tggggggccg ctcatcgacc  3240
tacttacaga agaccccccg ccttataggg acccaagacc acccccttcc gacagggacg  3300
gaaatggtgg agaagcgacc cctgcgggag aggcaccgga cccctcccca atggcatctc  3360
gcctacgtgg gagacgggag ccccctgtgg ccgactccac tacctcgcag gcattccccc  3420
tccgcgcagg aggaaacgga cagcttcaat actggccgtt ctcctcttct gacctttaca  3480
actggaaaaa taataaccct tctttttctg aagatccagg taaactgaca gctctgatcg  3540
agtctgttct catcacccat cagcccacct gggacgactg tcagcagctg ttggggactc  3600
tgctgaccgg agaagaaaaa caacgggtgc tcttagaggc tagaaaggcg gtgcggggcg  3660
atgatgggcg ccccactcaa ctgcccaatg aagtcgatgc cgcttttccc ctcgagcgcc  3720
cagactggga ttacaccacc caggcaggta ggaaccacct agtccactat cgccagttgc  3780
tcctagcggg tctccaaaac gcgggcagaa gccccaccaa tttggccaag gtaaaaggaa  3840
taacacaagg gcccaatgag tctccctcgg ccttcctaga gagacttaag gaagcctatc  3900
```

-continued

```
gcaggtacac tccttatgac cctgaggacc cagggcaaga aactaatgtg tctatgtctt  3960
tcatttggca gtctgcccca gacattggga gaaagttaga gaggttagaa gatttaaaaa  4020
acaagacgct tggagatttg gttagagagg cagaaaagat ctttaataaa cgagaaaccc  4080
cggaagaaag agaggaacgt atcaggagag aaacagagga aaaagaagaa cgccgtagga  4140
cagaggatga gcagaaagag aaagaaagag atcgtaggag acatagagag atgagcaagc  4200
tattggccac tgtcgttagt ggacagaaac aggatagaca gggaggagaa cgaaggaggt  4260
cccaactcga tcgcgaccag tgtgcctact gcaaagaaaa ggggcactgg gctaaagatt  4320
gtcccaagaa accacgagga cctcggggac caagacccca gacctccctc ctgaccctag  4380
atgactaggg aggtcagggt caggagcccc cccctgaacc caggataacc ctcaaagtcg  4440
gggggcaacc cgtcaccttc ctggtagata ctggggccca acactccgtg ctgacccaaa  4500
atcctggacc cctaagtgat aagtctgcct gggtccaagg ggctactgga ggaaagcggt  4560
atcgctggac cacggatcgc aaagtacatc tagctaccgg taaggtcacc cactctttcc  4620
tccatgtacc agactgtccc tatcctctgt taggaagaga tttgctgact aaactaaaag  4680
cccaaatcca ctttgaggga tcaggagctc aggttatggg accaatgggg cagcccctgc  4740
aagtgttgac cctaaatata gaagatgagc atcggctaca tgagacctca aaagagccag  4800
atgtttctct agggtccaca tggctgtctg attttcctca ggcctgggcg gaaaccgggg  4860
gcatgggact ggcagttcgc caagctcctc tgatcatacc tctgaaagca acctctaccc  4920
ccgtgtccat aaaacaatac cccatgtcac aagaagccag actggggatc aagccccaca  4980
tacagagact gttggaccag ggaatactgg taccctgcca gtcccccctgg aacacgcccc  5040
tgctacccgt taagaaacca gggactaatg attataggcc tgtccaggat ctgagagaag  5100
tcaacaagcg ggtggaagac atccacccca ccgtgcccaa cccttacaac ctcttgagcg  5160
ggctcccacc gtcccaccag tggtacactg tgcttgattt aaaggatgcc tttttctgcc  5220
tgagactcca ccccaccagt cagcctctct tcgcctttga gtggagagat ccagagatgg  5280
gaatctcagg acaattgacc tggaccagac tcccacaggg tttcaaaaac agtcccaccc  5340
tgtttgatga ggcactgcac agagacctag cagacttccg gatccagcac ccagacttga  5400
tcctgctaca gtacgtggat gacttactgc tggccgccac ttctgagcta gactgccaac  5460
aaggtactcg ggccctgtta caaaccctag ggaacctcgg gtatcgggcc tcggccaaga  5520
aagcccaaat ttgccagaaa caggtcaagt atctggggta tcttctaaaa gagggtcaga  5580
gatggctgac tgaggccaga aaagagactg tgatggggca gcctactccg aagacccctc  5640
gacaactaag ggagttccta gggacggcag gcttctgtcg cctctggatc cctgggtttg  5700
cagaaatggc agccccttg taccctctca ccaaaacggg gactctgttt aattggggcc  5760
cagaccaaca aaaggcctat caagaaatca agcaagctct tctaactgcc ccagccctgg  5820
ggttgccaga tttgactaag ccctttgaac tctttgtcga cgagaagcag ggctacgcca  5880
aaggtgtcct aacgcaaaaa ctgggacctt ggcgtcggcc ggtggcctac ctgtccaaaa  5940
agctagaccc agtagcagct gggtggcccc cttgcctacg gatggtagca gccattgccg  6000
tactgacaaa ggatgcaggc aagctaacca tgggacagcc actagtcatt ctggcccccc  6060
atgcagtaga ggcactagtc aaacaacccc ccgaccgctg gctttccaac gcccggatga  6120
ctcactatca ggccttgctt ttggacacgg accgggtcca gttcggaccg gtggtagccc  6180
tgaacccggc tacgctgctc ccactgcctg aggaagggct gcaacacaac tgccttgata  6240
tcctggccga agcccacgga acccgacccg acctaacgga ccagccgctc ccagacgccg  6300
accacacctg gtacacggat ggaagcagtc tcttacaaga gggacagcgt aaggcgggag  6360
ctgcggtgac caccgagacc gaggtaatct gggctaaagc cctgccagcc gggacatccg  6420
ctcagcgggc tgaactgata gcactcaccc aggccctaaa gatggcagaa ggtaagaagc  6480
taaatgttta tactgatagc cgttatgctt ttgctactgc ccatatccat ggagaaatat  6540
acagaaggcg tgggttgctc acatcagaag gcaaagagat caaaaataaa gacgagatct  6600
tggccctact aaaagccctc tttctgccca aaagacttag cataatccat tgtccaggac  6660
atcaaaaggg acacagcgcc gaggctagag gcaaccggat ggctgaccaa gcggcccgaa  6720
aggcagccat cacagagact ccagacacct ctaccctcct catagaaaat tcatcaccct  6780
acacctcaga acattttcat tacacagtga ctgatataaa ggacctaacc aagttggggg  6840
ccatttatga taaaacaaag aagtattggg tctaccaagg aaaacctgtg atgcctgacc  6900
agtttacttt tgaattatta gactttcttc atcagctgac tcacctcagc ttctcaaaaa  6960
tgaaggctct cctagagaga agccacagtc cctactacat gctgaaccgg gatcgaacac  7020
tcaaaaatat cactgagacc tgcaaagctt gtgcacaagt caacgccagc aagtctgccg  7080
ttaaacaggg aactagggtc cgcgggcatc ggcccggcac tcattgggag atcgatttca  7140
ccgagataaa gcccggattg tatggctata aatatcttct agtttttata gataccttttt  7200
ctggctggat agaagccttc ccaaccaaga aagaaaccgc caaggtcgta accaagaagc  7260
tactagagga gatcttcccc aggttcggca tgcctcaggt attgggaact gacaatgggc  7320
ctgccttcgt ctccaaggtg agtcagacag tggccgatct gttggggatt gattggaaat  7380
tacattgtgc atacagaccc caaagctcag gccaggtaga aagaatgaat agaaccatca  7440
aggagacttt aactaaatta acgcttgcaa ctggctctag agactgggtg ctcctactcc  7500
ccttagccct gtaccgagcc cgcaacacgc cgggccccca tggcctcacc ccatatgaga  7560
tcttatatgg ggcacccccg ccccttgtaa acttccctga ccctgacatg acaagagtta  7620
ctaacagccc ctctctccaa gctcacttac aggctctcta cttagtccag cacgaagtct  7680
ggagacctct ggcggcagcc taccaagaac aactggaccg accggtggta cctcaccctt  7740
accgagtcgg cgacacagtg tgggtccgcc gacaccagac taagaaccta gaacctcgct  7800
ggaaaggacc ttacacagtc ctgctgacca cccccaccgc cctcaaagta gacggcatcg  7860
cagcttggat acacgccgcc cacgtgaagg ctgccgaccc cgggggtgga ccatcctcta  7920
gactgacatg gcgcgttcaa cgctctcaaa acccccttaaa aataaggtta acccgcgagg  7980
ccccctaatc cccttaattc ttctgatgct cagaggggtc agtaaacgaa ttcgggcaga  8040
gcgcacatcg cccgcagtcc ccgagaagtt gggggaggg gtcggcaatt gatccggtgc  8100
ctagagaagg tggcgcgggg taaactggga aagtgatgtc gtgtactggc tccgcctttt  8160
tcccgagggt gggggagaac cgtatataag tgcagtagtc gccgtgaacg ttctttttcg  8220
caacgggttt gccgccagaa cacaggcggc cgcatggtta ctgggggaat ggcatctaag  8280
tgggatcaga aaggtatgga catcgcttat gaagaggctg ctctcggcta caaagagggt  8340
ggagtgccta tcggagggtg cctgatcaac aacaaggacg gcagtgtgct ggggagggc  8400
cacaatatga ggttccaaaa aggctccgcc actctccacg ggaaattag taccctcgag  8460
aattgcggac gattggaagg gaaggtgtac aaggatacaa cactgtacac caccctgtca  8520
ccctgtgata tgtgcacagg cgccattatc atgtacggaa tccctagatg tgtcgtgggg  8580
gagaatgtaa acttcaaaag taagggggag aaatatctcc agacccgggg gcacgaagtc  8640
```

-continued

```
gtcgttgtgg acgatgaacg gtgtaagaag atcatgaagc agtttatcga tgagaggccc  8700
caggactggt tcgaagacat cggggaataa gtttaaacga attcataaaa taaaagattt  8760
tatttagtct ccagaaaaag gggggaatga aagaccccac ctgtaggttt ggcaagctag  8820
cttaagtaac gccattttgc aaggcatgga aaaatacata actgagaata gagaagttca  8880
gatcaaggtc aggaacagat ggaacagctg aatatgggcc aaacaggata tctgtggtaa  8940
gcagttcctg ccccggctca gggccaagaa cagatggaac agctgaatat gggccaaaca  9000
ggatatctgt ggtaagcagt tcctgccccg gctcagggcc aagaacagat ggtccccaga  9060
tgcggtccag ccctcagcag tttctagaga accatcagat gtttccaggg tgccccaagg  9120
acctgaaatg accctgtgcc ttatttgaac taaccaatca gttcgcttct cgcttctgtt  9180
cgcgcgcttc tgctccccga gctcaataaa agagcccaca acccctcact cggggcgcca  9240
gtcctccgat tgactgagtc gcccgggtac ccgtgtatcc aataaaccct cttgcagttg  9300
catccgactt gtggtctcgc tgttccttgg gagggtctcc tctgagtgat tgactacccg  9360
tcagcggggg tctttcattg ttacttaaag ttacattggc ttccttgaaa taaacatgga  9420
gtattcagaa tgtgtcataa atatttctaa ttttaagata gtatctccat tggctttcta  9480
ctttttcttt tattttttt tgtcctctgt cttccatttg ttgttgttgt tgtttgtttg  9540
tttgtttgtt ggttggttgg ttaatttttt tttaaagatc ctacactata gttcaagcta  9600
gactattagc tactctgtaa cccagggtga ccttgaagtc atgggtagcc tgctgtttta  9660
gccttcccac atctaagatt acaggtatga gctatcattt ttggtatatt gattgattga  9720
ttgattgatg tgtgtgtgtg tgattgtgtt tgtgtgtgtg actgtgaaaa tgtgtgtatg  9780
ggtgtgtgtg aatgtgtgta tgtatgtgtg tgtgtgagtg tgtgtgtgtg tgtgtgcatg  9840
tgtgtgtgtg tgactgtgtc tatgtgtatg actgtgtgtg tgtgtgtgtg tgtgtgtgtg  9900
tgtgtgtgtg tgtgtgtgtt gtgaaaaaat attctatggt agtgagagcc aacgctccgg  9960
ctcaggtgtc aggttggttt ttgagacaga gtctttcact tagcttgg              10008

SEQ ID NO: 33           moltype = DNA  length = 10108
FEATURE                 Location/Qualifiers
misc_feature            1..10108
                        note = sRRVe-TK vector
source                  1..10108
                        mol_type = other DNA
                        organism = synthetic construct
SEQUENCE: 33
aacgccattt tgcaaggcat ggaaaaatac ataactgaga atagaaaagt tcagatcaag  60
gtcaggaaca gatggaacag ctgaatatgg gccaaacagg atatctgtgg taagcagttc  120
ctgccccggc tcagggccaa gaacagatgg aacagctgaa tatgggccaa acaggatatc  180
tgtggtaagc agttcctgcc ccggctcagg gccaagaaca gatggtcccc agatgcggtc  240
cagccctcag cagtttctag agaaccatca gatgtttcca gggtgcccca aggacctgaa  300
atgaccctgt gccttatttg aactaaccaa tcagttcgct tctcgcttct gttcgcgcgc  360
ttatgctccc cgagctcaat aaaagagccc acaacccctc actcggggcg ccagtcctcc  420
gattgactga gtcgcccggg tacccgtgta tccaataaac cctcttgcag ttgcatccga  480
cttgtggtct cgctgttcct tgggagggtc tcctctgagt gattgactac ccgtcagcgg  540
gggtctttca tttgggggct cgtccgggat cgggagaccc ctgcccaggg accaccgacc  600
caccaccggg aggtaagctg gccagcaact tatctgtgtc tgtccgattg tctagtgtct  660
atgactgatt ttatgcgcct gcgtcggtac tagttagcta actagctctg tatctggcgg  720
acccgtggtg gaactgacga gttcggaaca cccggccgca accctgggag acgtcccagg  780
gacttcgggg gccgtttttg tggcccgacc tgagtcctaa aatcccgatc gtttaggact  840
ctttggtgca cccccctag aggagggata tgtggttctg gtaggagacg agaacctaaa  900
acagttcccg cctccgtctg aatttttgct ttcggtttgg gaccgaagcc gcgccgcgcg  960
tcttgtctgc tgcagcatcg ttctgtgttg tctctgtctg actgtgtttc tgtatttgtc  1020
tgaaaatatg ggcccgggct agcctgttac cactccctta agtttgacct taggtcactg  1080
gaaagatgtc gagcggatcg ctcacaacca gtcggtagat gtcaagaaga gacgttgggt  1140
taccttctgc tctgcagaat ggccaacctt taacgtcgga tggccgcgag acggcacctt  1200
taaccgagac ctcactaccc aggttaagat caaggtcttt tcacctggcc cgcatggaca  1260
cccagaccag gtggggtaca tcgtgacctg ggaagccttg gcttttgacc cccctccctg  1320
ggtcaagccc tttgtacacc ctaagcctcc gcctcctctt cctccatccg ccccgtctct  1380
ccccttgaa cctcctcgtt cgacccgcc tcgatcctcc ctttatccag ccctcactcc  1440
ttctctaggc gcccccatat ggccatatga gatcttatat ggggcacccc cgccccttgt  1500
aaacttccct gaccctgaca tgacaagagt tactaacagc cctctctctcc aagctcactt  1560
acaggctctc tacttagtcc agcacgaagt ctggagacct ctggcggcag cctaccaaga  1620
acaactggac cgaccggtgg tacctcaccc ttaccgagtc ggcgacacag tgtgggtccg  1680
ccgacaccag actaagaacc tagaacctcg ctggaaagga ccttacacag tcctgctgac  1740
cacccccacc gccctcaaag tagacggcat cgcagcttgg atacacgccg cccacgtgat  1800
ggcgcgttca acgctctcaa aacccctca agataagatt aaccccgtgga agcccttaat  1860
agtcatggga gtcctgttag gagtagggat ggcagagagc ccccatcagg tctttaatgt  1920
aacctggaga gtcaccaacc tgatgactgg gcgtaccgcc aatgccacct ccctcctggg  1980
aactgtacaa gatgccttcc caaaattata ttttgatcta tgtgatctgg tcggagagga  2040
gtgggaccct tcagaccagg aaccgtatgt cgggtatggc tgcaagtacc ccgcagggag  2100
acagcggacc cggacttttg acttttacgt gtgccctggg cataccgtaa agtcggggtg  2160
tgggggacca ggagagggct actgtggtaa atgggggtgt gaaaccaccg gacaggctta  2220
ctggaagccc acatcatcgt gggacctaat ctcccttaag cgcggtaaca cccccctggga  2280
cacgggatgc tctaaagttg cctgtggccc ctgctacgac ctctccaaag tatccaattc  2340
cttccaaggg gctactcgag gggcagatg caaccctcta gtcctagaat tcactgatgc  2400
aggaaaaaag gctaactggg acgggcccaa atcgtgggga ctgagactgt accggacagg  2460
aacagatcct attaccatgt tctccctgac ccggcaggtc cttaatgtgg gaccccgagt  2520
ccccataggg cccaacccag tattacccga ccaaagactc ccttcctcac caatagagat  2580
tgtaccggct ccacagccac ctagccccct caataccagt taccccctt ccactaccag  2640
tacaccctca acctcccta caagtccaag tgtcccacag ccacccccag gaactggaga  2700
tagactacta gctctagtca aaggagccta tcaggcgctt aacctcacca atcccgacaa  2760
gacccaagaa tgttggctgt gcttagtgtc gggacctcct tattacgaag gagtagcggt  2820
```

-continued

```
cgtgggcact tataccaatc attccaccgc tccggccaac tgtacggcca cttcccaaca  2880
taagcttacc ctatctgaag tgacaggaca gggcctatgc atgggggcag tacctaaaac  2940
tcaccaggcc ttatgtaaca ccacccaaag cgccggctca ggatcctact accttgcagc  3000
acccgccgga acaatgtggg cttgcagcac tggattgact ccctgcttgt ccaccacggt  3060
gctcaatcta accacagatt attgtgtatt agttgaactc tggcccagag taatttacca  3120
ctcccccgat tatatgtatg gtcagcttga acagcgtacc aaatataaaa gagagccagt  3180
atcattgacc ctggcccttc tactaggagg attaaccatg ggagggattg cagctggaat  3240
agggacgggg accactgcct taattaaaac ccagcagttt gagcagcttc atgccgctat  3300
ccagacagac ctcaacgaag tcgaaaagtc aattaccaac ctagaaaagt cactgacctc  3360
gttgtctgaa gtagtcctac agaaccgcag aggcctagat ttgctattcc taaaggaggg  3420
aggtctctgc gcagccctaa aagaagaatg ttgtttttat gcagaccaca cggggctagt  3480
gagagacagc atggccaaat taagagaaag gcttaatcag agacaaaaac tatttgagac  3540
aggccaagga tggttcgaag ggctgtttaa tagatccccc tggtttacca ccttaatctc  3600
caccatcatg ggacctctaa tagtactctt actgatctta ctctttggac cttgcattct  3660
caatcgatta gtccaatttg ttaaagacag gatatcagtg gtccaggctc tagttttgac  3720
tcaacaatat caccagctga agcctataga gtacgagcca tagcacgtga aggctgccga  3780
ccccgggggt ggacatcctc tagactgcca tggcgcggat ctcgacgttt aaacaacagg  3840
aaagttccat tggagccaag tacattgagt caatagggac tttccaatgg gttttgccca  3900
gtacataagg tcaatgggag gtaagccaat gggtttttcc cattactggc acgtatactg  3960
agtcattagg gactttccaa tgggttttgc ccagtacata aggtcaatag gggtgaatca  4020
acaggaaagt cccattggag ccaagtacac tgagtcaata gggactttcc attgggtttt  4080
gcccagtaca aaaggtcaat agggggtgag tcaatgggtt tttcccatta ttggcacgta  4140
cataaggtca ataggggtga gtcattgggt ttttccagcc aatttaatta aaacgccatg  4200
tactttccca ccattgacgt caatgggcta ttgaaactaa tgcaacgtga cctttaaacg  4260
gtactttccc atagctgatt aatgggaaag taccgttctc gagccaatac acgtcaatgg  4320
gaagtgaaag ggcagccaaa acgtaacacc gccccggttt tccctggaaa ttccatattg  4380
gcacgcattc tattggctga gctgcgttct acgtgggtat aagaggcgcg accagcgtcg  4440
gtaccgtcgc agtcttcggt ctgaccaccg tagaacgcag aactctagaa ctagtggatc  4500
cgttaacatt tgcggccgct ttagtttatg gtgacatggc ttcgtacccc tgccatcaac  4560
acgcgtctgc gttcgaccag gctgcgcgtt ctcgcggcca tagcaaccga cgtacggcgt  4620
tgcgccctcg ccggcagcaa gaagccacgg aagtccgcct ggagcagaaa atgcccacgc  4680
tactgcgggt ttatatagac ggtcctcacg ggatggggaa aaccaccacc acgcaactgc  4740
tggtggccct gggttcgcgc gacgatatcg tctacgtacc cgagccgatg acttactggc  4800
aggtgctggg ggcttccgag acaatcgcga acatctacac cacacaacac cgcctcgacc  4860
agggtgagat atcggccggg gacgcggcgg tggtaatgac aagcgcccag ataacaatgg  4920
gcatgcctta tgccgtgacc gacgccgttc tggctcctca tatcgggggg gaggctggga  4980
gctcacatgc cccgcccccg gccctcaccc tcatcttcga ccgccatccc atcgccgccc  5040
tcctgtgcta cccggccgcg cgatacctta tgggcagcat gaccccccag gccgtgctgg  5100
cgttcgtggc cctcatcccg ccgaccttgc ccggcacaaa catcgtgttg gggcccttc   5160
cggaggacag acacatcgac cgcctggcca aacgccagcg ccccggcgag cggcttgacc  5220
tggctatgct ggccgcgatt cgccgcgttt acgggctgct tgccaatacg gtgcggtatc  5280
tgcagggcgg cgggtcgtgg cgggaggatt ggggacagct ttcggggacg gccgtgccgc  5340
cccagggtgc cgagccccag agcaacgcgg gcccacgacc ccatatcggg gacacgttat  5400
ttaccctgtt tcgggccccc gagttgctgg cccccaacgg cgacctgtac aacgtgtttg  5460
cctgggcctt ggacgtcttg gccaaacgcc tccgtcccat gcacgtcttt atcctggatt  5520
acgaccaatc gcccgccggc tgccgggacg ccctgctgca acttacctcc gggatggtcc  5580
agacccacgt caccaccccc ggctccatac cgacgatctg cgacctggcg cgcacgtttg  5640
cccgggagat gggggaggct aactgatcga gaaacgcgtc gacccatcga acatcgatgg  5700
taccagatcc gataaaataa aagattttat ttagtctcca gaaaaagggg ggaatgaaag  5760
accccacctg taggtttggc aagctagctt aagtaacgcc attttgcaag gcatggaaaa  5820
atacataact gagaatagag aagttcagat caaggtcagg aacagatgga acagctgaat  5880
atgggccaaa caggatatct gtggtaagca gttcctgccc cggctcaggg ccaagaacag  5940
atggaacagc tgaatatggg ccaaacagga tatctgtggt aagcagttcc tgccccggct  6000
cagggccaag aacagatggt ccccagatgc ggtccagccc tcagcagttt ctagagaacc  6060
atcagatgtt tccagggtgc cccaaggacc tgaaatgacc ctgtgcctta tttgaactaa  6120
ccaatcagtt cgcttctcgc ttctgttcgc gcgcttctgc tccccgagct caataaaaga  6180
gcccacaacc cctcactcgg ggcgccagtc ctccgattga ctgagtcgcc cgggtacccg  6240
tgtatccaat aaaccctctt gcagttgcat ccgacttgtg gtctcgctgt tccttgggag  6300
ggtctcctct gagtgattga ctacccgtca gcgggggtct ttcacacatg cagcatgtat  6360
caaaattaat ttggtttttt ttcttaagta tttacattaa atggccatag tacttaaagt  6420
tacattggct tccttgaaat aaacatggag tattcagaat gtgtcataaa tatttctaat  6480
tttaagatag tatctccatt ggctttctac tttttctttt attttttttt gtcctctgtc  6540
ttccatttgt tgttgttgtt gtttgtttgt ttgtttgttg gttggttggt taattttttt  6600
ttaaagatcc tacactatag ttcaagctag actattagct actctgtaac ccagggtgac  6660
cttgaagtca tgggtagcct gctgttttag ccttcccaca tctaagatta caggtatgag  6720
ctatcatttt tggtatatga ttgattgatt gattgatgtg tgtgtgtgtg attgtgtttg  6780
tgtgtgtgac tgtgaaaatg tgtgtatggg tgtgtgtgaa tgtgtgtatg tatgtgtgtg  6840
tgtgagtgtg tgtgtgtgtg tgtgcatgtg tgtgtgtgtg actgtgtcta tgtgtatgac  6900
tgtgtgtgtg tgtgtgtgtg tgtgtgtgtg tgtgtgtgtg tgtgtgttgt gaaaaaatat  6960
tctatggtag tgagagccaa cgctccggct caggtgtcag gttggttttt gagacagagt  7020
ctttcactta gcttggaatt cactggccgt cgttttacaa cgtcgtgact gggaaaaccc  7080
tggcgttacc caacttaatc gccttgcagc acatccccct ttcgccagct ggcgtaatag  7140
cgaagaggcc cgcaccgatc gcccttccca acagttgcgc agcctgaatg gcgaatggcg  7200
cctgatgcgg tattttctcc ttacgcatct gtgcggtatt tcacaccgca tatggtgcac  7260
tctcagtaca atctgctctg atgccgcata gttaagccag ccccgacacc cgccaacacc  7320
cgctgacgcg ccctgacggg cttgtctgct cccggcatcc gcttacagac aagctgtgac  7380
cgtctccggg agctgcatgt gtcagaggtt ttcaccgtca tcaccgaaac gcgcgagacg  7440
aaagggcctc gtgatacgcc tatttttata ggttaatgtc atgataataa tggtttctta  7500
gacgtcaggt ggcacttttc ggggaaatgt gcgcggaacc cctatttgtt tatttttcta  7560
```

```
aatacattca aatatgtatc cgctcatgag acaataaccc tgataaatgc ttcaataata  7620
ttgaaaaagg aagagtatga gtattcaaca tttccgtgtc gcccttattc cctttttttgc  7680
ggcattttgc cttcctgttt ttgctcaccc agaaacgctg gtgaaagtaa aagatgctga  7740
agatcagttg ggtgcacgag tgggttacat cgaactggat ctcaacagcg gtaagatcct  7800
tgagagtttt cgccccgaag aacgttttcc aatgatgagc acttttaaag ttctgctatg  7860
tggcgcggta ttatcccgta ttgacgccgg gcaagagcaa ctcggtcgcc gcatacacta  7920
ttctcagaat gacttggttg agtactcacc agtcacagaa aagcatctta cggatggcat  7980
gacagtaaga gaattatgca gtgctgccat aaccatgagt gataacactg cggccaactt  8040
acttctgaca acgatcggag gaccgaagga gctaaccgct tttttgcaca acatggggga  8100
tcatgtaact cgccttgatc gttgggaacc ggagctgaat gaagccatac caaacgacga  8160
gcgtgacacc acgatgcctg tagcaatggc aacaacgttg cgcaaactat taactggcga  8220
actacttact ctagcttccc ggcaacaatt aatagactgg atggaggcgg ataaagttgc  8280
aggaccactt ctgcgctcgg cccttccggc tggctggttt attgctgata aatctggagc  8340
cggtgagcgt gggtctcgcg gtatcattgc agcactgggg ccagatggta agccctcccg  8400
tatcgtagtt atctacacga cggggagtca ggcaactatg gatgaacgaa atagacagat  8460
cgctgagata ggtgcctcac tgattaagca ttggtaactg tcagaccaag tttactcata  8520
tatactttag attgatttaa aacttcattt ttaatttaaa aggatctagg tgaagatcct  8580
ttttgataat ctcatgacca aaatccctta acgtgagttt tcgttccact gagcgtcaga  8640
ccccgtagaa aagatcaaag gatcttcttg agatcctttt tttctgcgcg taatctgctg  8700
cttgcaaaca aaaaaaccac cgctaccagc ggtggtttgt ttgccggatc aagagctacc  8760
aactcttttt ccgaaggtaa ctggcttcag cagagcgcag ataccaaata ctgttcttct  8820
agtgtagccg tagttaggcc accacttcaa gaactctgta gcaccgccta catacctcgc  8880
tctgctaatc ctgttaccag tggctgctgc cagtggcgat aagtcgtgtc ttaccgggtt  8940
ggactcaaga cgatagttac cggataaggc gcagcggtcg ggctgaacgg ggggttcgtg  9000
cacacagccc agcttggagc gaacgaccta caccgaactg agatacctac agcgtgagct  9060
atgagaaagc gccacgcttc ccgaagggag aaaggcggac aggtatccgg taagcggcag  9120
ggtcggaaca ggagagcgca cgagggagct tccaggggga aacgcctggt atctttatag  9180
tcctgtcggg tttcgccacc tctgacttga gcgtcgattt ttgtgatgct cgtcaggggg  9240
gcggagccta tggaaaaacg ccagcaacgc ggccttttta cggttcctgg ccttttgctg  9300
gccttttgct cacatgttct ttcctgcgtt atcccctgat tctgtggata accgtattac  9360
cgcctttgag tgagctgata ccgctcgccg cagccgaacg accgagcgca gcgagtcagt  9420
gagcgaggaa gcggaagagc gcccaatacg caaaccgcct ctccccgcgc gttggccgat  9480
tcattaatgc agctggcacg acaggtttcc cgactggaaa gcgggcagtg agcgcaacgc  9540
aattaatgtg agttagctca ctcattaggc accccaggct ttacacttta tgcttccggc  9600
tcgtatgttg tgtggaattg tgagcggata acaatttcac acaggaaaca gctatgacca  9660
tgattacgcc aagctttgct cctaggagtt tcctaatact tcccaaactc aaatatataa  9720
agcatttgac ttgttctatg ccctaggggg cgggggggaag ctaagccagc tttttttaac  9780
atttaaaatg ttaattccat tttaaatgca cagatgtttt tatttcataa gggtttcaat  9840
gtgcatgaat gctgcaatat tcctgttacc aaagctagta taaataaaaa tagataaacg  9900
tggaaattac ttagagtttc tgtcattaac gtttccttcc tcagttgaca acataaatgc  9960
gctgctgagc aagccagttt gcatctgtca ggatcaattt cccattatgc cagtcatatt  10020
aattactagt caattagttg atttttattt ttgacatata catgtgaatg aaagacccca  10080
cctgtaggtt tggcaagcta gcttaagt                                    10108
```

```
SEQ ID NO: 34           moltype = DNA  length = 9901
FEATURE                 Location/Qualifiers
misc_feature            1..9901
                        note = sRRVe-F1-TK vector
source                  1..9901
                        mol_type = other DNA
                        organism = synthetic construct
SEQUENCE: 34
aacgccattt tgcaaggcat ggaaaaatac ataactgaga atagaaaagt tcagatcaag  60
gtcaggaaca gatggaacag ctgaatatgg gccaaacagg atatctgtgg taagcagttc  120
ctgccccggc tcagggccaa gaacagatgg aacagctgaa tatgggccaa acaggatatc  180
tgtggtaagc agttcctgcc ccggctcagg gccaagaaca gatggtcccc agatgcggtc  240
cagccctcag cagtttctag agaaccatca gatgtttcca gggtgcccca aggacctgaa  300
atgaccctgt gccttatttg aactaaccaa tcagttcgct tctcgcttct gttcgcgcgc  360
ttatgctccc cgagctcaat aaaagagccc acaacccctc actcggggcg ccagtcctcc  420
gattgactga gtcgcccggg tacccgtgta tccaataaac cctcttgcag ttgcatccga  480
cttgtggtct cgctgttcct tgggagggtc tcctctgagt gattgactac ccgtcagcgg  540
gggtctttca tttgggggct cgtccgggat cgggagaccc ctgcccaggg accaccgacc  600
caccaccggg aggtaagctg gccagcaact tatctgtgtc tgtccgattg tctagtgtct  660
atgactgatt ttatgcgcct gcgtcggtac tagttagcta actagctctg tatctggcgg  720
acccgtggtg gaactgacga gttcggaaca cccggccgca accctgggag acgtcccagg  780
gacttcgggg gccgtttttg tggcccgacc tgagtcctaa aatcccgatc gtttaggact  840
ctttggtgca cccccctttag aggagggata tgtggttctg gtaggagacg agaacctaaa  900
acagttcccg cctccgtctg aatttttgct ttcggtttgg gaccgaagcc gcgccgcgcg  960
tcttgtctgc tgcagcatcg ttctgtgttg tctctgtctg actgtgtttc tgtatttgtc  1020
tgaaaatatg ggcccgggct agcctgttac cactccctta agtttgacct taggtcactg  1080
gaaagatgtc gagcggatcg ctcacaacca gtcggtagat gtcaagaaga gacgttgggt  1140
taccttctgc tctgcagaat ggccaacctt taacgtcgga tggccgcgag acggcacctt  1200
taaccgagac ctcactaccc aggttaagat caaggtcttt tcacctggcc cgcatggaca  1260
cccagaccag gtggggtaca tcgtgacctg ggaagccttg gcttttgacc cccctccctg  1320
ggtcaagccc tttgtacacc ctaagcctcc gcctcctctt cctccatccg ccccgtctct  1380
ccccccttgaa cctcctcgtt cgaccccgcc tcgatcctcc ctttatccag ccctcactcc  1440
ttctctaggc gcccccatat ggccatatga gatcttatat ggggcacccc cgccccttgt  1500
aaacttccct gaccctgaca tgacaagagt tactaacagc ccctctctcc aagctcactt  1560
acaggctctc tacttagtcc agcacgaagt ctggagacct ctggcggcag cctaccaaga  1620
```

-continued

```
acaactggac cgaccggtgg tacctcaccc ttaccgagtc ggcgacacag tgtgggtccg  1680
ccgacaccag actaagaacc tagaacctcg ctggaaagga ccttacacag tcctgctgac  1740
cacccccacc gccctcaaag tagacggcat cgcagcttgg atacacgccg cccacgtgat  1800
ggcgcgttca acgctctcaa aaccccctca agataagatt aacccgtgga agcccttaat  1860
agtcatggga gtcctgttag gagtagggat ggcagagagc cccccatcagg tctttaatgt  1920
aacctggaga gtcaccaacc tgatgactgg gcgtaccgcc aatgccacct ccctcctggg  1980
aactgtacaa gatgccttcc caaaattata ttttgatcta tgtgatctgg tcggagagga  2040
gtgggaccct tcagaccagg aaccgtatgt cgggtatggc tgcaagtacc ccgcagggag  2100
acagcggacc cggacttttg acttttacgt gtgccctggg cataccgtaa agtcggggtg  2160
tgggggacca ggagagggct actgtggtaa atgggggtgt gaaaccaccg gacaggctta  2220
ctggaagccc acatcatcgt gggacctaat ctcccttaag cgcggtaaca ccccctggga  2280
cacgggatgc tctaaagttg cctgtggccc ctgctacgac ctctccaaag tatccaattc  2340
cttccaaggg gctactcgag ggggcagatg caaccctcta gtcctagaat tcactgatgc  2400
aggaaaaaag gctaactggg acgggcccaa atcgtgggga ctgagactgt accggacagg  2460
aacagatcct attaccatgt tctccctgac ccggcaggtc cttaatgtgg gaccccgagt  2520
ccccataggg cccaacccag tattacccga ccaaagactc ccttcctcac caatagagat  2580
tgtaccggct ccacagccac ctagcccccct caataccagt tacccccctt ccactaccag  2640
tacaccctca acctccccta caagtccaag tgtcccacag ccacccccag gaactggaga  2700
tagactacta gctctagtca aaggagccta tcaggcgctt aacctcacca atcccgacaa  2760
gacccaagaa tgttggctgt gcttagtgtc gggacctcct tattacgaag gagtagcggt  2820
cgtgggcact tataccaatc attccaccgc tccggccaac tgtacggcca cttcccaaca  2880
taagcttacc ctatctgaag tgacaggaca gggcctatgc atgggggcag tacctaaaac  2940
tcaccaggcc ttatgtaaca ccacccaaag cgccggctca ggatcctact accttgcagc  3000
acccgccgga acaatgtggg cttgcagcac tggattgact ccctgcttgt ccaccacggt  3060
gctcaatcta accacagatt attgtgtatt agttgaactc tggcccagag taatttacca  3120
ctcccccgat tatatgtatg gtcagcttga acagcgtacc aaatataaaa gagagccagt  3180
atcattgacc ctggcccttc tactaggagg attaaccatg ggagggattg cagctggaat  3240
agggacgggg accactgcct taattaaaac ccagcagttt gagcagcttc atgccgctat  3300
ccagacagac ctcaacgaag tcgaaaagtc aattaccaac ctagaaaagt cactgacctc  3360
gttgtctgaa gtagtcctac agaaccgcag aggcctagat ttgctattcc taaaggaggg  3420
aggtctctgc gcagccctaa aagaagaatg ttgtttttat gcagaccaca cggggctagt  3480
gagagacagc atggccaaat taagagaaag gcttaatcag agacaaaaac tatttgagac  3540
aggccaagga tggttcgaag ggctgtttaa tagatccccc tggtttacca ccttaatctc  3600
caccatcatg ggacctctaa tagtactctt actgatctta ctctttggac cttgcattct  3660
caatcgatta gtccaatttg ttaaagacag gatatcagtg gtccaggctc tagttttgac  3720
tcaacaatat caccagctga agcctataga gtacgagcca tagcacgtga aggctgccga  3780
ccccggggt ggacatcctc tagactgcca tggcgcggat ctcgacgttt aaacgggtga  3840
atcaacagga aagtcccatt ggagccaagt acactgagtc aatagggact ttccattggg  3900
ttttgcccag tacaaaaggt caatagggg tgagtcaatg ggtttttccc attattggca  3960
cgtacataag gtcaataggg gtgagtcatt gggtttttcc agccaattta attaaaacgc  4020
catgtacttt cccaccattg acgtcaatgg gctattgaaa ctaatgcaac gtgaccttta  4080
aacggtactt tcccatagct gattaatggg aaagtaccgt tctcgagcca atacacgtca  4140
atgggaagtg aaagggcagc caaaacgtaa caccgccccg gttttccctg gaaattccat  4200
attggcacgc attctattgg ctgagctgcg ttcacgtggg tataagaggc gcgaccagcg  4260
tcggtaccgt cgcagtcttc ggtctgacca ccgtagaacg cagagcggcc gctttagttt  4320
atggtgacat ggcttcgtac ccctgccatc aacacgcgtc tgcgttcgac caggctgcgc  4380
gttctcgcgg ccatagcaac cgacgtacgg cgttgcgccc tcgccggcag caagaagcca  4440
cggaagtccg cctggagcag aaaatgccca cgctactgcg ggtttatata gacggtcctc  4500
acgggatggg gaaaaccacc accacgcaac tgctggtggc cctgggttcg cgcgacgata  4560
tcgtctacgt acccgagccg atgacttact ggcaggtgct gggggcttcc gagacaatcg  4620
cgaacatcta caccacacaa caccgcctcg accagggtga gatatcggcc ggggacgcgg  4680
cggtggtaat gacaagcgcc cagataacaa tgggcatgcc ttatgccgtg accgacgccg  4740
ttctggctcc tcatatcggg ggggaggctg ggagctcaca tgccccgccc ccggccctca  4800
ccctcatctt cgaccgccat cccatcgccg ccctcctgtg ctacccggcc gcgcgatacc  4860
ttatgggcag catgaccccc caggccgtgc tggcgttcgt ggccctcatc ccgccgacct  4920
tgcccggcac aaacatcgtg ttgggggccc ttccggagga cagacacatc gaccgcctgg  4980
ccaaacgcca gcgccccggc gagcggcttg acctggctat gctggccgcg attcgccgcg  5040
tttacgggct gcttgccaat acggtgcggt atctgcaggg cggcgggtcg tggcgggagg  5100
attggggaca gctttcgggg acggccgtgc cgccccaggg tgccgagccc cagagcaacg  5160
cgggcccacg accccatatc ggggacacgt tatttaccct gtttcgggcc cccgagttgc  5220
tggcccccaa cggcgacctg tacaacgtgt ttgcctgggc cttggacgtc ttggccaaac  5280
gcctccgtcc catgcacgtc tttatcctgg attacgacca atcgcccgcc ggctgccggg  5340
acgccctgct gcaacttacc tccgggatgg tccagaccca cgtcaccacc cccggctcca  5400
taccgacgat ctgcgacctg gcgcgcacgt ttgcccggga gatgggggag gctaactgat  5460
cgagaaacgc gtcgacccat cgaacatcga tggtaccaga tccgataaaa taaaagattt  5520
tatttagtct ccagaaaaag gggggaatga aagaccccac ctgtaggttt ggcaagctag  5580
cttaagtaac gccattttgc aaggcatgga aaaatacata actgagaata gagaagttca  5640
gatcaaggtc aggaacagat ggaacagctg aatatgggcc aaacaggata tctgtggtaa  5700
gcagttcctg ccccggctca gggccaagaa cagatggaac agctgaatat gggccaaaca  5760
ggatatctgt ggtaagcagt tcctgccccg gctcagggcc aagaacagat ggtccccaga  5820
tgcggtccag ccctcagcag tttctagaga accatcagat gtttccaggg tgccccaagg  5880
acctgaaatg accctgtgcc ttatttgaac taaccaatca gttcgcttct cgcttctgtt  5940
cgcgcgcttc tgctccccga gctcaataaa agagcccaca acccctcact cggggcgcca  6000
gtcctccgat tgactgagtc gcccgggtac ccgtgtatcc aataaaccct cttgcagttg  6060
catccgactt gtggtctcgc tgttccttgg gagggtctcc tctgagtgat tgactacccg  6120
tcagcggggg tctttcacac atgcagcatg tatcaaaatt aatttggttt tttttcttaa  6180
gtatttacat taaatggcca tagtacttaa agttacattg gcttccttga aataaacatg  6240
gagtattcag aatgtgtcat aaatatttct aattttaaga tagtatctcc attggctttc  6300
tactttttct tttatttttt tttgtcctct gtcttccatt tgttgttgtt gttgtttgtt  6360
```

-continued

```
tgtttgtttg ttggttggtt ggttaatttt tttttaaaga tcctacacta tagttcaagc  6420
tagactatta gctactctgt aacccagggt gaccttgaag tcatgggtag cctgctgttt  6480
tagccttccc acatctaaga ttacaggtat gagctatcat ttttggtata tgattgattg  6540
attgattgat gtgtgtgtgt gtgattgtgt ttgtgtgtgt gactgtgaaa atgtgtgtat  6600
gggtgtgtgt gaatgtgtgt atgtatgtgt gtgtgtgagt gtgtgtgtgt gtgtgtgcat  6660
gtgtgtgtgt gtgactgtgt ctatgtgtat gactgtgtgt gtgtgtgtgt gtgtgtgtgt  6720
gtgtgtgtgt gtgtgtgtgt tgtgaaaaaa tattctatgg tagtgagagc caacgctccg  6780
gctcaggtgt caggttggtt tttgagacag agtctttcac ttagcttgga attcactggc  6840
cgtcgtttta caacgtcgtg actgggaaaa ccctggcgtt acccaactta atcgccttgc  6900
agcacatccc cctttcgcca gctggcgtaa tagcgaagag gcccgcaccg atcgcccttc  6960
ccaacagttg cgcagcctga atggcgaatg gcgcctgatg cggtattttc tccttacgca  7020
tctgtgcggt atttcacacc gcatatggtg cactctcagt acaatctgct ctgatgccgc  7080
atagttaagc cagccccgac acccgccaac acccgctgac gcgccctgac gggcttgtct  7140
gctcccggca tccgcttaca gacaagctgt gaccgtctcc gggagctgca tgtgtcagag  7200
gttttcaccg tcatcaccga aacgcgcgag acgaaagggc ctcgtgatac gcctattttt  7260
ataggttaat gtcatgataa taatggtttc ttagacgtca ggtggcactt ttcggggaaa  7320
tgtgcgcgga acccctattt gtttattttt ctaaatacat tcaaatatgt atccgctcat  7380
gagacaataa ccctgataaa tgcttcaata atattgaaaa aggaagagta tgagtattca  7440
acatttccgt gtcgccctta ttcccttttt tgcggcattt tgccttcctg tttttgctca  7500
cccagaaacg ctggtgaaag taaaagatgc tgaagatcag ttgggtgcac gagtgggtta  7560
catcgaactg gatctcaaca gcggtaagat ccttgagagt tttcgccccg aagaacgttt  7620
tccaatgatg agcactttta aagttctgct atgtggcgcg gtattatccc gtattgacgc  7680
cgggcaagag caactcggtc gccgcataca ctattctcag aatgacttgg ttgagtactc  7740
accagtcaca gaaaagcatc ttacggatgg catgacagta agagaattat gcagtgctgc  7800
cataaccatg agtgataaca ctgcggccaa cttacttctg acaacgatcg gaggaccgaa  7860
ggagctaacc gcttttttgc acaacatggg ggatcatgta actcgccttg atcgttggga  7920
accggagctg aatgaagcca taccaaacga cgagcgtgac accacgatgc ctgtagcaat  7980
ggcaacaacg ttgcgcaaac tattaactgg cgaactactt actctagctt cccggcaaca  8040
attaatagac tggatggagg cggataaagt tgcaggacca cttctgcgct cggcccttcc  8100
ggctggctgg tttattgctg ataaatctgg agccggtgag cgtgggtctc gcggtatcat  8160
tgcagcactg gggccagatg gtaagccctc ccgtatcgta gttatctaca cgacggggag  8220
tcaggcaact atggatgaac gaaatagaca gatcgctgag ataggtgcct cactgattaa  8280
gcattggtaa ctgtcagacc aagtttactc atatatactt tagattgatt taaaacttca  8340
tttttaattt aaaaggatct aggtgaagat cctttttgat aatctcatga ccaaaatccc  8400
ttaacgtgag ttttcgttcc actgagcgtc agaccccgta gaaaagatca aaggatcttc  8460
ttgagatcct ttttttctgc gcgtaatctg ctgcttgcaa acaaaaaaac caccgctacc  8520
agcggtggtt tgtttgccgg atcaagagct accaactctt tttccgaagg taactggctt  8580
cagcagagcg cagataccaa atactgttct tctagtgtag ccgtagttag gccaccactt  8640
caagaactct gtagcaccgc ctacatacct cgctctgcta atcctgttac cagtggctgc  8700
tgccagtggc gataagtcgt gtcttaccgg gttggactca agacgatagt taccggataa  8760
ggcgcagcgg tcgggctgaa cggggggttc gtgcacacag cccagcttgg agcgaacgac  8820
ctacaccgaa ctgagatacc tacagcgtga gctatgagaa agcgccacgc ttcccgaagg  8880
gagaaaggcg gacaggtatc cggtaagcgg cagggtcgga acaggagagc gcacgaggga  8940
gcttccaggg ggaaacgcct ggtatcttta tagtcctgtc gggtttcgcc acctctgact  9000
tgagcgtcga tttttgtgat gctcgtcagg ggggcggagc ctatggaaaa acgccagcaa  9060
cgcggccttt ttacggttcc tggccttttg ctggcctttt gctcacatgt tctttcctgc  9120
gttatcccct gattctgtgg ataaccgtat taccgccttt gagtgagctg ataccgctcg  9180
ccgcagccga acgaccgagc gcagcgagtc agtgagcgag gaagcggaag agcgcccaat  9240
acgcaaaccg cctctccccg cgcgttggcc gattcattaa tgcagctggc acgacaggtt  9300
tcccgactgg aaagcgggca gtgagcgcaa cgcaattaat gtgagttagc tcactcatta  9360
ggcaccccag gctttacact ttatgcttcc ggctcgtatg ttgtgtggaa ttgtgagcgg  9420
ataacaattt cacacaggaa acagctatga ccatgattac gccaagcttt gctcctagga  9480
gtttcctaat acttcccaaa ctcaaatata taaagcattt gacttgttct atgccctagg  9540
gggcgggggg aagctaagcc agcttttttt aacatttaaa atgttaattc cattttaaat  9600
gcacagatgt ttttatttca taagggtttc aatgtgcatg aatgctgcaa tattcctgtt  9660
accaaagcta gtataaataa aaatagataa acgtggaaat tacttagagt ttctgtcatt  9720
aacgtttcct tcctcagttg acaacataaa tgcgctgctg agcaagccag tttgcatctg  9780
tcaggatcaa tttcccatta tgccagtcat attaattact agtcaattag ttgattttta  9840
tttttgacat atacatgtga atgaaagacc ccacctgtag gtttggcaag ctagcttaag  9900
t                                                                  9901

SEQ ID NO: 35          moltype = DNA  length = 9768
FEATURE                Location/Qualifiers
misc_feature           1..9768
                       note = sRRVe-F2-TK vector
source                 1..9768
                       mol_type = other DNA
                       organism = synthetic construct
SEQUENCE: 35
aacgccattt tgcaaggcat ggaaaaatac ataactgaga atagaaaagt tcagatcaag  60
gtcaggaaca gatggaacag ctgaatatgg gccaaacagg atatctgtgg taagcagttc  120
ctgccccggc tcagggccaa gaacagatgg aacagctgaa tatgggccaa acaggatatc  180
tgtggtaagc agttcctgcc ccggctcagg gccaagaaca gatggtcccc agatgcggtc  240
cagccctcag cagtttctag agaaccatca gatgtttcca gggtgcccca aggacctgaa  300
atgaccctgt gccttatttg aactaaccaa tcagttcgct tctcgcttct gttcgcgcgc  360
ttatgctccc cgagctcaat aaaagagccc acaacccctc actcggggcg ccagtcctcc  420
gattgactga gtcgcccggg tacccgtgta tccaataaac cctcttgcag ttgcatccga  480
cttgtggtct cgctgttcct tgggagggtc tcctctgagt gattgactac ccgtcagcgg  540
gggtctttca tttgggggct cgtccgggat cgggagaccc ctgcccaggg accaccgacc  600
```

-continued

```
caccaccggg aggtaagctg gccagcaact tatctgtgtc tgtccgattg tctagtgtct  660
atgactgatt ttatgcgcct gcgtcggtac tagttagcta actagctctg tatctggcgg  720
acccgtggtg gaactgacga gttcggaaca cccggccgca accctgggag acgtcccagg  780
gacttcgggg gccgtttttg tggcccgacc tgagtcctaa aatcccgatc gtttaggact  840
ctttggtgca cccccccttag aggagggata tgtggttctg gtaggagacg agaacctaaa  900
acagttcccg cctccgtctg aatttttgct ttcggtttgg gaccgaagcc gcgccgcgcg  960
tcttgtctgc tgcagcatcg ttctgtgttg tctctgtctg actgtgtttc tgtatttgtc  1020
tgaaaatatg ggcccgggct agcctgttac cactccctta agtttgacct taggtcactg  1080
gaaagatgtc gagcggatcg ctcacaacca gtcggtagat gtcaagaaga gacgttgggt  1140
taccttctgc tctgcagaat ggccaacctt taacgtcgga tggccgcgag acggcacctt  1200
taaccgagac ctcactaccc aggttaagat caaggtcttt tcacctggcc cgcatggaca  1260
cccagaccag gtggggtaca tcgtgacctg ggaagccttg gcttttgacc cccctccctg  1320
ggtcaagccc tttgtacacc ctaagcctcc gcctcctctt cctccatccg ccccgtctct  1380
ccccccttgaa cctcctcgtt cgaccccgcc tcgatcctcc ctttatccag ccctcactcc  1440
ttctctaggc gcccccatat ggccatatga gatcttatat ggggcacccc cgccccttgt  1500
aaacttccct gaccctgaca tgacaagagt tactaacagc ccctctctcc aagctcactt  1560
acaggctctc tacttagtcc agcacgaagt ctggagacct ctggcggcag cctaccaaga  1620
acaactggac cgaccggtgg tacctcaccc ttaccgagtc ggcgacacag tgtgggtccg  1680
ccgacaccag actaagaacc tagaacctcg ctggaaagga ccttacacag tcctgctgac  1740
caccccccacc gccctcaaag tagacggcat cgcagcttgg atacacgccg cccacgtgat  1800
ggcgcgttca acgctctcaa aacccccctca agataagatt aaccccgtgga agcccttaat  1860
agtcatggga gtcctgttag gagtagggat ggcagagagc cccccatcagg tctttaatgt  1920
aacctggaga gtcaccaacc tgatgactgg gcgtaccgcc aatgccacct ccctcctggg  1980
aactgtacaa gatgccttcc caaaattata ttttgatcta tgtgatctgg tcggagagga  2040
gtgggaccct tcagaccagg aaccgtatgt cgggtatggc tgcaagtacc ccgcagggag  2100
acagcggacc cggacttttg acttttacgt gtgccctggg cataccgtaa agtcggggtg  2160
tgggggacca ggagagggct actgtggtaa atggggggtgt gaaaccaccg gacaggctta  2220
ctggaagccc acatcatcgt gggacctaat ctcccttaag cgcggtaaca cccccctggga  2280
cacgggatgc tctaaagttg cctgtggccc ctgctacgac ctctccaaag tatccaattc  2340
cttccaaggg gctactcgag gggcagatg caaccctcta gtcctagaat tcactgatgc  2400
aggaaaaaag gctaactggg acgggcccaa atcgtgggga ctgagactgt accggacagg  2460
aacagatcct attaccatgt tctccctgac ccggcaggtc cttaatgtgg gaccccgagt  2520
ccccataggg cccaacccag tattacccga ccaaagactc ccttcctcac caatagagat  2580
tgtaccggct ccacagccac ctagcccccct caataccagt tacccccctt ccactaccag  2640
tacaccctca acctccccta caagtccaag tgtcccacag ccacccccag gaactggaga  2700
tagactacta gctctagtca aaggagccta tcaggcgctt aacctcacca atcccgacaa  2760
gacccaagaa tgttggctgt gcttagtgtc gggacctcct tattacgaag gagtagcggt  2820
cgtgggcact tataccaatc attccaccgc tccggccaac tgtacggcca cttcccaaca  2880
taagcttacc ctatctgaag tgacaggaca gggcctatgc atgggggcag tacctaaaac  2940
tcaccaggcc ttatgtaaca ccacccaaag cgccggctca ggatcctact accttgcagc  3000
acccgccgga acaatgtggg cttgcagcac tggattgact ccctgcttgt ccaccacggt  3060
gctcaatcta accacagatt attgtgtatt agttgaactc tggcccagag taatttacca  3120
ctccccccgat tatatgtatg gtcagcttga acagcgtacc aaatataaaa gagagccagt  3180
atcattgacc ctggcccttc tactaggagg attaaccatg ggagggattg cagctggaat  3240
agggacgggg accactgcct taattaaaac ccagcagttt gagcagcttc atgccgctat  3300
ccagacagac ctcaacgaag tcgaaaagtc aattaccaac ctagaaaagt cactgacctc  3360
gttgtctgaa gtagtcctac agaaccgcag aggcctagat ttgctattcc taaaggaggg  3420
aggtctctgc gcagccctaa aagaagaatg ttgtttttat gcagaccaca cggggctagt  3480
gagagacagc atggccaaat taagagaaag gcttaatcag agacaaaaac tatttgagac  3540
aggccaagga tggttcgaag ggctgtttaa tagatccccc tggtttacca ccttaatctc  3600
caccatcatg ggacctctaa tagtactctt actgatctta ctctttggac cttgcattct  3660
caatcgatta gtccaatttg ttaaagacag gatatcagtg gtccaggctc tagttttgac  3720
tcaacaatat caccagctga agcctataga gtacgagcca tagcacgtga aggctgccga  3780
ccccgggggt ggacatcctc tagactgcca tggcgcggat ctcgacgttt aaacaaggtc  3840
aatagggggtg agtcattggg tttttccagc caatttaatt aaaacgccat gtactttccc  3900
accattgacg tcaatgggct attgaaacta atgcaacgtg acctttaaac ggtactttcc  3960
catagctgat taatgggaaa gtaccgttct cgagccaata cacgtcaatg ggaagtgaaa  4020
gggcagccaa aacgtaacac cgccccggtt ttccctggaa attccatatt ggcacgcatt  4080
ctattggctg agctgcgttc acgtgggtat aagaggcgcg accagcgtcg gtaccgtcgc  4140
agtcttcggt ctgaccaccg tagaacgcag agcggccgct ttagtttatg gtgacatggc  4200
ttcgtacccc tgccatcaac acgcgtctgc gttcgaccag gctgcgcgtt ctcgcggcca  4260
tagcaaccga cgtacggcgt tgcgccctcg ccggcagcaa gaagccacgg aagtccgcct  4320
ggagcagaaa atgcccacgc tactgcgggt ttatatagac ggtcctcacg ggatggggaa  4380
aaccaccacc acgcaactgc tggtggccct gggttcgcgc gacgatatcg tctacgtacc  4440
cgagccgatg acttactggc aggtgctggg ggcttccgag acaatcgcga acatctacac  4500
cacacaacac cgcctcgacc agggtgagat atcggccggg gacgcggcgg tggtaatgac  4560
aagcgcccag ataacaatgg gcatgcctta tgccgtgacc gacgccgttc tggctcctca  4620
tatcgggggg gaggctggga gctcacatgc cccgcccccg gccctcaccc tcatcttcga  4680
ccgccatccc atcgccgccc tcctgtgcta cccggccgcg cgatacctta tgggcagcat  4740
gaccccccag gccgtgctgg cgttcgtggc cctcatcccg ccgaccttgc ccggcacaaa  4800
catcgtgttg ggggcccttc cggaggacag acacatcgac cgcctggcca aacgccagcg  4860
ccccggcgag cggcttgacc tggctatgct ggccgcgatt cgccgcgttt acgggctgct  4920
tgccaatacg gtgcggtatc tgcagggcgg cgggtcgtgg cgggaggatt ggggacagct  4980
ttcggggacg gccgtgccgc cccagggtgc cgagccccag agcaacgcgg gcccacgacc  5040
ccatatcggg gacacgttat ttaccctgtt tcgggccccc gagttgctgg cccccaacgg  5100
cgacctgtac aacgtgtttg cctgggcctt ggacgtcttg gccaaacgcc tccgtcccat  5160
gcacgtcttt atcctggatt acgaccaatc gcccgccggc tgccgggacg ccctgctgca  5220
acttacctcc gggatggtcc agacccacgt caccaccccc ggctccatac cgacgatctg  5280
cgacctggcg cgcacgtttg cccgggagat gggggaggct aactgatcga gaaacgcgtc  5340
```

-continued gacccatcga acatcgatgg taccagatcc gataaaataa aagattttat ttagtctcca 5400
gaaaaagggg ggaatgaaag accccacctg taggtttggc aagctagctt aagtaacgcc 5460
attttgcaag gcatggaaaa atacataact gagaatagag aagttcagat caaggtcagg 5520
aacagatgga acagctgaat atgggccaaa caggatatct gtggtaagca gttcctgccc 5580
cggctcaggg ccaagaacag atggaacagc tgaatatggg ccaaacagga tatctgtggt 5640
aagcagttcc tgccccggct cagggccaag aacagatggt ccccagatgc ggtccagccc 5700
tcagcagttt ctagagaacc atcagatgtt tccagggtgc cccaaggacc tgaaatgacc 5760
ctgtgcctta tttgaactaa ccaatcagtt cgcttctcgc ttctgttcgc gcgcttctgc 5820
tccccgagct caataaaaga gcccacaacc cctcactcgg ggcgccagtc ctccgattga 5880
ctgagtcgcc cgggtacccg tgtatccaat aaaccctctt gcagttgcat ccgacttgtg 5940
gtctcgctgt tccttgggag ggtctcctct gagtgattga ctacccgtca gcgggggtct 6000
ttcacacatg cagcatgtat caaaattaat ttggtttttt ttcttaagta tttacattaa 6060
atggccatag tacttaaagt tacattggct tccttgaaat aaacatggag tattcagaat 6120
gtgtcataaa tatttctaat tttaagatag tatctccatt ggctttctac tttttctttt 6180
attttttttt gtcctctgtc ttccatttgt tgttgttgtt gtttgtttgt ttgtttgttg 6240
gttggttggt taattttttt ttaaagatcc tacactatag ttcaagctag actattagct 6300
actctgtaac ccagggtgac cttgaagtca tgggtagcct gctgttttag ccttcccaca 6360
tctaagatta caggtatgag ctatcatttt tggtatatga ttgattgatt gattgatgtg 6420
tgtgtgtgtg attgtgtttg tgtgtgtgac tgtgaaaatg tgtgtatggg tgtgtgtgaa 6480
tgtgtgtatg tatgtgtgtg tgtgagtgtg tgtgtgtgtg tgtgcatgtg tgtgtgtgtg 6540
actgtgtcta tgtgtatgac tgtgtgtgtg tgtgtgtgtg tgtgtgtgtg tgtgtgtgtg 6600
tgtgtgttgt gaaaaaatat tctatggtag tgagagccaa cgctccggct caggtgtcag 6660
gttggttttt gagacagagt ctttcactta gcttggaatt cactggccgt cgttttacaa 6720
cgtcgtgact gggaaaaccc tggcgttacc caacttaatc gccttgcagc acatccccct 6780
ttcgccagct ggcgtaatag cgaagaggcc cgcaccgatc gcccttccca acagttgcgc 6840
agcctgaatg gcgaatggcg cctgatgcgg tattttctcc ttacgcatct gtgcggtatt 6900
tcacaccgca tatggtgcac tctcagtaca atctgctctg atgccgcata gttaagccag 6960
ccccgacacc cgccaacacc cgctgacgcg ccctgacggg cttgtctgct cccggcatcc 7020
gcttacagac aagctgtgac cgtctccggg agctgcatgt gtcagaggtt ttcaccgtca 7080
tcaccgaaac gcgcgagacg aaagggcctc gtgatacgcc tatttttata ggttaatgtc 7140
atgataataa tggtttctta gacgtcaggt ggcacttttc ggggaaatgt gcgcggaacc 7200
cctatttgtt tatttttcta aatacattca aatatgtatc cgctcatgag acaataaccc 7260
tgataaatgc ttcaataata ttgaaaaagg aagagtatga gtattcaaca tttccgtgtc 7320
gcccttattc ccttttttgc ggcattttgc cttcctgttt ttgctcaccc agaaacgctg 7380
gtgaaagtaa aagatgctga agatcagttg ggtgcacgag tgggttacat cgaactggat 7440
ctcaacagcg gtaagatcct tgagagtttt cgccccgaag aacgttttcc aatgatgagc 7500
acttttaaag ttctgctatg tggcgcggta ttatcccgta ttgacgccgg gcaagagcaa 7560
ctcggtcgcc gcatacacta ttctcagaat gacttggttg agtactcacc agtcacagaa 7620
aagcatctta cggatggcat gacagtaaga gaattatgca gtgctgccat aaccatgagt 7680
gataacactg cggccaactt acttctgaca acgatcggag gaccgaagga gctaaccgct 7740
tttttgcaca acatggggga tcatgtaact cgccttgatc gttgggaacc ggagctgaat 7800
gaagccatac caaacgacga gcgtgacacc acgatgcctg tagcaatggc aacaacgttg 7860
cgcaaactat taactggcga actacttact ctagcttccc ggcaacaatt aatagactgg 7920
atggaggcgg ataaagttgc aggaccactt ctgcgctcgg cccttccggc tggctggttt 7980
attgctgata aatctggagc cggtgagcgt gggtctcgcg gtatcattgc agcactgggg 8040
ccagatggta agccctcccg tatcgtagtt atctacacga cggggagtca ggcaactatg 8100
gatgaacgaa atagacagat cgctgagata ggtgcctcac tgattaagca ttggtaactg 8160
tcagaccaag tttactcata tatactttag attgatttaa aacttcattt ttaatttaaa 8220
aggatctagg tgaagatcct ttttgataat ctcatgacca aaatccctta acgtgagttt 8280
tcgttccact gagcgtcaga ccccgtagaa aagatcaaag gatcttcttg agatcctttt 8340
tttctgcgcg taatctgctg cttgcaaaca aaaaaaccac cgctaccagc ggtggtttgt 8400
ttgccggatc aagagctacc aactcttttt ccgaaggtaa ctggcttcag cagagcgcag 8460
ataccaaata ctgttcttct agtgtagccg tagttaggcc accacttcaa gaactctgta 8520
gcaccgccta catacctcgc tctgctaatc ctgttaccag tggctgctgc cagtggcgat 8580
aagtcgtgtc ttaccgggtt ggactcaaga cgatagttac cggataaggc gcagcggtcg 8640
ggctgaacgg ggggttcgtg cacacagccc agcttggagc gaacgaccta caccgaactg 8700
agatacctac agcgtgagct atgagaaagc gccacgcttc ccgaagggag aaaggcggac 8760
aggtatccgg taagcggcag ggtcggaaca ggagagcgca cgagggagct tccaggggga 8820
aacgcctggt atctttatag tcctgtcggg tttcgccacc tctgacttga gcgtcgattt 8880
ttgtgatgct cgtcaggggg gcggagccta tggaaaaacg ccagcaacgc ggccttttta 8940
cggttcctgg ccttttgctg gccttttgct cacatgttct ttcctgcgtt atcccctgat 9000
tctgtggata accgtattac cgcctttgag tgagctgata ccgctcgccg cagccgaacg 9060
accgagcgca gcgagtcagt gagcgaggaa gcggaagagc gcccaatacg caaaccgcct 9120
ctccccgcgc gttggccgat tcattaatgc agctggcacg acaggtttcc cgactggaaa 9180
gcgggcagtg agcgcaacgc aattaatgtg agttagctca ctcattaggc accccaggct 9240
ttacacttta tgcttccggc tcgtatgttg tgtggaattg tgagcggata acaatttcac 9300
acaggaaaca gctatgacca tgattacgcc aagctttgct cctaggagtt tcctaatact 9360
tcccaaactc aaatatataa agcatttgac ttgttctatg ccctaggggg cgggggggaag 9420
ctaagccagc ttttttaac atttaaaatg ttaattccat tttaaatgca cagatgtttt 9480
tatttcataa gggtttcaat gtgcatgaat gctgcaatat tcctgttacc aaagctagta 9540
taaataaaaa tagataaacg tggaaattac ttagagtttc tgtcattaac gtttccttcc 9600
tcagttgaca acataaatgc gctgctgagc aagccagttt gcatctgtca ggatcaattt 9660
cccattatgc cagtcatatt aattactagt caattagttg atttttattt ttgacatata 9720
catgtgaatg aaagacccca cctgtaggtt tggcaagcta gcttaagt 9768

SEQ ID NO: 36 moltype = DNA length = 9668
FEATURE Location/Qualifiers
misc_feature 1..9668
note = sRRVe-F3-TK vector

```
source                  1..9668
                        mol_type = other DNA
                        organism = synthetic construct
SEQUENCE: 36
aacgccattt tgcaaggcat ggaaaaatac ataactgaga atagaaaagt tcagatcaag  60
gtcaggaaca gatggaacag ctgaatatgg gccaaacagg atatctgtgg taagcagttc  120
ctgccccggc tcagggccaa gaacagatgg aacagctgaa tatgggccaa acaggatatc  180
tgtggtaagc agttcctgcc ccggctcagg gccaagaaca gatggtcccc agatgcggtc  240
cagccctcag cagtttctag agaaccatca gatgtttcca gggtgcccca aggacctgaa  300
atgaccctgt gccttatttg aactaaccaa tcagttcgct tctcgcttct gttcgcgcgc  360
ttatgctccc cgagctcaat aaaagagccc acaacccctc actcggggcg ccagtcctcc  420
gattgactga gtcgcccggg tacccgtgta tccaataaac cctcttgcag ttgcatccga  480
cttgtggtct cgctgttcct tgggagggtc tcctctgagt gattgactac ccgtcagcgg  540
gggtctttca tttgggggct cgtccgggat cgggagaccc ctgcccaggg accaccgacc  600
caccaccggg aggtaagctg gccagcaact tatctgtgtc tgtccgattg tctagtgtct  660
atgactgatt ttatgcgcct gcgtcggtac tagttagcta actagctctg tatctggcgg  720
acccgtggtg gaactgacga gttcggaaca cccggccgca accctgggag acgtcccagg  780
gacttcgggg gccgtttttg tggcccgacc tgagtcctaa aatcccgatc gtttaggact  840
ctttggtgca cccccccttag aggagggata tgtggttctg gtaggagacg agaacctaaa  900
acagttcccg cctccgtctg aatttttgct ttcggtttgg gaccgaagcc gcgccgcgcg  960
tcttgtctgc tgcagcatcg ttctgtgttg tctctgtctg actgtgtttc tgtatttgtc  1020
tgaaaatatg ggcccgggct agcctgttac cactccctta agtttgacct taggtcactg  1080
gaaagatgtc gagcggatcg ctcacaacca gtcggtagat gtcaagaaga gacgttgggt  1140
taccttctgc tctgcagaat ggccaacctt taacgtcgga tggccgcgag acggcacctt  1200
taaccgagac ctcactaccc aggttaagat caaggtcttt tcacctggcc cgcatggaca  1260
cccagaccag gtggggtaca tcgtgacctg ggaagccttg gcttttgacc cccctccctg  1320
ggtcaagccc tttgtacacc ctaagcctcc gcctcctctt cctccatccg ccccgtctct  1380
ccccccttgaa cctcctcgtt cgaccccgcc tcgatcctcc ctttatccag ccctcactcc  1440
ttctctaggc gcccccatat ggccatatga gatcttatat ggggcacccc cgccccttgt  1500
aaacttccct gaccctgaca tgacaagagt tactaacagc ccctctctcc aagctcactt  1560
acaggctctc tacttagtcc agcacgaagt ctggagacct ctggcggcag cctaccaaga  1620
acaactggac cgaccggtgg tacctcaccc ttaccgagtc ggcgacacag tgtgggtccg  1680
ccgacaccag actaagaacc tagaacctcg ctggaaagga ccttacacag tcctgctgac  1740
cacccccacc gccctcaaag tagacggcat cgcagcttgg atacacgccg cccacgtgat  1800
ggcgcgttca acgctctcaa aacccctca agataagatt aacccgtgga agcccttaat  1860
agtcatggga gtcctgttag gagtagggat ggcagagagc cccccatcagg tctttaatgt  1920
aacctggaga gtcaccaacc tgatgactgg gcgtaccgcc aatgccacct ccctcctggg  1980
aactgtacaa gatgccttcc caaaattata ttttgatcta tgtgatctgg tcggagagga  2040
gtgggaccct tcagaccagg aaccgtatgt cgggtatggc tgcaagtacc ccgcagggag  2100
acagcggacc cggacttttg actttttacgt gtgccctggg cataccgtaa agtcggggtg  2160
tgggggacca ggagagggct actgtggtaa atgggggtgt gaaaccaccg gacaggctta  2220
ctggaagccc acatcatcgt gggacctaat ctcccttaag cgcggtaaca cccccctgga  2280
cacgggatgc tctaaagttg cctgtggccc ctgctacgac ctctccaaag tatccaattc  2340
cttccaaggg gctactcgag ggggcagatg caaccctcta gtcctagaat tcactgatgc  2400
aggaaaaaag gctaactggg acgggcccaa atcgtgggga ctgagactgt accggacagg  2460
aacagatcct attaccatgt tctccctgac ccggcaggtc cttaatgtgg gaccccgagt  2520
ccccataggg cccaacccag tattacccga ccaaagactc ccttcctcac caatagagat  2580
tgtaccggct ccacagccac ctagcccccct caataccagt taccccccctt ccactaccag  2640
tacaccctca acctccccta caagtccaag tgtcccacag ccacccccag gaactggaga  2700
tagactacta gctctagtca aaggagccta tcaggcgctt aacctcacca atcccgacaa  2760
gacccaagaa tgttggctgt gcttagtgtc gggacctcct tattacgaag gagtagcggt  2820
cgtgggcact tataccaatc attccaccgc tccggccaac tgtacggcca cttcccaaca  2880
taagcttacc ctatctgaag tgacaggaca gggcctatgc atgggggcag tacctaaaac  2940
tcaccaggcc ttatgtaaca ccacccaaag cgccggctca ggatcctact accttgcagc  3000
acccgccgga acaatgtggg cttgcagcac tggattgact ccctgcttgt ccaccacggt  3060
gctcaatcta accacagatt attgtgtatt agttgaactc tggcccagag taatttacca  3120
ctcccccgat tatatgtatg gtcagcttga acagcgtacc aaatataaaa gagagccagt  3180
atcattgacc ctggcccttc tactaggagg attaaccatg ggagggattg cagctggaat  3240
agggacgggg accactgcct taattaaaac ccagcagttt gagcagcttc atgccgctat  3300
ccagacagac ctcaacgaag tcgaaaagtc aattaccaac ctagaaaagt cactgacctc  3360
gttgtctgaa gtagtcctac agaaccgcag aggcctagat ttgctattcc taaaggaggg  3420
aggtctctgc gcagccctaa aagaagaatg ttgtttttat gcagaccaca cggggctagt  3480
gagagacagc atggccaaat taagagaaag gcttaatcag agacaaaaac tatttgagac  3540
aggccaagga tggttcgaag ggctgtttaa tagatccccc tggtttacca ccttaatctc  3600
caccatcatg ggacctctaa tagtactctt actgatctta ctctttggac cttgcattct  3660
caatcgatta gtccaatttg ttaaagacag gatatcagtg gtccaggctc tagttttgac  3720
tcaacaatat caccagctga agcctataga gtacgagcca tagcacgtga aggctgccga  3780
ccccgggggt ggacatcctc tagactgcca tggcgcggat ctcgacgttt aaacaacgtg  3840
acctttaaac ggtactttcc catagctgat taatgggaaa gtaccgttct cgagccaata  3900
cacgtcaatg ggaagtgaaa gggcagccaa aacgtaacac cgccccggtt ttccctggaa  3960
attccatatt ggcacgcatt ctattggctg agctgcgttc acgtgggtat aagaggcgcg  4020
accagcgtcg gtaccgtcgc agtcttcggt ctgaccaccg tagaacgcag agcggccgct  4080
ttagtttatg gtgacatggc ttcgtacccc tgccatcaac acgcgtctgc gttcgaccag  4140
gctgcgcgtt ctcgcggcca tagcaaccga cgtacggcgt tgcgccctcg ccggcagcaa  4200
gaagccacgg aagtccgcct ggagcagaaa atgcccacgc tactgcgggt ttatatagac  4260
ggtcctcacg ggatggggaa aaccaccacc acgcaactgc tggtggccct gggttcgcgc  4320
gacgatatcg tctacgtacc cgagccgatg acttactggc aggtgctggg ggcttccgag  4380
acaatcgcga acatctacac cacacaacac cgcctcgacc agggtgagat atcggccggg  4440
gacgcggcgg tggtaatgac aagcgcccag ataacaatgg gcatgcctta tgccgtgacc  4500
```

-continued

```
gacgccgttc tggctcctca tatcgggggg gaggctggga gctcacatgc cccgcccccg  4560
gccctcaccc tcatcttcga ccgccatccc atcgccgccc tcctgtgcta cccggccgcg  4620
cgataccttg tgggcagcat gaccccccag gccgtgctgg cgttcgtggc cctcatcccg  4680
ccgaccttgc ccggcacaaa catcgtgttg ggggcccttc cggaggacag acacatcgac  4740
cgcctggcca aacgccagcg ccccggcgag cggcttgacc tggctatgct ggccgcgatt  4800
cgccgcgttt acgggctgct tgccaatacg gtgcggtatc tgcagggcgg cgggtcgtgg  4860
cgggaggatt ggggacagct ttcggggacg gccgtgccgc cccagggtgc cgagccccag  4920
agcaacgcgg gcccacgacc ccatatcggg gacacgttat ttaccctgtt tcgggccccc  4980
gagttgctgg cccccaacgg cgacctgtac aacgtgtttg cctgggcctt ggacgtcttg  5040
gccaaacgcc tccgtcccat gcacgtcttt atcctggatt acgaccaatc gcccgccggc  5100
tgccgggacg ccctgctgca acttacctcc gggatggtcc agacccacgt caccaccccc  5160
ggctccatac cgacgatctg cgacctggcg cgcacgtttg cccgggagat gggggaggct  5220
aactgatcga gaaacgcgtc gacccatcga acatcgatgg taccagatcc gataaaataa  5280
aagattttat ttagtctcca gaaaaagggg ggaatgaaag accccacctg taggtttggc  5340
aagctagctt aagtaacgcc attttgcaag gcatggaaaa atacataact gagaatagag  5400
aagttcagat caaggtcagg aacagatgga acagctgaat atgggccaaa caggatatct  5460
gtggtaagca gttcctgccc cggctcaggg ccaagaacag atggaacagc tgaatatggg  5520
ccaaacagga tatctgtggt aagcagttcc tgccccggct cagggccaag aacagatggt  5580
ccccagatgc ggtccagccc tcagcagttt ctagagaacc atcagatgtt tccagggtgc  5640
cccaaggacc tgaaatgacc ctgtgcctta tttgaactaa ccaatcagtt cgcttctcgc  5700
ttctgttcgc gcgcttctgc tccccgagct caataaaaga gcccacaacc cctcactcgg  5760
ggcgccagtc ctccgattga ctgagtcgcc cgggtacccg tgtatccaat aaaccctctt  5820
gcagttgcat ccgacttgtg gtctcgctgt tccttgggag ggtctcctct gagtgattga  5880
ctacccgtca gcgggggtct ttcacacatg cagcatgtat caaaattaat ttggtttttt  5940
ttcttaagta tttacattaa atggccatag tacttaaagt tacattggct tccttgaaat  6000
aaacatggag tattcagaat gtgtcataaa tatttctaat tttaagatag tatctccatt  6060
ggctttctac tttttctttt attttttttt gtcctctgtc ttccatttgt tgttgttgtt  6120
gtttgtttgt ttgtttgttg gttggttggt taattttttt ttaaagatcc tacactatag  6180
ttcaagctag actattagct actctgtaac ccagggtgac cttgaagtca tgggtagcct  6240
gctgttttag ccttcccaca tctaagatta caggtatgag ctatcatttt tggtatatga  6300
ttgattgatt gattgatgtg tgtgtgtgtg attgtgtttg tgtgtgtgac tgtgaaaatg  6360
tgtgtatggg tgtgtgtgaa tgtgtgtatg tatgtgtgtg tgtgagtgtg tgtgtgtgtg  6420
tgtgcatgtg tgtgtgtgtg actgtgtcta tgtgtatgac tgtgtgtgtg tgtgtgtgtg  6480
tgtgtgtgtg tgtgtgtgtg tgtgtgttgt gaaaaaatat tctatggtag tgagagccaa  6540
cgctccggct caggtgtcag gttggttttt gagacagagt ctttcactta gcttggaatt  6600
cactggccgt cgttttacaa cgtcgtgact gggaaaaccc tggcgttacc caacttaatc  6660
gccttgcagc acatccccct ttcgccagct ggcgtaatag cgaagaggcc cgcaccgatc  6720
gcccttccca acagttgcgc agcctgaatg gcgaatggcg cctgatgcgg tattttctcc  6780
ttacgcatct gtgcggtatt tcacaccgca tatggtgcac tctcagtaca atctgctctg  6840
atgccgcata gttaagccag ccccgacacc cgccaacacc cgctgacgcg ccctgacggg  6900
cttgtctgct cccggcatcc gcttacagac aagctgtgac cgtctccggg agctgcatgt  6960
gtcagaggtt ttcaccgtca tcaccgaaac gcgcgagacg aaagggcctc gtgatacgcc  7020
tatttttata ggttaatgtc atgataataa tggtttctta gacgtcaggt ggcacttttc  7080
ggggaaatgt gcgcggaacc cctatttgtt tatttttcta aatacattca aatatgtatc  7140
cgctcatgag acaataaccc tgataaatgc ttcaataata ttgaaaaagg aagagtatga  7200
gtattcaaca tttccgtgtc gcccttattc cctttttgc ggcattttgc cttcctgttt  7260
ttgctcaccc agaaacgctg gtgaaagtaa aagatgctga agatcagttg ggtgcacgag  7320
tgggttacat cgaactggat ctcaacagcg gtaagatcct tgagagtttt cgccccgaag  7380
aacgttttcc aatgatgagc acttttaaag ttctgctatg tggcgcggta ttatcccgta  7440
ttgacgccgg gcaagagcaa ctcggtcgcc gcatacacta ttctcagaat gacttggttg  7500
agtactcacc agtcacagaa aagcatctta cggatggcat gacagtaaga gaattatgca  7560
gtgctgccat aaccatgagt gataacactg cggccaactt acttctgaca acgatcggag  7620
gaccgaagga gctaaccgct tttttgcaca acatggggga tcatgtaact cgccttgatc  7680
gttgggaacc ggagctgaat gaagccatac caaacgacga gcgtgacacc acgatgcctg  7740
tagcaatggc aacaacgttg cgcaaactat taactggcga actacttact ctagcttccc  7800
ggcaacaatt aatagactgg atggaggcgg ataaagttgc aggaccactt ctgcgctcgg  7860
cccttccggc tggctggttt attgctgata aatctggagc cggtgagcgt gggtctcgcg  7920
gtatcattgc agcactgggg ccagatggta agccctcccg tatcgtagtt atctacacga  7980
cggggagtca ggcaactatg gatgaacgaa atagacagat cgctgagata ggtgcctcac  8040
tgattaagca ttggtaactg tcagaccaag tttactcata tatactttag attgatttaa  8100
aacttcattt ttaatttaaa aggatctagg tgaagatcct ttttgataat ctcatgacca  8160
aaatccctta acgtgagttt tcgttccact gagcgtcaga ccccgtagaa aagatcaaag  8220
gatcttcttg agatcctttt tttctgcgcg taatctgctg cttgcaaaca aaaaaaccac  8280
cgctaccagc ggtggtttgt ttgccggatc aagagctacc aactcttttt ccgaaggtaa  8340
ctggcttcag cagagcgcag ataccaaata ctgttcttct agtgtagccg tagttaggcc  8400
accacttcaa gaactctgta gcaccgccta catacctcgc tctgctaatc ctgttaccag  8460
tggctgctgc cagtggcgat aagtcgtgtc ttaccgggtt ggactcaaga cgatagttac  8520
cggataaggc gcagcggtcg ggctgaacgg ggggttcgtg cacacagccc agcttggagc  8580
gaacgaccta caccgaactg agatacctac agcgtgagct atgagaaagc gccacgcttc  8640
ccgaagggag aaaggcggac aggtatccgg taagcggcag ggtcggaaca ggagagcgca  8700
cgagggagct tccaggggga aacgcctggt atctttatag tcctgtcggg tttcgccacc  8760
tctgacttga gcgtcgattt ttgtgatgct cgtcaggggg gcggagccta tggaaaaacg  8820
ccagcaacgc ggccttttta cggttcctgg ccttttgctg gccttttgct cacatgttct  8880
ttcctgcgtt atcccctgat tctgtggata accgtattac cgcctttgag tgagctgata  8940
ccgctcgccg cagccgaacg accgagcgca gcgagtcagt gagcgaggaa gcggaagagc  9000
gcccaatacg caaaccgcct ctccccgcgc gttggccgat tcattaatgc agctggcacg  9060
acaggtttcc cgactggaaa gcgggcagtg agcgcaacgc aattaatgtg agttagctca  9120
ctcattaggc accccaggct ttacacttta tgcttccggc tcgtatgttg tgtggaattg  9180
tgagcggata acaatttcac acaggaaaca gctatgacca tgattacgcc aagctttgct  9240
```

-continued

```
cctaggagtt tcctaatact tcccaaactc aaatatataa agcatttgac ttgttctatg  9300
ccctaggggg cgggggggaag ctaagccagc tttttttaac atttaaaatg ttaattccat  9360
tttaaatgca cagatgtttt tatttcataa gggtttcaat gtgcatgaat gctgcaatat  9420
tcctgttacc aaagctagta taaataaaaa tagataaacg tggaaattac ttagagtttc  9480
tgtcattaac gtttccttcc tcagttgaca acataaatgc gctgctgagc aagccagttt  9540
gcatctgtca ggatcaattt cccattatgc cagtcatatt aattactagt caattagttg  9600
atttttattt ttgacatata catgtgaatg aaagacccca cctgtaggtt tggcaagcta  9660
gcttaagt                                                           9668

SEQ ID NO: 37          moltype = DNA  length = 9592
FEATURE                Location/Qualifiers
misc_feature           1..9592
                       note = sRRVe-F4-TK vector
source                 1..9592
                       mol_type = other DNA
                       organism = synthetic construct
SEQUENCE: 37
aacgccattt tgcaaggcat ggaaaaatac ataactgaga atagaaaagt tcagatcaag  60
gtcaggaaca gatggaacag ctgaatatgg gccaaacagg atatctgtgg taagcagttc  120
ctgccccggc tcagggccaa gaacagatgg aacagctgaa tatgggccaa acaggatatc  180
tgtggtaagc agttcctgcc ccggctcagg gccaagaaca gatggtcccc agatgcggtc  240
cagccctcag cagtttctag agaaccatca gatgtttcca gggtgcccca aggacctgaa  300
atgaccctgt gccttatttg aactaaccaa tcagttcgct tctcgcttct gttcgcgcgc  360
ttatgctccc cgagctcaat aaaagagccc acaacccctc actcggggcg ccagtcctcc  420
gattgactga gtcgcccggg tacccgtgta tccaataaac cctcttgcag ttgcatccga  480
cttgtggtct cgctgttcct tgggagggtc tcctctgagt gattgactac ccgtcagcgg  540
gggtctttca tttgggggct cgtccgggat cgggagaccc ctgcccaggg accaccgacc  600
caccaccggg aggtaagctg gccagcaact tatctgtgtc tgtccgattg tctagtgtct  660
atgactgatt ttatgcgcct gcgtcggtac tagttagcta actagctctg tatctggcgg  720
acccgtggtg gaactgacga gttcggaaca cccggccgca accctgggag acgtcccagg  780
gacttcgggg gccgtttttg tggcccgacc tgagtcctaa aatcccgatc gtttaggact  840
ctttggtgca cccccccttag aggagggata tgtggttctg gtaggagacg agaacctaaa  900
acagttcccg cctccgtctg aatttttgct ttcggtttgg gaccgaagcc gcgccgcgcg  960
tcttgtctgc tgcagcatcg ttctgtgttg tctctgtctg actgtgtttc tgtatttgtc  1020
tgaaaatatg ggcccgggct agcctgttac cactccctta agtttgacct taggtcactg  1080
gaaagatgtc gagcggatcg ctcacaacca gtcggtagat gtcaagaaga gacgttgggt  1140
taccttctgc tctgcagaat ggccaacctt taacgtcgga tggccgcgag acggcacctt  1200
taaccgagac ctcactaccc aggttaagat caaggtcttt tcacctggcc cgcatggaca  1260
cccagaccag gtggggtaca tcgtgacctg ggaagccttg gcttttgacc cccctccctg  1320
ggtcaagccc tttgtacacc ctaagcctcc gcctcctctt cctccatccg ccccgtctct  1380
ccccttgaa cctcctcgtt cgaccccgcc tcgatcctcc ctttatccag ccctcactcc  1440
ttctctaggc gcccccatat ggccatatga gatcttatat ggggcacccc cgccccttgt  1500
aaacttccct gaccctgaca tgacaagagt tactaacagc ccctctctcc aagctcactt  1560
acaggctctc tacttagtcc agcacgaagt ctggagacct ctggcggcag cctaccaaga  1620
acaactggac cgaccggtgg tacctcaccc ttaccgagtc ggcgacacag tgtgggtccg  1680
ccgacaccag actaagaacc tagaacctcg ctggaaagga ccttacacag tcctgctgac  1740
cacccccacc gccctcaaag tagacggcat cgcagcttgg atacacgccg cccacgtgat  1800
ggcgcgttca acgctctcaa aacccctca agataagatt aacccgtgga agcccttaat  1860
agtcatggga gtcctgttag gagtagggat ggcagagagc cccccatcagg tctttaatgt  1920
aacctggaga gtcaccaacc tgatgactgg gcgtaccgcc aatgccacct ccctcctggg  1980
aactgtacaa gatgccttcc caaaattata ttttgatcta tgtgatctgg tcggagagga  2040
gtgggaccct tcagaccagg aaccgtatgt cgggtatggc tgcaagtacc ccgcagggag  2100
acagcggacc cggacttttg acttttacgt gtgccctggg cataccgtaa agtcggggtg  2160
tgggggacca ggagagggct actgtggtaa atgggggtgt gaaaccaccg gacaggctta  2220
ctggaagccc acatcatcgt gggacctaat ctcccttaag cgcggtaaca ccccctggga  2280
cacgggatgc tctaaagttg cctgtggccc ctgctacgac ctctccaaag tatccaattc  2340
cttccaaggg gctactcgag gggcagatg caaccctcta gtcctagaat tcactgatgc  2400
aggaaaaaag gctaactggg acgggcccaa atcgtgggga ctgagactgt accggacagg  2460
aacagatcct attaccatgt tctccctgac ccggcaggtc cttaatgtgg gaccccgagt  2520
ccccataggg cccaacccag tattacccga ccaaagactc ccttcctcac caatagagat  2580
tgtaccggct ccacagccac ctagcccct caataccagt tacccccctt ccactaccag  2640
tacaccctca acctccccta caagtccaag tgtcccacag ccacccccag gaactggaga  2700
tagactacta gctctagtca aaggagccta tcaggcgctt aacctcacca atcccgacaa  2760
gacccaagaa tgttggctgt gcttagtgtc gggacctcct tattacgaag gagtagcggt  2820
cgtgggcact tataccaatc attccaccgc tccggccaac tgtacggcca cttcccaaca  2880
taagcttacc ctatctgaag tgacaggaca gggcctatgc atgggggcag tacctaaaac  2940
tcaccaggcc ttatgtaaca ccacccaaag cgccggctca ggatcctact accttgcagc  3000
acccgccgga acaatgtggg cttgcagcac tggattgact ccctgcttgt ccaccacggt  3060
gctcaatcta accacagatt attgtgtatt agttgaactc tggcccagag taatttacca  3120
ctcccccgat tatatgtatg gtcagcttga acagcgtacc aaatataaaa gagagccagt  3180
atcattgacc ctggcccttc tactaggagg attaaccatg ggagggattg cagctggaat  3240
agggacgggg accactgcct taattaaaac ccagcagttt gagcagcttc atgccgctat  3300
ccagacagac ctcaacgaag tcgaaaagtc aattaccaac ctagaaaagt cactgacctc  3360
gttgtctgaa gtagtcctac agaaccgcag aggcctagat ttgctattcc taaaggaggg  3420
aggtctctgc gcagccctaa aagaagaatg ttgtttttat gcagaccaca cggggctagt  3480
gagagacagc atggccaaat taagagaaag gcttaatcag agacaaaaac tatttgagac  3540
aggccaagga tggttcgaag ggctgtttaa tagatccccc tggtttacca ccttaatctc  3600
caccatcatg ggacctctaa tagtactctt actgatctta ctctttggac cttgcattct  3660
caatcgatta gtccaatttg ttaaagacag gatatcagtg gtccaggctc tagttttgac  3720
```

-continued

```
tcaacaatat caccagctga agcctataga gtacgagcca tagcacgtga aggctgccga  3780
ccccgggggt ggacatcctc tagactgcca tggcgcggat ctcgacgttt aaacggaagt  3840
gaaagggcag ccaaaacgta acaccgcccc ggttttccct ggaaattcca tattggcacg  3900
cattctattg gctgagctgc gttcacgtgg gtataagagg cgcgaccagc gtcggtaccg  3960
tcgcagtctt cggtctgacc accgtagaac gcagagcggc cgctttagtt tatggtgaca  4020
tggcttcgta cccctgccat caacacgcgt ctgcgttcga ccaggctgcg cgttctcgcg  4080
gccatagcaa ccgacgtacg gcgttgcgcc ctcgccggca gcaagaagcc acggaagtcc  4140
gcctggagca gaaaatgccc acgctactgc gggtttatat agacggtcct cacgggatgg  4200
ggaaaaccac caccacgcaa ctgctggtgg ccctgggttc gcgcgacgat atcgtctacg  4260
tacccgagcc gatgacttac tggcaggtgc tgggggcttc cgagacaatc gcgaacatct  4320
acaccacaca acaccgcctc gaccagggtg agatatcggc cggggacgcg gcggtggtaa  4380
tgacaagcgc ccagataaca atgggcatgc cttatgccgt gaccgacgcc gttctggctc  4440
ctcatatcgg gggggaggct gggagctcac atgccccgcc cccggccctc accctcatct  4500
tcgaccgcca tcccatcgcc gccctcctgt gctacccggc cgcgcgatac cttatgggca  4560
gcatgacccc ccaggccgtg ctggcgttcg tggccctcat cccgccgacc ttgcccggca  4620
caaacatcgt gttgggggcc cttccggagg acagacacat cgaccgcctg gccaaacgcc  4680
agcgccccgg cgagcggctt gacctggcta tgctggccgc gattcgccgc gtttacgggc  4740
tgcttgccaa tacggtgcgg tatctgcagg gcggcgggtc gtggcgggag gattggggac  4800
agctttcggg gacggccgtg ccgccccagg gtgccgagcc ccagagcaac gcgggcccac  4860
gaccccatat cggggacacg ttatttaccc tgtttcgggc ccccgagttg ctggcccccca  4920
acggcgacct gtacaacgtg tttgcctggg ccttggacgt cttggccaaa cgcctccgtc  4980
ccatgcacgt ctttatcctg gattacgacc aatcgcccgc cggctgccgg gacgccctgc  5040
tgcaacttac ctccgggatg gtccagaccc acgtcaccac ccccggctcc ataccgacga  5100
tctgcgacct ggcgcgcacg tttgcccggg agatggggga ggctaactga tcgagaaacg  5160
cgtcgaccca tcgaacatcg atggtaccag atccgataaa ataaaagatt ttatttagtc  5220
tccagaaaaa ggggggaatg aaagacccca cctgtaggtt tggcaagcta gcttaagtaa  5280
cgccattttg caaggcatgg aaaaatacat aactgagaat agagaagttc agatcaaggt  5340
caggaacaga tggaacagct gaatatgggc caaacaggat atctgtggta agcagttcct  5400
gccccggctc agggccaaga acagatggaa cagctgaata tgggccaaac aggatatctg  5460
tggtaagcag ttcctgcccc ggctcagggc caagaacaga tggtccccag atgcggtcca  5520
gccctcagca gtttctagag aaccatcaga tgtttccagg gtgccccaag gacctgaaat  5580
gaccctgtgc cttatttgaa ctaaccaatc agttcgcttc tcgcttctgt tcgcgcgctt  5640
ctgctccccg agctcaataa aagagcccac aacccctcac tcggggcgcc agtcctccga  5700
ttgactgagt cgcccgggta cccgtgtatc caataaaccc tcttgcagtt gcatccgact  5760
tgtggtctcg ctgttccttg ggagggtctc ctctgagtga ttgactaccc gtcagcgggg  5820
gtctttcaca catgcagcat gtatcaaaat taatttggtt ttttttctta agtatttaca  5880
ttaaatggcc atagtactta aagttacatt ggcttccttg aaataaacat ggagtattca  5940
gaatgtgtca taaatatttc taattttaag atagtatctc cattggcttt ctactttttc  6000
ttttattttt ttttgtcctc tgtcttccat ttgttgttgt tgttgtttgt ttgtttgttt  6060
gttggttggt tggttaattt tttttaaag atcctacact atagttcaag ctagactatt  6120
agctactctg taacccaggg tgaccttgaa gtcatgggta gcctgctgtt ttagccttcc  6180
cacatctaag attacaggta tgagctatca tttttggtat atgattgatt gattgattga  6240
tgtgtgtgtg tgtgattgtg tttgtgtgtg tgactgtgaa aatgtgtgta tgggtgtgtg  6300
tgaatgtgtg tatgtatgtg tgtgtgtgag tgtgtgtgtg tgtgtgtgca tgtgtgtgtg  6360
tgtgactgtg tctatgtgta tgactgtgtg tgtgtgtgtg tgtgtgtgtg tgtgtgtgtg  6420
tgtgtgtgtg ttgtgaaaaa atattctatg gtagtgagag ccaacgctcc ggctcaggtg  6480
tcaggttggt ttttgagaca gagtctttca cttagcttgg aattcactgg ccgtcgtttt  6540
acaacgtcgt gactgggaaa accctggcgt tacccaactt aatcgccttg cagcacatcc  6600
ccctttcgcc agctggcgta atagcgaaga ggcccgcacc gatcgccctt cccaacagtt  6660
gcgcagcctg aatggcgaat ggcgcctgat gcggtatttt ctccttacgc atctgtgcgg  6720
tatttcacac cgcatatggt gcactctcag tacaatctgc tctgatgccg catagttaag  6780
ccagccccga cacccgccaa cacccgctga cgcgccctga cgggcttgtc tgctcccggc  6840
atccgcttac agacaagctg tgaccgtctc cgggagctgc atgtgtcaga ggttttcacc  6900
gtcatcaccg aaacgcgcga gacgaaaggg cctcgtgata cgcctatttt tataggttaa  6960
tgtcatgata ataatggttt cttagacgtc aggtggcact tttcggggaa atgtgcgcgg  7020
aacccctatt tgtttatttt tctaaataca ttcaaatatg tatccgctca tgagacaata  7080
accctgataa atgcttcaat aatattgaaa aaggaagagt atgagtattc aacatttccg  7140
tgtcgccctt attccctttt ttgcggcatt ttgccttcct gtttttgctc acccagaaac  7200
gctggtgaaa gtaaaagatg ctgaagatca gttgggtgca cgagtgggtt acatcgaact  7260
ggatctcaac agcggtaaga tccttgagag ttttcgcccc gaagaacgtt ttccaatgat  7320
gagcactttt aaagttctgc tatgtggcgc ggtattatcc cgtattgacg ccgggcaaga  7380
gcaactcggt cgccgcatac actattctca gaatgacttg gttgagtact caccagtcac  7440
agaaaagcat cttacggatg gcatgacagt aagagaatta tgcagtgctg ccataaccat  7500
gagtgataac actgcggcca acttacttct gacaacgatc ggaggaccga aggagctaac  7560
cgcttttttg cacaacatgg gggatcatgt aactcgcctt gatcgttggg aaccggagct  7620
gaatgaagcc ataccaaacg acgagcgtga caccacgatg cctgtagcaa tggcaacaac  7680
gttgcgcaaa ctattaactg gcgaactact tactctagct tcccggcaac aattaataga  7740
ctggatggag gcggataaag ttgcaggacc acttctgcgc tcggcccttc cggctggctg  7800
gtttattgct gataaatctg gagccggtga gcgtgggtct cgcggtatca ttgcagcact  7860
ggggccagat ggtaagccct cccgtatcgt agttatctac acgacgggga gtcaggcaac  7920
tatggatgaa cgaaatagac agatcgctga gataggtgcc tcactgatta agcattggta  7980
actgtcagac caagtttact catatatact ttagattgat ttaaaacttc atttttaatt  8040
taaaaggatc taggtgaaga tcctttttga taatctcatg accaaaatcc cttaacgtga  8100
gttttcgttc cactgagcgt cagaccccgt agaaaagatc aaaggatctt cttgagatcc  8160
tttttttctg cgcgtaatct gctgcttgca aacaaaaaaa ccaccgctac cagcggtggt  8220
ttgtttgccg gatcaagagc taccaactct ttttccgaag gtaactggct tcagcagagc  8280
gcagatacca aatactgttc ttctagtgta gccgtagtta ggccaccact tcaagaactc  8340
tgtagcaccg cctacatacc tcgctctgct aatcctgtta ccagtggctg ctgccagtgg  8400
cgataagtcg tgtcttaccg ggttggactc aagacgatag ttaccggata aggcgcagcg  8460
```

-continued

```
gtcgggctga acgggggggtt cgtgcacaca gcccagcttg gagcgaacga cctacaccga  8520
actgagatac ctacagcgtg agctatgaga aagcgccacg cttcccgaag ggagaaaggc  8580
ggacaggtat ccggtaagcg gcagggtcgg aacaggagag cgcacgaggg agcttccagg  8640
gggaaacgcc tggtatcttt atagtcctgt cgggtttcgc cacctctgac ttgagcgtcg  8700
atttttgtga tgctcgtcag gggggcggag cctatggaaa aacgccagca acgcggcctt  8760
tttacggttc ctggcctttt gctggccttt tgctcacatg ttctttcctg cgttatcccc  8820
tgattctgtg gataaccgta ttaccgcctt tgagtgagct gataccgctc gccgcagccg  8880
aacgaccgag cgcagcgagt cagtgagcga ggaagcggaa gagcgcccaa tacgcaaacc  8940
gcctctcccc gcgcgttggc cgattcatta atgcagctgg cacgacaggt ttcccgactg  9000
gaaagcgggc agtgagcgca acgcaattaa tgtgagttag ctcactcatt aggcacccca  9060
ggctttacac tttatgcttc cggctcgtat gttgtgtgga attgtgagcg gataacaatt  9120
tcacacagga aacagctatg accatgatta cgccaagctt tgctcctagg agtttcctaa  9180
tacttcccaa actcaaatat ataaagcatt tgacttgttc tatgccctag gggggcggggg  9240
gaagctaagc cagctttttt taacatttaa aatgttaatt ccattttaaa tgcacagatg  9300
tttttatttc ataagggttt caatgtgcat gaatgctgca atattcctgt taccaaagct  9360
agtataaata aaaatagata aacgtggaaa ttacttagag tttctgtcat taacgtttcc  9420
ttcctcagtt gacaacataa atgcgctgct gagcaagcca gtttgcatct gtcaggatca  9480
atttcccatt atgccagtca tattaattac tagtcaatta gttgattttt atttttgaca  9540
tatacatgtg aatgaaagac cccacctgta ggtttggcaa gctagcttaa gt          9592

SEQ ID NO: 38          moltype = DNA  length = 29
FEATURE                Location/Qualifiers
misc_feature           1..29
                       note = MCMV(F4)-EcoRI-F
source                 1..29
                       mol_type = other DNA
                       organism = synthetic construct
SEQUENCE: 38
cggaattcgg aagtgaaagg gcagccaaa                                    29

SEQ ID NO: 39          moltype = DNA  length = 48
FEATURE                Location/Qualifiers
misc_feature           1..48
                       note = MCMV-NotI-MluI-EcoRI-R
source                 1..48
                       mol_type = other DNA
                       organism = synthetic construct
SEQUENCE: 39
cggaattcac gcgtgcgcgg ccgctctgcg ttctacggtg gtcagacc               48

SEQ ID NO: 40          moltype = DNA  length = 30
FEATURE                Location/Qualifiers
misc_feature           1..30
                       note = hopt-yCD-NotI-F
source                 1..30
                       mol_type = other DNA
                       organism = synthetic construct
SEQUENCE: 40
cggcggccgc atggttactg ggggaatggc                                   30

SEQ ID NO: 41          moltype = DNA  length = 27
FEATURE                Location/Qualifiers
misc_feature           1..27
                       note = hopt-yCD-MluI-R
source                 1..27
                       mol_type = other DNA
                       organism = synthetic construct
SEQUENCE: 41
acgcgtttat tccccgatgt cttcgaa                                      27

SEQ ID NO: 42          moltype = DNA  length = 22
FEATURE                Location/Qualifiers
misc_feature           1..22
                       note = AmEnv961F
source                 1..22
                       mol_type = other DNA
                       organism = synthetic construct
SEQUENCE: 42
acaagaccca agaatgttgg ct                                           22

SEQ ID NO: 43          moltype = DNA  length = 1671
FEATURE                Location/Qualifiers
misc_feature           1..1671
                       note = hCD19 variant 2
source                 1..1671
                       mol_type = other DNA
                       organism = synthetic construct
SEQUENCE: 43
atgccacctc ctcgcctcct cttcttcctc ctcttcctca cccccatgga agtcaggccc  60
```

```
gaggaacctc tagtggtgaa ggtggaagag ggagataacg ctgtgctgca gtgcctcaag  120
gggacctcag atggccccac tcagcagctg acctggtctc gggagtcccc gcttaaaccc  180
ttcttaaaac tcagcctggg gctgccaggc ctgggaatcc acatgaggcc cctggccatc  240
tggcttttca tcttcaacgt ctctcaacag atgggggggct tctacctgtg ccagccgggg  300
ccccccctctg agaaggcctg gcagcctggc tggacagtca atgtggaggg cagcggggag  360
ctgttccggt ggaatgtttc ggacctaggt ggcctgggct gtggcctgaa gaacaggtcc  420
tcagagggcc ccagctcccc ttccgggaag ctcatgagcc ccaagctgta tgtgtgggcc  480
aaagaccgcc ctgagatctg ggagggagag cctccgtgtc tcccaccgag ggacagcctg  540
aaccagagcc tcagccagga cctcaccatg gcccctggct ccacactctg gctgtcctgt  600
ggggtacccc ctgactctgt gtccaggggc cccctctcct ggacccatgt gcaccccaag  660
gggcctaagt cattgctgag cctagagctg aaggacgatc gcccggccag agatatgtgg  720
gtaatggaga cgggtctgtt gttgccccgg gccacagctc aagacgctgg aaagtattat  780
tgtcaccgtg gcaacctgac catgtcattc cacctggaga tcactgctcg gccagtacta  840
tggcactggc tgctgaggac tggtggctgg aaggtctcag ctgtgacttt ggcttatctg  900
atcttctgcc tgtgttccct tgtgggcatt cttcatcttc aaagagccct ggtcctgagg  960
aggaaaagaa agcgaatgac tgaccccacc aggagattct tcaaagtgac gcctccccca  1020
ggaagcgggc cccagaacca gtacgggaac gtgctgtctc tccccacacc cacctcaggc  1080
ctcggacgcg cccagcgttg ggccgcaggc ctggggggca ctgccccgtc ttatggaaac  1140
ccgagcagcg acgtccaggc ggatggagcc ttggggtccc ggagcccgcc gggagtgggc  1200
ccagaagaag aggaagggga gggctatgag gaacctgaca gtgaggagga ctccgagttc  1260
tatgagaacg actccaacct tgggcaggac cagctctccc aggatggcag cggctacgag  1320
aaccctgagg atgagcccct gggtcctgag gatgaagact ccttctccaa cgctgagtct  1380
tatgagaacg aggatgaaga gctgacccag ccggtcgcca ggacaatgga cttcctgagc  1440
cctcatgggt cagcctggga ccccagccgg gaagcaacct ccctggggtc ccagtcctat  1500
gaggatatga gaggaatcct gtatgcagcc ccccagctcc gctccattcg gggccagcct  1560
ggacccaatc atgaggaaga tgcagactct tatgagaaca tggataatcc cgatgggcca  1620
gacccagcct ggggaggagg gggccgcatg ggcacctgga gcaccaggtg a           1671

SEQ ID NO: 44          moltype = DNA  length = 11157
FEATURE                Location/Qualifiers
misc_feature           1..11157
                       note = sRRVgp-F4-hCD19 vector
source                 1..11157
                       mol_type = other DNA
                       organism = synthetic construct
SEQUENCE: 44
catgtgagca aaaggccagc aaaaggccag gaaccgtaaa aaggccgcgt tgctggcgtt  60
tttccatagg ctccgccccc ctgacgagca tcacaaaaat cgacgctcaa gtcagaggtg  120
gcgaaacccg acaggactat aaagatacca ggcgtttccc cctggaagct ccctcgtgcg  180
ctctcctgtt ccgaccctgc cgcttaccgg atacctgtcc gcctttctcc cttcgggaag  240
cgtggcgctt tctcatagct cacgctgtag gtatctcagt tcggtgtagg tcgttcgctc  300
caagctgggc tgtgtgcacg aaccccccgt tcagcccgac cgctgcgcct tatccggtaa  360
ctatcgtctt gagtccaacc cggtaagaca cgacttatcg ccactggcag cagccactgg  420
taacaggatt agcagagcga ggtatgtagg cggtgctaca gagttcttga agtggtggcc  480
taactacggc tacactagaa ggacagtatt tggtatctgc gctctgctga agccagttac  540
cttcggaaaa agagttggta gctcttgatc cggcaaacaa accaccgctg gtagcggtgg  600
tttttttgtt tgcaagcagc agattacgcg cagaaaaaaa ggatctcaag aagatccttt  660
gatcttttct acggggtctg acgctcagtg gaacgaaaac tcacgttaag ggattttggt  720
catgagatta tcaaaaagga tcttcaccta gatcctttta aattaaaaat gaagttttaa  780
atcaatctaa agtatatatg agtaaacctga tcaggactct tcctttttcat gaacaataaa  840
actgtctgct tacataaaca gtaatacaag gggtgttatg agccatattc aacgggaaac  900
gtcttgctct aggccgcgat taaattccaa catggatgct gatttatatg ggtataaatg  960
ggctcgcgat aatgtcgggc aatcaggtgc gacaatctat cgattgtatg ggaagcccga  1020
tgcgccagag ttgtttctga aacatggcaa aggtagcgtt gccaatgatg ttacagatga  1080
gatggtcaga ctaaactggc tgacggaatt tatgcctctt ccgaccatca agcattttat  1140
ccgtactcct gatgatgcat ggttactcac cactgcgatc cccgggaaaa cagcattcca  1200
ggtattagaa gaatatcctg attcaggtga aaatattgtt gatgcgctgg cagtgttcct  1260
gcgccggttg cattcgattc ctgtttgtaa ttgtcctttt aacagcgatc gcgtatttcg  1320
tctcgctcag gcgcaatcac gaatgaataa cggtttggtt gatgcgagtg attttgatga  1380
cgagcgtaat ggctggcctg ttgaacaagt ctggaaagaa atgcataaac ttttgccatt  1440
ctcaccggat tcagtcgtca ctcatggtga tttctcactt gataacctta tttttgacga  1500
ggggaaatta ataggttgta ttgatgttgg acgagtcgga atcgcagacc gataccagga  1560
tcttgccatc ctatggaact gcctcggtga gttttctcct tcattacaga aacggctttt  1620
tcaaaaatat ggtattgata atcctgatat gaataaattg cagtttcatt tgatgctcga  1680
tgagtttttc taagaatttg tgaatgaaag accccacctg taggtttggc aagctagctt  1740
aagtaacgcc attttgcaag gcatggaaaa atacataact gagaatagaa aagttcagat  1800
caaggtcagg aacagatgga acagctgaat atgggccaaa caggatatct gtggtaagca  1860
gttcctgccc cggctcaggg ccaagaacag atggaacagc tgaatatggg ccaaacagga  1920
tatctgtggt aagcagttcc tgccccggct cagggccaag aacagatggt ccccagatgc  1980
ggtccagccc tcagcagttt ctagagaacc atcagatgtt tccagggtgc cccaaggacc  2040
tgaaatgacc ctgtgcctta tttgaactaa ccaatcagtt cgcttctcgc ttctgttcgc  2100
gcgcttatgc tccccgagct caataaaaga gcccacaacc cctcactcgg ggcgccagtc  2160
ctccgattga ctgagtcgcc cgggtacccg tgtatccaat aaaccctctt gcagttgcat  2220
ccgacttgtg gtctcgctgt tccttgggag ggtctcctct gagtgattga ctacccgtca  2280
gcgggggtct ttcatttggg ggctcgtccg ggatcgggag acccctgccc agggaccacc  2340
gacccaccac cgggaggtaa gctggccagc aacttatctg tgtctgtccg attgtctagt  2400
gtctatgact gattttatgc gcctgcgtcg gtactagtta gctaactagc tctgtatctg  2460
gcggacccgt ggtggaactg acgagttcgg aacacccggc cgcaaccctg ggagacgtcc  2520
cagggacttc gggggccgtt tttgtggccc gacctgagtc caaaaatccc gatcgttttg  2580
```

-continued

```
gactctttgg tgcacccccc ttagaggagg gatatgtggt tctggtagga gacgagaacc  2640
taaaacagtt cccgcctccg tctgaatttt tgctttcggt ttgggaccga agccgcgccg  2700
cgcgtcttgt ctgctgcagc atcgttctgt gttgtctctg tctgactgtg tttctgtatt  2760
tgtctgagaa tatgggccag actgttacca ctcccttaag tttgacctta ggtcactgga  2820
aagatgtcga gcggatcgct cacaaccagt cggtagatgt caagaagaga cgttgggtta  2880
ccttctgctc tgcagaatgg ccaaccttta acgtcggatg gccgcgagac ggcaccttta  2940
accgagacct catcacccag gttaagatca aggtcttttc acctggcccg catggacacc  3000
cagaccaggt cccctacatc gtgacctggg aagccttggc ttttgacccc cctccctggg  3060
tcaagccctt tgtacaccct aagcctccgc ctcctcttcc tccatccgcc ccgtctctcc  3120
cccttgaacc tcctcgttcg accccgcctc gatcctccct ttatccagcc ctcactcctt  3180
ctctaggcgc caaacctaaa cctcaagttc tttctgacag tggggggccg ctcatcgacc  3240
tacttacaga agaccccccg ccttataggg acccaagacc accccccttcc gacagggacg  3300
gaaatggtgg agaagcgacc cctgcgggag aggcaccgga cccctcccca atggcatctc  3360
gcctacgtgg gagacgggag ccccctgtgg ccgactccac tacctcgcag gcattccccc  3420
tccgcgcagg aggaaacgga cagcttcaat actggccgtt ctcctcttct gacctttaca  3480
actggaaaaa taataaccct tctttttctg aagatccagg taaactgaca gctctgatcg  3540
agtctgttct catcacccat cagcccacct gggacgactg tcagcagctg ttggggactc  3600
tgctgaccgg agaagaaaaa caacgggtgc tcttagaggc tagaaaggcg gtgcggggcg  3660
atgatgggcg ccccactcaa ctgcccaatg aagtcgatgc cgcttttccc ctcgagcgcc  3720
cagactggga ttacaccacc caggcaggta ggaaccacct agtccactat cgccagttgc  3780
tcctagcggg tctccaaaac gcgggcagaa gccccaccaa tttggccaag gtaaaaggaa  3840
taacacaagg gcccaatgag tctccctcgg ccttcctaga gagacttaag gaagcctatc  3900
gcaggtacac tccttatgac cctgaggacc cagggcaaga aactaatgtg tctatgtctt  3960
tcatttggca gtctgcccca gacattggga gaaagttaga gaggttagaa gatttaaaaa  4020
acaagacgct tggagatttg gttagagagg cagaaaagat ctttaataaa cgagaaaccc  4080
cggaagaaag agaggaacgt atcaggagag aaacagagga aaaagaagaa cgccgtagga  4140
cagaggatga gcagaaagag aaagaaagag atcgtaggag acatagagag atgagcaagc  4200
tattggccac tgtcgttagt ggacagaaac aggatagaca gggaggagaa cgaaggaggt  4260
cccaactcga tcgcgaccag tgtgcctact gcaaagaaaa ggggcactgg gctaaagatt  4320
gtcccaagaa accacgagga cctcggggac caagacccca gacctccctc ctgaccctag  4380
atgactaggg aggtcagggt caggagcccc cccctgaacc caggataacc ctcaaagtcg  4440
gggggcaacc cgtcaccttc ctggtagata ctggggccca acactccgtg ctgacccaaa  4500
atcctggacc cctaagtgat aagtctgcct gggtccaagg ggctactgga ggaaagcggt  4560
atcgctggac cacggatcgc aaagtacatc tagctaccgg taaggtcacc cactctttcc  4620
tccatgtacc agactgtccc tatcctctgt taggaagaga tttgctgact aaactaaaag  4680
cccaaatcca ctttgaggga tcaggagctc aggttatggg accaatgggg cagcccctgc  4740
aagtgttgac cctaaatata gaagatgagc atcggctaca tgagacctca aaagagccag  4800
atgtttctct agggtccaca tggctgtctg attttcctca ggcctgggcg gaaaccgggg  4860
gcatgggact ggcagttcgc caagctcctc tgatcatacc tctgaaagca acctctaccc  4920
ccgtgtccat aaaacaatac cccatgtcac aagaagccag actggggatc aagccccaca  4980
tacagagact gttggaccag ggaatactgg taccctgcca gtccccctgg aacacgcccc  5040
tgctacccgt taagaaacca gggactaatg attataggcc tgtccaggat ctgagagaag  5100
tcaacaagcg ggtggaagac atccacccca ccgtgcccaa cccttacaac ctcttgagcg  5160
ggctcccacc gtcccaccag tggtacactg tgcttgattt aaaggatgcc tttttctgcc  5220
tgagactcca ccccaccagt cagcctctct tcgcctttga gtggagagat ccagagatgg  5280
gaatctcagg acaattgacc tggaccagac tcccacaggg tttcaaaaac agtcccaccc  5340
tgtttgatga ggcactgcac agagacctag cagacttccg gatccagcac ccagacttga  5400
tcctgctaca gtacgtggat gacttactgc tggccgccac ttctgagcta gactgccaac  5460
aaggtactcg ggccctgtta caaaccctag ggaacctcgg gtatcgggcc tcggccaaga  5520
aagcccaaat ttgccagaaa caggtcaagt atctggggta tcttctaaaa gagggtcaga  5580
gatggctgac tgaggccaga aaagagactg tgatggggca gcctactccg aagacccctc  5640
gacaactaag ggagttccta gggacggcag gcttctgtcg cctctggatc cctgggtttg  5700
cagaaatggc agccccccttg taccctctca ccaaaacggg gactctgttt aattggggcc  5760
cagaccaaca aaaggcctat caagaaatca agcaagctct tctaactgcc ccagccctgg  5820
ggttgccaga tttgactaag cccttttgaac tctttgtcga cgagaagcag ggctacgcca  5880
aaggtgtcct aacgcaaaaa ctgggacctt ggcgtcggcc ggtggcctac ctgtccaaaa  5940
agctagaccc agtagcagct gggtggcccc cttgcctacg gatggtagca gccattgccg  6000
tactgacaaa ggatgcaggc aagctaacca tgggacagcc actagtcatt ctggcccccc  6060
atgcagtaga ggcactagtc aaacaacccc ccgaccgctg gctttccaac gcccggatga  6120
ctcactatca ggccttgctt ttggacacgg accgggtcca gttcggaccg gtggtagccc  6180
tgaacccggc tacgctgctc ccactgcctg aggaagggct gcaacacaac tgccttgata  6240
tcctggccga agcccacgga acccgacccg acctaacgga ccagccgctc ccagacgccg  6300
accacacctg gtacacggat ggaagcagtc tcttacaaga gggacagcgt aaggcgggag  6360
ctgcggtgac caccgagacc gaggtaatct gggctaaagc cctgccagcc gggacatccg  6420
ctcagcgggc tgaactgata gcactcaccc aggccctaaa gatggcagaa ggtaagaagc  6480
taaatgttta tactgatagc cgttatgctt ttgctactgc ccatatccat ggagaaatat  6540
acagaaggcg tgggttgctc acatcagaag gcaaagagat caaaaataaa gacgagatct  6600
tggccctact aaaagccctc tttctgccca aaagacttag cataatccat tgtccaggac  6660
atcaaaaggg acacagcgcc gaggctagag gcaaccggat ggctgaccaa gcggcccgaa  6720
aggcagccat cacagagact ccagacacct ctaccctcct catagaaaat tcatcaccct  6780
acacctcaga acattttcat tacacagtga ctgatataaa ggacctaacc aagttggggg  6840
ccatttatga taaaacaaag aagtattggg tctaccaagg aaaacctgtg atgcctgacc  6900
agtttacttt tgaattatta gactttcttc atcagctgac tcacctcagc ttctcaaaaa  6960
tgaaggctct cctagagaga agccacagtc cctactacat gctgaaccgg gatcgaacac  7020
tcaaaaatat cactgagacc tgcaaagctt gtgcacaagt caacgccagc aagtctgccg  7080
ttaaacaggg aactagggtc cgcgggcatc ggcccggcac tcattgggag atcgatttca  7140
ccgagataaa gcccggattg tatggctata aatatcttct agtttttata gatacctttt  7200
ctggctggat agaagccttc ccaaccaaga aagaaaccgc caaggtcgta accaagaagc  7260
tactagagga gatcttcccc aggttcggca tgcctcaggt attgggaact gacaatgggc  7320
```

```
ctgccttcgt ctccaaggtg agtcagacag tggccgatct gttggggatt gattggaaat  7380
tacattgtgc atacagaccc caaagctcag gccaggtaga aagaatgaat agaaccatca  7440
aggagacttt aactaaatta acgcttgcaa ctggctctag agactgggtg ctcctactcc  7500
ccttagccct gtaccgagcc cgcaacacgc cgggccccca tggcctcacc ccatatgaga  7560
tcttatatgg ggcacccccg ccccttgtaa acttccctga ccctgacatg acaagagtta  7620
ctaacagccc ctctctccaa gctcacttac aggctctcta cttagtccag cacgaagtct  7680
ggagacctct ggcggcagcc taccaagaac aactggaccg accggtggta cctcaccctt  7740
accgagtcgg cgacacagtg tgggtccgcc gacaccagac taagaaccta gaacctcgct  7800
ggaaaggacc ttacacagtc ctgctgacca cccccaccgc cctcaaagta gacggcatcg  7860
cagcttggat acacgccgcc cacgtgaagg ctgccgaccc cgggggtgga ccatcctcta  7920
gactgacatg gcgcgttcaa cgctctcaaa accccttaaa aataaggtta acccgcgagg  7980
ccccctaatc cccttaattc ttctgatgct cagaggggtc agtaaacgaa ttcggaagtg  8040
aaagggcagc caaaacgtaa caccgccccg gttttccctg gaaattccat attggcacgc  8100
attctattgg ctgagctgcg ttcacgtggg tataagaggc gcgaccagcg tcggtaccgt  8160
cgcagtcttc ggtctgacca ccgtagaacg cagagcggcc gcatgccacc tcctcgcctc  8220
ctcttcttcc tcctcttcct cacccccatg gaagtcaggc ccgaggaacc tctagtggtg  8280
aaggtggaag agggagataa cgctgtgctg cagtgcctca aggggacctc agatggcccc  8340
actcagcagc tgacctggtc tcgggagtcc ccgcttaaac ccttcttaaa actcagcctg  8400
gggctgccag gcctgggaat ccacatgagg cccctggcca tctggctttt catcttcaac  8460
gtctctcaac agatgggggg cttctacctg tgccagccgg ggcccccctc tgagaaggcc  8520
tggcagcctg gctggacagt caatgtggag ggcagcgggg agctgttccg gtggaatgtt  8580
tcggacctag gtggcctggg ctgtggcctg aagaacaggt cctcagaggg ccccagctcc  8640
ccttccggga agctcatgag ccccaagctg tatgtgtggg ccaaagaccg ccctgagatc  8700
tgggagggag agcctccgtg tctcccaccg agggacagcc tgaaccagag cctcagccag  8760
gacctcacca tggcccctgg ctccacactc tggctgtcct gtggggtacc ccctgactct  8820
gtgtccaggg gccccctctc ctggacccat gtgcacccca aggggcctaa gtcattgctg  8880
agcctagagc tgaaggacga tcgcccggcc agagatatgt gggtaatgga gacgggtctg  8940
ttgttgcccc gggccacagc tcaagacgct ggaaagtatt attgtcaccg tggcaacctg  9000
accatgtcat tccacctgga gatcactgct cggccagtac tatggcactg gctgctgagg  9060
actggtggct ggaaggtctc agctgtgact ttggcttatc tgatcttctg cctgtgttcc  9120
cttgtgggca ttcttcatct tcaaagagcc ctggtcctga ggaggaaaag aaagcgaatg  9180
actgacccca ccaggagatt cttcaaagtg acgcctcccc caggaagcgg gccccagaac  9240
cagtacggga acgtgctgtc tctccccaca cccacctcag gcctcggacg cgcccagcgt  9300
tgggccgcag gcctgggggg cactgccccg tcttatggaa acccgagcag cgacgtccag  9360
gcggatggag ccttggggtc ccggagcccg ccgggagtgg gcccagaaga agaggaaggg  9420
gagggctatg aggaacctga cagtgaggag gactccgagt tctatgagaa cgactccaac  9480
cttgggcagg accagctctc ccaggatggc agcggctacg agaaccctga ggatgagccc  9540
ctgggtcctg aggatgaaga ctccttctcc aacgctgagt cttatgagaa cgaggatgaa  9600
gagctgaccc agccggtcgc caggacaatg gacttcctga gccctcatgg gtcagcctgg  9660
gaccccagcc gggaagcaac ctccctgggg tcccagtcct atgaggatat gagaggaatc  9720
ctgtatgcag ccccccagct ccgctccatt cggggccagc ctggacccaa tcatgaggaa  9780
gatgcagact cttatgagaa catggataat cccgatgggc cagacccagc ctggggagga  9840
gggggccgca tgggcacctg gagcaccagg tgagtttaaa cacgcgtgaa ttcataaaat  9900
aaaagatttt atttagtctc cagaaaaagg ggggaatgaa agaccccacc tgtaggtttg  9960
gcaagctagc ttaagtaacg ccattttgca aggcatggaa aaatacataa ctgagaatag  10020
agaagttcag atcaaggtca ggaacagatg gaacagctga atatgggcca aacaggatat  10080
ctgtggtaag cagttcctgc cccggctcag ggccaagaac agatggaaca gctgaatatg  10140
ggccaaacag gatatctgtg gtaagcagtt cctgccccgg ctcagggcca agaacagatg  10200
gtccccagat gcggtccagc cctcagcagt ttctagagaa ccatcagatg tttccagggt  10260
gccccaagga cctgaaatga ccctgtgcct tatttgaact aaccaatcag ttcgcttctc  10320
gcttctgttc gcgcgcttct gctccccgag ctcaataaaa gagcccacaa cccctcactc  10380
ggggcgccag tcctccgatt gactgagtcg cccgggtacc cgtgtatcca ataaaccctc  10440
ttgcagttgc atccgacttg tggtctcgct gttccttggg agggtctcct ctgagtgatt  10500
gactacccgt cagcgggggt ctttcattgt tacttaaagt tacattggct tccttgaaat  10560
aaacatggag tattcagaat gtgtcataaa tatttctaat tttaagatag tatctccatt  10620
ggctttctac tttttctttt attttttttt gtcctctgtc ttccatttgt tgttgttgtt  10680
gtttgtttgt ttgtttgttg gttggttggt taattttttt ttaaagatcc tacactatag  10740
ttcaagctag actattagct actctgtaac ccagggtgac cttgaagtca tgggtagcct  10800
gctgttttag ccttcccaca tctaagatta caggtatgag ctatcatttt tggtatattg  10860
attgattgat tgattgatgt gtgtgtgtgt gattgtgttt gtgtgtgtga ctgtgaaaat  10920
gtgtgtatgg gtgtgtgtga atgtgtgtat gtatgtgtgt gtgtgagtgt gtgtgtgtgt  10980
gtgtgcatgt gtgtgtgtgt gactgtgtct atgtgtatga ctgtgtgtgt gtgtgtgtgt  11040
gtgtgtgtgt gtgtgtgtgt gtgtgtgttg tgaaaaaata ttctatggta gtgagagcca  11100
acgctccggc tcaggtgtca ggttggtttt tgagacagag tctttcactt agcttgg     11157
```

```
SEQ ID NO: 45           moltype = DNA  length = 10105
FEATURE                 Location/Qualifiers
misc_feature            1..10105
                        note = sRRVe-F4-hCD19 vector
source                  1..10105
                        mol_type = other DNA
                        organism = synthetic construct
SEQUENCE: 45
aacgccattt tgcaaggcat ggaaaaatac ataactgaga atagaaaagt tcagatcaag  60
gtcaggaaca gatggaacag ctgaatatgg gccaaacagg atatctgtgg taagcagttc  120
ctgccccggc tcagggccaa gaacagatgg aacagctgaa tatgggccaa acaggatatc  180
tgtggtaagc agttcctgcc ccggctcagg gccaagaaca gatggtcccc agatgcggtc  240
cagccctcag cagtttctag agaaccatca gatgtttcca gggtgcccca aggacctgaa  300
atgaccctgt gccttatttg aactaaccaa tcagttcgct tctcgcttct gttcgcgcgc  360
```

-continued

```
ttatgctccc cgagctcaat aaaagagccc acaacccctc actcggggcg ccagtcctcc  420
gattgactga gtcgcccggg tacccgtgta tccaataaac cctcttgcag ttgcatccga  480
cttgtggtct cgctgttcct tgggagggtc tcctctgagt gattgactac ccgtcagcgg  540
gggtctttca tttgggggct cgtccgggat cgggagaccc ctgcccaggg accaccgacc  600
caccaccggg aggtaagctg gccagcaact tatctgtgtc tgtccgattg tctagtgtct  660
atgactgatt ttatgcgcct gcgtcggtac tagttagcta actagctctg tatctggcgg  720
acccgtggtg gaactgacga gttcggaaca cccggccgca accctgggag acgtcccagg  780
gacttcgggg gccgtttttg tggcccgacc tgagtcctaa aatcccgatc gtttaggact  840
ctttggtgca cccccccttag aggagggata tgtggttctg gtaggagacg agaacctaaa  900
acagttcccg cctccgtctg aatttttgct ttcggtttgg gaccgaagcc gcgccgcgcg  960
tcttgtctgc tgcagcatcg ttctgtgttg tctctgtctg actgtgtttc tgtatttgtc  1020
tgaaaatatg ggcccgggct agcctgttac cactccctta agtttgacct taggtcactg  1080
gaaagatgtc gagcggatcg ctcacaacca gtcggtagat gtcaagaaga gacgttgggt  1140
taccttctgc tctgcagaat ggccaacctt taacgtcgga tggccgcgag acggcacctt  1200
taaccgagac ctcactaccc aggttaagat caaggtcttt tcacctggcc cgcatggaca  1260
cccagaccag gtggggtaca tcgtgacctg ggaagccttg gcttttgacc cccctccctg  1320
ggtcaagccc tttgtacacc ctaagcctcc gcctcctctt cctccatccg ccccgtctct  1380
ccccccttgaa cctcctcgtt cgaccccgcc tcgatcctcc ctttatccag ccctcactcc  1440
ttctctaggc gcccccatat ggccatatga gatcttatat ggggcacccc cgccccttgt  1500
aaacttccct gaccctgaca tgacaagagt tactaacagc ccctctctcc aagctcactt  1560
acaggctctc tacttagtcc agcacgaagt ctggagacct ctggcggcag cctaccaaga  1620
acaactggac cgaccggtgg tacctcaccc ttaccgagtc ggcgacacag tgtgggtccg  1680
ccgacaccag actaagaacc tagaacctcg ctggaaagga ccttacacag tcctgctgac  1740
cacccccacc gccctcaaag tagacggcat cgcagcttgg atacacgccg cccacgtgat  1800
ggcgcgttca acgctctcaa aacccctca agataagatt aacccgtgga agcccttaat  1860
agtcatggga gtcctgttag gagtagggat ggcagagagc ccccatcagg tctttaatgt  1920
aacctggaga gtcaccaacc tgatgactgg gcgtaccgcc aatgccacct ccctcctggg  1980
aactgtacaa gatgccttcc caaaattata ttttgatcta tgtgatctgg tcggagagga  2040
gtgggaccct tcagaccagg aaccgtatgt cgggtatggc tgcaagtacc ccgcagggag  2100
acagcggacc cggacttttg acttttacgt gtgccctggg cataccgtaa agtcggggtg  2160
tgggggacca ggagagggct actgtggtaa atgggggtgt gaaaccaccg gacaggctta  2220
ctggaagccc acatcatcgt gggacctaat ctcccttaag cgcggtaaca cccccctggga  2280
cacgggatgc tctaaagttg cctgtggccc ctgctacgac ctctccaaag tatccaattc  2340
cttccaaggg gctactcgag gggcagatg caaccctcta gtcctagaat tcactgatgc  2400
aggaaaaaag gctaactggg acgggcccaa atcgtgggga ctgagactgt accggacagg  2460
aacagatcct attaccatgt tctccctgac ccggcaggtc cttaatgtgg gaccccgagt  2520
ccccataggg cccaacccag tattacccga ccaaagactc ccttcctcac caatagagat  2580
tgtaccggct ccacagccac ctagccccct caataccagt taccccccctt ccactaccag  2640
tacaccctca acctccccta caagtccaag tgtcccacag ccacccccag gaactggaga  2700
tagactacta gctctagtca aaggagccta tcaggcgctt aacctcacca atcccgacaa  2760
gacccaagaa tgttggctgt gcttagtgtc gggacctcct tattacgaag gagtagcggt  2820
cgtgggcact tataccaatc attccaccgc tccggccaac tgtacggcca cttcccaaca  2880
taagcttacc ctatctgaag tgacaggaca gggcctatgc atgggggcag tacctaaaac  2940
tcaccaggcc ttatgtaaca ccacccaaag cgccggctca ggatcctact accttgcagc  3000
acccgccgga acaatgtggg cttgcagcac tggattgact ccctgcttgt ccaccacggt  3060
gctcaatcta accacagatt attgtgtatt agttgaactc tggcccagag taatttacca  3120
ctcccccgat tatatgtatg gtcagcttga acagcgtacc aaatataaaa gagagccagt  3180
atcattgacc ctggcccttc tactaggagg attaaccatg ggagggattg cagctggaat  3240
agggacgggg accactgcct taattaaaac ccagcagttt gagcagcttc atgccgctat  3300
ccagacagac ctcaacgaag tcgaaaagtc aattaccaac ctagaaaagt cactgacctc  3360
gttgtctgaa gtagtcctac agaaccgcag aggcctagat ttgctattcc taaaggaggg  3420
aggtctctgc gcagccctaa aagaagaatg ttgtttttat gcagaccaca cggggctagt  3480
gagagacagc atggccaaat taagagaaag gcttaatcag agacaaaaac tatttgagac  3540
aggccaagga tggttcgaag ggctgtttaa tagatccccc tggtttacca ccttaatctc  3600
caccatcatg ggacctctaa tagtactctt actgatctta ctctttggac cttgcattct  3660
caatcgatta gtccaatttg ttaaagacag gatatcagtg gtccaggctc tagttttgac  3720
tcaacaatat caccagctga agcctataga gtacgagcca tagcacgtga aggctgccga  3780
ccccgggggt ggacatcctc tagactgcca tggcgcggat ctcgacgttt aaacggaagt  3840
gaaagggcag ccaaaacgta acaccgcccc ggttttccct ggaaattcca tattggcacg  3900
cattctattg gctgagctgc gttcacgtgg gtataagagg cgcgaccagc gtcggtaccg  3960
tcgcagtctt cggtctgacc accgtagaac gcagagcggc cgcatgccac ctcctcgcct  4020
cctcttcttc ctcctcttcc tcacccccat ggaagtcagg cccgaggaac ctctagtggt  4080
gaaggtggaa gagggagata acgctgtgct gcagtgcctc aaggggacct cagatggccc  4140
cactcagcag ctgacctggt ctcgggagtc cccgcttaaa cccttcttaa aactcagcct  4200
ggggctgcca ggcctgggaa tccacatgag gcccctggcc atctggcttt tcatcttcaa  4260
cgtctctcaa cagatggggg gcttctacct gtgccagccg gggcccccct ctgagaaggc  4320
ctggcagcct ggctggacag tcaatgtgga gggcagcggg gagctgttcc ggtggaatgt  4380
ttcggaccta ggtggcctgg gctgtggcct gaagaacagg tcctcagagg gccccagctc  4440
cccttccggg aagctcatga gccccaagct gtatgtgtgg gccaaagacc gccctgagat  4500
ctgggaggga gagcctccgt gtctcccacc gagggacagc ctgaaccaga gcctcagcca  4560
ggacctcacc atggcccctg gctccacact ctggctgtcc tgtggggtac cccctgactc  4620
tgtgtccagg ggcccccctct cctggaccca tgtgcacccc aaggggccta agtcattgct  4680
gagcctagag ctgaaggacg atcgcccggc cagagatatg tgggtaatgg agacgggtct  4740
gttgttgccc cgggccacag ctcaagacgc tggaaagtat tattgtcacc gtggcaacct  4800
gaccatgtca ttccacctgg agatcactgc tcggccagta ctatggcact ggctgctgag  4860
gactggtggc tggaaggtct cagctgtgac tttggcttat ctgatcttct gcctgtgttc  4920
ccttgtgggc attcttcatc ttcaaagagc cctggtcctg aggaggaaaa gaaagcgaat  4980
gactgacccc accaggagat tcttcaaagt gacgcctccc ccaggaagcg ggccccagaa  5040
ccagtacggg aacgtgctgt ctctccccac acccacctca ggcctcggac gcgcccagcg  5100
```

-continued

```
ttgggccgca ggcctggggg gcactgcccc gtcttatgga aacccgagca gcgacgtcca  5160
ggcggatgga gccttggggt cccggagccc gccgggagtg ggcccagaag aagaggaagg  5220
ggagggctat gaggaacctg acagtgagga ggactccgag ttctatgaga acgactccaa  5280
ccttgggcag gaccagctct cccaggatgg cagcggctac gagaaccctg aggatgagcc  5340
cctgggtcct gaggatgaag actccttctc caacgctgag tcttatgaga acgaggatga  5400
agagctgacc cagccggtcg ccaggacaat ggacttcctg agccctcatg ggtcagcctg  5460
ggaccccagc cgggaagcaa cctccctggg gtcccagtcc tatgaggata tgagaggaat  5520
cctgtatgca gccccccagc tccgctccat tcggggccag cctggaccca atcatgagga  5580
agatgcagac tcttatgaga acatggataa tcccgatggg ccagacccag cctggggagg  5640
agggggccgc atgggcacct ggagcaccag gtgagtcgac ccatcgaaca tcgatggtac  5700
cagatccgat aaaataaaag attttattta gtctccagaa aaagggggga atgaaagacc  5760
ccacctgtag gtttggcaag ctagcttaag taacgccatt ttgcaaggca tggaaaaata  5820
cataactgag aatagagaag ttcagatcaa ggtcaggaac agatggaaca gctgaatatg  5880
ggccaaacag gatatctgtg gtaagcagtt cctgccccgg ctcagggcca agaacagatg  5940
gaacagctga atatgggcca aacaggatat ctgtggtaag cagttcctgc cccggctcag  6000
ggccaagaac agatggtccc cagatgcggt ccagccctca gcagtttcta gagaaccatc  6060
agatgtttcc agggtgcccc aaggacctga aatgaccctg tgccttattt gaactaacca  6120
atcagttcgc ttctcgcttc tgttcgcgcg cttctgctcc ccgagctcaa taaaagagcc  6180
cacaacccct cactcggggc gccagtcctc cgattgactg agtcgcccgg gtacccgtgt  6240
atccaataaa ccctcttgca gttgcatccg acttgtggtc tcgctgttcc ttgggagggt  6300
ctcctctgag tgattgacta cccgtcagcg ggggtctttc acacatgcag catgtatcaa  6360
aattaatttg gttttttttc ttaagtattt acattaaatg gccatagtac ttaaagttac  6420
attggcttcc ttgaaataaa catggagtat tcagaatgtg tcataaatat ttctaatttt  6480
aagatagtat ctccattggc tttctacttt ttcttttatt tttttttgtc ctctgtcttc  6540
catttgttgt tgttgttgtt tgtttgtttg tttgttggtt ggttggttaa tttttttta  6600
aagatcctac actatagttc aagctagact attagctact ctgtaaccca gggtgacctt  6660
gaagtcatgg gtagcctgct gttttagcct tcccacatct aagattacag gtatgagcta  6720
tcatttttgg tatatgattg attgattgat tgatgtgtgt gtgtgtgatt gtgtttgtgt  6780
gtgtgactgt gaaaatgtgt gtatgggtgt gtgtgaatgt gtgtatgtat gtgtgtgtgt  6840
gagtgtgtgt gtgtgtgtgt gcatgtgtgt gtgtgtgact gtgtctatgt gtatgactgt  6900
gtgtgtgtgt gtgtgtgtgt gtgtgtgtgt gtgtgtgtgt gtgttgtgaa aaaatattct  6960
atggtagtga gagccaacgc tccggctcag gtgtcaggtt ggtttttgag acagagtctt  7020
tcacttagct tggaattcac tggccgtcgt tttacaacgt cgtgactggg aaaaccctgg  7080
cgttacccaa cttaatcgcc ttgcagcaca tccccctttc gccagctggc gtaatagcga  7140
agaggcccgc accgatcgcc cttcccaaca gttgcgcagc ctgaatggcg aatggcgcct  7200
gatgcggtat tttctcctta cgcatctgtg cggtatttca caccgcatat ggtgcactct  7260
cagtacaatc tgctctgatg ccgcatagtt aagccagccc cgacacccgc caacacccgc  7320
tgacgcgccc tgacgggctt gtctgctccc ggcatccgct tacagacaag ctgtgaccgt  7380
ctccgggagc tgcatgtgtc agaggttttc accgtcatca ccgaaacgcg cgagacgaaa  7440
gggcctcgtg atacgcctat ttttataggt taatgtcatg ataataatgg tttcttagac  7500
gtcaggtggc acttttcggg gaaatgtgcg cggaacccct atttgtttat ttttctaaat  7560
acattcaaat atgtatccgc tcatgagaca ataaccctga taaatgcttc aataatattg  7620
aaaaaggaag agtatgagta ttcaacattt ccgtgtcgcc cttattccct tttttgcggc  7680
attttgcctt cctgtttttg ctcacccaga aacgctggtg aaagtaaaag atgctgaaga  7740
tcagttgggt gcacgagtgg gttacatcga actggatctc aacagcggta agatccttga  7800
gagttttcgc cccgaagaac gttttccaat gatgagcact tttaaagttc tgctatgtgg  7860
cgcggtatta tcccgtattg acgccgggca agagcaactc ggtcgccgca tacactattc  7920
tcagaatgac ttggttgagt actcaccagt cacagaaaag catcttacgg atggcatgac  7980
agtaagagaa ttatgcagtg ctgccataac catgagtgat aacactgcgg ccaacttact  8040
tctgacaacg atcggaggac cgaaggagct aaccgctttt ttgcacaaca tgggggatca  8100
tgtaactcgc cttgatcgtt gggaaccgga gctgaatgaa gccataccaa acgacgagcg  8160
tgacaccacg atgcctgtag caatggcaac aacgttgcgc aaactattaa ctggcgaact  8220
acttactcta gcttcccggc aacaattaat agactggatg gaggcggata aagttgcagg  8280
accacttctg cgctcggccc ttccggctgg ctggtttatt gctgataaat ctggagccgg  8340
tgagcgtggg tctcgcggta tcattgcagc actggggcca gatggtaagc cctcccgtat  8400
cgtagttatc tacacgacgg ggagtcaggc aactatggat gaacgaaata gacagatcgc  8460
tgagataggt gcctcactga ttaagcattg gtaactgtca gaccaagttt actcatatat  8520
actttagatt gatttaaaac ttcattttta atttaaaagg atctaggtga agatcctttt  8580
tgataatctc atgaccaaaa tcccttaacg tgagttttcg ttccactgag cgtcagaccc  8640
cgtagaaaag atcaaaggat cttcttgaga tccttttttt ctgcgcgtaa tctgctgctt  8700
gcaaacaaaa aaaccaccgc taccagcggt ggtttgtttg ccggatcaag agctaccaac  8760
tctttttccg aaggtaactg gcttcagcag agcgcagata ccaaatactg ttcttctagt  8820
gtagccgtag ttaggccacc acttcaagaa ctctgtagca ccgcctacat acctcgctct  8880
gctaatcctg ttaccagtgg ctgctgccag tggcgataag tcgtgtctta ccgggttgga  8940
ctcaagacga tagttaccgg ataaggcgca gcggtcgggc tgaacggggg gttcgtgcac  9000
acagcccagc ttggagcgaa cgacctacac cgaactgaga tacctacagc gtgagctatg  9060
agaaagcgcc acgcttcccg aagggagaaa ggcggacagg tatccggtaa gcggcagggt  9120
cggaacagga gagcgcacga gggagcttcc agggggaaac gcctggtatc tttatagtcc  9180
tgtcgggttt cgccacctct gacttgagcg tcgatttttg tgatgctcgt caggggggcg  9240
gagcctatgg aaaaacgcca gcaacgcggc ctttttacgg ttcctggcct tttgctggcc  9300
ttttgctcac atgttctttc ctgcgttatc ccctgattct gtggataacc gtattaccgc  9360
ctttgagtga gctgataccg ctcgccgcag ccgaacgacc gagcgcagcg agtcagtgag  9420
cgaggaagcg gaagagcgcc caatacgcaa accgcctctc cccgcgcgtt ggccgattca  9480
ttaatgcagc tggcacgaca ggtttcccga ctggaaagcg ggcagtgagc gcaacgcaat  9540
taatgtgagt tagctcactc attaggcacc ccaggcttta cactttatgc ttccggctcg  9600
tatgttgtgt ggaattgtga gcggataaca atttcacaca ggaaacagct atgaccatga  9660
ttacgccaag ctttgctcct aggagtttcc taatacttcc caaactcaaa tatataaagc  9720
atttgacttg ttctatgccc tagggggcgg ggggaagcta agccagcttt ttttaacatt  9780
taaaatgtta attccatttt aaatgcacag atgtttttat ttcataaggg tttcaatgtg  9840
```

```
catgaatgct gcaatattcc tgttaccaaa gctagtataa ataaaaatag ataaacgtgg  9900
aaattactta gagtttctgt cattaacgtt tccttcctca gttgacaaca taaatgcgct  9960
gctgagcaag ccagtttgca tctgtcagga tcaatttccc attatgccag tcatattaat  10020
tactagtcaa ttagttgatt tttatttttg acatatacat gtgaatgaaa gaccccacct  10080
gtaggtttgg caagctagct taagt                                        10105

SEQ ID NO: 46          moltype = DNA  length = 9955
FEATURE                Location/Qualifiers
misc_feature           1..9955
                       note = sRRVgp-F4-hopt-yCD
source                 1..9955
                       mol_type = other DNA
                       organism = synthetic construct
SEQUENCE: 46
catgtgagca aaaggccagc aaaaggccag gaaccgtaaa aaggccgcgt tgctggcgtt  60
tttccatagg ctccgccccc ctgacgagca tcacaaaaat cgacgctcaa gtcagaggtg  120
gcgaaacccg acaggactat aaagatacca ggcgtttccc cctggaagct ccctcgtgcg  180
ctctcctgtt ccgaccctgc cgcttaccgg atacctgtcc gcctttctcc cttcgggaag  240
cgtggcgctt tctcatagct cacgctgtag gtatctcagt tcggtgtagg tcgttcgctc  300
caagctgggc tgtgtgcacg aaccccccgt tcagcccgac cgctgcgcct tatccggtaa  360
ctatcgtctt gagtccaacc cggtaagaca cgacttatcg ccactggcag cagccactgg  420
taacaggatt agcagagcga ggtatgtagg cggtgctaca gagttcttga agtggtggcc  480
taactacggc tacactagaa ggacagtatt tggtatctgc gctctgctga agccagttac  540
cttcggaaaa agagttggta gctcttgatc cggcaaacaa accaccgctg gtagcggtgg  600
tttttttgtt tgcaagcagc agattacgcg cagaaaaaaa ggatctcaag aagatccttt  660
gatcttttct acggggtctg acgctcagtg gaacgaaaac tcacgttaag ggattttggt  720
catgagatta tcaaaaagga tcttcaccta gatcctttta aattaaaaat gaagttttaa  780
atcaatctaa agtatatatg agtaacctga tcaggactct tccttttcat gaacaataaa  840
actgtctgct tacataaaca gtaatacaag ggtgttatg agccatattc aacgggaaac  900
gtcttgctct aggccgcgat taaattccaa catggatgct gatttatatg ggtataaatg  960
ggctcgcgat aatgtcgggc aatcaggtgc gacaatctat cgattgtatg ggaagcccga  1020
tgcgccagag ttgtttctga aacatggcaa aggtagcgtt gccaatgatg ttacagatga  1080
gatggtcaga ctaaactggc tgacggaatt tatgcctctt ccgaccatca agcattttat  1140
ccgtactcct gatgatgcat ggttactcac cactgcgatc cccgggaaaa cagcattcca  1200
ggtattagaa gaatatcctg attcaggtga aaatattgtt gatgcgctgg cagtgttcct  1260
gcgccggttg cattcgattc ctgtttgtaa ttgtcctttt aacagcgatc gcgtatttcg  1320
tctcgctcag gcgcaatcac gaatgaataa cggtttggtt gatgcgagtg attttgatga  1380
cgagcgtaat ggctggcctg ttgaacaagt ctggaaagaa atgcataaac ttttgccatt  1440
ctcaccggat tcagtcgtca ctcatggtga tttctcactt gataacctta tttttgacga  1500
ggggaaatta ataggttgta ttgatgttgg acgagtcgga atcgcagacc gataccagga  1560
tcttgccatc ctatggaact gcctcggtga gttttctcct tcattacaga aacggctttt  1620
tcaaaaatat ggtattgata atcctgatat gaataaattg cagtttcatt tgatgctcga  1680
tgagtttttc taagaatttg tgaatgaaag accccacctg taggtttggc aagctagctt  1740
aagtaacgcc attttgcaag gcatggaaaa atacataact gagaatagaa aagttcagat  1800
caaggtcagg aacagatgga acagctgaat atgggccaaa caggatatct gtggtaagca  1860
gttcctgccc cggctcaggg ccaagaacag atggaacagc tgaatatggg ccaaacagga  1920
tatctgtggt aagcagttcc tgccccggct cagggccaag aacagatggt ccccagatgc  1980
ggtccagccc tcagcagttt ctagagaacc atcagatgtt tccagggtgc cccaaggacc  2040
tgaaatgacc ctgtgcctta tttgaactaa ccaatcagtt cgcttctcgc ttctgttcgc  2100
gcgcttatgc tccccgagct caataaaaga gcccacaacc cctcactcgg ggcgccagtc  2160
ctccgattga ctgagtcgcc cgggtacccg tgtatccaat aaaccctctt gcagttgcat  2220
ccgacttgtg gtctcgctgt tccttgggag ggtctcctct gagtgattga ctacccgtca  2280
gcgggggtct ttcatttggg ggctcgtccg ggatcgggag acccctgccc agggaccacc  2340
gacccaccac cgggaggtaa gctggccagc aacttatctg tgtctgtccg attgtctagt  2400
gtctatgact gattttatgc gcctgcgtcg gtactagtta gctaactagc tctgtatctg  2460
gcggacccgt ggtggaactg acgagttcgg aacacccggc cgcaaccctg ggagacgtcc  2520
cagggacttc gggggccgtt tttgtggccc gacctgagtc caaaaatccc gatcgttttg  2580
gactctttgg tgcacccccc ttagaggagg gatatgtggt tctggtagga gacgagaacc  2640
taaaacagtt cccgcctccg tctgaatttt tgctttcggt ttgggaccga agccgcgccg  2700
cgcgtcttgt ctgctgcagc atcgttctgt gttgtctctg tctgactgtg tttctgtatt  2760
tgtctgagaa tatgggccag actgttacca ctcccttaag tttgacctta ggtcactgga  2820
aagatgtcga gcggatcgct cacaaccagt cggtagatgt caagaagaga cgttgggtta  2880
ccttctgctc tgcagaatgg ccaaccttta acgtcggatg gccgcgagac ggcaccttta  2940
accgagacct catcacccag gttaagatca aggtcttttc acctggcccg catggacacc  3000
cagaccaggt ccccctacatc gtgacctggg aagccttggc ttttgacccc cctccctggg  3060
tcaagccctt tgtacaccct aagcctccgc ctcctcttcc tccatccgcc ccgtctctcc  3120
cccttgaacc tcctcgttcg accccgcctc gatcctccct ttatccagcc ctcactcctt  3180
ctctaggcgc caaacctaaa cctcaagttc tttctgacag tgggggggccg ctcatcgacc  3240
tacttacaga agaccccccg ccttataggg acccaagacc acccccttcc gacagggacg  3300
gaaatggtgg agaagcgacc cctgcgggag aggcaccgga cccctcccca atggcatctc  3360
gcctacgtgg gagacgggag ccccctgtgg ccgactccac tacctcgcag gcattccccc  3420
tccgcgcagg aggaaacgga cagcttcaat actggccgtt ctcctcttct gacctttaca  3480
actggaaaaa taataaccct tctttttctg aagatccagg taaactgaca gctctgatcg  3540
agtctgttct catcacccat cagcccacct gggacgactg tcagcagctg ttggggactc  3600
tgctgaccgg agaagaaaaa caacgggtgc tcttagaggc tagaaaggcg gtgcggggcg  3660
atgatgggcg ccccactcaa ctgcccaatg aagtcgatgc cgcttttccc ctcgagcgcc  3720
cagactggga ttacaccacc caggcaggta ggaaccacct agtccactat cgccagttgc  3780
tcctagcggg tctccaaaac gcgggcagaa gccccaccaa tttggccaag gtaaaaggaa  3840
taacacaagg gcccaatgag tctccctcgg ccttcctaga gagacttaag gaagcctatc  3900
```

-continued

```
gcaggtacac tccttatgac cctgaggacc cagggcaaga aactaatgtg tctatgtctt  3960
tcatttggca gtctgcccca gacattggga gaaagttaga gaggttagaa gatttaaaaa  4020
acaagacgct tggagatttg gttagagagg cagaaaagat ctttaataaa cgagaaaccc  4080
cggaagaaag agaggaacgt atcaggagag aaacagagga aaaagaagaa cgccgtagga  4140
cagaggatga gcagaaagag aaagaaagag atcgtaggag acatagagag atgagcaagc  4200
tattggccac tgtcgttagt ggacagaaac aggatagaca gggaggagaa cgaaggaggt  4260
cccaactcga tcgcgaccag tgtgcctact gcaaagaaaa ggggcactgg gctaaagatt  4320
gtcccaagaa accacgagga cctcggggac caagacccca gacctccctc ctgaccctag  4380
atgactaggg aggtcagggt caggagcccc cccctgaacc caggataacc ctcaaagtcg  4440
gggggcaacc cgtcaccttc ctggtagata ctggggccca acactccgtg ctgacccaaa  4500
atcctggacc cctaagtgat aagtctgcct gggtccaagg ggctactgga ggaaagcggt  4560
atcgctggac cacggatcgc aaagtacatc tagctaccgg taaggtcacc cactctttcc  4620
tccatgtacc agactgtccc tatcctctgt taggaagaga tttgctgact aaactaaaag  4680
cccaaatcca ctttgaggga tcaggagctc aggttatggg accaatgggg cagcccctgc  4740
aagtgttgac cctaaatata gaagatgagc atcggctaca tgagacctca aaagagccag  4800
atgtttctct agggtccaca tggctgtctg attttcctca ggcctgggcg gaaaccgggg  4860
gcatgggact ggcagttcgc caagctcctc tgatcatacc tctgaaagca acctctaccc  4920
ccgtgtccat aaaacaatac cccatgtcac aagaagccag actggggatc aagcccccaca  4980
tacagagact gttggaccag ggaatactgg taccctgcca gtccccctgg aacacgcccc  5040
tgctacccgt taagaaacca gggactaatg attataggcc tgtccaggat ctgagagaag  5100
tcaacaagcg ggtggaagac atccacccca ccgtgcccaa cccttacaac ctcttgagcg  5160
ggctcccacc gtcccaccag tggtacactg tgcttgattt aaaggatgcc tttttctgcc  5220
tgagactcca ccccaccagt cagcctctct tcgcctttga gtggagagat ccagagatgg  5280
gaatctcagg acaattgacc tggaccagac tcccacaggg tttcaaaaac agtcccaccc  5340
tgtttgatga ggcactgcac agagacctag cagacttccg gatccagcac ccagacttga  5400
tcctgctaca gtacgtggat gacttactgc tggccgccac ttctgagcta gactgccaac  5460
aaggtactcg ggccctgtta caaaccctag ggaacctcgg gtatcgggcc tcggccaaga  5520
aagcccaaat ttgccagaaa caggtcaagt atctggggta tcttctaaaa gagggtcaga  5580
gatggctgac tgaggccaga aaagagactg tgatggggca gcctactccg aagacccctc  5640
gacaactaag ggagttccta gggacggcag gcttctgtcg cctctggatc cctgggtttg  5700
cagaaatggc agcccccttg taccctctca ccaaaacggg gactctgttt aattggggcc  5760
cagaccaaca aaaggcctat caagaaatca agcaagctct tctaactgcc ccagccctgg  5820
ggttgccaga tttgactaag ccctttgaac tctttgtcga cgagaagcag ggctacgcca  5880
aaggtgtcct aacgcaaaaa ctgggacctt ggcgtcggcc ggtggcctac ctgtccaaaa  5940
agctagaccc agtagcagct gggtggcccc cttgcctacg gatggtagca gccattgccg  6000
tactgacaaa ggatgcaggc aagctaacca tgggacagcc actagtcatt ctggcccccc  6060
atgcagtaga ggcactagtc aaacaacccc ccgaccgctg gctttccaac gcccggatga  6120
ctcactatca ggccttgctt ttggacacgg accgggtcca gttcggaccg gtggtagccc  6180
tgaacccggc tacgctgctc ccactgcctg aggaagggct gcaacacaac tgccttgata  6240
tcctggccga agcccacgga acccgacccg acctaacgga ccagccgctc ccagacgccg  6300
accacacctg gtacacggat ggaagcagtc tcttacaaga gggacagcgt aaggcgggag  6360
ctgcggtgac caccgagacc gaggtaatct gggctaaagc cctgccagcc gggacatccg  6420
ctcagcgggc tgaactgata gcactcaccc aggccctaaa gatggcagaa ggtaagaagc  6480
taaatgttta tactgatagc cgttatgctt ttgctactgc ccatatccat ggagaaatat  6540
acagaaggcg tgggttgctc acatcagaag gcaaagagat caaaaataaa gacgagatct  6600
tggccctact aaaagccctc tttctgccca aaagacttag cataatccat tgtccaggac  6660
atcaaaaggg acacagcgcc gaggctagag gcaaccggat ggctgaccaa gcggcccgaa  6720
aggcagccat cacagagact ccagacacct ctaccctcct catagaaaat tcatcaccct  6780
acacctcaga acattttcat tacacagtga ctgatataaa ggacctaacc aagttggggg  6840
ccatttatga taaaacaaag aagtattggg tctaccaagg aaaacctgtg atgcctgacc  6900
agtttacttt tgaattatta gactttcttc atcagctgac tcacctcagc ttctcaaaaa  6960
tgaaggctct cctagagaga agccacagtc cctactacat gctgaaccgg gatcgaacac  7020
tcaaaaatat cactgagacc tgcaaagctt gtgcacaagt caacgccagc aagtctgccg  7080
ttaaacaggg aactagggtc cgcgggcatc ggcccggcac tcattgggag atcgatttca  7140
ccgagataaa gcccggattg tatggctata aatatcttct agtttttata gatacctttt  7200
ctggctggat agaagccttc ccaaccaaga aagaaaccgc caaggtcgta accaagaagc  7260
tactagagga gatcttcccc aggttcggca tgcctcaggt attgggaact gacaatgggc  7320
ctgccttcgt ctccaaggtg agtcagacag tggccgatct gttggggatt gattggaaat  7380
tacattgtgc atacagaccc caaagctcag gccaggtaga aagaatgaat agaaccatca  7440
aggagacttt aactaaatta acgcttgcaa ctggctctag agactgggtg ctcctactcc  7500
ccttagccct gtaccgagcc cgcaacacgc cgggcccccca tggcctcacc ccatatgaga  7560
tcttatatgg ggcacccccg cccctgtaa acttccctga ccctgacatg acaagagtta  7620
ctaacagccc ctctctccaa gctcacttac aggctctcta cttagtccag cacgaagtct  7680
ggagacctct ggcggcagcc taccaagaac aactggaccg accggtggta cctcaccctt  7740
accgagtcgg cgacacagtg tgggtccgcc gacaccagac taagaaccta gaacctcgct  7800
ggaaaggacc ttacacagtc ctgctgacca cccccaccgc cctcaaagta gacggcatcg  7860
cagcttggat acacgccgcc cacgtgaagg ctgccgaccc cgggggtgga ccatcctcta  7920
gactgacatg gcgcgttcaa cgctctcaaa accccttaaa aataaggtta acccgcgagg  7980
ccccctaatc cccttaattc ttctgatgct cagaggggtc agtaaacgaa ttcggaagtg  8040
aaagggcagc caaaacgtaa caccgccccg gttttccctg gaaattccat attggcacgc  8100
attctattgg ctgagctgcg ttcacgtggg tataagaggc gcgaccagcg tcggtaccgt  8160
cgcagtcttc ggtctgacca ccgtagaacg cagagcggcc gcatggttac tgggggaatg  8220
gcatctaagt gggatcagaa aggtatggac atcgcttatg aagaggctgc tctcggctac  8280
aaagagggtg gagtgcctat cggagggtgc ctgatcaaca acaaggacgg cagtgtgctg  8340
gggaggggcc acaatatgag gttccaaaaa ggctccgcca ctctccacgg ggaaattagt  8400
accctcgaga attgcggacg attggaaggg aaggtgtaca aggatacaac actgtacacc  8460
accctgtcac cctgtgatat gtgcacaggc gccattatca tgtacggaat ccctagatgt  8520
gtcgtggggg agaatgtaaa cttcaaaagt aagggggaga aatatctcca gacccggggg  8580
cacgaagtcg tcgttgtgga cgatgaacgg tgtaagaaga tcatgaagca gtttatcgat  8640
```

-continued

```
gagaggcccc aggactggtt cgaagacatc ggggaataaa cgcgtgaatt cataaaataa  8700
aagattttat ttagtctcca gaaaaagggg ggaatgaaag accccacctg taggtttggc  8760
aagctagctt aagtaacgcc attttgcaag gcatggaaaa atacataact gagaatagag  8820
aagttcagat caaggtcagg aacagatgga acagctgaat atgggccaaa caggatatct  8880
gtggtaagca gttcctgccc cggctcaggg ccaagaacag atggaacagc tgaatatggg  8940
ccaaacagga tatctgtggt aagcagttcc tgccccggct cagggccaag aacagatggt  9000
ccccagatgc ggtccagccc tcagcagttt ctagagaacc atcagatgtt tccagggtgc  9060
cccaaggacc tgaaatgacc ctgtgcctta tttgaactaa ccaatcagtt cgcttctcgc  9120
ttctgttcgc gcgcttctgc tccccgagct caataaaaga gcccacaacc cctcactcgg  9180
ggcgccagtc ctccgattga ctgagtcgcc cgggtacccg tgtatccaat aaaccctctt  9240
gcagttgcat ccgacttgtg gtctcgctgt tccttgggag ggtctcctct gagtgattga  9300
ctacccgtca gcgggggtct ttcattgtta cttaaagtta cattggcttc cttgaaataa  9360
acatggagta ttcagaatgt gtcataaata tttctaattt taagatagta tctccattgg  9420
ctttctactt tttcttttat ttttttttgt cctctgtctt ccatttgttg ttgttgttgt  9480
ttgtttgttt gtttgttggt tggttggtta attttttttt aaagatccta cactatagtt  9540
caagctagac tattagctac tctgtaaccc agggtgacct tgaagtcatg ggtagcctgc  9600
tgttttagcc ttcccacatc taagattaca ggtatgagct atcatttttg gtatattgat  9660
tgattgattg attgatgtgt gtgtgtgtga ttgtgtttgt gtgtgtgact gtgaaaatgt  9720
gtgtatgggt gtgtgtgaat gtgtgtatgt atgtgtgtgt gtgagtgtgt gtgtgtgtgt  9780
gtgcatgtgt gtgtgtgtga ctgtgtctat gtgtatgact gtgtgtgtgt gtgtgtgtgt  9840
gtgtgtgtgt gtgtgtgtgt gtgtgttgtg aaaaaaatatt ctatggtagt gagagccaac  9900
gctccggctc aggtgtcagg ttggtttttg agacagagtc tttcacttag cttgg       9955

SEQ ID NO: 47          moltype = DNA  length = 28
FEATURE                Location/Qualifiers
misc_feature           1..28
                       note = MCMV-F-EcoRI
source                 1..28
                       mol_type = other DNA
                       organism = synthetic construct
SEQUENCE: 47
cggaattcaa caggaaagtc ccattgga                                     28

SEQ ID NO: 48          moltype = DNA  length = 37
FEATURE                Location/Qualifiers
misc_feature           1..37
                       note = MCMV-R-PmeI-EcoRI
source                 1..37
                       mol_type = other DNA
                       organism = synthetic construct
SEQUENCE: 48
cggaattcgt ttaaacctgc gttctacggt ggtcaga                           37

SEQ ID NO: 49          moltype = DNA  length = 32
FEATURE                Location/Qualifiers
misc_feature           1..32
                       note = TK-F-PmeI
source                 1..32
                       mol_type = other DNA
                       organism = synthetic construct
SEQUENCE: 49
cggtttaaac atggcttcgt acccctgcca tc                                32

SEQ ID NO: 50          moltype = DNA  length = 32
FEATURE                Location/Qualifiers
misc_feature           1..32
                       note = TK-R-PmeI
source                 1..32
                       mol_type = other DNA
                       organism = synthetic construct
SEQUENCE: 50
cggtttaaac tcagttagcc tcccccatct cc                                32

SEQ ID NO: 51          moltype = DNA  length = 34
FEATURE                Location/Qualifiers
misc_feature           1..34
                       note = hCD19t-NotI-F
source                 1..34
                       mol_type = other DNA
                       organism = synthetic construct
SEQUENCE: 51
cggcggccgc atgccacctc ctcgcctcct cttc                              34

SEQ ID NO: 52          moltype = DNA  length = 33
FEATURE                Location/Qualifiers
misc_feature           1..33
                       note = hCD19t-MluI-R
source                 1..33
                       mol_type = other DNA
```

```
                         organism = synthetic construct
SEQUENCE: 52
caacgcgttc atcttttcct cctcaggacc agg                              33

SEQ ID NO: 53            moltype = DNA  length = 972
FEATURE                  Location/Qualifiers
misc_feature             1..972
                         note = hCD19t polynucleotide sequence
source                   1..972
                         mol_type = other DNA
                         organism = synthetic construct
SEQUENCE: 53
atgccacctc ctcgcctcct cttcttcctc ctcttcctca cccccatgga agtcaggccc  60
gaggaacctc tagtggtgaa ggtggaagag ggagataacg ctgtgctgca gtgcctcaag  120
gggacctcag atggccccac tcagcagctg acctggtctc gggagtcccc gcttaaaccc  180
ttcttaaaac tcagcctggg gctgccaggc ctgggaatcc acatgaggcc cctggccatc  240
tggcttttca tcttcaacgt ctctcaacag atgggggct tctacctgtg ccagccgggg  300
ccccctctg agaaggcctg gcagcctggc tggacagtca atgtggaggg cagcggggag  360
ctgttccggt ggaatgtttc ggacctaggt ggcctgggct gtggcctgaa gaacaggtcc  420
tcagagggcc ccagctcccc ttccgggaag ctcatgagcc ccaagctgta tgtgtgggcc  480
aaagaccgcc ctgagatctg ggagggagag cctccgtgtc tcccaccgag ggacagcctg  540
aaccagagcc tcagccagga cctcaccatg gcccctggct ccacactctg gctgtcctgt  600
ggggtacccc ctgactctgt gtccaggggc cccctctcct ggacccatgt gcaccccaag  660
gggcctaagt cattgctgag cctagagctg aaggacgatc gcccggccag agatatgtgg  720
gtaatggaga cgggtctgtt gttgccccgg gccacagctc aagacgctgg aaagtattat  780
tgtcaccgtg gcaacctgac catgtcattc cacctggaga tcactgctcg gccagtacta  840
tggcactggc tgctgaggac tggtggctgg aaggtctcag ctgtgacttt ggcttatctg  900
atcttctgcc tgtgttccct tgtgggcatt cttcatcttc aaagagccct ggtcctgagg  960
aggaaaagat ga                                                     972

SEQ ID NO: 54            moltype = DNA  length = 10450
FEATURE                  Location/Qualifiers
misc_feature             1..10450
                         note = sRRVgp-F4-hCD19t vector
source                   1..10450
                         mol_type = other DNA
                         organism = synthetic construct
SEQUENCE: 54
catgtgagca aaaggccagc aaaaggccag gaaccgtaaa aaggccgcgt tgctggcgtt  60
tttccatagg ctccgccccc ctgacgagca tcacaaaaat cgacgctcaa gtcagaggtg  120
gcgaaacccg acaggactat aaagatacca ggcgtttccc cctggaagct ccctcgtgcg  180
ctctcctgtt ccgaccctgc cgcttaccgg atacctgtcc gcctttctcc cttcgggaag  240
cgtggcgctt tctcatagct cacgctgtag gtatctcagt tcggtgtagg tcgttcgctc  300
caagctgggc tgtgtgcacg aaccccccgt tcagcccgac cgctgcgcct tatccggtaa  360
ctatcgtctt gagtccaacc cggtaagaca cgacttatcg ccactggcag cagccactgg  420
taacaggatt agcagagcga ggtatgtagg cggtgctaca gagttcttga agtggtggcc  480
taactacggc tacactagaa ggacagtatt tggtatctgc gctctgctga agccagttac  540
cttcggaaaa agagttggta gctcttgatc cggcaaacaa accaccgctg gtagcggtgg  600
tttttttgtt tgcaagcagc agattacgcg cagaaaaaaa ggatctcaag aagatccttt  660
gatcttttct acggggtctg acgctcagtg gaacgaaaac tcacgttaag ggattttggt  720
catgagatta tcaaaaagga tcttcaccta gatcctttta aattaaaaat gaagttttaa  780
atcaatctaa agtatatatg agtaacctga tcaggactct tccttttcat gaacaataaa  840
actgtctgct tacataaaca gtaatacaag gggtgttatg agccatattc aacgggaaac  900
gtcttgctct aggccgcgat taaattccaa catggatgct gatttatatg ggtataaatg  960
ggctcgcgat aatgtcgggc aatcaggtgc gacaatctat cgattgtatg ggaagcccga  1020
tgcgccagag ttgtttctga aacatggcaa aggtagcgtt gccaatgatg ttacagatga  1080
gatggtcaga ctaaactggc tgacggaatt tatgcctctt ccgaccatca agcattttat  1140
ccgtactcct gatgatgcat ggttactcac cactgcgatc cccgggaaaa cagcattcca  1200
ggtattagaa gaatatcctg attcaggtga aaatattgtt gatgcgctgg cagtgttcct  1260
gcgccggttg cattcgattc ctgtttgtaa ttgtcctttt aacagcgatc gcgtatttcg  1320
tctcgctcag gcgcaatcac gaatgaataa cggtttggtt gatgcgagtg attttgatga  1380
cgagcgtaat ggctggcctg ttgaacaagt ctggaaagaa atgcataaac ttttgccatt  1440
ctcaccggat tcagtcgtca ctcatggtga tttctcactt gataacctta tttttgacga  1500
ggggaaatta ataggttgta ttgatgttgg acgagtcgga atcgcagacc gataccagga  1560
tcttgccatc ctatggaact gcctcggtga gttttctcct tcattacaga aacggctttt  1620
tcaaaaatat ggtattgata atcctgatat gaataaattg cagtttcatt tgatgctcga  1680
tgagtttttc taagaatttg tgaatgaaag accccacctg taggtttggc aagctagctt  1740
aagtaacgcc attttgcaag gcatggaaaa atacataact gagaatagaa aagttcagat  1800
caaggtcagg aacagatgga acagctgaat atgggccaaa caggatatct gtggtaagca  1860
gttcctgccc cggctcaggg ccaagaacag atggaacagc tgaatatggg ccaaacagga  1920
tatctgtggt aagcagttcc tgccccggct cagggccaag aacagatggt ccccagatgc  1980
ggtccagccc tcagcagttt ctagagaacc atcagatgtt tccagggtgc cccaaggacc  2040
tgaaatgacc ctgtgcctta tttgaactaa ccaatcagtt cgcttctcgc ttctgttcgc  2100
gcgcttatgc tccccgagct caataaaaga gcccacaacc cctcactcgg ggcgccagtc  2160
ctccgattga ctgagtcgcc cgggtacccg tgtatccaat aaaccctctt gcagttgcat  2220
ccgacttgtg gtctcgctgt tccttgggag ggtctcctct gagtgattga ctacccgtca  2280
gcgggggtct ttcatttggg ggctcgtccg ggatcgggag acccctgccc agggaccacc  2340
gacccaccac cgggaggtaa gctggccagc aacttatctg tgtctgtccg attgtctagt  2400
gtctatgact gattttatgc gcctgcgtcg gtactagtta gctaactagc tctgtatctg  2460
```

-continued

```
gcggacccgt ggtggaactg acgagttcgg aacacccggc cgcaaccctg ggagacgtcc  2520
cagggacttc gggggccgtt tttgtggccc gacctgagtc caaaaatccc gatcgttttg  2580
gactctttgg tgcacccccc ttagaggagg gatatgtggt tctggtagga gacgagaacc  2640
taaaacagtt cccgcctccg tctgaatttt tgctttcggt ttgggaccga agccgcgccg  2700
cgcgtcttgt ctgctgcagc atcgttctgt gttgtctctg tctgactgtg tttctgtatt  2760
tgtctgagaa tatgggccag actgttacca ctcccttaag tttgacctta ggtcactgga  2820
aagatgtcga gcggatcgct cacaaccagt cggtagatgt caagaagaga cgttgggtta  2880
ccttctgctc tgcagaatgg ccaaccttta acgtcggatg gccgcgagac ggcaccttta  2940
accgagacct catcacccag gttaagatca aggtcttttc acctggcccg catggacacc  3000
cagaccaggt cccctacatc gtgacctggg aagccttggc ttttgacccc cctccctggg  3060
tcaagccctt tgtacaccct aagcctccgc ctcctcttcc tccatccgcc ccgtctctcc  3120
cccttgaacc tcctcgttcg accccgcctc gatcctccct ttatccagcc ctcactcctt  3180
ctctaggcgc caaacctaaa cctcaagttc tttctgacag tgggggccg ctcatcgacc  3240
tacttacaga agaccccccg ccttataggg acccaagacc accccccttcc gacagggacg  3300
gaaatggtgg agaagcgacc cctgcgggag aggcaccgga cccctcccca atggcatctc  3360
gcctacgtgg gagacgggag ccccctgtgg ccgactccac tacctcgcag gcattccccc  3420
tccgcgcagg aggaaacgga cagcttcaat actggccgtt ctcctcttct gacctttaca  3480
actggaaaaa taataaccct tctttttctg aagatccagg taaactgaca gctctgatcg  3540
agtctgttct catcacccat cagcccacct gggacgactg tcagcagctg ttggggactc  3600
tgctgaccgg agaagaaaaa caacgggtgc tcttagaggc tagaaaggcg gtgcggggcg  3660
atgatgggcg ccccactcaa ctgcccaatg aagtcgatgc cgcttttccc ctcgagcgcc  3720
cagactggga ttacaccacc caggcaggta ggaaccacct agtccactat cgccagttgc  3780
tcctagcggg tctccaaaac gcgggcagaa gccccaccaa tttggccaag gtaaaaggaa  3840
taacacaagg gcccaatgag tctccctcgg ccttcctaga gagacttaag gaagcctatc  3900
gcaggtacac tccttatgac cctgaggacc cagggcaaga aactaatgtg tctatgtctt  3960
tcatttggca gtctgcccca gacattggga gaaagttaga gaggttagaa gatttaaaaa  4020
acaagacgct tggagatttg gttagagagg cagaaaagat ctttaataaa cgagaaaccc  4080
cggaagaaag agaggaacgt atcaggagag aaacagagga aaaagaagaa cgccgtagga  4140
cagaggatga gcagaaagag aaagaaagag atcgtaggag acatagagag atgagcaagc  4200
tattggccac tgtcgttagt ggacagaaac aggatagaca gggaggagaa cgaaggaggt  4260
cccaactcga tcgcgaccag tgtgcctact gcaaagaaaa ggggcactgg gctaaagatt  4320
gtcccaagaa accacgagga cctcggggac caagacccca gacctccctc ctgaccctag  4380
atgactaggg aggtcagggt caggagcccc cccctgaacc caggataacc ctcaaagtcg  4440
gggggcaacc cgtcaccttc ctggtagata ctggggccca acactccgtg ctgacccaaa  4500
atcctggacc cctaagtgat aagtctgcct gggtccaagg ggctactgga ggaaagcggt  4560
atcgctggac cacggatcgc aaagtacatc tagctaccgg taaggtcacc cactctttcc  4620
tccatgtacc agactgtccc tatcctctgt taggaagaga tttgctgact aaactaaaag  4680
cccaaatcca ctttgaggga tcaggagctc aggttatggg accaatgggg cagcccctgc  4740
aagtgttgac cctaaatata gaagatgagc atcggctaca tgagacctca aaagagccag  4800
atgtttctct agggtccaca tggctgtctg attttcctca ggcctgggcg gaaaccgggg  4860
gcatgggact ggcagttcgc caagctcctc tgatcatacc tctgaaagca acctctaccc  4920
ccgtgtccat aaaacaatac cccatgtcac aagaagccag actggggatc aagccccaca  4980
tacagagact gttggaccag ggaatactgg taccctgcca gtccccctgg aacacgcccc  5040
tgctacccgt taagaaacca gggactaatg attataggcc tgtccaggat ctgagagaag  5100
tcaacaagcg ggtggaagac atccacccca ccgtgcccaa cccttacaac ctcttgagcg  5160
ggctcccacc gtcccaccag tggtacactg tgcttgattt aaaggatgcc tttttctgcc  5220
tgagactcca ccccaccagt cagcctctct tcgcctttga gtggagagat ccagagatgg  5280
gaatctcagg acaattgacc tggaccagac tcccacaggg tttcaaaaac agtcccaccc  5340
tgtttgatga ggcactgcac agagacctag cagacttccg gatccagcac ccagacttga  5400
tcctgctaca gtacgtggat gacttactgc tggccgccac ttctgagcta gactgccaac  5460
aaggtactcg ggccctgtta caaaccctag ggaacctcgg gtatcgggcc tcggccaaga  5520
aagcccaaat ttgccagaaa caggtcaagt atctggggta tcttctaaaa gagggtcaga  5580
gatggctgac tgaggccaga aaagagactg tgatggggca gcctactccg aagacccctc  5640
gacaactaag ggagttccta gggacggcag gcttctgtcg cctctggatc cctgggtttg  5700
cagaaatggc agccccttg taccctctca ccaaaacggg gactctgttt aattggggcc  5760
cagaccaaca aaaggcctat caagaaatca agcaagctct tctaactgcc ccagccctgg  5820
ggttgccaga tttgactaag ccctttgaac tctttgtcga cgagaagcag ggctacgcca  5880
aaggtgtcct aacgcaaaaa ctgggacctt ggcgtcggcc ggtggcctac ctgtccaaaa  5940
agctagaccc agtagcagct gggtggcccc cttgcctacg gatggtagca gccattgccg  6000
tactgacaaa ggatgcaggc aagctaacca tgggacagcc actagtcatt ctggcccccc  6060
atgcagtaga ggcactagtc aaacaacccc ccgaccgctg gctttccaac gcccggatga  6120
ctcactatca ggccttgctt ttggacacgg accgggtcca gttcggaccg gtggtagccc  6180
tgaacccggc tacgctgctc ccactgcctg aggaagggct gcaacacaac tgccttgata  6240
tcctggccga agcccacgga acccgacccg acctaacgga ccagccgctc ccagacgccg  6300
accacacctg gtacacggat ggaagcagtc tcttacaaga gggacagcgt aaggcgggag  6360
ctgcggtgac caccgagacc gaggtaatct gggctaaagc cctgccagcc gggacatccg  6420
ctcagcgggc tgaactgata gcactcaccc aggccctaaa gatggcagaa ggtaagaagc  6480
taaatgttta tactgatagc cgttatgctt ttgctactgc ccatatccat ggagaaatat  6540
acagaaggcg tgggttgctc acatcagaag gcaaagagat caaaaataaa gacgagatct  6600
tggccctact aaaagccctc tttctgccca aaagacttag cataatccat tgtccaggac  6660
atcaaaaggg acacagcgcc gaggctagag gcaaccggat ggctgaccaa gcggcccgaa  6720
aggcagccat cacagagact ccagacacct ctaccctcct catagaaaat tcatcaccct  6780
acacctcaga acattttcat tacacagtga ctgatataaa ggacctaacc aagttggggg  6840
ccatttatga taaaacaaag aagtattggg tctaccaagg aaaacctgtg atgcctgacc  6900
agtttacttt tgaattatta gactttcttc atcagctgac tcacctcagc ttctcaaaaa  6960
tgaaggctct cctagagaga agccacagtc cctactacat gctgaaccgg gatcgaacac  7020
tcaaaaatat cactgagacc tgcaaagctt gtgcacaagt caacgccagc aagtctgccg  7080
ttaaacaggg aactagggtc cgcgggcatc ggcccggcac tcattgggag atcgatttca  7140
ccgagataaa gcccggattg tatggctata aatatcttct agtttttata gatacctttt  7200
```

```
ctggctggat agaagccttc ccaaccaaga aagaaaccgc caaggtcgta accaagaagc  7260
tactagagga gatcttcccc aggttcggca tgcctcaggt attgggaact gacaatgggc  7320
ctgccttcgt ctccaaggtg agtcagacag tggccgatct gttggggatt gattggaaat  7380
tacattgtgc atacagaccc caaagctcag gccaggtaga aagaatgaat agaaccatca  7440
aggagacttt aactaaatta acgcttgcaa ctggctctag agactgggtg ctcctactcc  7500
ccttagccct gtaccgagcc cgcaacacgc cgggccccca tggcctcacc ccatatgaga  7560
tcttatatgg ggcaccccg cccttgtaa acttccctga ccctgacatg acaagagtta  7620
ctaacagccc ctctctccaa gctcacttac aggctctcta cttagtccag cacgaagtct  7680
ggagacctct ggcggcagcc taccaagaac aactggaccg accggtggta cctcaccctt  7740
accgagtcgg cgacacagtg tgggtccgcc gacaccagac taagaaccta gaacctcgct  7800
ggaaaggacc ttacacagtc ctgctgacca cccccaccgc cctcaaagta gacggcatcg  7860
cagcttggat acacgccgcc cacgtgaagg ctgccgaccc cgggggtgga ccatcctcta  7920
gactgacatg gcgcgttcaa cgctctcaaa accccttaaa aataaggtta acccgcgagg  7980
ccccctaatc cccttaattc ttctgatgct cagaggggtc agtaaacgaa ttcggaagtg  8040
aaagggcagc caaaacgtaa caccgccccg gttttccctg gaaattccat attggcacgc  8100
attctattgg ctgagctgcg ttcacgtggg tataagaggc gcgaccagcg tcggtaccgt  8160
cgcagtcttc ggtctgacca ccgtagaacg cagagcggcc gcatgccacc tcctcgcctc  8220
ctcttcttcc tcctcttcct cacccccatg gaagtcaggc ccgaggaacc tctagtggtg  8280
aaggtggaag agggagataa cgctgtgctg cagtgcctca aggggacctc agatggcccc  8340
actcagcagc tgacctggtc tcgggagtcc ccgcttaaac ccttcttaaa actcagcctg  8400
gggctgccag gcctgggaat ccacatgagg cccctggcca tctggctttt catcttcaac  8460
gtctctcaac agatgggggg cttctacctg tgccagccgg ggcccccctc tgagaaggcc  8520
tggcagcctg gctggacagt caatgtggag ggcagcgggg agctgttccg gtggaatgtt  8580
tcggacctag gtggcctggg ctgtggcctg aagaacaggt cctcagaggg ccccagctcc  8640
ccttccggga agctcatgag ccccaagctg tatgtgtggg ccaaagaccg ccctgagatc  8700
tgggagggag agcctccgtg tctcccaccg agggacagcc tgaaccagag cctcagccag  8760
gacctcacca tggcccctgg ctccacactc tggctgtcct gtggggtacc ccctgactct  8820
gtgtccaggg gcccccctctc ctggacccat gtgcacccca aggggcctaa gtcattgctg  8880
agcctagagc tgaaggacga tcgcccggcc agagatatgt gggtaatgga gacgggtctg  8940
ttgttgcccc gggccacagc tcaagacgct ggaaagtatt attgtcaccg tggcaacctg  9000
accatgtcat tccacctgga gatcactgct cggccagtac tatggcactg gctgctgagg  9060
actggtggct ggaaggtctc agctgtgact ttggcttatc tgatcttctg cctgtgttcc  9120
cttgtgggca ttcttcatct tcaaagagcc ctggtcctga ggaggaaaag atgaacgcgt  9180
gaattcataa aataaaagat tttatttagt ctccagaaaa agggggggaat gaaagacccc  9240
acctgtaggt ttggcaagct agcttaagta acgccatttt gcaaggcatg gaaaaataca  9300
taactgagaa tagagaagtt cagatcaagg tcaggaacag atggaacagc tgaatatggg  9360
ccaaacagga tatctgtggt aagcagttcc tgccccggct cagggccaag aacagatgga  9420
acagctgaat atgggccaaa caggatatct gtggtaagca gttcctgccc cggctcaggg  9480
ccaagaacag atggtcccca gatgcggtcc agccctcagc agtttctaga gaaccatcag  9540
atgtttccag ggtgccccaa ggacctgaaa tgaccctgtg ccttatttga actaaccaat  9600
cagttcgctt ctcgcttctg ttcgcgcgct tctgctcccc gagctcaata aaagagccca  9660
caacccctca ctcggggcgc cagtcctccg attgactgag tcgcccgggt acccgtgtat  9720
ccaataaacc ctcttgcagt tgcatccgac ttgtggtctc gctgttcctt gggagggtct  9780
cctctgagtg attgactacc cgtcagcggg ggtctttcat tgttacttaa agttacattg  9840
gcttccttga aataaacatg gagtattcag aatgtgtcat aaatatttct aattttaaga  9900
tagtatctcc attggctttc tactttttct tttatttttt tttgtcctct gtcttccatt  9960
tgttgttgtt gttgtttgtt tgtttgtttg ttggttggtt ggttaatttt tttttaaaga  10020
tcctacacta tagttcaagc tagactatta gctactctgt aacccagggt gaccttgaag  10080
tcatgggtag cctgctgttt tagccttccc acatctaaga ttacaggtat gagctatcat  10140
ttttggtata ttgattgatt gattgattga tgtgtgtgtg tgtgattgtg tttgtgtgtg  10200
tgactgtgaa aatgtgtgta tgggtgtgtg tgaatgtgtg tatgtatgtg tgtgtgtgag  10260
tgtgtgtgtg tgtgtgtgca tgtgtgtgtg tgtgactgtg tctatgtgta tgactgtgtg  10320
tgtgtgtgtg tgtgtgtgtg tgtgtgtgtg tgtgtgtgtg ttgtgaaaaa atattctatg  10380
gtagtgagag ccaacgctcc ggctcaggtg tcaggttggt ttttgagaca gagtctttca  10440
cttagcttgg                                                        10450

SEQ ID NO: 55          moltype = DNA  length = 33
FEATURE                Location/Qualifiers
misc_feature           1..33
                       note = hCD19t-SalI-R
source                 1..33
                       mol_type = other DNA
                       organism = synthetic construct
SEQUENCE: 55
tggtcgactc atcttttcct cctcaggacc agg                              33

SEQ ID NO: 56          moltype = DNA  length = 9406
FEATURE                Location/Qualifiers
misc_feature           1..9406
                       note = sRRVe-F4-hCD19t vector
source                 1..9406
                       mol_type = other DNA
                       organism = synthetic construct
SEQUENCE: 56
aacgccattt tgcaaggcat ggaaaaatac ataactgaga atagaaaagt tcagatcaag  60
gtcaggaaca gatggaacag ctgaatatgg gccaaacagg atatctgtgg taagcagttc  120
ctgccccggc tcagggccaa gaacagatgg aacagctgaa tatgggccaa acaggatatc  180
tgtggtaagc agttcctgcc ccggctcagg gccaagaaca gatggtcccc agatgcggtc  240
cagccctcag cagtttctag agaaccatca gatgtttcca gggtgcccca aggacctgaa  300
```

-continued

```
atgaccctgt gccttatttg aactaaccaa tcagttcgct tctcgcttct gttcgcgcgc  360
ttatgctccc cgagctcaat aaaagagccc acaacccctc actcggggcg ccagtcctcc  420
gattgactga gtcgcccggg tacccgtgta tccaataaac cctcttgcag ttgcatccga  480
cttgtggtct cgctgttcct tgggagggtc tcctctgagt gattgactac ccgtcagcgg  540
gggtctttca tttgggggct cgtccgggat cgggagaccc ctgcccaggg accaccgacc  600
caccaccggg aggtaagctg gccagcaact tatctgtgtc tgtccgattg tctagtgtct  660
atgactgatt ttatgcgcct gcgtcggtac tagttagcta actagctctg tatctggcgg  720
acccgtggtg gaactgacga gttcggaaca cccggccgca accctgggag acgtcccagg  780
gacttcgggg gccgtttttg tggcccgacc tgagtcctaa aatcccgatc gtttaggact  840
ctttggtgca cccccccttag aggagggata tgtggttctg gtaggagacg agaacctaaa  900
acagttcccg cctccgtctg aatttttgct ttcggtttgg gaccgaagcc gcgccgcgcg  960
tcttgtctgc tgcagcatcg ttctgtgttg tctctgtctg actgtgtttc tgtatttgtc  1020
tgaaaatatg ggcccgggct agcctgttac cactccctta agtttgacct taggtcactg  1080
gaaagatgtc gagcggatcg ctcacaacca gtcggtagat gtcaagaaga gacgttgggt  1140
taccttctgc tctgcagaat ggccaacctt taacgtcgga tggccgcgag acggcacctt  1200
taaccgagac ctcactaccc aggttaagat caaggtcttt tcacctggcc cgcatggaca  1260
cccagaccag gtggggtaca tcgtgacctg ggaagccttg gcttttgacc cccctccctg  1320
ggtcaagccc tttgtacacc ctaagcctcc gcctcctctt cctccatccg ccccgtctct  1380
ccccccttgaa cctcctcgtt cgaccccgcc tcgatcctcc ctttatccag ccctcactcc  1440
ttctctaggc gcccccatat ggccatatga gatcttatat ggggcacccc cgccccttgt  1500
aaacttccct gaccctgaca tgacaagagt tactaacagc ccctctctcc aagctcactt  1560
acaggctctc tacttagtcc agcacgaagt ctggagacct ctggcggcag cctaccaaga  1620
acaactggac cgaccggtgg tacctcaccc ttaccgagtc ggcgacacag tgtgggtccg  1680
ccgacaccag actaagaacc tagaacctcg ctggaaagga ccttacacag tcctgctgac  1740
cacccccacc gccctcaaag tagacggcat cgcagcttgg atacacgccg cccacgtgat  1800
ggcgcgttca acgctctcaa aacccccctca agataagatt aacccgtgga agcccttaat  1860
agtcatggga gtcctgttag gagtagggat ggcagagagc cccccatcagg tctttaatgt  1920
aacctggaga gtcaccaacc tgatgactgg gcgtaccgcc aatgccacct ccctcctggg  1980
aactgtacaa gatgccttcc caaaattata ttttgatcta tgtgatctgg tcggagagga  2040
gtgggaccct tcagaccagg aaccgtatgt cgggtatggc tgcaagtacc ccgcagggag  2100
acagcggacc cggacttttg acttttacgt gtgccctggg cataccgtaa agtcggggtg  2160
tgggggacca ggagagggct actgtggtaa atgggggtgt gaaaccaccg gacaggctta  2220
ctggaagccc acatcatcgt gggacctaat ctcccttaag cgcggtaaca cccccctggga  2280
cacgggatgc tctaaagttg cctgtggccc ctgctacgac ctctccaaag tatccaattc  2340
cttccaaggg gctactcgag gggcagatg caaccctcta gtcctagaat tcactgatgc  2400
aggaaaaaag gctaactggg acgggcccaa atcgtgggga ctgagactgt accggacagg  2460
aacagatcct attaccatgt tctccctgac ccggcaggtc cttaatgtgg gaccccgagt  2520
ccccataggg cccaacccag tattacccga ccaaagactc ccttcctcac caatagagat  2580
tgtaccggct ccacagccac ctagcccccct caataccagt taccccccctt ccactaccag  2640
tacaccctca acctccccta caagtccaag tgtcccacag ccacccccag gaactggaga  2700
tagactacta gctctagtca aaggagccta tcaggcgctt aacctcacca atcccgacaa  2760
gacccaagaa tgttggctgt gcttagtgtc gggacctcct tattacgaag gagtagcggt  2820
cgtgggcact tataccaatc attccaccgc tccggccaac tgtacggcca cttcccaaca  2880
taagcttacc ctatctgaag tgacaggaca gggcctatgc atgggggcag tacctaaaac  2940
tcaccaggcc ttatgtaaca ccacccaaag cgccggctca ggatcctact accttgcagc  3000
acccgccgga acaatgtggg cttgcagcac tggattgact ccctgcttgt ccaccacggt  3060
gctcaatcta accacagatt attgtgtatt agttgaactc tggcccagag taatttacca  3120
ctcccccgat tatatgtatg gtcagcttga acagcgtacc aaatataaaa gagagccagt  3180
atcattgacc ctggcccttc tactaggagg attaaccatg ggagggattg cagctggaat  3240
agggacgggg accactgcct taattaaaac ccagcagttt gagcagcttc atgccgctat  3300
ccagacagac ctcaacgaag tcgaaaagtc aattaccaac ctagaaaagt cactgacctc  3360
gttgtctgaa gtagtcctac agaaccgcag aggcctagat ttgctattcc taaaggaggg  3420
aggtctctgc gcagccctaa aagaagaatg ttgtttttat gcagaccaca cggggctagt  3480
gagagacagc atggccaaat taagagaaag gcttaatcag agacaaaaac tatttgagac  3540
aggccaagga tggttcgaag ggctgtttaa tagatccccc tggtttacca ccttaatctc  3600
caccatcatg ggacctctaa tagtactctt actgatctta ctctttggac cttgcattct  3660
caatcgatta gtccaatttg ttaaagacag gatatcagtg gtccaggctc tagttttgac  3720
tcaacaatat caccagctga agcctataga gtacgagcca tagcacgtga aggctgccga  3780
ccccggggggt ggacatcctc tagactgcca tggcgcggat ctcgacgttt aaacggaagt  3840
gaaagggcag ccaaaacgta acaccgcccc ggttttccct ggaaattcca tattggcacg  3900
cattctattg gctgagctgc gttcacgtgg gtataagagg cgcgaccagc gtcggtaccg  3960
tcgcagtctt cggtctgacc accgtagaac gcagagcggc cgcatgccac ctcctcgcct  4020
cctcttcttc ctcctcttcc tcacccccat ggaagtcagg cccgaggaac ctctagtggt  4080
gaaggtggaa gagggagata acgctgtgct gcagtgcctc aaggggacct cagatggccc  4140
cactcagcag ctgacctggt ctcgggagtc cccgcttaaa cccttcttaa aactcagcct  4200
ggggctgcca ggcctgggaa tccacatgag gcccctggcc atctggcttt tcatcttcaa  4260
cgtctctcaa cagatggggg gcttctacct gtgccagccg gggcccccct ctgagaaggc  4320
ctggcagcct ggctggacag tcaatgtgga gggcagcggg gagctgttcc ggtggaatgt  4380
ttcggaccta ggtggcctgg gctgtggcct gaagaacagg tcctcagagg gccccagctc  4440
cccttccggg aagctcatga gccccaagct gtatgtgtgg gccaaagacc gccctgagat  4500
ctgggaggga gagcctccgt gtctcccacc gagggacagc ctgaaccaga gcctcagcca  4560
ggacctcacc atggcccctg gctccacact ctggctgtcc tgtggggtac cccctgactc  4620
tgtgtccagg ggcccccctct cctggaccca tgtgcacccc aaggggccta agtcattgct  4680
gagcctagag ctgaaggacg atcgcccggc cagagatatg tgggtaatgg agacgggtct  4740
gttgttgccc cgggccacag ctcaagacgc tggaaagtat tattgtcacc gtggcaacct  4800
gaccatgtca ttccacctgg agatcactgc tcggccagta ctatggcact ggctgctgag  4860
gactggtggc tggaaggtct cagctgtgac tttggcttat ctgatcttct gcctgtgttc  4920
ccttgtgggc attcttcatc ttcaaagagc cctggtcctg aggaggaaaa gatgagtcga  4980
cccatcgaac atcgatggta ccagatccga taaaataaaa gatttattt agtctccaga  5040
```

-continued

```
aaaagggggg aatgaaagac cccacctgta ggtttggcaa gctagcttaa gtaacgccat  5100
tttgcaaggc atggaaaaat acataactga gaatagagaa gttcagatca aggtcaggaa  5160
cagatggaac agctgaatat gggccaaaca ggatatctgt ggtaagcagt tcctgccccg  5220
gctcagggcc aagaacagat ggaacagctg aatatgggcc aaacaggata tctgtggtaa  5280
gcagttcctg ccccggctca gggccaagaa cagatggtcc ccagatgcgg tccagccctc  5340
agcagtttct agagaaccat cagatgtttc cagggtgccc caaggacctg aaatgaccct  5400
gtgccttatt tgaactaacc aatcagttcg cttctcgctt ctgttcgcgc gcttctgctc  5460
cccgagctca ataaaagagc ccacaacccc tcactcgggg cgccagtcct ccgattgact  5520
gagtcgcccg ggtacccgtg tatccaataa accctcttgc agttgcatcc gacttgtggt  5580
ctcgctgttc cttgggaggg tctcctctga gtgattgact acccgtcagc gggggtcttt  5640
cacacatgca gcatgtatca aaattaattt ggtttttttt cttaagtatt tacattaaat  5700
ggccatagta cttaaagtta cattggcttc cttgaaataa acatggagta ttcagaatgt  5760
gtcataaata tttctaattt taagatagta tctccattgg ctttctactt tttcttttat  5820
ttttttttgt cctctgtctt ccatttgttg ttgttgttgt ttgtttgttt gtttgttggt  5880
tggttggtta attttttttt aaagatccta cactatagtt caagctagac tattagctac  5940
tctgtaaccc agggtgacct tgaagtcatg ggtagcctgc tgttttagcc ttcccacatc  6000
taagattaca ggtatgagct atcatttttg gtatatgatt gattgattga ttgatgtgtg  6060
tgtgtgtgat tgtgtttgtg tgtgtgactg tgaaaatgtg tgtatgggtg tgtgtgaatg  6120
tgtgtatgta tgtgtgtgtg tgagtgtgtg tgtgtgtgtg tgcatgtgtg tgtgtgtgac  6180
tgtgtctatg tgtatgactg tgtgtgtgtg tgtgtgtgtg tgtgtgtgtg tgtgtgtgtg  6240
tgtgttgtga aaaaatattc tatggtagtg agagccaacg ctccggctca ggtgtcaggt  6300
tggtttttga gacagagtct ttcacttagc ttggaattca ctggccgtcg ttttacaacg  6360
tcgtgactgg gaaaaccctg gcgttaccca acttaatcgc cttgcagcac atcccccttt  6420
cgccagctgg cgtaatagcg aagaggcccg caccgatcgc ccttcccaac agttgcgcag  6480
cctgaatggc gaatggcgcc tgatgcggta ttttctcctt acgcatctgt gcggtatttc  6540
acaccgcata tggtgcactc tcagtacaat ctgctctgat gccgcatagt taagccagcc  6600
ccgacacccg ccaacacccg ctgacgcgcc ctgacgggct tgtctgctcc cggcatccgc  6660
ttacagacaa gctgtgaccg tctccgggag ctgcatgtgt cagaggtttt caccgtcatc  6720
accgaaacgc gcgagacgaa agggcctcgt gatacgccta tttttatagg ttaatgtcat  6780
gataataatg gtttcttaga cgtcaggtgg cacttttcgg ggaaatgtgc gcggaacccc  6840
tatttgttta tttttctaaa tacattcaaa tatgtatccg ctcatgagac aataaccctg  6900
ataaatgctt caataatatt gaaaaaggaa gagtatgagt attcaacatt tccgtgtcgc  6960
ccttattccc ttttttgcgg cattttgcct tcctgttttt gctcacccag aaacgctggt  7020
gaaagtaaaa gatgctgaag atcagttggg tgcacgagtg ggttacatcg aactggatct  7080
caacagcggt aagatccttg agagttttcg ccccgaagaa cgttttccaa tgatgagcac  7140
ttttaaagtt ctgctatgtg gcgcggtatt atcccgtatt gacgccgggc aagagcaact  7200
cggtcgccgc atacactatt ctcagaatga cttggttgag tactcaccag tcacagaaaa  7260
gcatcttacg gatggcatga cagtaagaga attatgcagt gctgccataa ccatgagtga  7320
taacactgcg gccaacttac ttctgacaac gatcggagga ccgaaggagc taaccgcttt  7380
tttgcacaac atgggggatc atgtaactcg ccttgatcgt tgggaaccgg agctgaatga  7440
agccatacca aacgacgagc gtgacaccac gatgcctgta gcaatggcaa caacgttgcg  7500
caaactatta actggcgaac tacttactct agcttcccgg caacaattaa tagactggat  7560
ggaggcggat aaagttgcag gaccacttct gcgctcggcc cttccggctg gctggtttat  7620
tgctgataaa tctggagccg gtgagcgtgg gtctcgcggt atcattgcag cactggggcc  7680
agatggtaag ccctcccgta tcgtagttat ctacacgacg gggagtcagg caactatgga  7740
tgaacgaaat agacagatcg ctgagatagg tgcctcactg attaagcatt ggtaactgtc  7800
agaccaagtt tactcatata tactttagat tgatttaaaa cttcattttt aatttaaaag  7860
gatctaggtg aagatccttt ttgataatct catgaccaaa atcccttaac gtgagttttc  7920
gttccactga gcgtcagacc ccgtagaaaa gatcaaagga tcttcttgag atcctttttt  7980
tctgcgcgta atctgctgct tgcaaacaaa aaaaccaccg ctaccagcgg tggtttgttt  8040
gccggatcaa gagctaccaa ctctttttcc gaaggtaact ggcttcagca gagcgcagat  8100
accaaatact gttcttctag tgtagccgta gttaggccac cacttcaaga actctgtagc  8160
accgcctaca tacctcgctc tgctaatcct gttaccagtg gctgctgcca gtggcgataa  8220
gtcgtgtctt accgggttgg actcaagacg atagttaccg gataaggcgc agcggtcggg  8280
ctgaacgggg ggttcgtgca cacagcccag cttggagcga acgacctaca ccgaactgag  8340
atacctacag cgtgagctat gagaaagcgc cacgcttccc gaagggagaa aggcggacag  8400
gtatccggta agcggcaggg tcggaacagg agagcgcacg agggagcttc cagggggaaa  8460
cgcctggtat ctttatagtc ctgtcgggtt tcgccacctc tgacttgagc gtcgattttt  8520
gtgatgctcg tcaggggggc ggagcctatg gaaaaacgcc agcaacgcgg cctttttacg  8580
gttcctggcc ttttgctggc cttttgctca catgttcttt cctgcgttat cccctgattc  8640
tgtggataac cgtattaccg cctttgagtg agctgatacc gctcgccgca gccgaacgac  8700
cgagcgcagc gagtcagtga gcgaggaagc ggaagagcgc ccaatacgca aaccgcctct  8760
ccccgcgcgt tggccgattc attaatgcag ctggcacgac aggtttcccg actggaaagc  8820
gggcagtgag cgcaacgcaa ttaatgtgag ttagctcact cattaggcac cccaggcttt  8880
acactttatg cttccggctc gtatgttgtg tggaattgtg agcggataac aatttcacac  8940
aggaaacagc tatgaccatg attacgccaa gctttgctcc taggagtttc ctaatacttc  9000
ccaaactcaa atatataaag catttgactt gttctatgcc ctaggggggcg gggggaagct  9060
aagccagctt tttttaacat ttaaaatgtt aattccattt taaatgcaca gatgttttta  9120
tttcataagg gtttcaatgt gcatgaatgc tgcaatattc ctgttaccaa agctagtata  9180
aataaaaata gataaacgtg gaaattactt agagtttctg tcattaacgt ttccttcctc  9240
agttgacaac ataaatgcgc tgctgagcaa gccagtttgc atctgtcagg atcaatttcc  9300
cattatgcca gtcatattaa ttactagtca attagttgat tttatttttt gacatataca  9360
tgtgaatgaa agaccccacc tgtaggtttg gcaagctagc ttaagt                9406

SEQ ID NO: 57           moltype = DNA  length = 9535
FEATURE                 Location/Qualifiers
misc_feature            1..9535
                        note = spRRVe-mGM-CSF
source                  1..9535
```

-continued mol_type = other DNA
organism = synthetic construct
SEQUENCE: 57
aacgccattt tgcaaggcat ggaaaaatac ataactgaga atagaaaagt tcagatcaag 60
gtcaggaaca gatggaacag ctgaatatgg gccaaacagg atatctgtgg taagcagttc 120
ctgccccggc tcagggccaa gaacagatgg aacagctgaa tatgggccaa acaggatatc 180
tgtggtaagc agttcctgcc ccggctcagg gccaagaaca gatggtcccc agatgcggtc 240
cagccctcag cagtttctag agaaccatca gatgtttcca gggtgcccca aggacctgaa 300
atgaccctgt gccttatttg aactaaccaa tcagttcgct tctcgcttct gttcgcgcgc 360
ttatgctccc cgagctcaat aaaagagccc acaacccctc actcggggcg ccagtcctcc 420
gattgactga gtcgcccggg tacccgtgta tccaataaac cctcttgcag ttgcatccga 480
cttgtggtct cgctgttcct tgggagggtc tcctctgagt gattgactac ccgtcagcgg 540
gggtctttca tttgggggct cgtccgggat cgggagaccc ctgcccaggg accaccgacc 600
caccaccggg aggtaagctg gccagcaact tatctgtgtc tgtccgattg tctagtgtct 660
atgactgatt ttatgcgcct gcgtcggtac tagttagcta actagctctg tatctggcgg 720
acccgtggtg gaactgacga gttcggaaca cccggccgca accctgggag acgtcccagg 780
gacttcgggg gccgtttttg tggcccgacc tgagtcctaa aatcccgatc gtttaggact 840
ctttggtgca cccccccttag aggagggata tgtggttctg gtaggagacg agaacctaaa 900
acagttcccg cctccgtctg aatttttgct ttcggtttgg gaccgaagcc gcgccgcgcg 960
tcttgtctgc tgcagcatcg ttctgtgttg tctctgtctg actgtgtttc tgtatttgtc 1020
tgaaaatatg ggcccgggct agcctgttac cactccctta agtttgacct taggtcactg 1080
gaaagatgtc gagcggatcg ctcacaacca gtcggtagat gtcaagaaga gacgttgggt 1140
taccttctgc tctgcagaat ggccaacctt taacgtcgga tggccgcgag acggcacctt 1200
taaccgagac ctcactaccc aggttaagat caaggtcttt tcacctggcc cgcatggaca 1260
cccagaccag gtggggtaca tcgtgacctg ggaagccttg gcttttgacc cccctccctg 1320
ggtcaagccc tttgtacacc ctaagcctcc gcctcctctt cctccatccg ccccgtctct 1380
ccccccttgaa cctcctcgtt cgaccccgcc tcgatcctcc ctttatccag ccctcactcc 1440
ttctctaggc gcccccatat ggccatatga gatcttatat ggggcacccc cgccccttgt 1500
aaacttccct gaccctgaca tgacaagagt tactaacagc ccctctctcc aagctcactt 1560
acaggctctc tacttagtcc agcacgaagt ctggagacct ctggcggcag cctaccaaga 1620
acaactggac cgaccggtgg tacctcaccc ttaccgagtc ggcgacacag tgtgggtccg 1680
ccgacaccag actaagaacc tagaacctcg ctggaaagga ccttacacag tcctgctgac 1740
caccccccacc gccctcaaag tagacggcat cgcagcttgg atacacgccg cccacaattc 1800
gatcatacct ggtgttgctg actaccccga ccgcggtaaa agtcgatggt attgctgcct 1860
gggtccatgc ttctcacctc aaacctgcac caccttcggc accagatgag tcctgggagc 1920
tggaaaagac tgatcatcct cttaagctgc gtattcggcg gcggcgggac gagtctgcaa 1980
aataagaacc cccaccagcc catgaccctc acttggcagg tactgtccca aactggagac 2040
gttgtctggg atacaaaggc agtccagccc ccttggactt ggtggcccac acttaaacct 2100
gatgtatgtg ccttggcggc tagtcttgag tcctgggata tcccgggaac cgatgtctcg 2160
tcctctaaac gagtcagacc tccggactca gactatactg ccgcttataa gcaaatcacc 2220
tggggagcca tagggtgcag ctaccctcgg gctaggacta gaatggcaag ctctaccttc 2280
tacgtatgtc cccgggatgg ccggaccctt tcagaagcta gaaggtgcgg ggggctagaa 2340
tccctatact gtaaagaatg ggattgtgag accacgggga ccggttattg gctatctaaa 2400
tcctcaaaag acctcataac tgtaaaatgg gaccaaaata gcgaatggac tcaaaaattt 2460
caacagtgtc accagaccgg ctggtgtaac cccccttaaaa tagatttcac agacaaagga 2520
aaattatcca aggactggat aacgggaaaa acctggggat taagattcta tgtgtctgga 2580
catccaggcg tacagttcac cattcgctta aaaatcacca acatgccagc tgtggcagta 2640
ggtcctgacc tcgtccttgt ggaacaagga cctcctagaa cgtccctcgc tctcccacct 2700
cctcttcccc caagggaagc gccaccgcca tctctccccg actctaactc cacagccctg 2760
gcgactagtg cacaaactcc cacggtgaga aaaacaattg ttaccctaaa cactccgcct 2820
cccaccacag gcgacagact tttgatcttt gtgcaggggg ccttcctaac cttaaatgct 2880
accaacccag gggccactga gtcttgctgg ctttgtttgg ccatgggccc cccttattat 2940
gaagcaatag cctcatcagg agaggtcgcc tactccaccg accttgaccg gtgccgctgg 3000
gggacccaag gaaagctcac cctcactgag gtctcaggac acgggttgtg cataggaaag 3060
gtgcccttta cccatcagca tctctgcaat cagaccctat ccatcaattc ctccggagac 3120
catcagtatc tgctcccctc caaccatagc tggtgggctt gcagcactgg cctcacccct 3180
tgcctctcca cctcagtttt taatcagact agagatttct gtatccaggt ccagctgatt 3240
cctcgcatct attactatcc tgaagaagtt ttgttacagg cctatgacaa ttctcacccc 3300
aggactaaaa gagaggctgt ctcacttacc ctagctgttt tactggggtt gggaatcacg 3360
gcgggaatag gtactggttc aactgcctta attaaaggac ctatagacct ccagcaaggc 3420
ctgacaagcc tccagatcgc catagatgct gacctccggg ccctccaaga ctcagtcagc 3480
aagttagagg actcactgac ttccctgtcc gaggtagtgc tccaaaatag gagaggcctt 3540
gacttgctgt ttctaaaaga aggtggcctc tgtgcggccc taaaggaaga gtgctgtttt 3600
tacatagacc actcaggtgc agtacgggac tccatgaaaa aactcaaaga aaaactggat 3660
aaaagacagt tagagcgcca gaaaagccaa aactggtatg aaggatggtt caataactcc 3720
ccttggttca ctaccctgct atcaaccatc gctgggcccc tattactcct ccttctgttg 3780
ctcatcctcg ggccatgcat catcaataag ttagttcaat tcatcaatga taggataagt 3840
gcagttaaaa ttctggtcct tagacaaaaa tatcaggccc tagagaacga aggtaacctt 3900
taacacgtga aggctgccga ccccgggggt ggaccatcct ctagactgtg ctcgacgttt 3960
aaaccgataa gcgttttttt caataacagg aaagtcccat tggagccaag tacattgagt 4020
caatagggac tttccaatgg gttttgccca gtacataagg tcaatgggag gtaagccaat 4080
gggtttttcc cattactggc acgtatactg agtcattagg gactttccaa tgggttttgc 4140
ccagtacata aggtcaatag ggggtgaatca acaggaaagt cccattggag ccaagtacac 4200
tgagtcaata gggactttcc attgggtttt gcccagtaca aaaggtcaat agggggtgag 4260
tcaatgggtt tttcccatta ttggcacgta cataaggtca ataggggtga gtcattgggt 4320
ttttccagcc aatttaatta aaacgccatg tactttccca ccattgacgt caatgggcta 4380
ttgaaactaa tgcaacgtga cctttaaacg gtactttccc atagctgatt aatgggaaag 4440
taccgttctc gagccaatac acgtcaatgg gaagtgaaag ggcagccaaa acgtaacacc 4500
gccccggttt tcccctggaa attccatatt ggcacgcatt ctattggctg agctgcgttc 4560

-continued

```
tacgtgggta taagaggcgc gaccagcgtc ggtaccgtcg cagtcttcgg tctgaccacc  4620
gtagaacgca gaactctaga actagtggat cccccgggct gcaggaattc aggatgtggc  4680
tgcagaattt acttttcctg ggcattgtgg tctacagcct ctcagcaccc acccgctcac  4740
ccatcactgt cacccggcct tggaagcatg tagaggccat caaagaagcc ctgaacctcc  4800
tggatgacat gcctgtcacg ttgaatgaag aggtagaagt cgtctctaac gagttctcct  4860
tcaagaagct aacatgtgtg cagacccgcc tgaagatatt cgagcagggt ctacggggca  4920
atttcaccaa actcaagggc gccttgaaca tgacagccag ctactaccag acatactgcc  4980
ccccaactcc ggaaacggac tgtgaaacac aagttaccac ctatgcggat ttcatagaca  5040
gccttaaaac ctttctgact gatatcccct ttgaatgcaa aaaaccagtc caaaaatgag  5100
aattcgatat caagcttatc gatggggtac cagatccgat aaaataaaag attttattta  5160
gtctccagaa aaagggggga atgaaagacc ccacctgtag gtttggcaag ctagcttaag  5220
taacgccatt ttgcaaggca tggaaaaata cataactgag aatagagaag ttcagatcaa  5280
ggtcaggaac agatggaaca gctgaatatg ggccaaacag gatatctgtg gtaagcagtt  5340
cctgccccgg ctcagggcca agaacagatg gaacagctga atatgggcca aacaggatat  5400
ctgtggtaag cagttcctgc cccggctcag ggccaagaac agatggtccc cagatgcggt  5460
ccagccctca gcagtttcta gagaaccatc agatgtttcc agggtgcccc aaggacctga  5520
aatgaccctg tgccttattt gaactaacca atcagttcgc ttctcgcttc tgttcgcgcg  5580
cttctgctcc ccgagctcaa taaaagagcc cacaacccct cactcggggc gccagtcctc  5640
cgattgactg agtcgcccgg gtacccgtgt atccaataaa ccctcttgca gttgcatccg  5700
acttgtggtc tcgctgttcc ttgggagggt ctcctctgag tgattgacta cccgtcagcg  5760
ggggtctttc acacatgcag catgtatcaa aattaatttg gttttttttc ttaagtattt  5820
acattaaatg gccatagtac ttaaagttac attggcttcc ttgaaataaa catggagtat  5880
tcagaatgtg tcataaatat ttctaatttt aagatagtat ctccattggc tttctacttt  5940
ttctttattt tttttttgtc ctctgtcttc catttgttgt tgttgttgtt tgtttgtttg  6000
tttgttggtt ggttggttaa tttttttta aagatcctac actatagttc aagctagact  6060
attagctact ctgtaaccca gggtgacctt gaagtcatgg gtagcctgct gttttagcct  6120
tcccacatct aagattacag gtatgagcta tcatttttgg tatatgattg attgattgat  6180
tgatgtgtgt gtgtgtgatt gtgtttgtgt gtgtgactgt gaaaatgtgt gtatgggtgt  6240
gtgtgaatgt gtgtatgtat gtgtgtgtgt gagtgtgtgt gtgtgtgtgt gcatgtgtgt  6300
gtgtgtgact gtgtctatgt gtatgactgt gtgtgtgtgt gtgtgtgtgt gtgtgtgtgt  6360
gtgtgtgtgt gtgttgtgaa aaaatattct atggtagtga gagccaacgc tccggctcag  6420
gtgtcaggtt ggtttttgag acagagtctt tcacttagct tggaattcac tggccgtcgt  6480
tttacaacgt cgtgactggg aaaaccctgg cgttacccaa cttaatcgcc ttgcagcaca  6540
tccccctttc gccagctggc gtaatagcga agaggcccgc accgatcgcc cttcccaaca  6600
gttgcgcagc ctgaatggcg aatggcgcct gatgcggtat tttctcctta cgcatctgtg  6660
cggtatttca caccgcatat ggtgcactct cagtacaatc tgctctgatg ccgcatagtt  6720
aagccagccc cgacacccgc caacacccgc tgacgcgccc tgacgggctt gtctgctccc  6780
ggcatccgct tacagacaag ctgtgaccgt ctccgggagc tgcatgtgtc agaggttttc  6840
accgtcatca ccgaaacgcg cgagacgaaa gggcctcgtg atacgcctat ttttataggt  6900
taatgtcatg ataataatgg tttcttagac gtcaggtggc acttttcggg gaaatgtgcg  6960
cggaacccct atttgtttat ttttctaaat acattcaaat atgtatccgc tcatgagaca  7020
ataaccctga taaatgcttc aataatattg aaaaaggaag agtatgagta ttcaacattt  7080
ccgtgtcgcc cttattccct tttttgcggc attttgcctt cctgtttttg ctcacccaga  7140
aacgctggtg aaagtaaaag atgctgaaga tcagttgggt gcacgagtgg gttacatcga  7200
actggatctc aacagcggta agatccttga gagttttcgc cccgaagaac gttttccaat  7260
gatgagcact tttaaagttc tgctatgtgg cgcggtatta tcccgtattg acgccgggca  7320
agagcaactc ggtcgccgca tacactattc tcagaatgac ttggttgagt actcaccagt  7380
cacagaaaag catcttacgg atggcatgac agtaagagaa ttatgcagtg ctgccataac  7440
catgagtgat aacactgcgg ccaacttact tctgacaacg atcggaggac cgaaggagct  7500
aaccgctttt ttgcacaaca tgggggatca tgtaactcgc cttgatcgtt gggaaccgga  7560
gctgaatgaa gccataccaa acgacgagcg tgacaccacg atgcctgtag caatggcaac  7620
aacgttgcgc aaactattaa ctggcgaact acttactcta gcttcccggc aacaattaat  7680
agactggatg gaggcggata aagttgcagg accacttctg cgctcggccc ttccggctgg  7740
ctggtttatt gctgataaat ctggagccgg tgagcgtggg tctcgcggta tcattgcagc  7800
actggggcca gatggtaagc cctcccgtat cgtagttatc tacacgacgg ggagtcaggc  7860
aactatggat gaacgaaata gacagatcgc tgagataggt gcctcactga ttaagcattg  7920
gtaactgtca gaccaagttt actcatatat actttagatt gatttaaaac ttcattttta  7980
atttaaaagg atctaggtga agatcctttt tgataatctc atgaccaaaa tcccttaacg  8040
tgagttttcg ttccactgag cgtcagaccc cgtagaaaag atcaaaggat cttcttgaga  8100
tccttttttt ctgcgcgtaa tctgctgctt gcaaacaaaa aaaccaccgc taccagcggt  8160
ggtttgtttg ccggatcaag agctaccaac tctttttccg aaggtaactg gcttcagcag  8220
agcgcagata ccaaatactg ttcttctagt gtagccgtag ttaggccacc acttcaagaa  8280
ctctgtagca ccgcctacat acctcgctct gctaatcctg ttaccagtgg ctgctgccag  8340
tggcgataag tcgtgtctta ccgggttgga ctcaagacga tagttaccgg ataaggcgca  8400
gcggtcgggc tgaacggggg gttcgtgcac acagcccagc ttggagcgaa cgacctacac  8460
cgaactgaga tacctacagc gtgagctatg agaaagcgcc acgcttcccg aagggagaaa  8520
ggcggacagg tatccggtaa gcggcagggt cggaacagga gagcgcacga gggagcttcc  8580
agggggaaac gcctggtatc tttatagtcc tgtcgggttt cgccacctct gacttgagcg  8640
tcgatttttg tgatgctcgt caggggggcg gagcctatgg aaaaacgcca gcaacgcggc  8700
ctttttacgg ttcctggcct tttgctggcc ttttgctcac atgttctttc ctgcgttatc  8760
ccctgattct gtggataacc gtattaccgc ctttgagtga gctgataccg ctcgccgcag  8820
ccgaacgacc gagcgcagcg agtcagtgag cgaggaagcg gaagagcgcc caatacgcaa  8880
accgcctctc cccgcgcgtt ggccgattca ttaatgcagc tggcacgaca ggtttcccga  8940
ctggaaagcg ggcagtgagc gcaacgcaat taatgtgagt tagctcactc attaggcacc  9000
ccaggcttta cactttatgc ttccggctcg tatgttgtgt ggaattgtga gcggataaca  9060
atttcacaca ggaaacagct atgaccatga ttacgccaag ctttgctcct aggagtttcc  9120
taatacttcc caaactcaaa tatataaagc atttgacttg ttctatgccc taggggggcgg  9180
ggggaagcta agccagcttt ttttaacatt taaaatgtta attccatttt aaatgcacag  9240
atgtttttat ttcataaggg tttcaatgtg catgaatgct gcaatattcc tgttaccaaa  9300
```

```
gctagtataa ataaaaatag ataaacgtgg aaattactta gagtttctgt cattaacgtt  9360
tccttcctca gttgacaaca taaatgcgct gctgagcaag ccagtttgca tctgtcagga  9420
tcaatttccc attatgccag tcatattaat tactagtcaa ttagttgatt tttatttttg  9480
acatatacat gtgaatgaaa gaccccacct gtaggtttgg caagctagct taagt       9535

SEQ ID NO: 58          moltype = DNA  length = 30
FEATURE                Location/Qualifiers
misc_feature           1..30
                       note = mGM-CSF-F-NotI
source                 1..30
                       mol_type = other DNA
                       organism = synthetic construct
SEQUENCE: 58
cggcggccgc aggatgtggc tgcagaattt                                   30

SEQ ID NO: 59          moltype = DNA  length = 28
FEATURE                Location/Qualifiers
misc_feature           1..28
                       note = mGM-CSF-R-MluI
source                 1..28
                       mol_type = other DNA
                       organism = synthetic construct
SEQUENCE: 59
tggtcgactc atttttggac tggttttt                                     28

SEQ ID NO: 60          moltype = DNA  length = 9907
FEATURE                Location/Qualifiers
misc_feature           1..9907
                       note = sRRVgp-F4-mGM-CSF vector
source                 1..9907
                       mol_type = other DNA
                       organism = synthetic construct
SEQUENCE: 60
catgtgagca aaaggccagc aaaaggccag gaaccgtaaa aaggccgcgt tgctggcgtt  60
tttccatagg ctccgccccc ctgacgagca tcacaaaaat cgacgctcaa gtcagaggtg  120
gcgaaacccg acaggactat aaagatacca ggcgtttccc cctggaagct ccctcgtgcg  180
ctctcctgtt ccgaccctgc cgcttaccgg atacctgtcc gcctttctcc cttcgggaag  240
cgtggcgctt tctcatagct cacgctgtag gtatctcagt tcggtgtagg tcgttcgctc  300
caagctgggc tgtgtgcacg aaccccccgt tcagcccgac cgctgcgcct tatccggtaa  360
ctatcgtctt gagtccaacc cggtaagaca cgacttatcg ccactggcag cagccactgg  420
taacaggatt agcagagcga ggtatgtagg cggtgctaca gagttcttga agtggtggcc  480
taactacggc tacactagaa ggacagtatt tggtatctgc gctctgctga agccagttac  540
cttcggaaaa agagttggta gctcttgatc cggcaaacaa accaccgctg gtagcggtgg  600
tttttttgtt tgcaagcagc agattacgcg cagaaaaaaa ggatctcaag aagatccttt  660
gatcttttct acggggtctg acgctcagtg gaacgaaaac tcacgttaag ggattttggt  720
catgagatta tcaaaaagga tcttcaccta gatcctttta aattaaaaat gaagttttaa  780
atcaatctaa agtatatatg agtaacctga tcaggactct tccttttcat gaacaataaa  840
actgtctgct tacataaaca gtaatacaag gggtgttatg agccatattc aacgggaaac  900
gtcttgctct aggccgcgat taaattccaa catggatgct gatttatatg ggtataaatg  960
ggctcgcgat aatgtcgggc aatcaggtgc gacaatctat cgattgtatg ggaagcccga  1020
tgcgccagag ttgtttctga aacatggcaa aggtagcgtt gccaatgatg ttacagatga  1080
gatggtcaga ctaaactggc tgacggaatt tatgcctctt ccgaccatca agcattttat  1140
ccgtactcct gatgatgcat ggttactcac cactgcgatc cccgggaaaa cagcattcca  1200
ggtattagaa gaatatcctg attcaggtga aaatattgtt gatgcgctgg cagtgttcct  1260
gcgccggttg cattcgattc ctgtttgtaa ttgtcctttt aacagcgatc gcgtatttcg  1320
tctcgctcag gcgcaatcac gaatgaataa cggtttggtt gatgcgagtg attttgatga  1380
cgagcgtaat ggctggcctg ttgaacaagt ctggaaagaa atgcataaac ttttgccatt  1440
ctcaccggat tcagtcgtca ctcatggtga tttctcactt gataacctta tttttgacga  1500
ggggaaatta ataggttgta ttgatgttgg acgagtcgga atcgcagacc gataccagga  1560
tcttgccatc ctatggaact gcctcggtga gttttctcct tcattacaga aacggctttt  1620
tcaaaaatat ggtattgata atcctgatat gaataaattg cagtttcatt tgatgctcga  1680
tgagtttttc taagaatttg tgaatgaaag accccacctg taggtttggc aagctagctt  1740
aagtaacgcc attttgcaag gcatggaaaa atacataact gagaatagaa aagttcagat  1800
caaggtcagg aacagatgga acagctgaat atgggccaaa caggatatct gtggtaagca  1860
gttcctgccc cggctcaggg ccaagaacag atggaacagc tgaatatggg ccaaacagga  1920
tatctgtggt aagcagttcc tgccccggct cagggccaag aacagatggt ccccagatgc  1980
ggtccagccc tcagcagttt ctagagaacc atcagatgtt tccagggtgc cccaaggacc  2040
tgaaatgacc ctgtgcctta tttgaactaa ccaatcagtt cgcttctcgc ttctgttcgc  2100
gcgcttatgc tccccgagct caataaaaga gcccacaacc cctcactcgg ggcgccagtc  2160
ctccgattga ctgagtcgcc cgggtacccg tgtatccaat aaaccctctt gcagttgcat  2220
ccgacttgtg gtctcgctgt tccttgggag ggtctcctct gagtgattga ctacccgtca  2280
gcgggggtct ttcatttggg ggctcgtccg ggatcgggag acccctgccc agggaccacc  2340
gacccaccac cgggaggtaa gctggccagc aacttatctg tgtctgtccg attgtctagt  2400
gtctatgact gattttatgc gcctgcgtcg gtactagtta gctaactagc tctgtatctg  2460
gcggacccgt ggtggaactg acgagttcgg aacacccggc cgcaaccctg ggagacgtcc  2520
cagggacttc gggggccgtt tttgtggccc gacctgagtc caaaaatccc gatcgttttg  2580
gactctttgg tgcacccccc ttagaggagg gatatgtggt tctggtagga gacgagaacc  2640
taaaacagtt cccgcctccg tctgaatttt tgctttcggt ttgggaccga agccgcgccg  2700
cgcgtcttgt ctgctgcagc atcgttctgt gttgtctctg tctgactgtg tttctgtatt  2760
```

-continued

```
tgtctgagaa tatgggccag actgttacca ctcccttaag tttgacctta ggtcactgga  2820
aagatgtcga gcggatcgct cacaaccagt cggtagatgt caagaagaga cgttgggtta  2880
ccttctgctc tgcagaatgg ccaaccttta acgtcggatg gccgcgagac ggcaccttta  2940
accgagacct catcacccag gttaagatca aggtcttttc acctggcccg catggacacc  3000
cagaccaggt cccctacatc gtgacctggg aagccttggc ttttgacccc cctccctggg  3060
tcaagccctt tgtacaccct aagcctccgc ctcctcttcc tccatccgcc ccgtctctcc  3120
cccttgaacc tcctcgttcg accccgcctc gatcctccct ttatccagcc ctcactcctt  3180
ctctaggcgc caaacctaaa cctcaagttc tttctgacag tggggggccg ctcatcgacc  3240
tacttacaga agaccccccg ccttataggg acccaagacc accccccttcc gacagggacg  3300
gaaatggtgg agaagcgacc cctgcgggag aggcaccgga cccctcccca atggcatctc  3360
gcctacgtgg gagacgggag ccccctgtgg ccgactccac tacctcgcag gcattccccc  3420
tccgcgcagg aggaaacgga cagcttcaat actggccgtt ctcctcttct gacctttaca  3480
actggaaaaa taataaccct tctttttctg aagatccagg taaactgaca gctctgatcg  3540
agtctgttct catcacccat cagcccacct gggacgactg tcagcagctg ttggggactc  3600
tgctgaccgg agaagaaaaa caacgggtgc tcttagaggc tagaaaggcg gtgcggggcg  3660
atgatgggcg ccccactcaa ctgcccaatg aagtcgatgc cgcttttccc ctcgagcgcc  3720
cagactggga ttacaccacc caggcaggta ggaaccacct agtccactat cgccagttgc  3780
tcctagcggg tctccaaaac gcgggcagaa gccccaccaa tttggccaag gtaaaaggaa  3840
taacacaagg gcccaatgag tctccctcgg ccttcctaga gagacttaag gaagcctatc  3900
gcaggtacac tccttatgac cctgaggacc cagggcaaga aactaatgtg tctatgtctt  3960
tcatttggca gtctgcccca gacattggga gaaagttaga gaggttagaa gatttaaaaa  4020
acaagacgct tggagatttg gttagagagg cagaaaagat ctttaataaa cgagaaaccc  4080
cggaagaaag agaggaacgt atcaggagag aaacagagga aaaagaagaa cgccgtagga  4140
cagaggatga gcagaaagag aaagaaagag atcgtaggag acatagagag atgagcaagc  4200
tattggccac tgtcgttagt ggacagaaac aggatagaca gggaggagaa cgaaggaggt  4260
cccaactcga tcgcgaccag tgtgcctact gcaaagaaaa ggggcactgg gctaaagatt  4320
gtcccaagaa accacgagga cctcggggac caagacccca gacctccctc ctgaccctag  4380
atgactaggg aggtcagggt caggagcccc cccctgaacc caggataacc ctcaaagtcg  4440
gggggcaacc cgtcaccttc ctggtagata ctggggccca acactccgtg ctgacccaaa  4500
atcctggacc cctaagtgat aagtctgcct gggtccaagg ggctactgga ggaaagcggt  4560
atcgctggac cacggatcgc aaagtacatc tagctaccgg taaggtcacc cactctttcc  4620
tccatgtacc agactgtccc tatcctctgt taggaagaga tttgctgact aaactaaaag  4680
cccaaatcca ctttgaggga tcaggagctc aggttatggg accaatgggg cagcccctgc  4740
aagtgttgac cctaaatata gaagatgagc atcggctaca tgagacctca aaagagccag  4800
atgtttctct agggtccaca tggctgtctg attttcctca ggcctgggcg gaaaccgggg  4860
gcatgggact ggcagttcgc caagctcctc tgatcatacc tctgaaagca acctctaccc  4920
ccgtgtccat aaaacaatac cccatgtcac aagaagccag actggggatc aagccccaca  4980
tacagagact gttggaccag ggaatactgg taccctgcca gtccccctgg aacacgcccc  5040
tgctacccgt taagaaacca gggactaatg attataggcc tgtccaggat ctgagagaag  5100
tcaacaagcg ggtggaagac atccacccca ccgtgcccaa cccttacaac ctcttgagcg  5160
ggctcccacc gtcccaccag tggtacactg tgcttgattt aaaggatgcc tttttctgcc  5220
tgagactcca ccccaccagt cagcctctct tcgcctttga gtggagagat ccagagatgg  5280
gaatctcagg acaattgacc tggaccagac tcccacaggg tttcaaaaac agtcccaccc  5340
tgtttgatga ggcactgcac agagacctag cagacttccg gatccagcac ccagacttga  5400
tcctgctaca gtacgtggat gacttactgc tggccgccac ttctgagcta gactgccaac  5460
aaggtactcg ggccctgtta caaaccctag ggaacctcgg gtatcgggcc tcggccaaga  5520
aagcccaaat ttgccagaaa caggtcaagt atctggggta tcttctaaaa gagggtcaga  5580
gatggctgac tgaggccaga aaagagactg tgatggggca gcctactccg aagacccctc  5640
gacaactaag ggagttccta gggacggcag gcttctgtcg cctctggatc cctgggtttg  5700
cagaaatggc agccccccttg taccctctca ccaaaacggg gactctgttt aattggggcc  5760
cagaccaaca aaaggcctat caagaaatca agcaagctct tctaactgcc ccagccctgg  5820
ggttgccaga tttgactaag ccctttgaac tctttgtcga cgagaagcag ggctacgcca  5880
aaggtgtcct aacgcaaaaa ctgggacctt ggcgtcggcc ggtggcctac ctgtccaaaa  5940
agctagaccc agtagcagct gggtggcccc cttgcctacg gatggtagca gccattgccg  6000
tactgacaaa ggatgcaggc aagctaacca tgggacagcc actagtcatt ctggcccccc  6060
atgcagtaga ggcactagtc aaacaacccc ccgaccgctg gctttccaac gcccggatga  6120
ctcactatca ggccttgctt ttggacacgg accgggtcca gttcggaccg gtggtagccc  6180
tgaacccggc tacgctgctc ccactgcctg aggaagggct gcaacacaac tgccttgata  6240
tcctggccga agcccacgga acccgacccg acctaacgga ccagccgctc ccagacgccg  6300
accacacctg gtacacggat ggaagcagtc tcttacaaga gggacagcgt aaggcgggag  6360
ctgcggtgac caccgagacc gaggtaatct gggctaaagc cctgccagcc gggacatccg  6420
ctcagcgggc tgaactgata gcactcaccc aggccctaaa gatggcagaa ggtaagaagc  6480
taaatgttta tactgatagc cgttatgctt ttgctactgc ccatatccat ggagaaatat  6540
acagaaggcg tgggttgctc acatcagaag gcaaagagat caaaaataaa gacgagatct  6600
tggccctact aaaagccctc tttctgccca aaagacttag cataatccat tgtccaggac  6660
atcaaaaggg acacagcgcc gaggctagag gcaaccggat ggctgaccaa gcggcccgaa  6720
aggcagccat cacagagact ccagacacct ctaccctcct catagaaaat tcatcaccct  6780
acacctcaga acattttcat tacacagtga ctgatataaa ggacctaacc aagttggggg  6840
ccatttatga taaaacaaag aagtattggg tctaccaagg aaaacctgtg atgcctgacc  6900
agtttacttt tgaattatta gactttcttc atcagctgac tcacctcagc ttctcaaaaa  6960
tgaaggctct cctagagaga agccacagtc cctactacat gctgaaccgg gatcgaacac  7020
tcaaaaatat cactgagacc tgcaaagctt gtgcacaagt caacgccagc aagtctgccg  7080
ttaaacaggg aactagggtc cgcgggcatc ggcccggcac tcattgggag atcgatttca  7140
ccgagataaa gcccggattg tatggctata aatatcttct agtttttata gataccttt  7200
ctggctggat agaagccttc ccaaccaaga aagaaaccgc caaggtcgta accaagaagc  7260
tactagagga gatcttcccc aggttcggca tgcctcaggt attgggaact gacaatgggc  7320
ctgccttcgt ctccaaggtg agtcagacag tggccgatct gttggggatt gattggaaat  7380
tacattgtgc atacagaccc caaagctcag gccaggtaga aagaatgaat agaaccatca  7440
aggagacttt aactaaatta acgcttgcaa ctggctctag agactgggtg ctcctactcc  7500
```

-continued

```
ccttagccct gtaccgagcc cgcaacacgc cgggccccca tggcctcacc ccatatgaga  7560
tcttatatgg ggcacccccg cccccttgtaa acttccctga ccctgacatg acaagagtta  7620
ctaacagccc ctctctccaa gctcacttac aggctctcta cttagtccag cacgaagtct  7680
ggagacctct ggcggcagcc taccaagaac aactggaccg accggtggta cctcaccctt  7740
accgagtcgg cgacacagtg tgggtccgcc gacaccagac taagaaccta gaacctcgct  7800
ggaaaggacc ttacacagtc ctgctgacca cccccaccgc cctcaaagta gacggcatcg  7860
cagcttggat acacgccgcc cacgtgaagg ctgccgaccc cgggggtgga ccatcctcta  7920
gactgacatg gcgcgttcaa cgctctcaaa accccttaaa aataaggtta acccgcgagg  7980
ccccctaatc cccttaattc ttctgatgct cagaggggtc agtaaacgaa ttcggaagtg  8040
aaagggcagc caaaacgtaa caccgccccg gttttccctg gaaattccat attggcacgc  8100
attctattgg ctgagctgcg ttcacgtggg tataagaggc gcgaccagcg tcggtaccgt  8160
cgcagtcttc ggtctgacca ccgtagaacg cagagcggcc gcaggatgtg gctgcagaat  8220
ttacttttcc tgggcattgt ggtctacagc ctctcagcac ccacccgctc acccatcact  8280
gtcacccggc cttggaagca tgtagaggcc atcaaagaag ccctgaacct cctggatgac  8340
atgcctgtca cgttgaatga agaggtagaa gtcgtctcta acgagttctc cttcaagaag  8400
ctaacatgtg tgcagacccg cctgaagata ttcgagcagg gtctacgggg caatttcacc  8460
aaactcaagg gcgccttgaa catgacagcc agctactacc agacatactg ccccccaact  8520
ccggaaacgg actgtgaaac acaagttacc acctatgcgg atttcataga cagccttaaa  8580
acctttctga ctgatatccc ctttgaatgc aaaaaaccag tccaaaaatg aacgcgtgaa  8640
ttcataaaat aaaagatttt atttagtctc cagaaaaagg ggggaatgaa agaccccacc  8700
tgtaggtttg gcaagctagc ttaagtaacg ccattttgca aggcatggaa aaatacataa  8760
ctgagaatag agaagttcag atcaaggtca ggaacagatg gaacagctga atatgggcca  8820
aacaggatat ctgtggtaag cagttcctgc cccggctcag ggccaagaac agatggaaca  8880
gctgaatatg ggccaaacag gatatctgtg gtaagcagtt cctgccccgg ctcagggcca  8940
agaacagatg gtccccagat gcggtccagc cctcagcagt ttctagagaa ccatcagatg  9000
tttccagggt gccccaagga cctgaaatga ccctgtgcct tatttgaact aaccaatcag  9060
ttcgcttctc gcttctgttc gcgcgcttct gctccccgag ctcaataaaa gagcccacaa  9120
cccctcactc ggggcgccag tcctccgatt gactgagtcg cccgggtacc cgtgtatcca  9180
ataaaccctc ttgcagttgc atccgacttg tggtctcgct gttccttggg agggtctcct  9240
ctgagtgatt gactacccgt cagcgggggt ctttcattgt tacttaaagt tacattggct  9300
tccttgaaat aaacatggag tattcagaat gtgtcataaa tatttctaat tttaagatag  9360
tatctccatt ggctttctac tttttctttt atttttttttt gtcctctgtc ttccatttgt  9420
tgttgttgtt gtttgtttgt ttgtttgttg gttggttggt taattttttt ttaaagatcc  9480
tacactatag ttcaagctag actattagct actctgtaac ccagggtgac cttgaagtca  9540
tgggtagcct gctgttttag ccttcccaca tctaagatta caggtatgag ctatcatttt  9600
tggtatattg attgattgat tgattgatgt gtgtgtgtgt gattgtgttt gtgtgtgtga  9660
ctgtgaaaat gtgtgtatgg gtgtgtgtga atgtgtgtat gtatgtgtgt gtgtgagtgt  9720
gtgtgtgtgt gtgtgcatgt gtgtgtgtgt gactgtgtct atgtgtatga ctgtgtgtgt  9780
gtgtgtgtgt gtgtgtgtgt gtgtgtgtgt gtgtgtgttg tgaaaaaata ttctatggta  9840
gtgagagcca acgctccggc tcaggtgtca ggttggtttt tgagacagag tctttcactt  9900
agcttgg                                                            9907
```

```
SEQ ID NO: 61           moltype = DNA  length = 9593
FEATURE                 Location/Qualifiers
misc_feature            1..9593
                        note = spRRVe-hGM-CSF
source                  1..9593
                        mol_type = other DNA
                        organism = synthetic construct
SEQUENCE: 61
aacgccattt tgcaaggcat ggaaaaatac ataactgaga atagaaaagt tcagatcaag  60
gtcaggaaca gatggaacag ctgaatatgg gccaaacagg atatctgtgg taagcagttc  120
ctgccccggc tcagggccaa gaacagatgg aacagctgaa tatgggccaa acaggatatc  180
tgtggtaagc agttcctgcc ccggctcagg gccaagaaca gatggtcccc agatgcggtc  240
cagccctcag cagtttctag agaaccatca gatgtttcca gggtgcccca aggacctgaa  300
atgaccctgt gccttatttg aactaaccaa tcagttcgct tctcgcttct gttcgcgcgc  360
ttatgctccc cgagctcaat aaaagagccc acaacccctc actcggggcg ccagtcctcc  420
gattgactga gtcgcccggg tacccgtgta tccaataaac cctcttgcag ttgcatccga  480
cttgtggtct cgctgttcct tgggagggtc tcctctgagt gattgactac ccgtcagcgg  540
gggtctttca tttgggggct cgtccgggat cgggagaccc ctgcccaggg accaccgacc  600
caccaccggg aggtaagctg gccagcaact tatctgtgtc tgtccgattg tctagtgtct  660
atgactgatt ttatgcgcct gcgtcggtac tagttagcta actagctctg tatctggcgg  720
acccgtggtg gaactgacga gttcggaaca cccggccgca accctgggag acgtcccagg  780
gacttcgggg gccgtttttg tggcccgacc tgagtcctaa aatcccgatc gtttaggact  840
ctttggtgca cccccttag aggagggata tgtggttctg gtaggagacg agaacctaaa  900
acagttcccg cctccgtctg aatttttgct ttcggtttgg gaccgaagcc gcgccgcgcg  960
tcttgtctgc tgcagcatcg ttctgtgttg tctctgtctg actgtgtttc tgtatttgtc  1020
tgaaaatatg ggcccgggct agcctgttac cactccctta agtttgacct taggtcactg  1080
gaaagatgtc gagcggatcg ctcacaacca gtcggtagat gtcaagaaga gacgttgggt  1140
taccttctgc tctgcagaat ggccaacctt taacgtcgga tggccgcgag acggcacctt  1200
taaccgagac ctcactaccc aggttaagat caaggtcttt tcacctggcc cgcatggaca  1260
cccagaccag gtggggtaca tcgtgacctg ggaagccttg gcttttgacc cccctccctg  1320
ggtcaagccc tttgtacacc ctaagcctcc gcctcctctt cctccatccg ccccgtctct  1380
ccccttgaa cctcctcgtt cgaccccgcc tcgatcctcc ctttatccag ccctcactcc  1440
ttctctaggc gcccccatat ggccatatga gatcttatat ggggcacccc cgccccttgt  1500
aaacttccct gaccctgaca tgacaagagt tactaacagc ccctctctcc aagctcactt  1560
acaggctctc tacttagtcc agcacgaagt ctggagacct ctggcggcag cctaccaaga  1620
acaactggac cgaccggtgg tacctcaccc ttaccgagtc ggcgacacag tgtgggtccg  1680
ccgacaccag actaagaacc tagaacctcg ctggaaagga ccttacacag tcctgctgac  1740
```

-continued

```
caccccacc gccctcaaag tagacggcat cgcagcttgg atacacgccg cccacaattc  1800
gatcatacct ggtgttgctg actaccccga ccgcggtaaa agtcgatggt attgctgcct  1860
gggtccatgc ttctcacctc aaacctgcac caccttcggc accagatgag tcctgggagc  1920
tggaaaagac tgatcatcct cttaagctgc gtattcggcg gcggcgggac gagtctgcaa  1980
aataagaacc cccaccagcc catgaccctc acttggcagg tactgtccca aactggagac  2040
gttgtctggg atacaaaggc agtccagccc ccttggactt ggtggcccac acttaaacct  2100
gatgtatgtg ccttggcggc tagtcttgag tcctgggata tcccgggaac cgatgtctcg  2160
tcctctaaac gagtcagacc tccggactca gactatactg ccgcttataa gcaaatcacc  2220
tggggagcca tagggtgcag ctaccctcgg gctaggacta gaatggcaag ctctaccttc  2280
tacgtatgtc cccgggatgg ccggaccctt tcagaagcta gaaggtgcgg ggggctagaa  2340
tccctatact gtaaagaatg ggattgtgag accacgggga ccggttattg gctatctaaa  2400
tcctcaaaag acctcataac tgtaaaatgg gaccaaaata gcgaatggac tcaaaaattt  2460
caacagtgtc accagaccgg ctggtgtaac cccccttaaaa tagatttcac agacaaagga  2520
aaattatcca aggactggat aacgggaaaa acctggggat taagattcta tgtgtctgga  2580
catccaggcg tacagttcac cattcgctta aaaatcacca acatgccagc tgtggcagta  2640
ggtcctgacc tcgtccttgt ggaacaagga cctcctagaa cgtccctcgc tctcccacct  2700
cctcttcccc caagggaagc gccaccgcca tctctccccg actctaactc cacagccctg  2760
gcgactagtg cacaaactcc cacggtgaga aaaacaattg ttaccctaaa cactccgcct  2820
cccaccacag gcgacagact tttgatcttt gtgcaggggg ccttcctaac cttaaatgct  2880
accaacccag gggccactga gtcttgctgg ctttgtttgg ccatgggccc cccttattat  2940
gaagcaatag cctcatcagg agaggtcgcc tactccaccg accttgaccg gtgccgctgg  3000
gggacccaag gaaagctcac cctcactgag gtctcaggac acgggttgtg cataggaaag  3060
gtgcccttta cccatcagca tctctgcaat cagaccctat ccatcaattc ctccggagac  3120
catcagtatc tgctcccctc caaccatagc tggtgggctt gcagcactgg cctcacccct  3180
tgcctctcca cctcagtttt taatcagact agagatttct gtatccaggt ccagctgatt  3240
cctcgcatct attactatcc tgaagaagtt ttgttacagg cctatgacaa ttctcacccc  3300
aggactaaaa gagaggctgt ctcacttacc ctagctgttt tactggggtt gggaatcacg  3360
gcgggaatag gtactggttc aactgcctta attaaaggac ctatagacct ccagcaaggc  3420
ctgacaagcc tccagatcgc catagatgct gacctccggg ccctccaaga ctcagtcagc  3480
aagttagagg actcactgac ttccctgtcc gaggtagtgc tccaaaatag gagaggcctt  3540
gacttgctgt ttctaaaaga aggtggcctc tgtgcggccc taaaggaaga gtgctgtttt  3600
tacatagacc actcaggtgc agtacgggac tccatgaaaa aactcaaaga aaaactggat  3660
aaaagacagt tagagcgcca gaaaagccaa aactggtatg aaggatggtt caataactcc  3720
ccttggttca ctaccctgct atcaaccatc gctgggcccc tattactcct ccttctgttg  3780
ctcatcctcg ggccatgcat catcaataag ttagttcaat tcatcaatga taggataagt  3840
gcagttaaaa ttctggtcct tagacaaaaa tatcaggccc tagagaacga aggtaacctt  3900
taattttgct ctaagattag agctattcac aagagaaatg ggatcacta gtgaattaaa  3960
caacaggaaa gttccattgg agccaagtac attgagtcaa tagggacttt ccaatgggtt  4020
ttgcccagta cataaggtca atgggaggta agccaatggg tttttcccat tactggcacg  4080
tatactgagt cattagggac tttccaatgg gttttgccca gtacataagg tcaatagggg  4140
tgaatcaaca ggaaagtccc attggagcca agtacactga gtcaataggg actttccatt  4200
gggttttgcc cagtacaaaa ggtcaatagg gggtgagtca atgggttttt cccattattg  4260
gcacgtacat aaggtcaata ggggtgagtc attgggtttt tccagccaat ttaattaaaa  4320
cgccatgtac tttcccacca ttgacgtcaa tgggctattg aaactaatgc aacgtgacct  4380
ttaaacggta ctttcccata gctgattaat gggaaagtac cgttctcgag ccaatacacg  4440
tcaatgggaa gtgaaagggc agccaaaacg taacaccgcc ccggttttcc ctggaaattc  4500
catattggca cgcattctat tggctgagct gcgttctacg tgggtataag aggcgcgacc  4560
agcgtcggta ccgtcgcagt cttcggtctg accaccgtag aacgcagaac tctagaacta  4620
gtcgggatcc gttaacatgt ggctgcagag cctgctgctc ttgggcactg tggcctgcag  4680
catctctgca cccgcccgct cgcccagccc cagcacgcag ccctgggagc atgtgaatgc  4740
catccaggag gcccggcgtc tcctgaacct gagtagagac actgctgctg agatgaatga  4800
aacagtagaa gtcatctcag aaatgtttga cctccaggag ccgacctgcc tacagacccg  4860
cctggagctg tacaagcagg gcctgcgggg cagcctcacc aagctcaagg gccccttgac  4920
catgatggcc agccactaca agcagcactg ccctccaacc ccggaaactt cctgtgcaac  4980
ccagattatc acctttgaaa gtttcaaaga gaacctgaag gactttctgc ttgtcatccc  5040
ctttgactgc tgggagccag tccaggagtg agttaacatc gatggggtac cagatccgga  5100
ttagtccaat ttgttaaaga caggatatca gtggtccagg ctctagtttt gactcaacaa  5160
tatcaccagc tgaagcctat agagtacgag ccatagataa aataaaagat tttatttagt  5220
ctccagaaaa agggggggaat gaaagacccc acctgtaggt ttggcaagct agcttaagta  5280
acgccatttt gcaaggcatg gaaaaataca taactgagaa tagagaagtt cagatcaagg  5340
tcaggaacag atggaacagc tgaatatggg ccaaacagga tatctgtggt aagcagttcc  5400
tgccccggct cagggccaag aacagatgga acagctgaat atgggccaaa caggatatct  5460
gtggtaagca gttcctgccc cggctcaggg ccaagaacag atggtcccca gatgcggtcc  5520
agccctcagc agtttctaga gaaccatcag atgtttccag ggtgccccaa ggacctgaaa  5580
tgaccctgtg ccttatttga actaaccaat cagttcgctt ctcgcttctg ttcgcgcgct  5640
tctgctcccc gagctcaata aaagagccca caacccctca ctcggggcgc cagtcctccg  5700
attgactgag tcgcccgggt acccgtgtat ccaataaacc ctcttgcagt tgcatccgac  5760
ttgtggtctc gctgttcctt gggagggtct cctctgagtg attgactacc cgtcagcggg  5820
ggtctttcac acatgcagca tgtatcaaaa ttaatttggt ttttttttctt aagtatttac  5880
attaaatggc catagtactt aaagttacat tggcttcctt gaaataaaca tggagtattc  5940
agaatgtgtc ataaatattt ctaattttaa gatagtatct ccattggctt tctacttttt  6000
cttttatttt tttttgtcct ctgtcttcca tttgttgttg ttgttgtttg tttgtttgtt  6060
tgttggttgg ttggttaatt ttttttttaaa gatcctacac tatagttcaa gctagactat  6120
tagctactct gtaacccagg gtgaccttga agtcatgggt agcctgctgt tttagccttc  6180
ccacatctaa gattacaggt atgagctatc atttttggta tatgattgat tgattgattg  6240
atgtgtgtgt gtgtgattgt gtttgtgtgt gtgactgtga aaatgtgtgt atgggtgtgt  6300
gtgaatgtgt gtatgtatgt gtgtgtgtga gtgtgtgtgt gtgtgtgtgc atgtgtgtgt  6360
gtgtgactgt gtctatgtgt atgactgtgt gtgtgtgtgt gtgtgtgtgt gtgtgtgtgt  6420
gtgtgtgtgt gttgtgaaaa aatattctat ggtagtgaga gccaacgctc cggctcaggt  6480
```

-continued

```
gtcaggttgg tttttgagac agagtctttc acttagcttg gaattcactg gccgtcgttt  6540
tacaacgtcg tgactgggaa aaccctggcg ttacccaact taatcgcctt gcagcacatc  6600
cccctttcgc cagctggcgt aatagcgaag aggcccgcac cgatcgccct tcccaacagt  6660
tgcgcagcct gaatggcgaa tggcgcctga tgcggtattt tctccttacg catctgtgcg  6720
gtatttcaca ccgcatatgg tgcactctca gtacaatctg ctctgatgcc gcatagttaa  6780
gccagccccg acacccgcca acacccgctg acgcgccctg acgggcttgt ctgctcccgg  6840
catccgctta cagacaagct gtgaccgtct ccgggagctg catgtgtcag aggttttcac  6900
cgtcatcacc gaaacgcgcg agacgaaagg gcctcgtgat acgcctattt ttataggtta  6960
atgtcatgat aataatggtt tcttagacgt caggtggcac ttttcgggga aatgtgcgcg  7020
gaacccctat ttgtttattt ttctaaatac attcaaatat gtatccgctc atgagacaat  7080
aaccctgata aatgcttcaa taatattgaa aaaggaagag tatgagtatt caacatttcc  7140
gtgtcgccct tattcccttt tttgcggcat tttgccttcc tgtttttgct cacccagaaa  7200
cgctggtgaa agtaaaagat gctgaagatc agttgggtgc acgagtgggt tacatcgaac  7260
tggatctcaa cagcggtaag atccttgaga gttttcgccc cgaagaacgt tttccaatga  7320
tgagcacttt taaagttctg ctatgtggcg cggtattatc ccgtattgac gccgggcaag  7380
agcaactcgg tcgccgcata cactattctc agaatgactt ggttgagtac tcaccagtca  7440
cagaaaagca tcttacggat ggcatgacag taagagaatt atgcagtgct gccataacca  7500
tgagtgataa cactgcggcc aacttacttc tgacaacgat cggaggaccg aaggagctaa  7560
ccgctttttt gcacaacatg ggggatcatg taactcgcct tgatcgttgg gaaccggagc  7620
tgaatgaagc cataccaaac gacgagcgtg acaccacgat gcctgtagca atggcaacaa  7680
cgttgcgcaa actattaact ggcgaactac ttactctagc ttcccggcaa caattaatag  7740
actggatgga ggcggataaa gttgcaggac cacttctgcg ctcggccctt ccggctggct  7800
ggtttattgc tgataaatct ggagccggtg agcgtgggtc tcgcggtatc attgcagcac  7860
tggggccaga tggtaagccc tcccgtatcg tagttatcta cacgacgggg agtcaggcaa  7920
ctatggatga acgaaataga cagatcgctg agataggtgc ctcactgatt aagcattggt  7980
aactgtcaga ccaagtttac tcatatatac tttagattga tttaaaactt catttttaat  8040
ttaaaaggat ctaggtgaag atcctttttg ataatctcat gaccaaaatc ccttaacgtg  8100
agttttcgtt ccactgagcg tcagaccccg tagaaaagat caaaggatct tcttgagatc  8160
cttttttctt gcgcgtaatc tgctgcttgc aaacaaaaaa accaccgcta ccagcggtgg  8220
tttgtttgcc ggatcaagag ctaccaactc tttttccgaa ggtaactggc ttcagcagag  8280
cgcagatacc aaatactgtt cttctagtgt agccgtagtt aggccaccac ttcaagaact  8340
ctgtagcacc gcctacatac ctcgctctgc taatcctgtt accagtggct gctgccagtg  8400
gcgataagtc gtgtcttacc gggttggact caagacgata gttaccggat aaggcgcagc  8460
ggtcgggctg aacggggggt tcgtgcacac agcccagctt ggagcgaacg acctacaccg  8520
aactgagata cctacagcgt gagctatgag aaagcgccac gcttcccgaa gggagaaagg  8580
cggacaggta tccggtaagc ggcagggtcg gaacaggaga gcgcacgagg gagcttccag  8640
ggggaaacgc ctggtatctt tatagtcctg tcgggtttcg ccacctctga cttgagcgtc  8700
gatttttgtg atgctcgtca ggggggcgga gcctatggaa aaacgccagc aacgcggcct  8760
ttttacggtt cctggccttt tgctggcctt ttgctcacat gttctttcct gcgttatccc  8820
ctgattctgt ggataaccgt attaccgcct ttgagtgagc tgataccgct cgccgcagcc  8880
gaacgaccga gcgcagcgag tcagtgagcg aggaagcgga agagcgccca atacgcaaac  8940
cgcctctccc cgcgcgttgg ccgattcatt aatgcagctg gcacgacagg tttcccgact  9000
ggaaagcggg cagtgagcgc aacgcaatta atgtgagtta gctcactcat taggcacccc  9060
aggctttaca ctttatgctt ccggctcgta tgttgtgtgg aattgtgagc ggataacaat  9120
ttcacacagg aaacagctat gaccatgatt acgccaagct ttgctcctag gagtttccta  9180
atacttccca aactcaaata tataaagcat ttgacttgtt ctatgcccta gggggcgggg  9240
ggaagctaag ccagcttttt ttaacattta aaatgttaat tccattttaa atgcacagat  9300
gtttttattt cataagggtt tcaatgtgca tgaatgctgc aatattcctg ttaccaaagc  9360
tagtataaat aaaaatagat aaacgtggaa attacttaga gtttctgtca ttaacgtttc  9420
cttcctcagt tgacaacata aatgcgctgc tgagcaagcc agtttgcatc tgtcaggatc  9480
aatttcccat tatgccagtc atattaatta ctagtcaatt agttgatttt tatttttgac  9540
atatacatgt gaatgaaaga ccccacctgt aggtttggca agctagctta agt         9593
```

```
SEQ ID NO: 62          moltype = DNA  length = 28
FEATURE                Location/Qualifiers
misc_feature           1..28
                       note = hGM-CSF-F-NotI
source                 1..28
                       mol_type = other DNA
                       organism = synthetic construct
SEQUENCE: 62
cggcggccgc aggatgtggc tgcagagc                                     28

SEQ ID NO: 63          moltype = DNA  length = 28
FEATURE                Location/Qualifiers
misc_feature           1..28
                       note = hGM-CSF-R-MluI
source                 1..28
                       mol_type = other DNA
                       organism = synthetic construct
SEQUENCE: 63
tggtcgactc actcctggac tggctccc                                     28

SEQ ID NO: 64          moltype = DNA  length = 9916
FEATURE                Location/Qualifiers
misc_feature           1..9916
                       note = sRRVgp-F4-hGM-CSF vector
source                 1..9916
                       mol_type = other DNA
```

-continued

```
                        organism = synthetic construct
SEQUENCE: 64
catgtgagca aaaggccagc aaaaggccag gaaccgtaaa aaggccgcgt tgctggcgtt  60
tttccatagg ctccgccccc ctgacgagca tcacaaaaat cgacgctcaa gtcagaggtg  120
gcgaaacccg acaggactat aaagatacca ggcgtttccc cctggaagct ccctcgtgcg  180
ctctcctgtt ccgaccctgc cgcttaccgg atacctgtcc gcctttctcc cttcgggaag  240
cgtggcgctt tctcatagct cacgctgtag gtatctcagt tcggtgtagg tcgttcgctc  300
caagctgggc tgtgtgcacg aaccccccgt tcagcccgac cgctgcgcct tatccggtaa  360
ctatcgtctt gagtccaacc cggtaagaca cgacttatcg ccactggcag cagccactgg  420
taacaggatt agcagagcga ggtatgtagg cggtgctaca gagttcttga agtggtggcc  480
taactacggc tacactagaa ggacagtatt tggtatctgc gctctgctga agccagttac  540
cttcggaaaa agagttggta gctcttgatc cggcaaacaa accaccgctg gtagcggtgg  600
tttttttgtt tgcaagcagc agattacgcg cagaaaaaaa ggatctcaag aagatccttt  660
gatcttttct acggggtctg acgctcagtg gaacgaaaac tcacgttaag ggattttggt  720
catgagatta tcaaaaagga tcttcaccta gatcctttta aattaaaaat gaagttttaa  780
atcaatctaa agtatatatg agtaacctga tcaggactct tccttttcat gaacaataaa  840
actgtctgct tacataaaca gtaatacaag gggtgttatg agccatattc aacgggaaac  900
gtcttgctct aggccgcgat taaattccaa catggatgct gatttatatg ggtataaatg  960
ggctcgcgat aatgtcgggc aatcaggtgc gacaatctat cgattgtatg ggaagcccga  1020
tgcgccagag ttgtttctga aacatggcaa aggtagcgtt gccaatgatg ttacagatga  1080
gatggtcaga ctaaactggc tgacggaatt tatgcctctt ccgaccatca agcattttat  1140
ccgtactcct gatgatgcat ggttactcac cactgcgatc cccgggaaaa cagcattcca  1200
ggtattagaa gaatatcctg attcaggtga aaatattgtt gatgcgctgg cagtgttcct  1260
gcgccggttg cattcgattc ctgtttgtaa ttgtcctttt aacagcgatc gcgtatttcg  1320
tctcgctcag gcgcaatcac gaatgaataa cggtttggtt gatgcgagtg attttgatga  1380
cgagcgtaat ggctggcctg ttgaacaagt ctggaaagaa atgcataaac ttttgccatt  1440
ctcaccggat tcagtcgtca ctcatggtga tttctcactt gataacctta tttttgacga  1500
ggggaaatta ataggttgta ttgatgttgg acgagtcgga atcgcagacc gataccagga  1560
tcttgccatc ctatggaact gcctcggtga gttttctcct tcattacaga aacggctttt  1620
tcaaaaatat ggtattgata atcctgatat gaataaattg cagtttcatt tgatgctcga  1680
tgagtttttc taagaatttg tgaatgaaag accccacctg taggtttggc aagctagctt  1740
aagtaacgcc attttgcaag gcatggaaaa atacataact gagaatagaa aagttcagat  1800
caaggtcagg aacagatgga acagctgaat atgggccaaa caggatatct gtggtaagca  1860
gttcctgccc cggctcaggg ccaagaacag atggaacagc tgaatatggg ccaaacagga  1920
tatctgtggt aagcagttcc tgccccggct cagggccaag aacagatggt ccccagatgc  1980
ggtccagccc tcagcagttt ctagagaacc atcagatgtt tccagggtgc cccaaggacc  2040
tgaaatgacc ctgtgcctta tttgaactaa ccaatcagtt cgcttctcgc ttctgttcgc  2100
gcgcttatgc tccccgagct caataaaaga gcccacaacc cctcactcgg ggcgccagtc  2160
ctccgattga ctgagtcgcc cgggtacccg tgtatccaat aaaccctctt gcagttgcat  2220
ccgacttgtg gtctcgctgt tccttgggag ggtctcctct gagtgattga ctacccgtca  2280
gcgggggtct ttcatttggg ggctcgtccg ggatcgggag acccctgccc agggaccacc  2340
gacccaccac cgggaggtaa gctggccagc aacttatctg tgtctgtccg attgtctagt  2400
gtctatgact gattttatgc gcctgcgtcg gtactagtta gctaactagc tctgtatctg  2460
gcggacccgt ggtggaactg acgagttcgg aacacccggc cgcaaccctg ggagacgtcc  2520
cagggacttc gggggccgtt tttgtggccc gacctgagtc caaaaatccc gatcgttttg  2580
gactctttgg tgcacccccc ttagaggagg gatatgtggt tctggtagga gacgagaacc  2640
taaaacagtt cccgcctccg tctgaatttt tgctttcggt ttgggaccga agccgcgccg  2700
cgcgtcttgt ctgctgcagc atcgttctgt gttgtctctg tctgactgtg tttctgtatt  2760
tgtctgagaa tatgggccag actgttacca ctcccttaag tttgacctta ggtcactgga  2820
aagatgtcga gcggatcgct cacaaccagt cggtagatgt caagaagaga cgttgggtta  2880
ccttctgctc tgcagaatgg ccaaccttta acgtcggatg gccgcgagac ggcaccttta  2940
accgagacct catcacccag gttaagatca aggtcttttc acctggcccg catggacacc  3000
cagaccaggt cccctacatc gtgacctggg aagccttggc ttttgacccc cctccctggg  3060
tcaagccctt tgtacaccct aagcctccgc ctcctcttcc tccatccgcc ccgtctctcc  3120
cccttgaacc tcctcgttcg accccgcctc gatcctccct ttatccagcc ctcactcctt  3180
ctctaggcgc caaacctaaa cctcaagttc tttctgacag tggggggccg ctcatcgacc  3240
tacttacaga agaccccccg ccttataggg acccaagacc accccttcc gacagggacg  3300
gaaatggtgg agaagcgacc cctgcgggag aggcaccgga cccctcccca atggcatctc  3360
gcctacgtgg gagacgggag ccccctgtgg ccgactccac tacctcgcag gcattccccc  3420
tccgcgcagg aggaaacgga cagcttcaat actggccgtt ctcctcttct gacctttaca  3480
actggaaaaa taataaccct tctttttctg aagatccagg taaactgaca gctctgatcg  3540
agtctgttct catcacccat cagcccacct gggacgactg tcagcagctg ttggggactc  3600
tgctgaccgg agaagaaaaa caacgggtgc tcttagaggc tagaaaggcg gtgcggggcg  3660
atgatgggcg ccccactcaa ctgcccaatg aagtcgatgc cgcttttccc ctcgagcgcc  3720
cagactggga ttacaccacc caggcaggta ggaaccacct agtccactat cgccagttgc  3780
tcctagcggg tctccaaaac gcgggcagaa gccccaccaa tttggccaag gtaaaaggaa  3840
taacacaagg gcccaatgag tctccctcgg ccttcctaga gagacttaag gaagcctatc  3900
gcaggtacac tccttatgac cctgaggacc cagggcaaga aactaatgtg tctatgtctt  3960
tcatttggca gtctgcccca gacattggga gaaagttaga gaggttagaa gatttaaaaa  4020
acaagacgct tggagatttg gttagagagg cagaaaagat ctttaataaa cgagaaaccc  4080
cggaagaaag agaggaacgt atcaggagag aaacagagga aaaagaagaa cgccgtagga  4140
cagaggatga gcagaaagag aaagaaagag atcgtaggag acatagagag atgagcaagc  4200
tattggccac tgtcgttagt ggacagaaac aggatagaca gggaggagaa cgaaggaggt  4260
cccaactcga tcgcgaccag tgtgcctact gcaaagaaaa ggggcactgg gctaaagatt  4320
gtcccaagaa accacgagga cctcggggac caagacccca gacctccctc ctgaccctag  4380
atgactaggg aggtcagggt caggagcccc cccctgaacc caggataacc ctcaaagtcg  4440
gggggcaacc cgtcaccttc ctggtagata ctggggccca acactccgtg ctgacccaaa  4500
atcctggacc cctaagtgat aagtctgcct gggtccaagg ggctactgga ggaaagcggt  4560
atcgctggac cacggatcgc aaagtacatc tagctaccgg taaggtcacc cactctttcc  4620
```

-continued

```
tccatgtacc agactgtccc tatcctctgt taggaagaga tttgctgact aaactaaaag  4680
cccaaatcca ctttgaggga tcaggagctc aggttatggg accaatgggg cagcccctgc  4740
aagtgttgac cctaaatata gaagatgagc atcggctaca tgagacctca aaagagccag  4800
atgtttctct agggtccaca tggctgtctg attttcctca ggcctgggcg gaaaccgggg  4860
gcatgggact ggcagttcgc caagctcctc tgatcatacc tctgaaagca acctctaccc  4920
ccgtgtccat aaaacaatac cccatgtcac aagaagccag actggggatc aagccccaca  4980
tacagagact gttggaccag ggaatactgg taccctgcca gtccccctgg aacacgcccc  5040
tgctacccgt taagaaacca gggactaatg attataggcc tgtccaggat ctgagagaag  5100
tcaacaagcg ggtggaagac atccacccca ccgtgcccaa cccttacaac ctcttgagcg  5160
ggctcccacc gtcccaccag tggtacactg tgcttgattt aaaggatgcc tttttctgcc  5220
tgagactcca ccccaccagt cagcctctct tcgcctttga gtggagagat ccagagatgg  5280
gaatctcagg acaattgacc tggaccagac tcccacaggg tttcaaaaac agtcccaccc  5340
tgtttgatga ggcactgcac agagacctag cagacttccg gatccagcac ccagacttga  5400
tcctgctaca gtacgtggat gacttactgc tggccgccac ttctgagcta gactgccaac  5460
aaggtactcg ggccctgtta caaaccctag ggaacctcgg gtatcgggcc tcggccaaga  5520
aagcccaaat ttgccagaaa caggtcaagt atctggggta tcttctaaaa gagggtcaga  5580
gatggctgac tgaggccaga aaagagactg tgatggggca gcctactccg aagacccctc  5640
gacaactaag ggagttccta gggacggcag gcttctgtcg cctctggatc cctgggtttg  5700
cagaaatggc agccccccttg taccctctca ccaaaacggg gactctgttt aattggggcc  5760
cagaccaaca aaaggcctat caagaaatca agcaagctct tctaactgcc ccagccctgg  5820
ggttgccaga tttgactaag ccctttgaac tctttgtcga cgagaagcag ggctacgcca  5880
aaggtgtcct aacgcaaaaa ctgggacctt ggcgtcggcc ggtggcctac ctgtccaaaa  5940
agctagaccc agtagcagct gggtggcccc cttgcctacg gatggtagca gccattgccg  6000
tactgacaaa ggatgcaggc aagctaacca tgggacagcc actagtcatt ctggcccccc  6060
atgcagtaga ggcactagtc aaacaacccc ccgaccgctg gctttccaac gcccggatga  6120
ctcactatca ggccttgctt ttggacacgg accgggtcca gttcggaccg gtggtagccc  6180
tgaacccggc tacgctgctc ccactgcctg aggaagggct gcaacacaac tgccttgata  6240
tcctggccga agcccacgga acccgacccg acctaacgga ccagccgctc ccagacgccg  6300
accacacctg gtacacggat ggaagcagtc tcttacaaga gggacagcgt aaggcgggag  6360
ctgcggtgac caccgagacc gaggtaatct gggctaaagc cctgccagcc gggacatccg  6420
ctcagcgggc tgaactgata gcactcaccc aggccctaaa gatggcagaa ggtaagaagc  6480
taaatgttta tactgatagc cgttatgctt ttgctactgc ccatatccat ggagaaatat  6540
acagaaggcg tgggttgctc acatcagaag gcaaagagat caaaaataaa gacgagatct  6600
tggccctact aaaagccctc tttctgccca aaagacttag cataatccat tgtccaggac  6660
atcaaaaggg acacagcgcc gaggctagag gcaaccggat ggctgaccaa gcggcccgaa  6720
aggcagccat cacagagact ccagacacct ctaccctcct catagaaaat tcatcaccct  6780
acacctcaga acattttcat tacacagtga ctgatataaa ggacctaacc aagttggggg  6840
ccatttatga taaaacaaag aagtattggg tctaccaagg aaaacctgtg atgcctgacc  6900
agtttacttt tgaattatta gactttcttc atcagctgac tcacctcagc ttctcaaaaa  6960
tgaaggctct cctagagaga agccacagtc cctactacat gctgaaccgg gatcgaacac  7020
tcaaaaatat cactgagacc tgcaaagctt gtgcacaagt caacgccagc aagtctgccg  7080
ttaaacaggg aactagggtc cgcgggcatc ggcccggcac tcattgggag atcgatttca  7140
ccgagataaa gcccggattg tatggctata aatatcttct agtttttata gatacctttt  7200
ctggctggat agaagccttc ccaaccaaga aagaaaccgc caaggtcgta accaagaagc  7260
tactagagga gatcttcccc aggttcggca tgcctcaggt attgggaact gacaatgggc  7320
ctgccttcgt ctccaaggtg agtcagacag tggccgatct gttggggatt gattggaaat  7380
tacattgtgc atacagaccc caaagctcag gccaggtaga aagaatgaat agaaccatca  7440
aggagacttt aactaaatta acgcttgcaa ctggctctag agactgggtg ctcctactcc  7500
ccttagccct gtaccgagcc cgcaacacgc cgggccccca tggcctcacc ccatatgaga  7560
tcttatatgg ggcacccccg ccccttgtaa acttccctga ccctgacatg acaagagtta  7620
ctaacagccc ctctctccaa gctcacttac aggctctcta cttagtccag cacgaagtct  7680
ggagacctct ggcggcagcc taccaagaac aactggaccg accggtggta cctcacccct  7740
accgagtcgg cgacacagtg tgggtccgcc gacaccagac taagaaccta gaacctcgct  7800
ggaaaggacc ttacacagtc ctgctgacca cccccaccgc cctcaaagta gacggcatcg  7860
cagcttggat acacgccgcc cacgtgaagg ctgccgaccc cgggggtgga ccatcctcta  7920
gactgacatg gcgcgttcaa cgctctcaaa accccttaaa aataaggtta acccgcgagg  7980
ccccctaatc cccttaattc ttctgatgct cagaggggtc agtaaacgaa ttcggaagtg  8040
aaagggcagc caaaacgtaa caccgccccg gttttccctg gaaattccat attggcacgc  8100
attctattgg ctgagctgcg ttcacgtggg tataagaggc gcgaccagcg tcggtaccgt  8160
cgcagtcttc ggtctgacca ccgtagaacg cagagcggcc gcaggatgtg gctgcagagc  8220
ctgctgctct tgggcactgt ggcctgcagc atctctgcac ccgcccgctc gcccagcccc  8280
agcacgcagc cctgggagca tgtgaatgcc atccaggagg cccggcgtct cctgaacctg  8340
agtagagaca ctgctgctga gatgaatgaa acagtagaag tcatctcaga aatgtttgac  8400
ctccaggagc cgacctgcct acagacccgc ctggagctgt acaagcaggg cctgcggggc  8460
agcctcacca agctcaaggg ccccttgacc atgatggcca gccactacaa gcagcactgc  8520
cctccaaccc cggaaacttc ctgtgcaacc cagattatca cctttgaaag tttcaaagag  8580
aacctgaagg actttctgct tgtcatcccc tttgactgct gggagccagt ccaggagtga  8640
acgcgtgaat tcataaaata aaagatttta tttagtctcc agaaaaaggg gggaatgaaa  8700
gaccccacct gtaggtttgg caagctagct taagtaacgc cattttgcaa ggcatggaaa  8760
aatacataac tgagaataga gaagttcaga tcaaggtcag gaacagatgg aacagctgaa  8820
tatgggccaa acaggatatc tgtggtaagc agttcctgcc ccggctcagg gccaagaaca  8880
gatggaacag ctgaatatgg gccaaacagg atatctgtgg taagcagttc ctgccccggc  8940
tcagggccaa gaacagatgg tccccagatg cggtccagcc ctcagcagtt tctagagaac  9000
catcagatgt ttccagggtg ccccaaggac ctgaaatgac cctgtgcctt atttgaacta  9060
accaatcagt tcgcttctcg cttctgttcg cgcgcttctg ctccccgagc tcaataaaag  9120
agcccacaac ccctcactcg gggcgccagt cctccgattg actgagtcgc ccgggtaccc  9180
gtgtatccaa taaaccctct tgcagttgca tccgacttgt ggtctcgctg ttccttggga  9240
gggtctcctc tgagtgattg actacccgtc agcgggggtc tttcattgtt acttaaagtt  9300
acattggctt ccttgaaata aacatggagt attcagaatg tgtcataaat atttctaatt  9360
```

-continued

```
ttaagatagt atctccattg gctttctact ttttctttta ttttttttg tcctctgtct  9420
tccatttgtt gttgttgttg tttgtttgtt tgtttgttgg ttggttggtt aatttttttt  9480
taaagatcct acactatagt tcaagctaga ctattagcta ctctgtaacc cagggtgacc  9540
ttgaagtcat gggtagcctg ctgttttagc cttcccacat ctaagattac aggtatgagc  9600
tatcattttt ggtatattga ttgattgatt gattgatgtg tgtgtgtgtg attgtgtttg  9660
tgtgtgtgac tgtgaaaatg tgtgtatggg tgtgtgtgaa tgtgtgtatg tatgtgtgtg  9720
tgtgagtgtg tgtgtgtgtg tgtgcatgtg tgtgtgtgtg actgtgtcta tgtgtatgac  9780
tgtgtgtgtg tgtgtgtgtg tgtgtgtgtg tgtgtgttgt gaaaaaatat  9840
tctatggtag tgagagccaa cgctccggct caggtgtcag gttggttttt gagacagagt  9900
ctttcactta gcttgg                                                 9916
```

```
SEQ ID NO: 65          moltype = DNA  length = 435
FEATURE                Location/Qualifiers
misc_feature           1..435
                       note = human codon optimized hGM-CSF polynucleotide sequence
source                 1..435
                       mol_type = other DNA
                       organism = synthetic construct
SEQUENCE: 65
atgtggcttc aaagtttgtt gctccttgga accgtcgctt gctctattag cgcacccgca  60
cgcagcccaa gtccttccac gcagccttgg gaacatgtta atgcgatcca agaagcacgg  120
cgcctcttga atctttcccg agacacggcg gcagaaatga atgagacagt tgaagtcatt  180
tcagagatgt ttgatctcca agaacctact tgtttgcaga ctcgactcga actttacaag  240
cagggtctcc ggggaagttt gaccaagctc aagggtcccc ttacgatgat ggcgtcccac  300
tacaagcaac actgcccccc gacaccagaa acgtcatgtg ctacccaaat cattaccttt  360
gaatcattca aggagaacct caaggatttt ctgttggtca taccattcga ctgttgggag  420
cccgtgcagg aatga                                                  435
```

```
SEQ ID NO: 66          moltype = DNA  length = 9913
FEATURE                Location/Qualifiers
misc_feature           1..9913
                       note = sRRVgp-F4-hopt-GM-CSF vector
source                 1..9913
                       mol_type = other DNA
                       organism = synthetic construct
SEQUENCE: 66
catgtgagca aaaggccagc aaaaggccag gaaccgtaaa aaggccgcgt tgctggcgtt  60
tttccatagg ctccgccccc ctgacgagca tcacaaaaat cgacgctcaa gtcagaggtg  120
gcgaaacccg acaggactat aaagatacca ggcgtttccc cctggaagct ccctcgtgcg  180
ctctcctgtt ccgaccctgc cgcttaccgg atacctgtcc gcctttctcc cttcgggaag  240
cgtggcgctt tctcatagct cacgctgtag gtatctcagt tcggtgtagg tcgttcgctc  300
caagctgggc tgtgtgcacg aaccccccgt tcagcccgac cgctgcgcct tatccggtaa  360
ctatcgtctt gagtccaacc cggtaagaca cgacttatcg ccactggcag cagccactgg  420
taacaggatt agcagagcga ggtatgtagg cggtgctaca gagttcttga agtggtggcc  480
taactacggc tacactagaa ggacagtatt tggtatctgc gctctgctga agccagttac  540
cttcggaaaa agagttggta gctcttgatc cggcaaacaa accaccgctg gtagcggtgg  600
tttttttgtt tgcaagcagc agattacgcg cagaaaaaaa ggatctcaag aagatccttt  660
gatcttttct acggggtctg acgctcagtg gaacgaaaac tcacgttaag ggattttggt  720
catgagatta tcaaaaagga tcttcaccta gatcctttta aattaaaaat gaagttttaa  780
atcaatctaa agtatatatg agtaacctga tcaggactct tccttttcat gaacaataaa  840
actgtctgct tacataaaca gtaatacaag gggtgttatg agccatattc aacgggaaac  900
gtcttgctct aggccgcgat taaattccaa catggatgct gatttatatg ggtataaatg  960
ggctcgcgat aatgtcgggc aatcaggtgc gacaatctat cgattgtatg ggaagcccga  1020
tgcgccagag ttgtttctga aacatggcaa aggtagcgtt gccaatgatg ttacagatga  1080
gatggtcaga ctaaactggc tgacggaatt tatgcctctt ccgaccatca agcattttat  1140
ccgtactcct gatgatgcat ggttactcac cactgcgatc cccgggaaaa cagcattcca  1200
ggtattagaa gaatatcctg attcaggtga aaatattgtt gatgcgctgg cagtgttcct  1260
gcgccggttg cattcgattc ctgtttgtaa ttgtcctttt aacagcgatc gcgtatttcg  1320
tctcgctcag gcgcaatcac gaatgaataa cggtttggtt gatgcgagtg attttgatga  1380
cgagcgtaat ggctggcctg ttgaacaagt ctggaaagaa atgcataaac ttttgccatt  1440
ctcaccggat tcagtcgtca ctcatggtga tttctcactt gataacctta tttttgacga  1500
ggggaaatta ataggttgta ttgatgttgg acgagtcgga atcgcagacc gataccagga  1560
tcttgccatc ctatggaact gcctcggtga gttttctcct tcattacaga aacggctttt  1620
tcaaaaatat ggtattgata atcctgatat gaataaattg cagtttcatt tgatgctcga  1680
tgagtttttc taagaatttg tgaatgaaag accccacctg taggtttggc aagctagctt  1740
aagtaacgcc attttgcaag gcatggaaaa atacataact gagaatagaa aagttcagat  1800
caaggtcagg aacagatgga acagctgaat atgggccaaa caggatatct gtggtaagca  1860
gttcctgccc cggctcaggg ccaagaacag atggaacagc tgaatatggg ccaaacagga  1920
tatctgtggt aagcagttcc tgccccggct cagggccaag aacagatggt ccccagatgc  1980
ggtccagccc tcagcagttt ctagagaacc atcagatgtt tccagggtgc cccaaggacc  2040
tgaaatgacc ctgtgcctta tttgaactaa ccaatcagtt cgcttctcgc ttctgttcgc  2100
gcgcttatgc tccccgagct caataaaaga gcccacaacc cctcactcgg ggcgccagtc  2160
ctccgattga ctgagtcgcc cgggtacccg tgtatccaat aaaccctctt gcagttgcat  2220
ccgacttgtg gtctcgctgt tccttgggag ggtctcctct gagtgattga ctacccgtca  2280
gcgggggtct ttcatttggg ggctcgtccg ggatcgggag acccctgccc agggaccacc  2340
gacccaccac cgggaggtaa gctggccagc aacttatctg tgtctgtccg attgtctagt  2400
gtctatgact gattttatgc gcctgcgtcg gtactagtta gctaactagc tctgtatctg  2460
gcggacccgt ggtggaactg acgagttcgg aacacccggc cgcaaccctg ggagacgtcc  2520
cagggacttc gggggccgtt tttgtggccc gacctgagtc caaaaatccc gatcgttttg  2580
```

-continued

```
gactctttgg tgcacccccc ttagaggagg gatatgtggt tctggtagga gacgagaacc  2640
taaaacagtt cccgcctccg tctgaatttt tgctttcggt ttgggaccga agccgcgccg  2700
cgcgtcttgt ctgctgcagc atcgttctgt gttgtctctg tctgactgtg tttctgtatt  2760
tgtctgagaa tatgggccag actgttacca ctcccttaag tttgacctta ggtcactgga  2820
aagatgtcga gcggatcgct cacaaccagt cggtagatgt caagaagaga cgttgggtta  2880
ccttctgctc tgcagaatgg ccaaccttta acgtcggatg gccgcgagac ggcaccttta  2940
accgagacct catcacccag gttaagatca aggtcttttc acctggcccg catggacacc  3000
cagaccaggt cccctacatc gtgacctggg aagccttggc ttttgacccc cctccctggg  3060
tcaagccctt tgtacaccct aagcctccgc ctcctcttcc tccatccgcc ccgtctctcc  3120
cccttgaacc tcctcgttcg accccgcctc gatcctccct ttatccagcc ctcactcctt  3180
ctctaggcgc caaacctaaa cctcaagttc tttctgacag tggggggccg ctcatcgacc  3240
tacttacaga agaccccccg ccttataggg acccaagacc accccccttcc gacagggacg  3300
gaaatggtgg agaagcgacc cctgcgggag aggcaccgga cccctcccca atggcatctc  3360
gcctacgtgg gagacgggag ccccctgtgg ccgactccac tacctcgcag gcattccccc  3420
tccgcgcagg aggaaacgga cagcttcaat actggccgtt ctcctcttct gacctttaca  3480
actggaaaaa taataaccct tctttttctg aagatccagg taaactgaca gctctgatcg  3540
agtctgttct catcacccat cagcccacct gggacgactg tcagcagctg ttggggactc  3600
tgctgaccgg agaagaaaaa caacgggtgc tcttagaggc tagaaaggcg gtgcggggcg  3660
atgatgggcg ccccactcaa ctgcccaatg aagtcgatgc cgcttttccc ctcgagcgcc  3720
cagactggga ttacaccacc caggcaggta ggaaccacct agtccactat cgccagttgc  3780
tcctagcggg tctccaaaac gcgggcagaa gccccaccaa tttggccaag gtaaaaggaa  3840
taacacaagg gcccaatgag tctccctcgg ccttcctaga gagacttaag gaagcctatc  3900
gcaggtacac tccttatgac cctgaggacc cagggcaaga aactaatgtg tctatgtctt  3960
tcatttggca gtctgcccca gacattggga gaaagttaga gaggttagaa gatttaaaaa  4020
acaagacgct tggagatttg gttagagagg cagaaaagat ctttaataaa cgagaaaccc  4080
cggaagaaag agaggaacgt atcaggagag aaacagagga aaaagaagaa cgccgtagga  4140
cagaggatga gcagaaagag aaagaaagag atcgtaggag acatagagag atgagcaagc  4200
tattggccac tgtcgttagt ggacagaaac aggatagaca gggaggagaa cgaaggaggt  4260
cccaactcga tcgcgaccag tgtgcctact gcaaagaaaa ggggcactgg gctaaagatt  4320
gtcccaagaa accacgagga cctcggggac caagacccca gacctccctc ctgaccctag  4380
atgactaggg aggtcagggt caggagcccc cccctgaacc caggataacc ctcaaagtcg  4440
gggggcaacc cgtcaccttc ctggtagata ctggggccca acactccgtg ctgacccaaa  4500
atcctggacc cctaagtgat aagtctgcct gggtccaagg ggctactgga ggaaagcggt  4560
atcgctggac cacggatcgc aaagtacatc tagctaccgg taaggtcacc cactctttcc  4620
tccatgtacc agactgtccc tatcctctgt taggaagaga tttgctgact aaactaaaag  4680
cccaaatcca ctttgaggga tcaggagctc aggttatggg accaatgggg cagcccctgc  4740
aagtgttgac cctaaatata gaagatgagc atcggctaca tgagacctca aaagagccag  4800
atgtttctct agggtccaca tggctgtctg attttcctca ggcctgggcg gaaaccgggg  4860
gcatgggact ggcagttcgc caagctcctc tgatcatacc tctgaaagca acctctaccc  4920
ccgtgtccat aaaacaatac cccatgtcac aagaagccag actggggatc aagccccaca  4980
tacagagact gttggaccag ggaatactgg taccctgcca gtccccctgg aacacgcccc  5040
tgctacccgt taagaaacca gggactaatg attataggcc tgtccaggat ctgagagaag  5100
tcaacaagcg ggtggaagac atccacccca ccgtgcccaa cccttacaac ctcttgagcg  5160
ggctcccacc gtcccaccag tggtacactg tgcttgattt aaaggatgcc tttttctgcc  5220
tgagactcca ccccaccagt cagcctctct tcgcctttga gtggagagat ccagagatgg  5280
gaatctcagg acaattgacc tggaccagac tcccacaggg tttcaaaaac agtcccaccc  5340
tgtttgatga ggcactgcac agagacctag cagacttccg gatccagcac ccagacttga  5400
tcctgctaca gtacgtggat gacttactgc tggccgccac ttctgagcta gactgccaac  5460
aaggtactcg ggccctgtta caaaccctag ggaacctcgg gtatcgggcc tcggccaaga  5520
aagcccaaat ttgccagaaa caggtcaagt atctggggta tcttctaaaa gagggtcaga  5580
gatggctgac tgaggccaga aaagagactg tgatggggca gcctactccg aagacccctc  5640
gacaactaag ggagttccta gggacggcag gcttctgtcg cctctggatc cctgggtttg  5700
cagaaatggc agccccccttg taccctctca ccaaaacggg gactctgttt aattggggcc  5760
cagaccaaca aaaggcctat caagaaatca agcaagctct tctaactgcc ccagccctgg  5820
ggttgccaga tttgactaag cccctttgaac tctttgtcga cgagaagcag ggctacgcca  5880
aaggtgtcct aacgcaaaaa ctgggacctt ggcgtcggcc ggtggcctac ctgtccaaaa  5940
agctagaccc agtagcagct gggtggcccc cttgcctacg gatggtagca gccattgccg  6000
tactgacaaa ggatgcaggc aagctaacca tgggacagcc actagtcatt ctggcccccc  6060
atgcagtaga ggcactagtc aaacaacccc ccgaccgctg gctttccaac gcccggatga  6120
ctcactatca ggccttgctt ttggacacgg accgggtcca gttcggaccg gtggtagccc  6180
tgaacccggc tacgctgctc ccactgcctg aggaagggct gcaacacaac tgccttgata  6240
tcctggccga agcccacgga acccgacccg acctaacgga ccagccgctc ccagacgccg  6300
accacacctg gtacacggat ggaagcagtc tcttacaaga gggacagcgt aaggcgggag  6360
ctgcggtgac caccgagacc gaggtaatct gggctaaagc cctgccagcc gggacatccg  6420
ctcagcgggc tgaactgata gcactcaccc aggccctaaa gatggcagaa ggtaagaagc  6480
taaatgttta tactgatagc cgttatgctt ttgctactgc ccatatccat ggagaaatat  6540
acagaaggcg tgggttgctc acatcagaag gcaaagagat caaaaataaa gacgagatct  6600
tggccctact aaaagccctc tttctgccca aaagacttag cataatccat tgtccaggac  6660
atcaaaaggg acacagcgcc gaggctagag gcaaccggat ggctgaccaa gcggcccgaa  6720
aggcagccat cacagagact ccagacacct ctaccctcct catagaaaat tcatcaccct  6780
acacctcaga acattttcat tacacagtga ctgatataaa ggacctaacc aagttggggg  6840
ccatttatga taaaacaaag aagtattggg tctaccaagg aaaacctgtg atgcctgacc  6900
agtttacttt tgaattatta gactttcttc atcagctgac tcacctcagc ttctcaaaaa  6960
tgaaggctct cctagagaga agccacagtc cctactacat gctgaaccgg gatcgaacac  7020
tcaaaaatat cactgagacc tgcaaagctt gtgcacaagt caacgccagc aagtctgccg  7080
ttaaacaggg aactagggtc cgcgggcatc ggcccggcac tcattgggag atcgatttca  7140
ccgagataaa gcccggattg tatggctata aatatcttct agtttttata gatacctttt  7200
ctggctggat agaagccttc ccaaccaaga aagaaaccgc caaggtcgta accaagaagc  7260
tactagagga gatcttcccc aggttcggca tgcctcaggt attgggaact gacaatgggc  7320
```

```
ctgccttcgt ctccaaggtg agtcagacag tggccgatct gttggggatt gattggaaat  7380
tacattgtgc atacagaccc caaagctcag gccaggtaga aagaatgaat agaaccatca  7440
aggagacttt aactaaatta acgcttgcaa ctggctctag agactgggtg ctcctactcc  7500
ccttagccct gtaccgagcc cgcaacacgc cgggccccca tggcctcacc ccatatgaga  7560
tcttatatgg ggcacccccg ccccttgtaa acttccctga ccctgacatg acaagagtta  7620
ctaacagccc ctctctccaa gctcacttac aggctctcta cttagtccag cacgaagtct  7680
ggagacctct ggcggcagcc taccaagaac aactggaccg accggtggta cctcaccctt  7740
accgagtcgg cgacacagtg tgggtccgcc gacaccagac taagaaccta gaacctcgct  7800
ggaaaggacc ttacacagtc ctgctgacca cccccaccgc cctcaaagta gacggcatcg  7860
cagcttggat acacgccgcc cacgtgaagg ctgccgaccc cgggggtgga ccatcctcta  7920
gactgacatg gcgcgttcaa cgctctcaaa acccccttaaa aataaggtta acccgcgagg  7980
ccccctaatc cccttaattc ttctgatgct cagaggggtc agtaaacgaa ttcggaagtg  8040
aaagggcagc caaaacgtaa caccgccccg gttttccctg gaaattccat attggcacgc  8100
attctattgg ctgagctgcg ttcacgtggg tataagaggc gcgaccagcg tcggtaccgt  8160
cgcagtcttc ggtctgacca ccgtagaacg cagagcggcc gcatgtggct tcaaagtttg  8220
ttgctccttg gaaccgtcgc ttgctctatt agcgcacccg cacgcagccc aagtccttcc  8280
acgcagcctt gggaacatgt taatgcgatc caagaagcac ggcgcctctt gaatctttcc  8340
cgagacacgg cggcagaaat gaatgagaca gttgaagtca tttcagagat gtttgatctc  8400
caagaaccta cttgtttgca gactcgactc gaactttaca agcagggtct ccggggaagt  8460
ttgaccaagc tcaagggtcc ccttacgatg atggcgtccc actacaagca acactgcccc  8520
ccgacaccag aaacgtcatg tgctacccaa atcattacct ttgaatcatt caaggagaac  8580
ctcaaggatt ttctgttggt cataccattc gactgttggg agcccgtgca ggaatgaacg  8640
cgtgaattca taaaataaaa gattttattt agtctccaga aaaagggggg aatgaaagac  8700
cccacctgta ggtttggcaa gctagcttaa gtaacgccat tttgcaaggc atggaaaaat  8760
acataactga gaatagagaa gttcagatca aggtcaggaa cagatggaac agctgaatat  8820
gggccaaaca ggatatctgt ggtaagcagt tcctgccccg gctcagggcc aagaacagat  8880
ggaacagctg aatatgggcc aaacaggata tctgtggtaa gcagttcctg ccccggctca  8940
gggccaagaa cagatggtcc ccagatgcgg tccagccctc agcagtttct agagaaccat  9000
cagatgtttc cagggtgccc caaggacctg aaatgaccct gtgccttatt tgaactaacc  9060
aatcagttcg cttctcgctt ctgttcgcgc gcttctgctc cccgagctca ataaaagagc  9120
ccacaacccc tcactcgggg cgccagtcct ccgattgact gagtcgcccg ggtacccgtg  9180
tatccaataa accctcttgc agttgcatcc gacttgtggt ctcgctgttc cttgggaggg  9240
tctcctctga gtgattgact acccgtcagc gggggtcttt cattgttact taaagttaca  9300
ttggcttcct tgaaataaac atggagtatt cagaatgtgt cataaatatt tctaatttta  9360
agatagtatc tccattggct ttctactttt tcttttattt ttttttgtcc tctgtcttcc  9420
atttgttgtt gttgttgttt gtttgtttgt ttgttggttg gttggttaat tttttttttaa  9480
agatcctaca ctatagttca agctagacta ttagctactc tgtaacccag ggtgaccttg  9540
aagtcatggg tagcctgctg ttttagcctt cccacatcta agattacagg tatgagctat  9600
catttttggt atattgattg attgattgat tgatgtgtgt gtgtgtgatt gtgtttgtgt  9660
gtgtgactgt gaaaatgtgt gtatgggtgt gtgtgaatgt gtgtatgtat gtgtgtgtgt  9720
gagtgtgtgt gtgtgtgtgt gcatgtgtgt gtgtgtgact gtgtctatgt gtatgactgt  9780
gtgtgtgtgt gtgtgtgtgt gtgtgtgtgt gtgtgtgtgt gtgttgtgaa aaaatattct  9840
atggtagtga gagccaacgc tccggctcag gtgtcaggtt ggtttttgag acagagtctt  9900
tcacttagct tgg                                                     9913

SEQ ID NO: 67          moltype =   length =
SEQUENCE: 67
000

SEQ ID NO: 68          moltype = DNA  length = 27
FEATURE                Location/Qualifiers
source                 1..27
                       mol_type = genomic DNA
                       organism = unidentified
SEQUENCE: 68
aatatcacca gctgaagcct atagagt                                      27

SEQ ID NO: 69          moltype = DNA  length = 21
FEATURE                Location/Qualifiers
source                 1..21
                       mol_type = genomic DNA
                       organism = unidentified
SEQUENCE: 69
aacaggaaag ttccattgga g                                            21

SEQ ID NO: 70          moltype = DNA  length = 21
FEATURE                Location/Qualifiers
source                 1..21
                       mol_type = genomic DNA
                       organism = unidentified
SEQUENCE: 70
atagggtgaa tcaacaggag t                                            21

SEQ ID NO: 71          moltype = DNA  length = 30
FEATURE                Location/Qualifiers
source                 1..30
                       mol_type = genomic DNA
                       organism = unidentified
SEQUENCE: 71
```

-continued

```
ataccacttt gtatacgacg ctgtctccat                                   30

SEQ ID NO: 72          moltype = DNA  length = 22
FEATURE                Location/Qualifiers
source                 1..22
                       mol_type = genomic DNA
                       organism = unidentified
SEQUENCE: 72
aagggggggaa tgaaagaccc ca                                          22

SEQ ID NO: 73          moltype = DNA  length = 27
FEATURE                Location/Qualifiers
source                 1..27
                       mol_type = genomic DNA
                       organism = unidentified
SEQUENCE: 73
ttcccatagc tgattaatgg gaaagta                                      27

SEQ ID NO: 74          moltype = DNA  length = 22
FEATURE                Location/Qualifiers
source                 1..22
                       mol_type = genomic DNA
                       organism = unidentified
SEQUENCE: 74
ggattggttt gaagatattg gt                                           22

SEQ ID NO: 75          moltype = DNA  length = 24
FEATURE                Location/Qualifiers
source                 1..24
                       mol_type = genomic DNA
                       organism = unidentified
SEQUENCE: 75
gcgtcggtac cgtggtagct cgaa                                         24

SEQ ID NO: 76          moltype = DNA  length = 25
FEATURE                Location/Qualifiers
source                 1..25
                       mol_type = genomic DNA
                       organism = unidentified
SEQUENCE: 76
tacgagccat agataaaata aaagg                                        25

SEQ ID NO: 77          moltype = DNA  length = 21
FEATURE                Location/Qualifiers
source                 1..21
                       mol_type = genomic DNA
                       organism = unidentified
SEQUENCE: 77
gaagtgaaag ggcagccaaa a                                            21

SEQ ID NO: 78          moltype = DNA  length = 23
FEATURE                Location/Qualifiers
source                 1..23
                       mol_type = genomic DNA
                       organism = unidentified
SEQUENCE: 78
aacttcaagt ccaagggcga gaa                                          23

SEQ ID NO: 79          moltype = DNA  length = 24
FEATURE                Location/Qualifiers
source                 1..24
                       mol_type = genomic DNA
                       organism = unidentified
SEQUENCE: 79
tgagtcatta gggactttcc aatg                                         24

SEQ ID NO: 80          moltype = DNA  length = 27
FEATURE                Location/Qualifiers
source                 1..27
                       mol_type = genomic DNA
                       organism = unidentified
SEQUENCE: 80
ggtcaatagg ggtgaatcaa caggaaa                                      27

SEQ ID NO: 81          moltype = DNA  length = 12
FEATURE                Location/Qualifiers
source                 1..12
                       mol_type = genomic DNA
                       organism = unidentified
```

-continued

```
SEQUENCE: 81
gggtttttcc ag                                                    12

SEQ ID NO: 82           moltype = DNA  length = 25
FEATURE                 Location/Qualifiers
source                  1..25
                        mol_type = genomic DNA
                        organism = unidentified
SEQUENCE: 82
caacaaggac ggcagtgtgc tgggg                                      25

SEQ ID NO: 83           moltype = DNA  length = 26
FEATURE                 Location/Qualifiers
source                  1..26
                        mol_type = genomic DNA
                        organism = unidentified
SEQUENCE: 83
ccctagagaa cgaaggtaac ctttaa                                     26

SEQ ID NO: 84           moltype = DNA  length = 27
FEATURE                 Location/Qualifiers
source                  1..27
                        mol_type = genomic DNA
                        organism = unidentified
SEQUENCE: 84
agctgaagcc tatagagtac gagccat                                    27
```

GENE THERAPY VECTOR WITH MINIMIZING RECOMBINATION, RECOMBINANT RETROVIRUS COMPRISING THE VECTOR, AND PHARMACEUTICAL COMPOSITION FOR PREVENTING OR TREATING CANCER COMPRISING THE RECOMBINANT RETROVIRUS

CROSS-REFERENCE TO RELATED APPLICATIONS

The present application is a continuation-in-part of International PCT Patent Application No. PCT/KR2021/012776, filed on Sep. 17, 2021 and entitled "Gene therapy vector with minimized recombination occurance, recombinant retrovirus comprising the vector, and pharmaceutical composition for preventing or treating cancer, comprising recombinant retrovirus," which claims priority to Korean Application No. 10-2021-0118834, filed on Sep. 7, 2021 and Korean Application No. 10-2020-0120797, filed on Sep. 18, 2020, all of which are hereby incorporated in their entireties by reference.

SEQUENCE LISTING XML

The instant application contains a sequence listing, which has been submitted in XML file format by electronic submission and is hereby incorporated by reference in its entirety. The XML file, created on Mar. 15, 2023, is named 2022fpo-12-004US_seq_0315.xml and is 344,653 bytes in size.

BACKGROUND OF THE INVENTION

1. Field of the Invention

The present invention relates to a replicating-retrovirus vector with minimized recombination occurrence that contains thymidine kinase (HSV-TK), yeast cytosine deaminase (yCD), human CD19 gene or granulocyte-macrophage colony-stimulating factor (GM-CSF) as a therapeutic gene for efficient cancer treatment and comprises a minimal MCMV promoter with minimizing recombination while maintaining a high expression rate of the therapeutic gene.

2. Description of the Related Art

Gene therapy refers to a technology for treating a disease by replacing an abnormal gene that causes a disease in a patient's cells or tissues or by inserting a gene helpful in treating a disease. In the early days of the development of gene therapy, the main concept of gene therapy was to insert foreign DNA into the chromosome of a target cell to express a specific gene. However, recently, antisense therapy, which inhibits the expression of a gene related to a specific disease using antisense oligodioxinucleotide, siRNA, and the like is also included in the category.

Such gene therapy is an approach with a completely different concept from previous treatment methods and can treat the root cause of a disease by identifying it at the molecular level. In addition, since gene therapy is a nucleotide sequence-specific action, unnecessary side effects that are problematic in other treatment methods can be minimized by removing genes related to major diseases. Such a method of targeting genes does not require any optimization in the production of a therapeutic agent if only the nucleotide sequence of a gene to control the level of expression is known, so the production process is very simple compared to antibodies or compound therapeutic agents. In addition, the target that is difficult for other therapeutic agents to target can be targeted as long as the gene that causes the disease is known and thus has sufficient potential as a next-generation therapeutic agent. In this regard, there are several research results that have increased the possibility of treatment by applying gene therapy to incurable diseases, cancer, AIDS, genetic diseases, and nervous system diseases that are difficult to treat with existing medical technology, and actual clinical trials are also being conducted (YOUNG et al, 2006).

Gene therapy consists of a gene carrier and a therapeutic gene. The gene carrier, a tool for delivering genes into the living body, can be largely divided into viral and non-viral carriers. The viral carrier is manufactured by eliminating most of the viral genes or some of the essential genes of the virus so that the virus cannot replicate itself, and inserting a therapeutic gene therein instead (Lotze M T et al., Cancer Gene Therapy, 9:692-699, 2002). The viral carrier can deliver genes with high efficiency, but has problems such as difficulty in mass production, induction of immune response, toxicity, or emergence of replicable viruses depending on the type of virus. Major the viral carriers currently used in the development of gene therapy include retrovirus, lentivirus, adenovirus, adeno-associated virus (AAV), herpes simplex virus, and poxvirus. On the other hand, the non-viral carrier does not induce immune reactions, has low toxicity, and is easy to mass-produce, but has low gene delivery efficiency and transient expression.

A retrovirus vector, one of the most widely used viral carriers in clinical practice, was used in the first clinical trial of gene therapy conducted by the U.S. National Institutes of Health in 1990 and is considered the most useful vector for stably inserting a therapeutic gene.

A relatively large gene can be inserted into a non-replicable retrovirus vector with limited self-replication, and the titer of the vector is about $10^6$~$10^7$ pfu/ml, so there is no major problem in infecting target cells. In addition, since a packaging cell line has been developed, the manufacturing method of the retrovirus vector is easy. Further, the retrovirus vector can be scaled up by inserting a therapeutic gene into a retrovirus plasmid and infecting packaging cells with the retrovirus plasmid to produce recombinant viruses and infecting target cells with the recombinant viruses. However, in the process of insertion into the chromosome, mutations may occur due to gene insertion.

The replicable retrovirus vector is highly controversial in terms of genome stability, and when developed as a self-replicating virus vector for gene therapy, it is difficult to introduce various therapeutic genes because the size of genes that can be introduced is limited to about 1.3 kb (J. of virology, Vol. 75, 6989-6998, 2001).

As a therapeutic gene used in anticancer gene therapy, a gene that induces suicide of cancer cells by prodrug administration such as herpes simplex virus thymidine kinase or cytosine deaminase, a cytokine gene that can promote immune responses such as interleukin-12 or GM-CSF, and a tumor-specific antigen gene such as CEA or Her-2, are widely used (Gottesman M M, Cancer Gene Therapy, 10:501-508, 2003). The suicide gene kills cancer after being delivered to cancer cells, and the cytokine gene or tumor-specific antigen gene attacks cancer cells by activating immune responses to cancer.

Recently, studies on synthesis techniques of enzymes/prodrugs that selectively exhibit antitumor effects on malignant tumors have been actively conducted. In fact, when a suicide gene is expressed in cancer tissue and its precursor is systemically administered to a living body, toxicity does not appear in normal cells and the precursor is converted into a toxic substance only in tumor cells in which the therapeutic gene is expressed and destroys the tumor cells.

One of the most widely used suicide genes is the herpes simplex virus thymidine kinase (HSV-TK). It has a bystander effect that induces apoptosis of cells with a suicide gene as well as adjacent cells through a gap junction by converting a prodrug called ganciclovir (GCV) that is harmless to cells into a cytotoxic substance through an enzyme reaction. Clinical trials up to phase 3 for the suicide gene were conducted to prove the efficacy and stability (human gene therapy, 4:725-731, 1993; molecular therapy, 1:195-203, 2000).

Another suicide gene is yeast cytosine deaminase (yCD), which deaminates 5-fluorocytosine (5-FC) to 5-fluorouracil (5-FU), a powerful anticancer agent. 5-FU is metabolized to 5-fluorouridine triphosphate (5-FUTP) and 5-fluorodeoxyuridine monophosphate (5-FdUMP). The 5-FUTP fused with ribonucleic acid interferes with the synthesis of ribosomal ribonucleic acid and carrier ribonucleic acid, and 5-FdUMP inhibits DNA synthesis by irreversibly inhibiting thymidine synthase. In addition, yCD has a bystander effect that kills surrounding cells to which yCD has not been delivered. Therefore, in tumor cells expressing TK or yCD, they selectively kill cancer cells by converting prodrugs such as GCV and 5-FC into toxic metabolites.

Recently, many studies have been conducted on immunotherapeutic agents to treat cancer, and an immunotherapy method, in which a receptor targeting an antigen specifically expressed in cancer cells, such as CAR-T, is loaded into a viral vector and delivered, has been developed and is being applied clinically. This immunotherapy method can reduce side effects as much as possible by using the characteristics of immune cells in the body, and can strengthen the immune response so that the patient's body fights against cancer cells. Examples of the antigen gene specifically expressed in cancer cells include CD19 (cluster of differentiation 19), CEA (carcinoembryonic antigen), or HER2 (human epidermal growth factor receptor 2). CD19, a cancer antigen gene is specifically expressed mainly in hematologic malignancies and is a 95 kDa-sized transmembrane glycoprotein composed of a total of 556 amino acids. It consists of cytosolic C-terminal, extracellular N-terminal, and transmembrane domain. Among them, the extracellular N-terminal plays a role in binding to CAR as a signaling peptide. Y391, Y482, and Y513 tyrosine residues at the cytosolic C-terminal are involved in intracellular signaling mechanisms such as Vav PLC (phospholipase C) and PI3K(phosphoinositide 3-kinase)/Lyn, respectively, and have extensive influence.

GM-CSF (granulocyte-macrophage colony-stimulating factor) is a cytokine that functions as a white blood cell growth factor as well as proliferation and production of granulocytes and increases immune response by rapidly increasing the number of macrophages to fight infection.

The technology of simultaneously applying two or more types of therapeutic genes to gene therapy is excellent in terms of therapeutic efficiency and is particularly useful when resistance to specific gene therapy is exhibited. In this regard, since cancers resistant to treatment by administration of TK and CD have recently been reported, a gene therapy vector system capable of simultaneously expressing TK and CD in cancer tissues has a great advantage. However, the introduction of both HSV-TK and CD into RRV (replicating-retrovirus vector) results in a genomic size of approximately 10 kb or more, making it virtually impossible to insert into a single retrovirus vector. In addition, since a foreign gene is introduced in addition to the genomic RNA of the original retrovirus into the replicating-retrovirus vector for gene therapy, the size of the genomic RNA is increased, non-homologous sequences are added, and gene recombination is likely to cause loss of therapeutic genes, making it difficult to construct the vector.

In order to solve this problem, the present inventors reduced the size of the gag-pol-env genome included in the replicating retrovirus to maintain the stability of the virus. In addition, a double replicating-retrovirus vector was constructed by including the gag-pol and env genes in separate vectors from the gag-pol-env vector composed of one genome to allow the introduction of other therapeutic genes.

It has been known that the promoter of the murine cytomegalovirus (MCMV) IE gene induces several to several dozen times higher expression in specific cells than the promoter of the HCMV IE gene (Lafemina R et al, J Gen Virol., 69, 355-374 (1988)), and induces uniformly stable expression in various cells (Aiba-Masago S et al., Am J Pathol. 154, 735-743 (1999)). In particular, it has been reported that the removal of the upstream region from the MCMV major immediate-early promoter (MIEP) region induces very strong expression in primates and mouse cells (Kim and Risser, J. Virol. 67, 239-248 (1993); and Kim, Biochem. Biophys. Res. Comm., 203, 1152-1159 (1994)). In addition, Korean Patent No. 10-0423022 discloses that the MCMV promoter can be used as an expression vector for animals because the promoter strongly and stably induces gene expression in human and mouse eukaryotic cells.

However, due to repetitive nucleotide sequences in the MCMV promoter, some of the MCMV nucleotide sequences are lost during viral replication, or virus vector nucleotide sequences at other locations starting from the MCMV promoter are lost together, resulting in a recombinant virus, which is a major problem in the production and infection of retrovirus vectors that continuously express therapeutic genes.

Accordingly, while developing a virus vector for gene therapy in which recombination does not occur, the present inventors constructed four variants containing HSV-TK, hopt-yCD, hCD19, or GM-CSF gene as a therapeutic gene by truncating the promoter based on the repetitive nucleotide sequence in the MCMV promoter, and developed a replicating-retrovirus vector in which the cleaved MCMV promoter was introduced and there was no loss of the therapeutic gene because recombination did not occur during virus infection. The present inventors completed this invention by confirming that viral recombination does not occur in the vector and that the vector has excellent therapeutic gene expression and drug sensitivity.

SUMMARY OF THE INVENTION

It is an object of the present invention to provide a replicating-retrovirus vector with minimized recombination occurrence that contains thymidine kinase, cytosine deaminase, human CD19 gene or granulocyte-macrophage colony-stimulating factor as a therapeutic gene, and an MCMV promoter for treating cancer.

It is another object of the present invention to provide a recombinant retrovirus containing the retrovirus vector, and a host cell infected with the recombinant retrovirus.

To achieve the above objects, the present invention provides a replicating recombinant retrovirus vector with minimized recombination occurrence, comprising a first recombinant expression vector containing a Gag-Pol gene of MuLV, a sEF1α promoter or an MCMV promoter, and a first therapeutic gene; and a second recombinant expression vector containing an Env gene of a virus, an MCMV promoter and a second therapeutic gene.

The present invention also provides a recombinant retrovirus comprising the vector.

The present invention also provides a host cell transfected with the recombinant retrovirus.

The present invention also provides a pharmaceutical composition and methods for preventing or treating cancer comprising the recombinant retrovirus as an active ingredient.

The present invention also provides a gene delivery composition and method of gene delivery for treating cancer comprising the recombinant retrovirus.

In addition, the present invention provides a method for preparing a replicating-retrovirus vector with minimized recombination occurrence, comprising the following steps:

1) a step of preparing a first recombinant expression vector containing a Gag-Pol gene of MuLV, a sEF1α promoter or an MCMV promoter, and a first therapeutic gene; and
2) a step of preparing a second recombinant expression vector containing an Env gene of a virus, an MCMV promoter, and a second therapeutic gene.

Advantageous Effect

The present invention relates to a gene therapy vector in which the occurrence of recombination is minimized. In order to minimize the occurrence of recombination, which is a major problem in the production and infection of a retroviral vector virus that continuously expresses a therapeutic gene during virus replication, in the present invention, a cleaved MCMV promoter was prepared by cutting the MCMV promoter on the basis of a repeat sequence, and the cleaved MCMV promoter was introduced to prepare a vector. It was confirmed that the vector having the cleaved MCMV promoter incorporated therein does not cause recombination even after being incubated multiple times, and shows a continuous expression of the therapeutic protein, and in cells transfected with the virus containing the vector, cell death effectively occurs when a prodrug is administered thereto. Accordingly, the vector with minimized recombination occurrence of the present invention can be advantageously used for the treatment of cancer.

BRIEF DESCRIPTION OF THE DRAWINGS

FIG. 6 is a diagram showing the 4 repetitive nucleotide sequences (1. AACAGGAAA, 2. GGGACTTTCCAATGGGTTTTGCCCAGTACA, 3. TGGGTTTTTCC, 4. GTACTTTCCCA) within the MCMV promoter nucleotide sequence.

FIG. 7 is a diagram showing the structures of spRRVe-TK, spRRVe-F1-TK, spRRVe-F2-TK, spRRVe-F3-TK and spRRVe-F4-TK vectors in which the cleaved MCMV promoter is introduced into GaLV Env.

DESCRIPTION OF THE PREFERRED EMBODIMENTS

Figure 1:
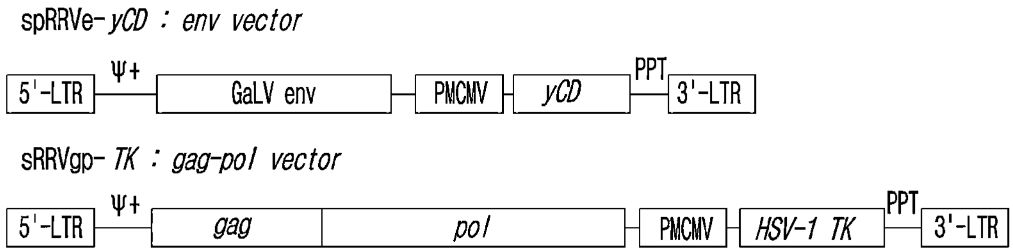
FIG. 1 is a schematic diagram of the GaLV env-pMCMV-yCD/gag-pol-pMCMV-HSV1-TK vector designed to confirm the infectivity and recombination type of the replicating-retrovirus vector.

Hereinafter, the present invention is described in detail.

The present invention provides a replicating-retrovirus vector with minimized recombination occurrence, comprising a first recombinant expression vector containing a Gag-Pol gene of MuLV (Murine Leukemia virus), a sEF1α promoter or a MCMV promoter, and a first therapeutic gene; and a second recombinant expression vector containing an Env gene of a virus, an MCMV promoter and a second therapeutic gene.

The MCMV promoter is a 646 bp polynucleotide having the nucleotide sequence represented by SEQ. ID. NO: 3.

The MCMV promoter is a murine cytomegalovirus promoter, and it has been known that it induces several to several dozen times higher expression in specific cells than the promoter of the human cytomegalovirus (HCMV) IE gene (Lafemina R et al, J Gen Virol., 69, 355-374 (1988)), and induces uniformly stable expression in various cells (Aiba-Masago S et al., Am J Pathol. 154, 735-743 (1999)). In particular, it has been reported that the MCMV promoter in which a region upstream of a major immediate-early promoter (MIEP) site is removed induces very strong expression in primate and mouse cells (Kim and Risser, J. Virol. 67, 239-248 (1993); and Kim, Biochem. Biophys. Res. Comm., 203, 1152-1159 (1994)).

However, due to the repetitive nucleotide sequences in the MCMV promoter at 4 locations, the virus vector nucleotide sequences at other sites starting from the MCMV promoter are lost or some of the nucleotide sequences are lost within the promoter, resulting in recombination, which causes the therapeutic gene to be lost and causes a major problem in the production and infection of retroviral vector virus that continuously express the therapeutic gene.

Therefore, in order to minimize the occurrence of recombination, the MCMV promoter is characterized in that it is a cleaved MCMV promoter.

The cleaved MCMV promoter can be any one selected from the group consisting of polynucleotides having the nucleotide sequences represented by SEQ. ID. NO: 4, NO: 5, NO: 6 and NO: 7, preferably any one selected from the group consisting of polynucleotides having the nucleotide sequences represented by SEQ. ID. NO: 5, NO: 6 and NO: 7 SEQ, more preferably can be a polynucleotide having the nucleotide sequence represented by SEQ. ID. NO: 6 or NO: 7, and most preferably can be a polynucleotide having the nucleotide sequence represented by SEQ. ID. NO: 7.

In a specific embodiment of the present invention, it was confirmed that gene recombination occurred due to the repetitive nucleotide sequences in the MCMV promoter in the vector (spRRVe-yCD) containing MCMV promoter full-length sequence, GaLV env and the gene encoding yeast cytosine deaminase protein and the vector (sRRVgp-TK) containing a MCMV promoter full-length sequence, a gag-pol gene and the gene encoding thymidine kinase (TK) protein (FIGS. 1 to 6).

The sEF1α (short elongation factor 1α) promoter is a polynucleotide having the nucleotide sequence represented by SEQ. ID. NO: 18.

The virus Env gene is any one derived from the group consisting of Gibbon ape Leukemia virus (GaLV), amphotropic MuLV, xenotropic MuLV, feline endogenous retrovirus (RD114), vesicular stomatitis virus (VSV) and measles virus (MV) Env genes. The polynucleotide can include a variant having the above-described characteristics.

The GaLV Env gene is a polynucleotide having the nucleotide sequence represented by SEQ. ID. NO: 19.

The MuLV Env gene is a polynucleotide having the nucleotide sequence represented by SEQ. ID. NO: 20.

The first therapeutic gene or the second therapeutic gene can be any one selected from the group consisting of a suicide gene inducing suicide of cancer cells by administration of prodrugs, a cytokine gene such as interleukin-12 or GM-CSF promoting immune responses, and a tumor-specific cancer antigen gene such as CD19, CEA or HER2.

The suicide gene can be a thymidine kinase (TK) gene or a yeast cytosine deaminase (yCD) gene.

The first therapeutic gene and the second therapeutic gene are at least one selected from the group consisting of a thymidine kinase (TK) gene, a yeast cytosine deaminase (yCD) gene and a human CD19 gene.

The thymidine kinase gene is a polynucleotide having the nucleotide sequence represented by SEQ. ID. NO: 21. The polynucleotide can include not only a polynucleotide sequence encoding the amino acid sequence of a thymidine kinase protein, but also a polynucleotide having the nucleotide sequence substantially identical to that of the polynucleotide, and a fragment thereof. The polynucleotide having the substantially identical nucleotide sequence can have 80% or more, specifically 90% or more, more specifically 95% or more homology with the polynucleotide of the present invention. As described above, the polynucleotide of the present invention can include a variant in which one or more nucleotide sequences are substituted, deleted, or inserted, as long as it encodes a protein having an activity equivalent thereto.

The yeast cytosine deaminase (yCD) gene is a polynucleotide having the nucleotide sequence represented by SEQ. ID. NO: 22.

The cytosine deaminase gene may be a gene optimized with human codons.

The term "optimized with human codons" used in this specification means that when DNA is transcribed and translated into proteins in host cells, there are preferred codons depending on the host between the codons designating amino acids, which are replaced with human codons to increase the expression efficiency of amino acids or proteins encoded by the nucleic acids.

The thymidine kinase gene or the yeast cytosine deaminase gene activates a precursor drug. The precursor drug is at least one selected from the group consisting of ganciclovir (GCV) and 5-fluorocytosine (5-FC). In one embodiment of the present invention, the thymidine kinase gene can activate ganciclovir, and the yeast cytosine deaminase gene can activate 5-fluorocytosine.

The granulocyte macrophage colony stimulating factor (GM-CSF) may be one optimized with human codons.

The term "optimized with human codons" used in this specification means that when DNA is transcribed and translated into proteins in host cells, there are preferred codons depending on the host between the codons designating amino acids, which are replaced with human codons to increase the expression efficiency of amino acids or proteins encoded by the nucleic acids.

The human CD19 (Cluster of Differentiation 19) gene can be a truncated human CD19 gene in which amino acids in the cytoplasmic domain are removed, and 233 amino acids in the cytoplasmic domain may be removed.

The human CD19 gene is a polynucleotide having the nucleotide sequence represented by SEQ. ID. NO: 43 or NO: 53.

The gag gene can be a polynucleotide encoding four types of proteins constituting the retrovirus core. Meanwhile, the pol gene is a polynucleotide encoding retrovirus reverse transcriptase, and the env gene is a polynucleotide encoding retrovirus envelope glycoprotein.

The MuLV-Gag gene is a Gag gene of murine leukemia virus and may be a polynucleotide composed of the nucleotide sequence represented by SEQ. ID. NO: 23. The MuLV-Pol gene is a Pol gene of murine leukemia virus and may be a polynucleotide composed of the nucleotide sequence represented by SEQ. ID. NO: 24. The MuLV Gag-Pol gene may be a polynucleotide composed of a nucleotide sequence in which the nucleotide sequences represented by SEQ. ID. NO: 23 and 24 are fused.

The term "replicable" used in this specification means that a virus vector can replicate itself in cells in which a viral genome containing a specific gene is transduced or infected with a virus vector containing animal cells or a specific gene.

As used herein, the term "replicating-retrovirus vector" is a vector that produces a non-lytic virus, and since it enters into the nucleus through a crack in the nuclear membrane, it can specifically infect dividing cells, that is, cancer cells, and thus the inserted gene can be prevented from being expressed in other normal cells. Therefore, the vector can safely deliver genes to cancer cells, and can increase gene delivery efficiency because it can replicate viruses.

Figure 10:
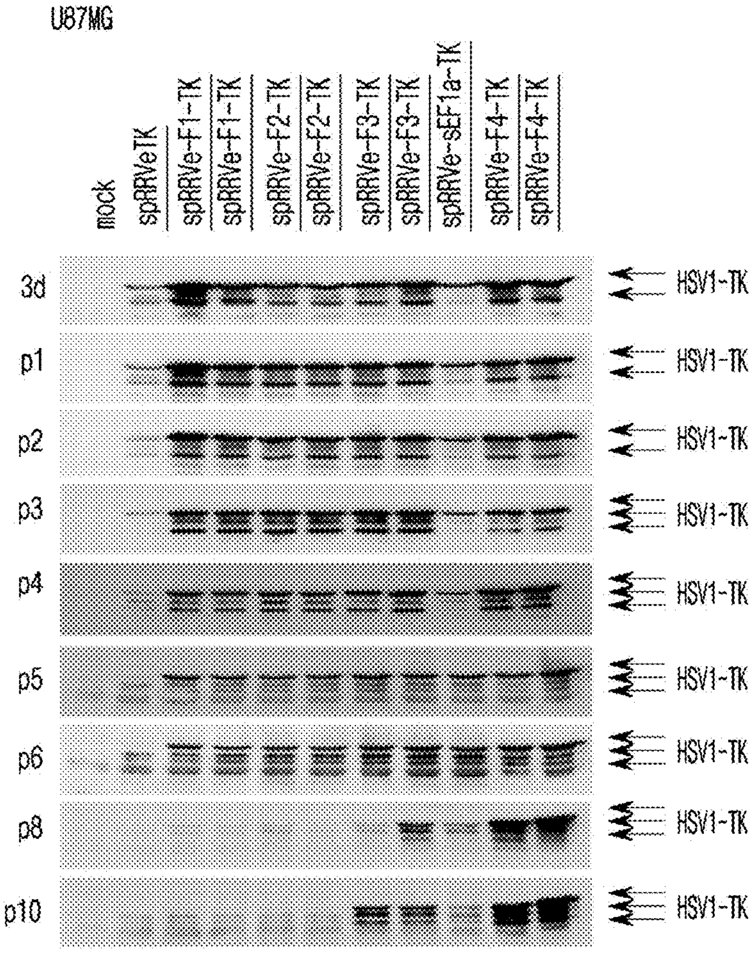
FIG. 10 is a diagram confirming that thymidine kinase (TK) protein is continuously expressed in spRRVe-TK, spRRVe-F1-TK, spRRVe-F2-TK, spRRVe-F3-TK and spRRVe-F4-TK vectors.
Figure 11:
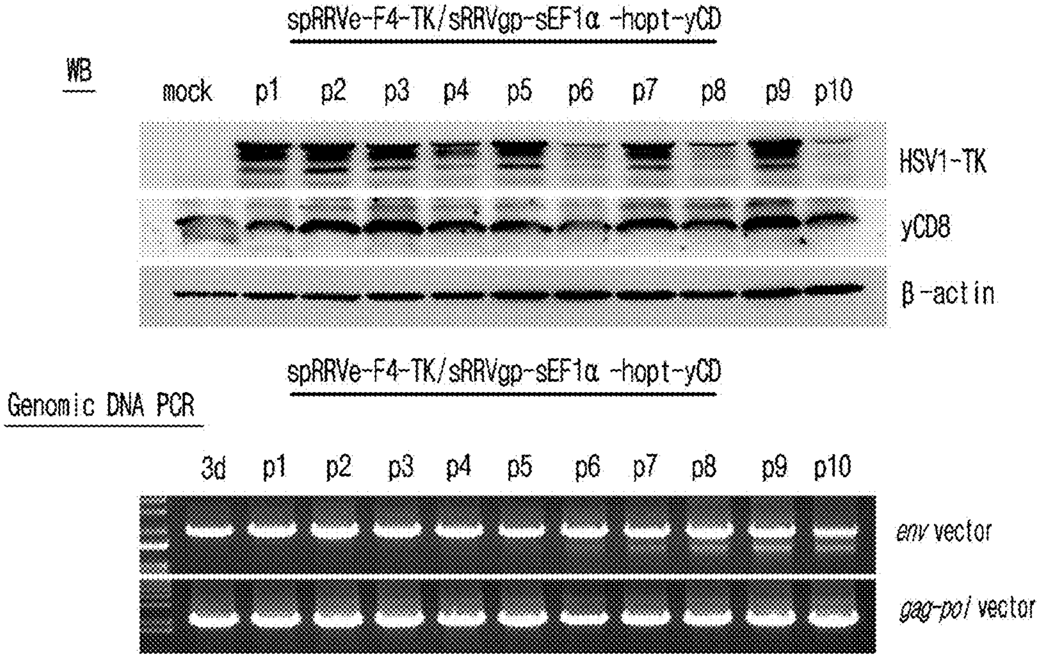
FIG. 11 is a diagram confirming that recombination of the spRRVe-F4-TK vector does not occur in the spRRVe-F4-TK/sRRVgp-sEF1a-hopt-yCD vector and yeast cytosine deaminase protein is continuously expressed therein.
Figure 13:
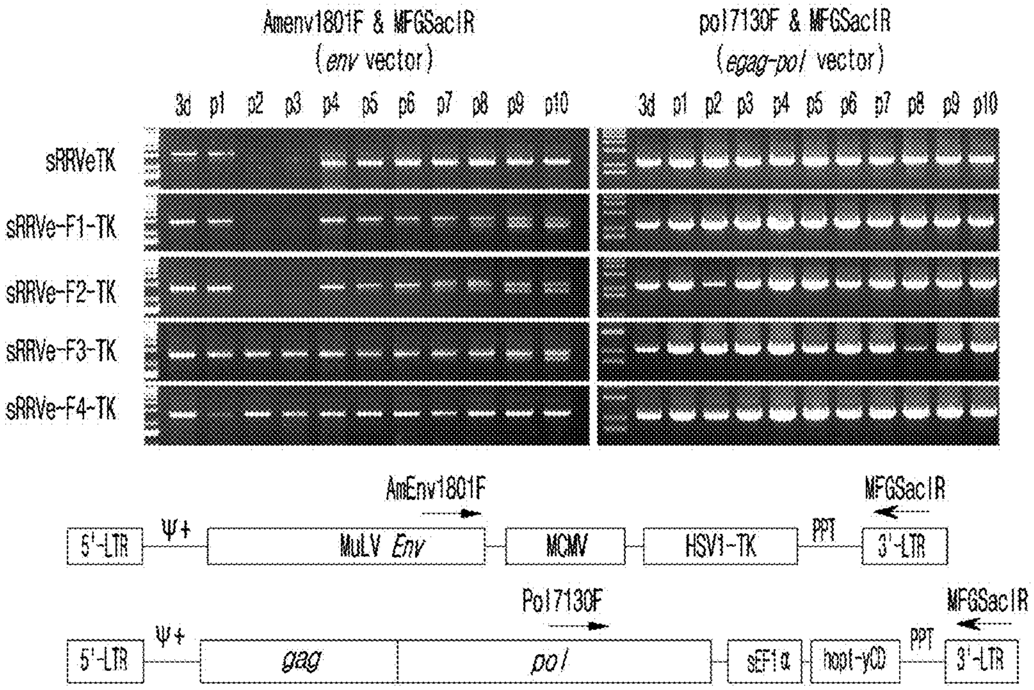
FIG. 13 is a diagram showing the locations of primers for confirming recombination in sRRVgp-sEF1a-hopt-yCD, sRRVe-TK, sRRVe-F1-TK, sRRVe-F2-TK, sRRVe-F3-TK and sRRVe-F4-TK vectors, and whether the recombination.

In a specific embodiment of the present invention, four cleaved MCMV promoters having the sizes of 470 bp, 337 bp, 237 bp, and 160 bp, respectively, were prepared by removing repetitive nucleotide sequences in the MCMV promoter to minimize recombination (Table 2). In addition, GaLV env-based vectors (spRRVe-TK, spRRVe-F1-TK, spRRVe-F2-TK, spRRVe-F3-TK and spRRVe-F4-TK) and MuLV-based vectors (sRRVe-TK, sRRVe-F1-TK, sRRVe-F2-TK, sRRVe-F3-TK and sRRVe-F4-TK) into which the cleaved MCMV promoter was introduced were constructed, and a sRRVe-sEF1α-hopt-yCD vector composed of gag-pol-sEF1α-hopt-yCD expressing yeast cytosine deaminase protein was constructed as a vector introduced together with the vector expressing thymidine kinase protein (FIGS. 7 and 8), followed by confirming the occurrence of recombination. As a result, it was confirmed that no recombination occurred in the sRRVe-sEF1α-hopt-yCD vector (see FIG. 9), and almost no recombination occurred in the spRVe-F4-TK vector in which most of the repetitive sequences in the MCMV promoter were removed (FIGS. 10, 11 and 13). In addition, it was confirmed that recombination did not occur even in the combination of sRRVgp-F4-hopt-yCD and the vector in which sEF1α of the sRRVe-sEF1α-hopt-yCD vector was substituted with the F4 truncated promoter of MCMV (see FIG. 14). It was also confirmed that recombination did not occur in the sRRVgp-F4-hopt-yCD/sRRVe-F4-hCD19 vector into which human CD19 gene was introduced as a therapeutic gene (see FIGS. 20 and 21). It was also confirmed that recombination did not occur even in the sRRVe-F4-hCD19t vector into which hCD19t with truncated amino acids of the cytoplasmic domain of human CD19 gene was introduced as a therapeutic gene (see FIGS. 23 and 25). It was also confirmed that recombination did not occur even in the sRRVgp-F4-mGM-CSF vector into which mouse GM-CSF was introduced as a therapeutic gene (see FIG. 27). It was also confirmed that recombination did not occur in the sRRVgp-F4-hopt-GM-CSF vector into which codon-optimized human GM-CSF was introduced as a therapeutic gene (see FIGS. 32 and 33).

Therefore, the occurrence of recombination in the vector of the present invention is minimized, and thus it can be usefully used to stably express a therapeutic gene without loss.

The present invention also provides a recombinant retrovirus comprising the vector. Meanwhile, the first recombinant expression vector containing a Gag-Pol gene of MuLV, a sEF1α promoter or a MCMV promoter, and a first therapeutic gene; and the second recombinant expression vector containing an Env gene of a virus, an MCMV promoter and a second therapeutic gene can be included in the recombinant retrovirus, respectively or together.

In a specific embodiment of the present invention, four cleaved MCMV promoters having the sizes of 470 bp, 337 bp, 237 bp, and 160 bp, respectively, were prepared by removing repetitive nucleotide sequences in the MCMV promoter to minimize recombination (Table 2). In addition, GaLV env-based vectors (spRRVe-TK, spRRVe-F1-TK, spRRVe-F2-TK, spRRVe-F3-TK and spRRVe-F4-TK) and MuLV-based vectors (sRRVe-TK, sRRVe-F1-TK, sRRVe-F2-TK, sRRVe-F3-TK and sRRVe-F4-TK) into which the cleaved MCMV promoter was introduced were constructed, and a sRRVe-sEF1α-hopt-yCD vector composed of gag-pol-sEF1α-hopt-yCD expressing yeast cytosine deaminase protein was constructed as a vector introduced together with the vector expressing thymidine kinase protein (FIGS. 7 and 8), followed by confirming the occurrence of recombination. As a result, it was confirmed that no recombination occurred in the sRRVe-sEF1α-hopt-yCD vector (see FIG. 9), and almost no recombination occurred in the spRVe-F4-TK vector in which most of the repetitive sequences in the MCMV promoter were removed (FIGS. 10, 11 and 13). In addition, it was confirmed that recombination did not occur even in the combination of sRRVgp-F4-hopt-yCD and the vector in which sEF1α of the sRRVe-sEF1α-hopt-yCD vector was substituted with the F4 truncated promoter of MCMV (see FIG. 14). It was also confirmed that recombination did not occur in the sRRVgp-F4-hopt-yCD/sRRVe-F4-hCD19 vector into which human CD19 gene was introduced as a therapeutic gene (see FIGS. 20 and 21). It was also confirmed that recombination did not occur even in the sRRVe-F4-hCD19t vector into which hCD19t with truncated amino acids of the cytoplasmic domain of human CD19 gene was introduced as a therapeutic gene (see FIGS. 23 and 25). It was also confirmed that recombination did not occur even in the sRRVgp-F4-mGM-CSF vector into which mouse GM-CSF was introduced as a therapeutic gene (see FIG. 27). It was also confirmed that recombination did not occur in the sRRVgp-F4-hopt-GM-CSF vector into which codon-optimized human GM-CSF was introduced as a therapeutic gene (see FIGS. 32 and 33).

Therefore, the occurrence of recombination in the vector of the present invention is minimized, and thus it can be usefully used to stably express a therapeutic gene without loss.

The present invention also provides a host cell transfected with the recombinant retrovirus.

The host cell can be NS/O myeloma cell, human 293T cell, Chinese hamster ovary cell (CHO cell), HeLa cell, CapT cell (human amniotic fluid-derived cell), COS cell, canine D17 cell, mouse NIH/3T3 cell, retrovirus packaging cell, human mesenchymal stem cell, or feline PG4 cell.

Transfection is performed by infecting the cells above with the recombinant viruses produced in cells transduced with the recombinant retrovirus vector plasmid.

The transfection can be performed according to the method known in the art. For example, the transfection can be performed by one or more methods selected from the group consisting of lipofectamine method, microinjection method, calcium phosphate precipitation method, electroporation method, liposome-mediated transfection method, DEAE-dextran treatment method and gene bombardment method. In one embodiment of the present invention, the transfection can be performed by lipofectamine method.

The transfected cells can be cultured using a medium commonly used for culturing animal cells. For example, the medium can be at least one selected from the group consisting of Eagles's MEM, a-MEM, Iscove's MEM, medium 199, CMRL 1066, RPMI 1640, F12, F10, DMEM, a mixed medium of DMEM and F12, Way-mouth's MB752/1, McCoy's 5A and MCDB series media. In one embodiment of the present invention, the medium can be DMEM.

The present invention also provides a pharmaceutical composition and methods for preventing or treating cancer comprising the recombinant retrovirus as an active ingredient.

On the other hand, the first recombinant expression vector containing a Gag-Pol gene of MuLV (Murine Leukemia virus), a sEF1α promoter and a yeast cytosine deaminase (yCD) gene; and the second recombinant expression vector containing an Env gene of a virus, an MCMV promoter and a thymidine kinase gene can be included in the recombinant retrovirus, respectively or together.

The retrovirus can target any dividing cell, and specifically, the cell may be a cancer cell. The cancer cell may include the cell derived from cancers such as mucinous cell carcinoma, round cell carcinoma, locally advanced tumor, metastatic cancer, Ewing's sarcoma, cancer metastasis, lymphoid metastasis, squamous cell carcinoma, esophageal squamous cell carcinoma, oral carcinoma, multiple myeloma, acute lymphocytic leukemia, acute nonlymphocytic leukemia, chronic lymphocytic leukemia, chronic myelocytic leukemia, hairy cell leukemia, effluent lymphoma (celiac lymphoma), thymic lymphoma lung cancer, small cell lung carcinoma, cutaneous T-cell lymphoma, Hodgkin's lymphoma, non-Hodgkin's lymphoma, adrenocortical cancer, ACTH-producing tumor, non-small cell lung cancer, breast cancer, small cell carcinoma, ductal carcinoma, stomach cancer, colon cancer, colorectal cancer, polyps associated with colorectal neoplasia, pancreatic cancer, liver cancer, bladder cancer, primary superficial bladder tumor, invasive metastatic cell bladder carcinoma of the bladder, muscle invasive bladder cancer, prostate cancer, colorectal cancer, kidney cancer, liver cancer, esophageal cancer, ovarian carcinoma, cervical cancer, endometrial cancer, choriocarcinoma, ovarian cancer, primary peritoneal epithelial neoplasia, cervical carcinoma, vaginal cancer, vulvar cancer, uterine cancer, follicular solid tumor, testicular cancer, penile cancer, renal cell carcinoma, brain cancer, head and neck cancer, neuroblastoma, brainstem glioma, glioma, metastatic tumor cell infiltration in the central nervous system, osteoma, osteosarcoma, malignant melanoma, tumor progression of human skin keratinocytes, squamous cell carcinoma, thyroid cancer, retinoblastoma, neuroblastoma, mesothelioma, Wilms' tumor, gallbladder cancer, trophoblastic tumor, hemangiopericytoma, or Kaposi's sarcoma.

In a specific embodiment of the present invention, it was confirmed that thymidine kinase and yeast cytosine deaminase used as therapeutic genes were stably expressed in the GaLV env-based vectors (spRRVe-TK, spRRVe-F1-TK, spRRVe-F2-TK, spRRVe-F3-TK, and spRRVe-F4-TK) and the MuLV-based vectors (sRRVe-TK, sRRVe-F1-TK, sRRVe-F2-TK, sRRVe-F3-TK, and sRRVe-F4-TK), and that the therapeutic genes could kill cells by acting on the prodrugs GCV and 5-FC.

Therefore, the recombinant retrovirus containing the vector according to the present invention can be effectively used for preventing or treating cancer.

The pharmaceutical composition of the present invention can be formulated as a parenteral preparation. Formulations for parenteral administration can include injections such as sterilized aqueous solutions, water-insoluble excipients, suspensions and emulsions.

Propylene glycol, polyethylene glycol, vegetable oil such as olive oil, and injectable ester such as ethyl oleate can be used as water insoluble excipients and suspensions.

Parenteral administration can be performed by a method selected from the group consisting of external skin application, intraperitoneal injection, rectal injection, subcutaneous injection, intravenous injection, intramuscular injection, and intrathoracic injection.

The composition of the present invention can be administered by the pharmaceutically effective amount. The effective amount can be determined according to the type of disease, the severity, the activity of the drug, the patient's sensitivity to the drug, the time of administration, the route of administration, the duration of treatment, the drugs being used simultaneously, and the like. The composition of the present invention can be administered alone or in combination with other therapeutic agents. In combination administration, the administration can be sequential or simultaneous.

The effective dose of the composition is $10^{11}$ to $10^{13}$ virus particles ($10^8$ to $10^{10}$ IU)/kg per 1 kg of body weight in the case of recombinant viruses and 103 to $10^6$ cells/kg in the case of cells, and the administration is carried out as a single administration.

The pharmaceutical composition according to the present invention can contain the replicating-retrovirus vector with minimized recombination occurrence by 10 to 95 weight % as an active ingredient based on the total weight of the composition. In addition, the pharmaceutical composition of the present invention can further include at least one active ingredient exhibiting the same or similar function in addition to the above active ingredient.

The present invention also provides a gene delivery composition and method of gene delivery for treating cancer comprising the recombinant retrovirus.

Meanwhile, the first recombinant expression vector containing a Gag-Pol gene of MuLV (Murine Leukemia virus), a sEF1α promoter or a MCMV promoter, and a first therapeutic gene; and the second recombinant expression vector containing an Env gene of a virus, an MCMV promoter and a second therapeutic gene can be included in the recombinant retrovirus, respectively or together.

The cancer may include cancer as described above.

The term "gene delivery composition" used in this specification refers to a composition capable of transferring a gene into a target cell.

In a specific embodiment of the present invention, it was confirmed that thymidine kinase and yeast cytosine deaminase used as therapeutic genes were stably expressed in the GaLV env-based vectors (spRRVe-TK, spRRVe-F1-TK, spRRVe-F2-TK, spRRVe-F3-TK, and spRRVe-F4-TK) and the MuLV-based vectors (sRRVe-TK, sRRVe-F1-TK, sRRVe-F2-TK, sRRVe-F3-TK, and sRRVe-F4-TK), and that the therapeutic genes could kill cells by acting on the prodrugs GCV and 5-FC.

Therefore, the recombinant retrovirus containing the vector according to the present invention can be effectively used for the delivery of genes for cancer treatment.

In addition, the present invention provides a method for preparing a replicating-retrovirus vector with minimized recombination occurrence, comprising the following steps:

1) a step of preparing a first recombinant expression vector containing a Gag-Pol gene of MuLV (Murine Leukemia virus), a sEF1α promoter or a MCMV promoter, and a first therapeutic gene; and
2) a step of preparing a second recombinant expression vector containing Env gene of a virus, an MCMV promoter and a second therapeutic gene.

The vector has the characteristics described above. For example, the MCMV promoter is selected from the group consisting of polynucleotides having the nucleotide sequences represented by SEQ. ID. NO: 3, NO: 4, NO: 5, NO: 6 and NO: 7, the sEF1α promoter is a polynucleotide having the nucleotide sequence represented by SEQ. ID. NO: 18, and the Env gene of a virus is a polynucleotide having the nucleotide sequence represented by SEQ. ID. NO: 19 or NO: 20.

In addition, the first therapeutic gene and the second therapeutic gene are at least one selected from the group consisting of a thymidine kinase (TK) gene, a yeast cytosine deaminase (yCD) gene and a human CD19 gene.

The thymidine kinase gene is a polynucleotide having the nucleotide sequence represented by SEQ. ID. NO: 21, the yeast cytosine deaminase (yCD) gene is a polynucleotide having the nucleotide sequence represented by SEQ. ID. NO: 22, and the human CD19 gene is a polynucleotide having the nucleotide sequence represented by SEQ. ID. NO: 43.

The thymidine kinase gene can activate the precursor drug ganciclovir, and the cytosine deaminase gene can activate the precursor drug 5-fluorocytosine.

In a specific embodiment of the present invention, four cleaved MCMV promoters having the sizes of 470 bp, 337 bp, 237 bp, and 160 bp, respectively, were prepared by removing repetitive nucleotide sequences in the MCMV promoter to minimize recombination (Table 2). In addition, GaLV env-based vectors (spRRVe-TK, spRRVe-F1-TK, spRRVe-F2-TK, spRRVe-F3-TK and spRRVe-F4-TK) and MuLV-based vectors (sRRVe-TK, sRRVe-F1-TK, sRRVe-F2-TK, sRRVe-F3-TK and sRRVe-F4-TK) into which the cleaved MCMV promoter was introduced were constructed, and a sRRVe-sEF1α-hopt-yCD vector composed of gag-pol-sEF1α-hopt-yCD expressing yeast cytosine deaminase protein was constructed as a vector introduced together with the vector expressing thymidine kinase protein (FIGS. 7 and 8), followed by confirming the occurrence of recombination. As a result, it was confirmed that no recombination occurred in the sRRVe-sEF1α-hopt-yCD vector (see FIG. 9), and almost no recombination occurred in the spRVe-F4-TK vector in which most of the repetitive sequences in the MCMV promoter were removed (FIGS. 10, 11 and 13). It was also confirmed that recombination did not occur even in the combination of sRRVgp-F4-hopt-yCD and the vector in which sEF1α of the sRRVe-sEF1α-hopt-yCD vector was substituted with the F4 truncated promoter of MCMV (see FIG. 14). It was also confirmed that recombination did not occur in the sRRVgp-F4-hopt-yCD/sRRVe-F4-hCD19 vector into which human CD19 gene was introduced as a therapeutic gene (see FIGS. 20 and 21). It was also confirmed that recombination did not occur even in the sRRVe-F4-hCD19t vector into which hCD19t with truncated amino acids of the cytoplasmic domain of human CD19 gene was introduced as a therapeutic gene (see FIGS. 23 and 25). It was also confirmed that recombination did not occur even in the sRRVgp-F4-mGM-CSF vector into which mouse GM-CSF was introduced as a therapeutic gene (see FIG. 27). It was also confirmed that recombination did not occur in the sRRVgp-F4-hopt-GM-CSF vector into which codon-optimized human GM-CSF was introduced as a therapeutic gene (see FIGS. 32 and 33).

Therefore, the occurrence of recombination in the vector prepared by the production method of the present invention is minimized, and thus it can be usefully used to stably express a therapeutic gene without loss.

Hereinafter, the present invention will be described in detail by the following examples.

However, the following examples are only for illustrating the present invention, and the contents of the present invention are not limited thereto.

<Example 1> Construction of Replicating-Retrovirus Vector

<1-1> Preparation of Virus Vector

If a foreign gene larger than 1.3 kb is inserted into a conventional RRV vector in which gag, pol and env genes are synthesized into a single genome, the genome size increases, making the vector structure unstable, so the virus vector in intact form cannot be multiplied. Therefore, two vectors were constructed so that the gag-pol gene and the env genes were expressed in independent vectors, respectively. At this time, the env was replaced with the env gene of MuLV (murine leukemia virus), which is friendly to mammalian infection, or the env gene of GaLV (Gibbon ape Leukemia virus), which is friendly to primate infection. As a therapeutic gene, HSV-TK (herpes simplex virus thymidine kinase) gene was cloned into the gag-pol vector and yCD (yeast cytosine deaminase) gene was cloned into the GaLV-env vector, respectively, and then vectors were constructed using a murine cytomegalovirus (MCMV) promoter as the promoter for gene expression control.

Specifically, virus vectors were constructed as follows.

1. spRRVe-yCD env vector (SEQ. ID. NO: 25): (FIG. 1)

PmeI existing in MCS (multi-cloning site) of the previously constructed spRRVeMCMV-MCS (GaLVEnv-MCMV-MCS-3'-LTR) vector was cut and treated with CIAP to prepare both ends of the truncated vector in a blunt form. The pcDNA-yCD vector into which yCD was inserted was digested with XhoI-HindIII to recover the yCD gene, and then treated with T4 DNA polymerase to prepare both ends of the vector in a blunt form. Then, the spRRVeMCMV (PmeI, CIAP) vector and yCD (XhoI-HindIII, T4 DNA polymerase) were ligated using T4 DNA ligase to prepare spRRVe-yCD.

2. sRRVgp-TK:gag-pol vector (SEQ. ID. NO: 26): (FIG. 1)

A promoter and transgene-free sRRVgp (vector with retrovirus gag-pol) vector was constructed. Then, MCMV-TK was introduced into the EcoRI site between gag-pol and 3'-LTR. Since sRRVgp-TK could not be completed in one cloning process, MCMV was first cloned, and then TK was introduced under MCMV to complete sRRVgp-TK, the final product. The method is as follows.

To clone MCMV into the EcoRI site between the gag-pol and 3'-LTR of sRRVgp, the MCMV promoter was amplified by PCR.

MCMV-F-EcoRI: 5'-cgGAATTCAACAGGAAAGTCCCATTGGA-3' (SEQ. ID. NO: 47)

MCMV—R-PmeI-EcoRI: 5'-cgGAATTCGTTTAAACCTGCGTTCTACGGTGGTCAGA-3' (SEQ. ID. NO: 48) The amplified MCMV promoter product was digested with EcoRI, and the sRRVgp vector was recovered by treatment with EcoRI and CIAP, and then ligated with T4 DNA ligase to complete sRRVgpMCMV. Then, in order to clone the TK gene into the PmeI site of the sRRVgpMCMV vector, the TK gene was amplified by PCR to include PmeI.

TK—F-PmeI: 5'-cgGTTTAAACATGGCTTCGTACCCCTGCCATC-3' (SEQ. ID. NO: 49)

TK—R-PmeI: 5'-CGGTTTAAACTCAGTTAGCCTCCCCCATCTCC-3' (SEQ. ID. NO: 50) By treating with PmeI and CIAP, sRRVgpMCMV was recovered and the TK gene was digested with PmeI and recovered, and then ligated with T4 DNA ligase to construct the final product, sRRVgp-TK.

<1-2> Virus Production

Figure 2:
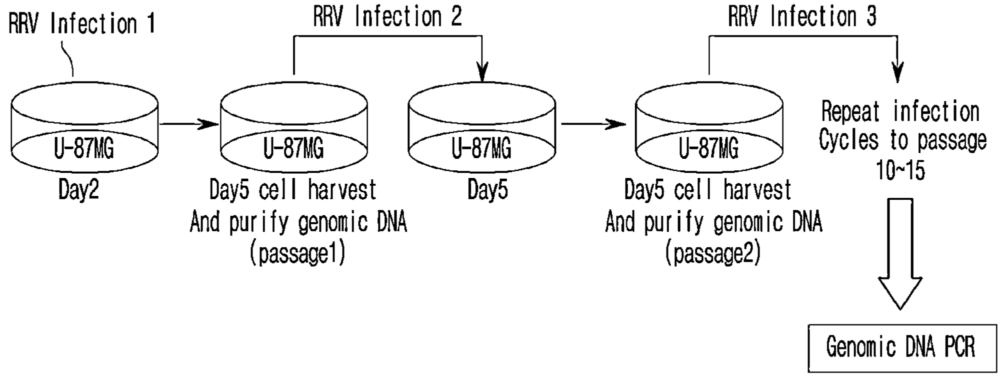
FIG. 2 is a schematic diagram showing the experimental procedure for confirming the infectivity and recombination type of the GaLV env-pMCMV-yCD/gag-pol-pMCMV-HSV1-TK vector.

In order to confirm the infectivity and recombination type of the replicating-retrovirus vector in which the therapeutic gene is expressed under the control of the MCMV promoter, viruses were produced using the vector constructed in Example <1-1> according to the procedure shown in the schematic diagram of FIG. 2.

Specifically, viruses were produced by transient transduction of the vector prepared in Example <1-1> into 293T cells, and the brain tumor cell line U87MG was infected with the virus of 2E7 gc (genome copies). After 3 days of initial infection, the cultured supernatant was taken and re-infected to new U87MG, and the infected U87MG cell line was recovered and genomic DNA was isolated.

<1-3> Confirmation of Recombination of spRRVe-yCD:env Vector

The replicating-retrovirus vector for gene therapy is highly likely to cause recombination because the size of genomic RNA is increased by the introduced foreign gene and non-homologous sequences are added. Therefore, in order to construct an efficient and stable replicating-retrovirus vector for gene therapy, it is very important to confirm the presence and degree of recombination at the development stage. To confirm whether the virus proliferation and infection progressed and whether the recombination occurred during the amplification process after the virus infection, polymerase chain reaction (PCR) was performed using the genomic DNA extracted from the virus produced in Example <1-2>.

Figure 3:
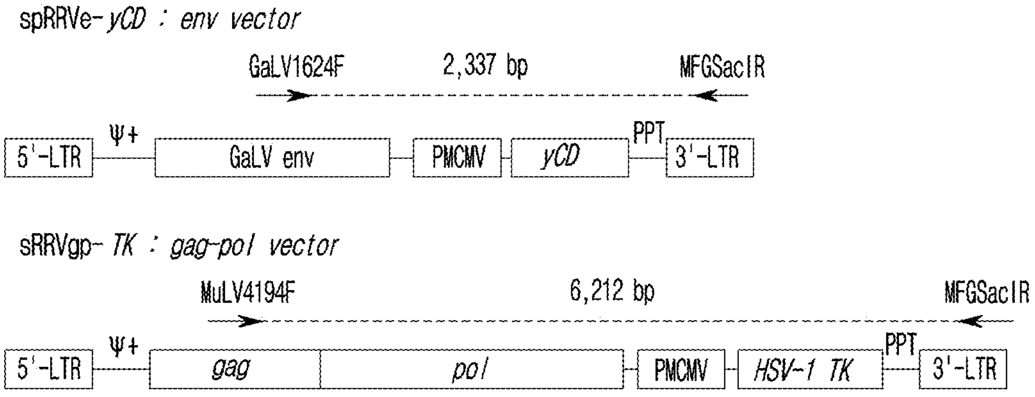
FIG. 3 is a schematic diagram showing the positions of primers used in polymerase chain reaction performed to confirm the recombination type of the GaLV env-pMCMV-yCD/gag-pol-pMCMV-HSV1-TK vector.

Specifically, polymerase chain reaction was performed using the primers listed in Table 1 below capable of specifically amplifying the env vector. As shown in FIG. 3, for the spRRVe-yCD:env vector, genomic DNA PCR was performed using the primers amplifying GaLV env and the 3' end as the target sites to confirm whether the gene was amplified to the expected size. 100 ng of genomic DNA, 1X reaction buffer, 0.25 mM dNTP, 0.2 pmol forward primer, 0.2 pmol reverse primer, and 0.2 unit Taq polymerase were added to a PCR reaction tube, and sterilized distilled water was added to make the final volume of 20 μℓ. Then, After PCR was performed under the conditions shown in Table 1 below, the amplified DNA was loaded on a 1% agarose gel to confirm the PCR amplification product, thereby confirming the infectivity of the virus and whether the recombination occurred.

TABLE 1

| | Sequence (5'→3') | SEQ. ID. NO: |
|---|---|---|
| GaLV 1624F | GACTCAGTCAGCAAGTTAGAG | 1 |
| MFGSacIR | CAATCG-GAGGACTGGCGCCCCGAGTGA | 2 |

Figure 4:
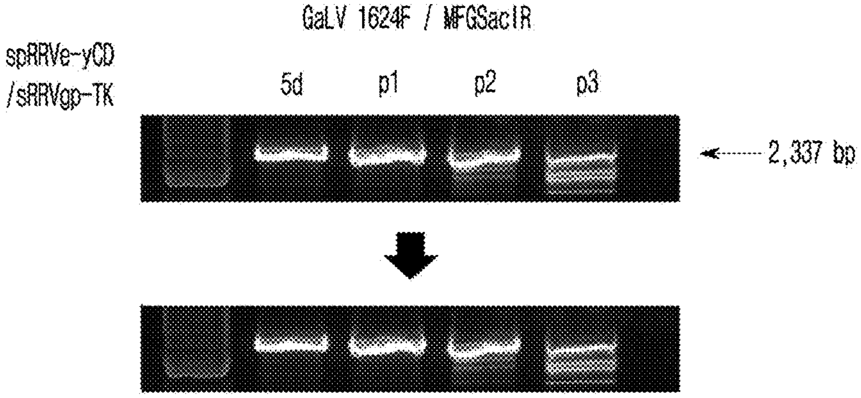
FIG. 4 is a diagram showing the results of polymerase chain reaction performed to confirm whether recombination occurred in the spRRVe-yCD:env vector, confirming that virus proliferation and infection progressed, but recombination occurred during the amplification process after virus infection.

As a result, as shown in FIG. 4, as a result of performing polymerase chain reaction of the spRRVe-yCD:env vector, PCR products were detected on the 3rd day of the initial infection and passages 1 to 3, confirming that the virus proliferation and infection progressed. However, since a large number of PCR products smaller than the expected 2,337 bp amplification product were detected from passage 2, it was confirmed that recombination occurred during the amplification process after virus infection. Specifically, only a single PCR band could be observed up to passage 1, but in passage 2 and passage 3, it was confirmed that several PCR bands were amplified.

<1-4> Analysis of Recombination Type of spRRVe-yCD:env Vector

Since retroviruses are synthesized through the process of reverse transcription, instability of the genome sequence during this process can create various types of recombination. Therefore, after the PCR reaction using the genomic DNA of the spRRVe-yCD:env vector in Example <1-3>, the PCR products of p2 and p3 stage recombination bands (bands indicated by red boxes in FIG. 4) were recovered and cloned into a pGEM-T vector for gene analysis, and the clone was purified and the nucleotide sequence of the gene was analyzed to analyze the recombination type.

Figure 5:
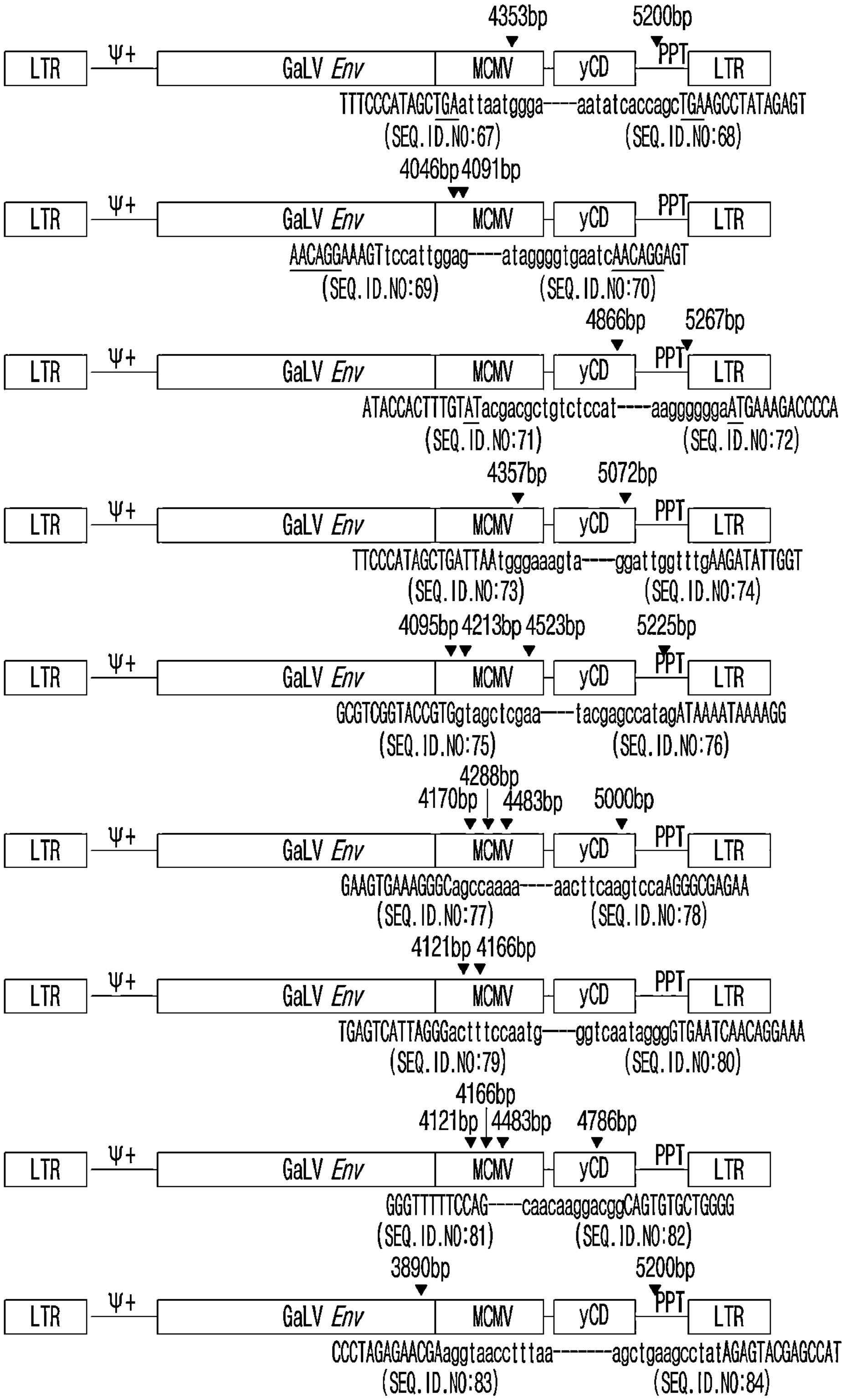
FIG. 5 is a diagram confirming the type of recombination occurred in GaLV env, MCMV promoter, yCD, and 3' nucleotide sequence.

As a result, as shown in FIG. 5, the clones in which recombination occurred within the GaLV env, MCMV promoter, yCD, and 3'-LTR sequences were confirmed in the recovered PCR products. In particular, it was confirmed that recombination occurred due to the loss of the virus vector nucleotide sequence at other sites starting from the MCMV promoter or some of the nucleotide sequence within the promoter caused by the four repetitive nucleotide sequences (1. AACAGGAAA, 2. GGGACTTTCCAATGGGTT TTGC CCAGTACA, 3. TGGGTTTTTCC, 4. GTACTTTCCCA) within the MCMV promoter shown in FIG. 6. Accordingly, four types of promoters with different sizes were designed by excising the MCMV promoter sequence to minimize the repetitive sequences of MCMV to prevent recombination and facilitate the expression of therapeutic genes.

<Example 2> Construction of Replicating-Retrovirus Vector with Minimized Recombination Occurrence

<2-1> Preparation of Truncated Form of MCMV Promoter for Construction of Vector with Minimized Recombination Occurrence In order to overcome recombination of the replicating-retrovirus vector caused by the repetitive sequences within the MCMV promoter, a cleaved MCMV promoter was constructed by removing the repetitive sequences within the MCMV promoter.

Specifically, 4 types of cleaved MCMV promoters were prepared by cutting the initially used MCMV promoter of about 646 bp based on the repetitive sequences (Table 2). Then, MCMV F1 (470 bp), F2 (337 bp), F3 (237 bp), and F4 (160 bp) were introduced into the 646 bp MCMV promoter sites of the sRRVe-TK and spRRVe-TK previously constructed in this laboratory. The cleaved MCMV promoters were obtained through PCR using the amplification primers containing the restriction enzyme sites described in Table 3 below.

TABLE 2

| | MCMV promoter (5'→3') |
|---|---|
| MCMV (SEQ. ID. NO: 3, 646 bp) | AACAGGAAAGTTCCATTGGAGCCAAGTACATTGAGTCAATAGGGAC TTTCCAATGGGTTTTGCCCAGTACATAAGGTCAATGGGAGGTAAGC CAATGGGTTTTTCCCATTACTGGCACGTATACTGAGTCATTAGGGA CTTTCCAATGGGTTTTGCCCAGTACATAAGGTCAATAGGGGTGAAT CAACAGGAAAGTCCCATTGGAGCCAAGTACACTGAGTCAATAGGGA CTTTCCATTGGGTTTTGCCCAGTACAAAAGGTCAATAGGGGGTGAG TCAATGGGTTTTTCCCATTATTGGCACGTACATAAGGTCAATAGGG GTGAGTCATTGGGTTTTTCCAGCCAATTTAATTAAAACGCCATGTA CTTTCCCACCATTGACGTCAATGGGCTATTGAAACTAATGCAACGT GACCTTTAAACGGTACTTTCCCATAGCTGATTAATGGGAAAGTACC GTTCTCGAGCCAATACACGTCAATGGGAAGTGAAAGGGCAGCCAAA ACGTAACACCGCCCCGGTTTTCCCTGGAAATTCCATATTGGCACGC ATTCTATTGGCTGAGCTGCGTTCACGTGGGTATAAGAGGCGCGACC AGCGTCGGTACCGTCGCAGTCTTCGGTCTGACCACCGTAGAACGCA GA |
| MCMV F1 (SEQ. ID. NO: 4, 470 bp) | GGGTGAATCAACAGGAAAGTCCCATTGGAGCCAAGTACACTGAGTC AATAGGGACTTTCCATTGGGTTTTGCCCAGTACAAAAGGTCAATAG GGGGTGAGTCAATGGGTTTTTCCCATTATTGGCACGTACATAAGGT CAATAGGGGTGAGTCATTGGGTTTTTCCAGCCAATTTAATTAAAAC GCCATGTACTTTCCCACCATTGACGTCAATGGGCTATTGAAACTAA TGCAACGTGACCTTTAAACGGTACTTTCCCATAGCTGATTAATGGG AAAGTACCGTTCTCGAGCCAATACACGTCAATGGGAAGTGAAAGGG CAGCCAAAACGTAACACCGCCCCGGTTTTCCCTGGAAATTCCATAT TGGCACGCATTCTATTGGCTGAGCTGCGTTCACGTGGGTATAAGAG GCGCGACCAGCGTCGGTACCGTCGCAGTCTTCGGTCTGACCACCGT AGAACGCAGA |

TABLE 2-continued

| | MCMV promoter (5'→3') |
|---|---|
| MCMV F2 (SEQ. ID. NO: 5, 337 bp) | AAGGTCAATAGGGGTGAGTCATTGGGTTTTTCCAGCCAATTTAATT<br>AAAACGCCATGTACTTTCCCACCATTGACGTCAATGGGCTATTGAA<br>ACTAATGCAACGTGACCTTTAAACGGTACTTTCCCATAGCTGATTA<br>ATGGGAAAGTACCGTTCTCGAGCCAATACACGTCAATGGGAAGTGA<br>AAGGGCAGCCAAAACGTAACACCGCCCCGGTTTTCCCTGGAAATTC<br>CATATTGGCACGCATTCTATTGGCTGAGCTGCGTTCACGTGGGTAT<br>AAGAGGCGCGACCAGCGTCGGTACCGTCGCAGTCTTCGGTCTGACC<br>ACCGTAGAACGCAGA |
| MCMV F3 (SEQ. ID. NO: 6, 237 bp) | AACGTGACCTTTAAACGGTACTTTCCCATAGCTGATTAATGGGAAA<br>GTACCGTTCTCGAGCCAATACACGTCAATGGGAAGTGAAAGGGCAG<br>CCAAAACGTAACACCGCCCCGGTTTTCCCTGGAAATTCCATATTGG<br>CACGCATTCTATTGGCTGAGCTGCGTTCACGTGGGTATAAGAGGCG<br>CGACCAGCGTCGGTACCGTCGCAGTCTTCGGTCTGACCACCGTAGA<br>ACGCAGA |
| MCMV F4 (SEQ. ID. NO: 7, 161 bp) | GGAAGTGAAAGGGCAGCCAAAACGTAACACCGCCCCGGTTTTCCCT<br>GGAAATTCCATATTGGCACGCATTCTATTGGCTGAGCTGCGTTCAC<br>GTGGGTATAAGAGGCGCGACCAGCGTCGGTACCGTCGCAGTCTTCG<br>GTCTGACCACCGTAGAACGCAGA |

TABLE 3

| | Primer | Sequence (5'→3') | SEQ. ID. NO: |
|---|---|---|---|
| SRRVe (MuLV)-based TK | MCMV F1-PmeI | cggtttaaacGGGTGAATC AACAGGAAAGTCCC | 8 |
| | MCMV F2-PmeI | cggtttaaacAAGGTCAAT AGGGGTGAGTCAT | 9 |
| | MCMV F3-PmeI | cggtttaaacAACGTGACC TTTAAACGGTACT | 10 |
| | MCMV F4-PmeI | cggtttaaacGGAAGTGAA AGGGCAGCCAAA | 11 |
| | MCMV-R-NotI | cggcggccgcTCTGCGTTC TACGGTGGTCAGACC | 12 |
| spRRVe (GaLV)-based-TK | MCMV F1-PmeI | cggtttaaacGGGTGAATC AACAGGAAAGTCCC | 8 |
| | MCMV F2-PmeI | cggtttaaacAAGGTCAAT AGGGGTGAGTCAT | 9 |
| | MCMV F3-PmeI | cggtttaaacAACGTGACC TTTAAACGGTACT | 10 |
| | MCMV F4-PmeI | cggtttaaacGGAAGTGAA AGGGCAGCCAAA | 11 |
| | MCMV-R-BamHI | cgggatccTCTGCGTTCTA CGGTGGTCAGACC | 13 |

<2-2> Construction of Replicating-Retrovirus Vector with Minimized Recombination Occurrence (spRRVe(GaLV)-TK/sRRVgp-sEF1α-Hopt-yCD)

The cleaved MCMV promoter digested with PmeI-BamHI was cloned into the promoter site of spRRVe (GaLV)-TK to complete spRRVe-TK (SEQ. ID. NO: 27), spRRVe-F1-TK (SEQ. ID. NO: 28), spRRVe-F2-TK (SEQ. ID. NO: 29), spRRVe-F3-TK (SEQ. ID. NO: 30), and spRRVe-F4-TK (SEQ. ID. NO: 31) vectors (FIG. 7). Then, to confirm the effectiveness of the constructed split-dual RRV vector and whether or not recombination occurred, viruses were synthesized with a combination of gag-pol vectors (sRRVgp-sEF1α-hopt-yCD, SEQ. ID. NO: 32) expressing hopt-yCD regulated by the sEF1α promoter, and then infected to U87MG cells to determine whether recombination occurred.

<2-3> Construction of Replicating-Retrovirus Vector with Minimized Recombination Occurrence (sRRVe (MuLV)-TK/sRRVgp-sEF1α-hopt-yCD)

Figure 8:
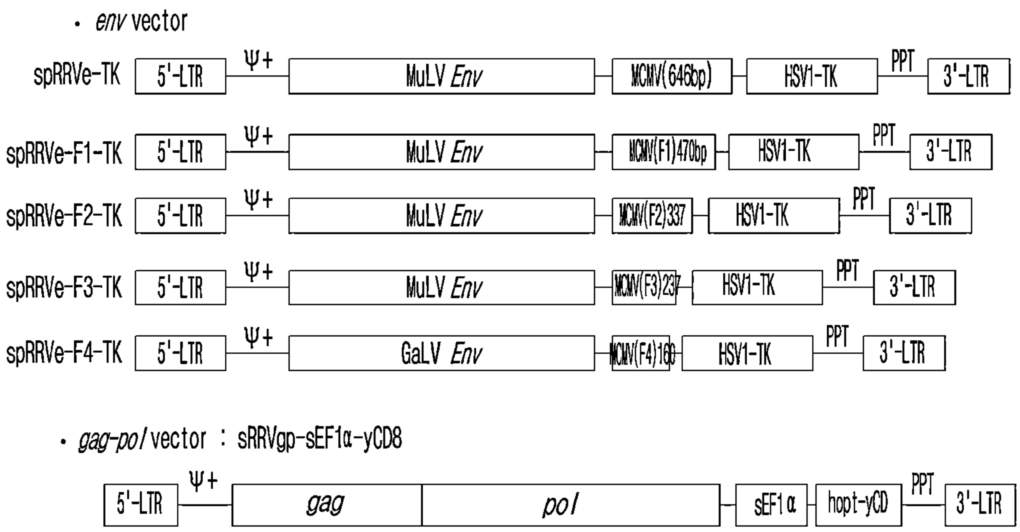
FIG. 8 is a diagram showing the structures of sRRVe-TK, sRRVe-F1-TK, sRRVe-F2-TK, sRRVe-F3-TK and sRRVe-F4-TK vectors in which the cleaved MCMV promoter is introduced into MuLV Env.

The cleaved MCMV promoter digested with PmeI-NotI was cloned into the promoter site of sRRVe(MuLV)-TK to complete sRRVe-TK (SEQ. ID. NO: 33), sRRVe-F1-TK (SEQ. ID. NO: 34), sRRVe-F2-TK (SEQ. ID. NO: 35), sRRVe-F3-TK (SEQ. ID. NO: 36), and sRRVe-F4-TK (SEQ. ID. NO: 37) vectors (FIG. 8). Then, to confirm the effectiveness of the constructed split-dual RRV vector and whether or not recombination occurred, viruses were synthesized with a combination of gag-pol vectors (sRRVgp-sEF1α-hopt-yCD) expressing hopt-yCD regulated by the sEF1α promoter, and then infected to U87MG cells to determine whether recombination occurred.

<Example 3> Confirmation of Recombination Type of Replicating-Retrovirus Vector with Minimized Recombination Occurrence (spRRVe (GaLV)-TK/sRRVgp-sEF1α-hopt-yCD)

The recombination type of the vector constructed in Example <2-2> was confirmed in the same manner as in Example <1-3>.

Specifically, the constructed GaLV env-based vectors (spRRVe-TK, spRRVe-F1-TK, spRRVe-F2-TK, spRRVe-F3-TK, and spRRVe-F4-TK) were used in combination with the sRRVgp-sEF1α-hopt-yCD vector to synthesize viruses in 293T cells, and then the recombination type was analyzed in the same manner as in Example <1-3>. GaLV1932F and MFGSacIR primers shown in Table 4 were used for env vector-specific amplification, and pol7130F and MFGSacIR primers were used for gag-pol vector-specific amplification.

Figure 9:
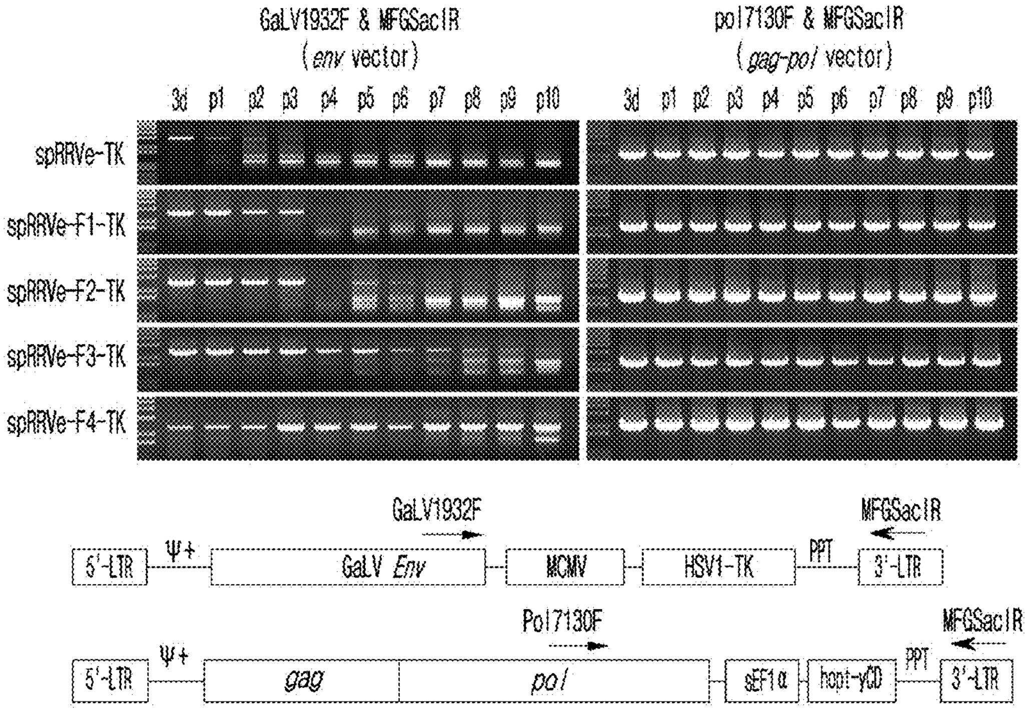
FIG. 9 is a diagram showing the locations of primers for confirming recombination in sRRVgp-sEF1a-hopt-yCD, spRRVe-TK, spRRVe-F1-TK, spRRVe-F2-TK, spRRVe-F3-TK and spRRVe-F4-TK vectors, and whether the recombination.

As a result, as shown in FIG. 9, as a result of genomic DNA PCR analysis, recombination did not occur in all 5 sets of the sRRVgp-sEF1α-hopt-yCD vector. On the other hand, recombination started to occur from p1 in spRRVe-TK, from p4 in spRRVe-F1-TK and spRRVe-F2-TK, from p5 in spRRVe-F3-TK, and recombination did not occur until p10 in spRRVe-F4-TK. However, in addition to the amplification bands in the PCR products of p6 to p10, a small band below was confirmed by gene sequencing, which indicates that the complete hopt-yCD of the gag-pol vector was reciprocally recombined and inserted into the TK site of the env vector.

TABLE 4

| Primer | Sequence (5'→3') | SEQ. ID. NO: |
|---|---|---|
| GaLV 1624F | GACTCAGTCAGCAAGTTAGAG | 1 |
| GaLV 1932F | GTTGCTCATCCTCGGGCCATG | 14 |
| Am1801F | ATCATTGACCCTGGCCCTTC | 15 |
| pol7130F | CGGCCCGGCACTCATTGGGAG | 16 |
| MuLV4194F | AGCAAGCTATTGGCCACTG | 17 |
| MFGSacIR | CAATCGGAGGACTGGCGC CCCGAGTGA | 2 |

<Example 4> Expression Levels of Thymidine Kinase (TK) and Yeast Cytosine Deaminase (yCD) Proteins in Cells Transfected with Viruses Containing Replicating-Retrovirus Vector with Minimized Recombination Occurrence (spRRVe (GaLV)-TK/sRRVgp-sEF1α-Hopt-yCD)

Thereafter, the protein expression levels of thymidine kinase (HSV1-TK) and yeast cytosine deaminase (yCD) in the U87MG cells obtained in the recombination test step were confirmed by Western blotting with.

Specifically, as shown in FIG. 2, a human brain tumor cell line U87MG was infected with a retrovirus vector combination of 0.1 MOI, and three days later, the virus-containing cell culture supernatant was taken and sequentially infected to a new brain tumor cell line U87MG. After 3 days of initial infection, p1(passage 1)~p10 cells were harvested and resuspended in 100 μℓ of T-PER tissue extraction agent (PIERCE, 78510)+1× proteinase inhibitor. Thereafter, the cells were broken by freezing-thawing three times, and the cytoplasmic supernatant was recovered by centrifugation at 13,000 rpm for 10 minutes. After quantifying the protein amount using BCA, 20 μg of cell lysate was taken and mixed with SDS sample loading dye to 1%. After reacting for 5 minutes in a 100° C. heat block, the reaction mixture was moved to ice and reacted for 2 minutes. Then, the reactant was loaded on 10% (TK) or 13.5% (yCD) SDS-PAGE gel, followed by electrophoresis. Upon completion of the electrophoresis, the protein was transferred to a NC (nitrocellulose) membrane at 90 V for 2 hours, and then put into a blocking solution (5% skim milk in 1X TBS-T), followed by reaction at room temperature for 1 hour. Then, the membrane was added to 1% skim milk/1X TBS-T containing the primary antibody (anti-rabbit-TK: Santa Cruze sc-28038, 1:500 dilution, anti-sheep yCD: Thermo Fisher Scientific PA1-85365, 1:500, anti-mouse b-actin: Sigma A2228, 1:1000), followed by reaction in a refrigerator at 4° C. overnight. Thereafter, the membrane was washed 4 times with 1× TBS-T at room temperature for 10 minutes, and then reacted with the horseradish peroxidase (HRP)-conjugated secondary antibody for 1 hour at room temperature. Then, the membrane was washed 4 times with 1× TBS-T at room temperature for 10 minutes, reacted in an ECL (enhanced chemiluminescence, Bio-rad Cat No. 170-5062) solution, and then analyzed in a chemiluminescence imaging system (ChemiDoc, Biorad CA).

As a result, as shown in FIGS. 10 and 11, consistent with the results of genomic DNA PCR, it was confirmed that the thymidine kinase (TK) protein expression continued stably as the promoter size decreased, and the yeast cytosine diaminase (yCD) protein in the gag-pol vector (sRRVgp-sEF1α-hopt-yCD) was also continuously expressed.

<Example 5> Confirmation of Cell Death Upon Administration of Prodrugs of Thymidine Kinase and Yeast Cytosine Deaminase The drug sensitivity of the spRRVe(GaLV)-TK/sRRVgp-sEF1α-hopt-yCD virus produced in Example <2-2> to ganciclovir (GCV) and 5-fluorocytosine (5-FC) was confirmed.

Specifically, the spRRVe-TK/sRRVgp-sEF1α-hopt-yCD virus was co-transfected into the 293T cell line using PLUS reagent (Invitrogen) and lipofectamine (Invitrogen). After 2 days, the supernatant of the virus was recovered, and U-87MG cells passaged in a 6-well plate at the density of $1.5\times10^5$ cells/well the previous day were infected with the virus and polybran at a concentration of 8 μg/mℓ for 8 hours. Five days after infection (postinfection 5d), the cell supernatant was taken and re-infected to U-87MG cells passaged in a 6-well plate at the density of $1.5\times10^5$ cells/well the previous day (p1), and then sequentially infected up to p4 in the same way. Cells at each stage of infection were treated with trypsin-EDTA to make single cells, and passaged in a 12-well plate at the density of $1.5\times10^5$ cells/well, and from the next day after the passage, 30 μg/mℓ of GCV and 1 mM 5-FC were treated for or 8 days, respectively, to confirm cell death.

Figure 12:
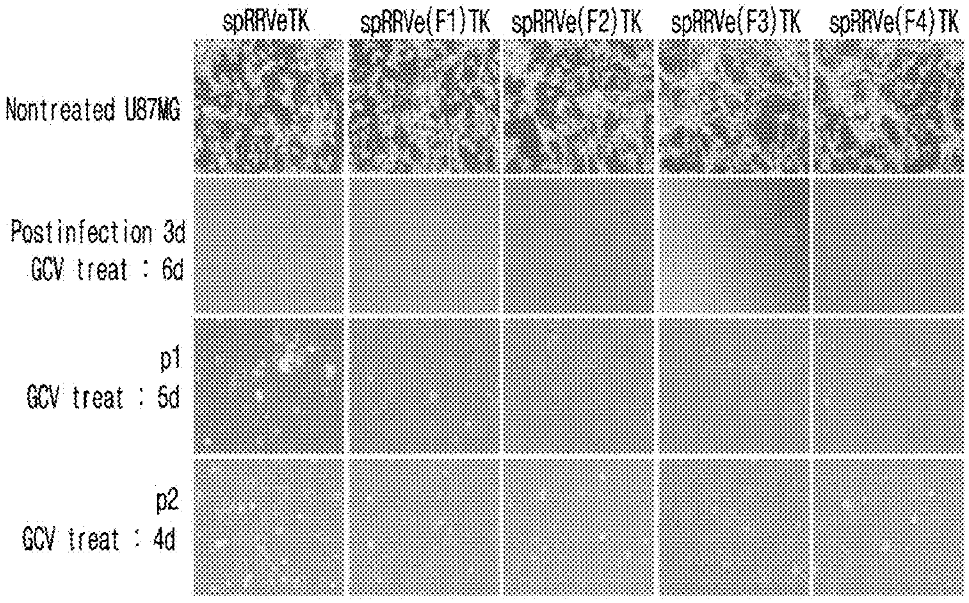
FIG. 12 is a diagram confirming that cell death is induced by thymidine kinase and yeast cytosine deaminase expressed in the sRRVgp-sEF1a-hopt-yCD, spRRVe-TK, spRRVe-F1-TK, spRRVe-F2-TK, spRRVe-F3-TK and spRRVe-F4-TK vectors when the vectors are treated with the prodrugs GCV and 5-FC.

As a result, as shown in FIG. 12, it was confirmed that the cells were killed when the virus-infected cells were treated with 30 μg/mℓ of ganciclovir (GCV) and 1 mM 5-fluorocytocin (5-FC), the pro-drugs.

<Example 6> Confirmation of Recombination Type of MuLV Env-Based Vector Containing Cleaved MCMV Promoter In the analysis test of the recombination occurrence of the spRVe-sEF1α-TK/sRRVgp-sEF1α-hopt-yCD combination, it was confirmed that recombination did not occur well in the gag-pol vector, but confirmed that the complete hopt-yCD of the gag-pol vector was reciprocally recombined and inserted into the TK site of the env vector. This is a phenomenon caused by homologous recombination between promoters when the promoters used in the gag-pol vector and the env vector are the same, and does not affect the expression of a therapeutic gene. On the other hand, in the case of the sRRVgp-sEF1α-hopt-yCD/spRRVe-F4-TK combination, non-homologous recombination occurs between promoters, which affects the expression of an effective therapeutic gene. To minimize the occurrence of such recombination, sRRVgp-F4-hopt-yCD was constructed by introducing F4 promoter into the sEF1α site of sRRVgp-sEF1α-hopt-yCD, and then the recombination type of the sRRVgp-F4-hopt-yCD/sRRV3 sRRVe-F4-TK vector was confirmed in the same manner as in Example <1-3>.

Specifically, the sRRVgp-sEF1α-TK vector was treated with EcoRI to produce sEF1α-TK, and PCR was performed using spRVe-TK as a template with MCMV(F4)-EcoRI-F and MCMV-NotI-M1uI-EcoRI-R primers shown in Table 5 below containing restriction enzyme recognition sequences for cloning other therapeutic genes to clone MCMVF4. Thereafter, the sRRVgp-sEF1α-TK and MCMV F4 PCR products were digested with EcoRI and cloned to construct a sRRVgp-MCMV F4 vector. Then, the hopet-yCD-NotI-F and hopet-yCD-NotI-R primers shown in Table 5 were constructed using hopet-yCD, and PCR was performed using the sRRVgp-sEF1α-hopt-yCD vector as a template.

TABLE 5

| Primer | Sequence (5'→3') | SEQ. ID. NO: |
|---|---|---|
| MCMV(F4)-ECORI-F | cggaattcGGAAGTGA AAGGGCAGCCAAA | 38 |
| MCMV-NotI-MluI-EcoRI-R | cggaattcacgcgtg cgcggccgcTCTGCGT TCTACGGTGGTCAGACC | 39 |
| hopt-yCD-NotI-F | cggcggccgcATGGTTAC TGGGGGAATGGC | 40 |
| hopt-yCD-MluI-R | acgcgtTTATTCCCCGAT GTCTTCGAA | 41 |

Thereafter, the sRRVgp-MCMV F4 vector and the hopt-yCD PCR product were recovered by treatment with NotI-MluI and cloned to complete a sRRVgp-F4-hopt-yCD vector. The constructed MuLV env-based sRRVe-F4-TK vector was used in combination with the sRRVgp-F4-hopt-yCD vector to synthesize viruses in 293T cells, and then the recombination type analysis test was performed in the same manner as in Example <1-3>. Am1801F and MFGSacIR primers shown in Table 4 were used for env vector-specific amplification, and pol7130F and MFGSacIR primers were used for gag-pol vector-specific amplification.

Figure 14:
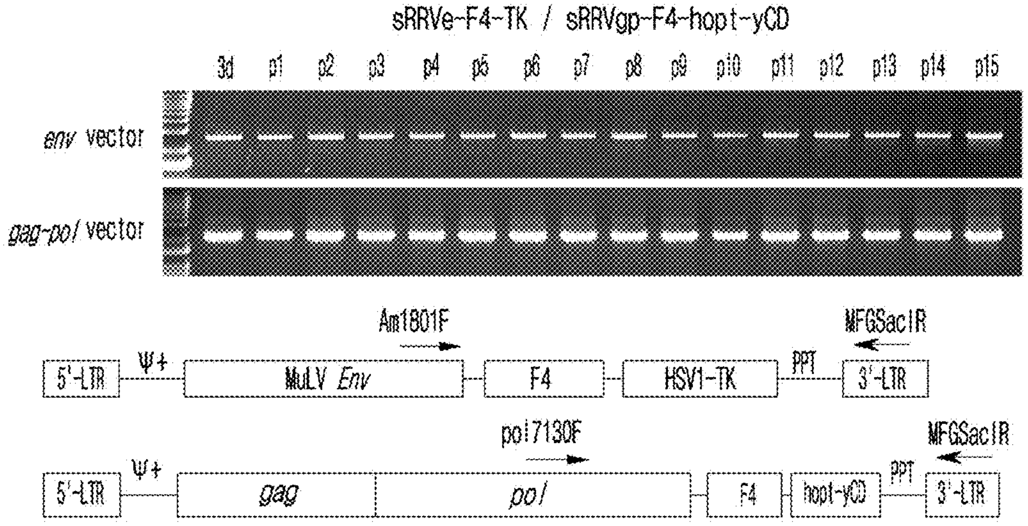
FIG. 14 is a diagram showing the locations of primers for confirming recombination in sRRVgp-F4-hopt-yCD and sRRVe-F4-TK vectors, and whether the recombination.

As a result, as shown in FIG. 13, as a result of genomic DNA PCR analysis, recombination did not occur in all 5 sets of the gag-pol vector. On the other hand, in the sRRVe-TK vector, it was confirmed that recombination in which the small size was lost started to occur from p2. It was also confirmed that recombination started to occur from p7 in sRRVe-F1-TK and sRRVe-F2-TK, and from p8 in sRRVe-F3-TK. On the other hand, in the sRRVe-F4-TK/sRRVgp-F4-hopt-yCD vector combination, recombination did not occur up to p10 in sRRVe-F4-TK, and recombination did not occur even after continuous infection up to p15 (FIG. 14).

That is, in the MuLV env-based RRV vector, recombination frequency decreased as the size of the MCMV promoter decreased, and recombination did not occur in the sRRVe-F4-TK vector in which most of the repetitive sequences of the MCMV promoter were removed. Therefore, it was confirmed that the replicating-retrovirus vector containing the cleaved MCMV promoter did not undergo recombination and thus the therapeutic gene could be delivered to target cells without loss.

<Example 7> Expression Level of Thymidine Kinase (TK) in Cells Transfected with Viruses Containing Replicating-Retrovirus Vector with Minimized Recombination Occurrence (sRRVe (MuLV)-TK/sRRVgp-sEF1α-hopt-yCD)

Then, the TK protein expression level in U87MG cells obtained in the recombination test step after sRRVe-F4-TK was confirmed by Western blotting under the same method and conditions as described in Example 4 above. It was confirmed that yCD protein was stably expressed because recombination did not occur in the gag-pol vector, and thus only the expression level of TK protein was confirmed.

Figure 15:
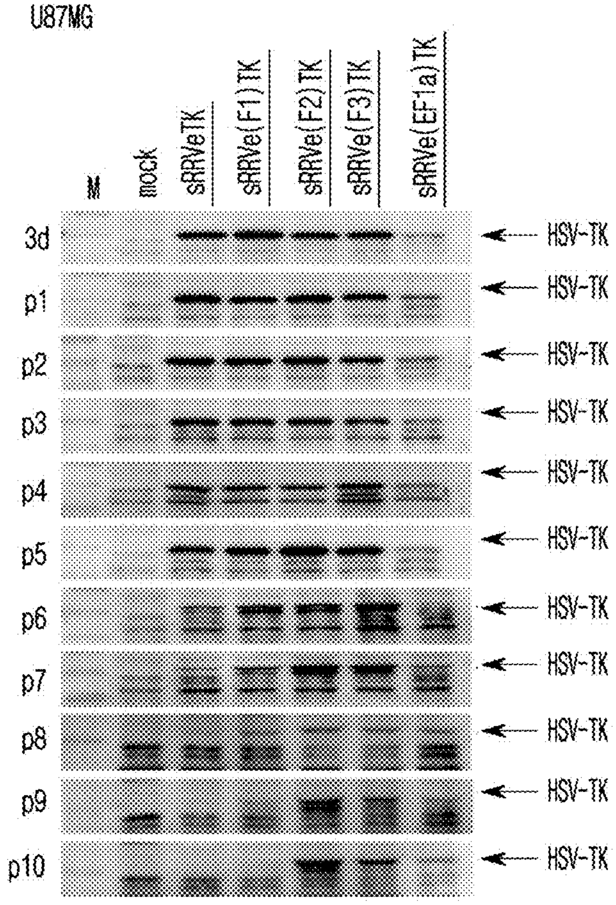
FIG. 15 is a diagram confirming that thymidine kinase (TK) protein is continuously expressed in sRRVe-TK, sRRVe-F1-TK, sRRVe-F2-TK, sRRVe-F3-TK and sRRVe-F4-TK vectors.

As a result, as shown in FIG. 15, it was confirmed that the thymidine kinase (TK) protein expression continued stably as the promoter size decreased consistent with the results of genomic DNA PCR.

<Example 8> Confirmation of Cell Death Upon Administration of Prodrugs of Thymidine Kinase (TK) and Yeast Cytosine Deaminase (yCD)

The drug sensitivity of the virus containing the sRRVe (MuLV)-TK/sRRVgp-F4-hopt-yCD vector produced in Example 6 to ganciclovir (GCV) and 5-fluorocytosine (5-FC) was confirmed.

Specifically, the virus containing spRRVe-F4-hopt-yCD/sRRVgp-TK, spRRVe-F4-hopt-yCD/sRRVgp-F1-TK, spRRVe-F4-hopt-yCD/sRRVgp-F2-TK, spRRVe-F4-hopt-yCD/sRRVgp-F3-TK and spRRVe-F4-hopt-yCD/sRRVgp-F4-TK was co-transfected into the 293T cell line using PLUS reagent (Invitrogen) and lipofectamine (Invitrogen). After 2 days, the supernatant of the virus was recovered, and U-87MG cells passaged in a 6-well plate at the density of $1.5\times10^5$ cells/well the previous day were infected with the virus and polybran at a concentration of 8 μg/mℓ for 8 hours. Five days after infection (postinfection 5d), the cell supernatant was taken and re-infected to U-87MG cells passaged in a 6-well plate at the density of $1.5\times10^5$ cells/well the previous day (p1), and then sequentially infected up to p4 in the same way. Cells at each stage of infection were treated with trypsin-EDTA to make single cells, and passaged in a 12-well plate at the density of $1.5\times10^5$ cells/well and from the next day after the passage, 30 μg/mℓ of GCV and 1 mM 5-FC were treated for 5 or 8 days, respectively, to confirm cell death.

Figure 16:
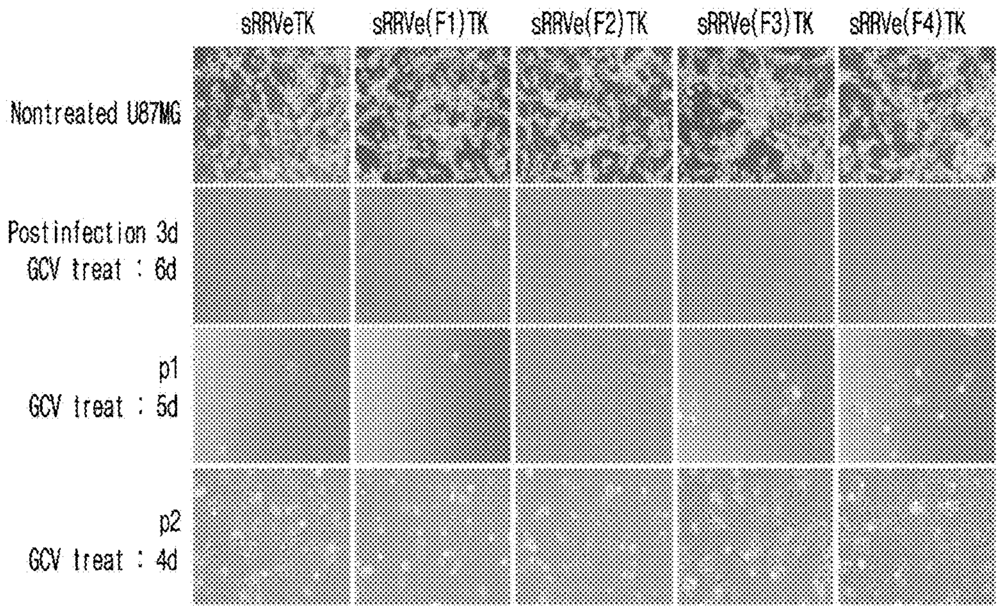
FIG. 16 is a diagram confirming that cell death is induced by thymidine kinase expressed in the sRRVgp-sEF1a-hopt-yCD, sRRVe-TK, sRRVe-F1-TK, sRRVe-F2-TK, sRRVe-F3-TK and sRRVe-F4-TK vectors when the vectors are treated with the prodrug GCV.
Figure 17:
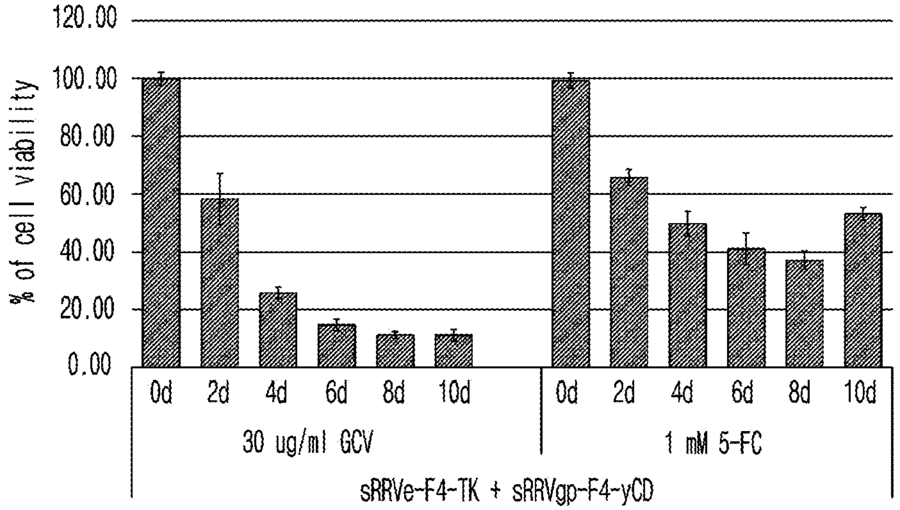
FIG. 17 is a diagram showing the cell viability quantitatively according to cell death in the cells transfected with viruses containing the sRRVgp-sEF1a-hopt-yCD and sRRVe-F4-TK vectors.

As a result, as shown in FIG. 16, it was confirmed that the cells were killed when the virus-infected cells were treated with 30 μg/mℓ of (GCV) and 1 mM 5-fluorocytocin (5-FC), the pro-drugs under an optical microscope. After infecting U87MG with 2E7 genome copies of the sRRVe-F4-TK/sRRVgp-F4-hopt-yCD virus for 7 days, 30 μg/mℓ of GCV and 1 mM 5-FC were treated to quantitatively evaluate cell death. As a result, when GCV was treated, the cell viability decreased by about 80% until 4 days after infection, and only about 10% of cells survived 10 days after infection, suggesting that GCV killed more than 90% of cells. When 5-FC was treated, the cell viability decreased by about 40% 2 days after infection, and only about 40% of cells survived 8 days after infection, suggesting that 5-FC killed more than 60% of cells (FIG. 17).

<Example 9> Construction of Self-Replicating Retrovirus Vector with Minimized Recombination Occurrence into which Human CD19, Cancer Antigen Gene, is Introduced <9-1> Construction of sRRVgp-F4-hCD19/sRRVe-F4-TK Vector and Confirmation of Recombination Occurrence Recently, many studies have been conducted on immunotherapy drugs to treat cancer, and in fact, an Immunotherapy method has been developed to load and deliver the receptor targeting an antigen specifically expressed in cancer cells, such as CAR-T, on a virus vector and is being applied in clinical practice. These immunotherapy methods can reduce side effects as much as possible by using the characteristics of immune cells in the body, and can strengthen the immune response so that the patient's body fights against cancer cells. Among them, active immunotherapy is to attack cancer cells by actively activating the immune system by administering tumor-specific antigens possessed by cancer cells to cancer patients. Accordingly, the human CD19 gene was introduced into a self-replicating retrovirus vector to be used as a gene therapy vector for cancer with minimized recombination.

Figure 18:
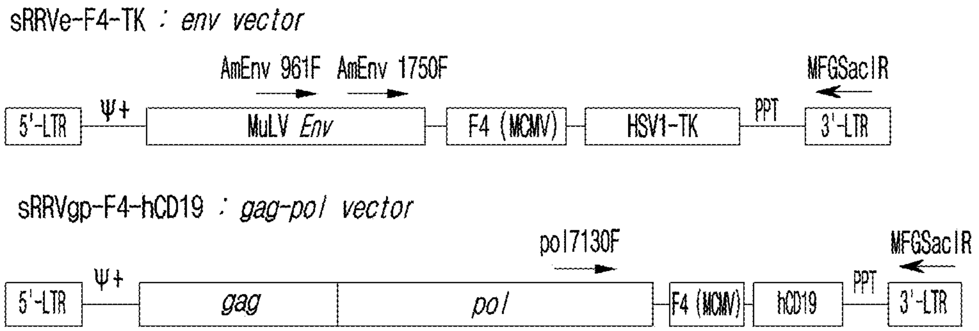
FIG. 18 is a diagram showing the amplification positions of primers for confirming whether recombination occurs in the sRRVe-F4-TK/sRRVgp-F4-hCD19 vector.

Specifically, to clone the hCD19 variant 2 into the hopt-yCD site of sRRVgp-F4-hopt-yCD, the NotI-hCD19-MluI gene containing a restriction enzyme site was synthesized. Thereafter, hCD19 and sRRVgp-F4-hopt-yCD were digested with NotI and MluI and recovered, respectively, and then cloned to construct a sRRVgp-F4-hCD19 vector (SEQ. ID. NO: 44). As shown in FIG. 18, viruses were synthesized with the combination of sRRVe-F4-TK (SEQ. ID. NO: 37) and sRRVgp-F4-hCD19, and the titer of the virus vector was quantified. After infecting the brain tumor cell line U87-MG with 0.1 MOI of the virus, the cells were passaged 13 times, and genomic DNA was purified from the infected cell line at each passage step. Thereafter, PCR was performed with the genomic DNA using the primers shown in Table 6 to analyze the type of recombination.

Figure 19:
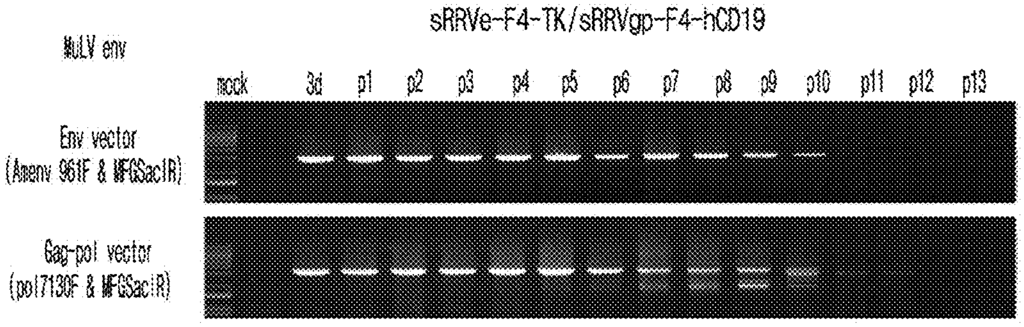
FIG. 19 is a diagram confirming by PCR that recombination occurred in the sRRVgp-F4-hCD19 vector from passage 3.

As a result, as shown in FIG. 19, it was confirmed that the recombinant PCR band was amplified from p3 of the vector into which hCD19 was introduced.

TABLE 6

| Primer | Sequence (5'→3') | SEQ. ID. NO: |
|---|---|---|
| AmEnv961F | ACAAGACCCAAGAA TGTTGGCT | 42 |
| Am 1801F | ATCATTGACCCTGG CCCTTC | 15 |
| pol 7130F | CGGCCCGGCACTCA TTGGGAG | 16 |
| MFGSacIR | CAATCGGAGGACTG GCGCCCCGAGTGA | 2 |

<9-2> Construction of sRRVgp-F4-Hopt-yCD/sRRVe-F4-hCD19 Vector and Confirmation of Recombination Occurrence As shown in Example <9-1>, it was confirmed that recombination occurred in the sRRVgp-F4-hCD19 vector into which hCD19 was inserted during virus replication in the sRRVgp-F4-hCD19/sRRVe-F4-TK vector combination. Therefore, the sRRVgp-F4-hopt-yCD gag-pol vector confirmed that no recombination occurred during virus replication was selected, and a sRRVe-F4-hCD19 vector in which the TK gene of the sRRVe-F4-TK vector was substituted with hCD19 was constructed.

Figure 20:
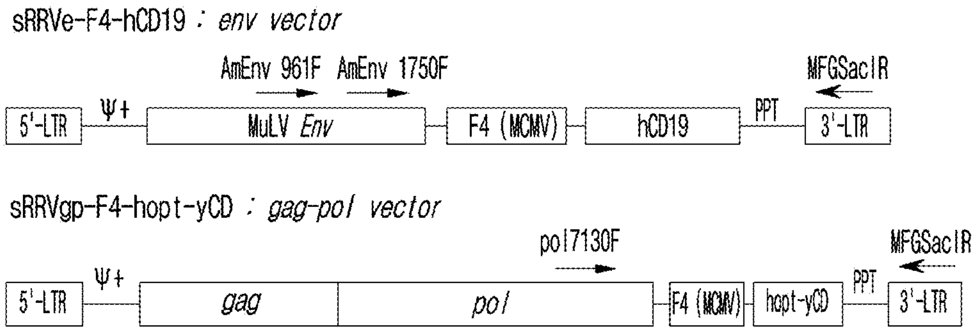
FIG. 20 is a diagram showing the amplification positions of primers for confirming whether recombination occurs in the sRRVe-F4-hCD19/sRRVgp-F4-hopt-yCD vector.

Specifically, to clone hCD19 into the TK site of sRRVe-F4-TK using the hCD19 variant 2, the NotI-hCD19-MluI gene containing a restriction enzyme site was synthesized. Thereafter, hCD19 and sRRVgp-F4-TK were digested with NotI and MluI and recovered, and then cloned to construct a sRRVe-F4-hCD19 vector (SEQ. ID. NO: 45). As shown in FIG. 20, viruses were synthesized with the combination of sRRVe-F4-hCD19 (SEQ. ID. NO: 45) and sRRVgp-F4-hopt-yCD (SEQ. ID. NO: 46), and the titer of the virus vector was quantified. A recombination type analysis experiment was performed using the primers shown in Table 6 by taking 0.1 MOI of the virus.

Figure 21:
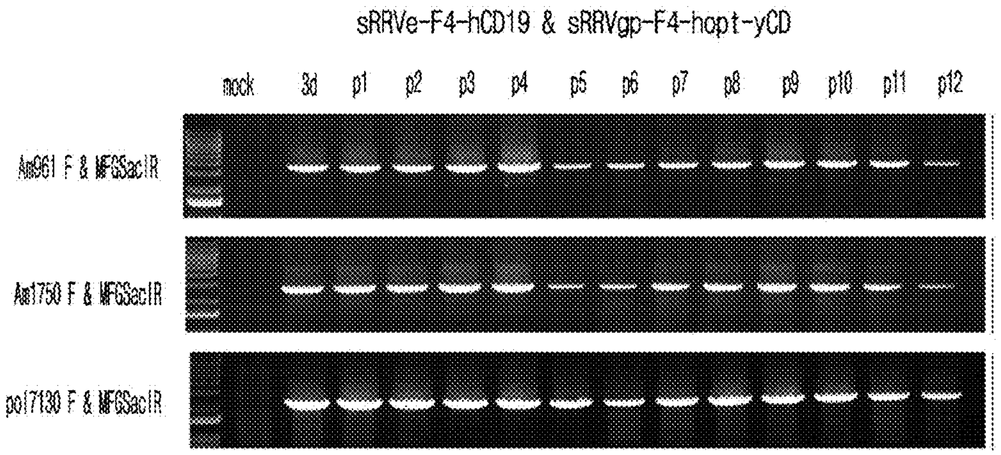
FIG. 21 is a diagram confirming by PCR that recombination did not occur in the sRRVe-F4-hCD19 vector.

As shown in FIG. 21, PCR was performed using the primers capable of confirming the replication and genome stability of the env vector. As a result, the size of the AmEnv961F/MFGSacIR amplification product was 3,460 bp, and the size of the AmEnv1801F/MFGSacIR amplification product was 3,030 bp. In addition, the size of the amplification product using the pol7130R/MFGSacIR primer capable of confirming the replication and genome stability of the gag-pol vector was 2,092 bp. Therefore, it was confirmed that recombination did not occur during virus replication in the combination of the sRRVe-F4-hCD19 vector into which hCD19 was introduced and the sRRVgp-F4-hopt-yCD vector.

<Example 10> Construction of Self-Replicating Retrovirus Vector with Minimized Recombination Occurrence into which Human CD19t (Truncated Human CD19, hCD19t), Cancer Antigen Gene, is Introduced <10-1> Construction of sRRVgp-F4-hCD19t Vector and Confirmation of Recombination Occurrence In addition to the CD19 N-terminal/CAR-T mechanism, in order to suppress intracellular signaling that may occur by the C-terminal of CD19, 233 amino acids of the cytoplasmic domain were removed and truncated CD19 (CD19t) composed of 323 amino acids was introduced into a self-replicating retrovirus vector to use it as a cancer gene therapy vector with minimized recombination. The CD19t consists of an extracellular N-terminal, a transmembrane domain, and a cytosolic C-terminus with only 19 amino acids.

The sRRVgp-F4-hCD19t vector was constructed as follows. To secure hCD19t, hCD19t was amplified using the hCD19 variant 2 as a template with the primers shown in Table 7 below.

TABLE 7

| Primer | Sequence (5'→3') | SEQ. ID. NO: |
|---|---|---|
| hCD19t-NotI-F | cggcggccgCATGCCACCTCC TCGCCTCCTCTTC | 51 |
| hCD19t-MluI-R | caacgcgtTCATCTTTTCCTC CTCAGGACCAGG | 52 |

Figure 22:
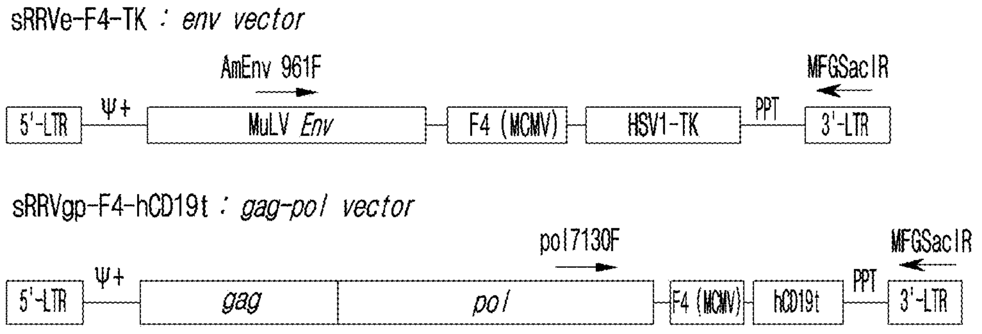
FIG. 22 is a schematic diagram of the sRRVe-F4-TK and sRRVgp-F4-hCD19t vectors.
Figure 23:
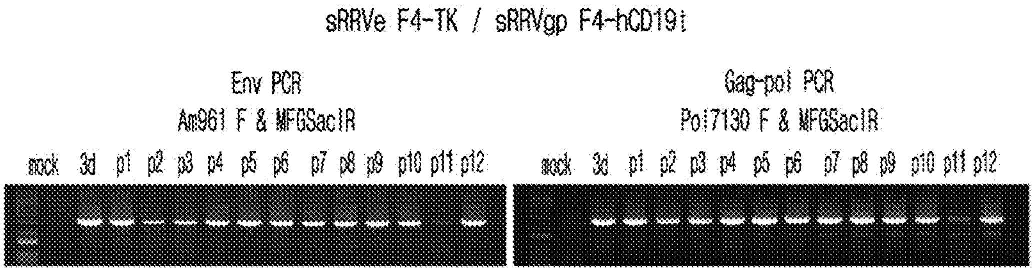
FIG. 23 is a diagram confirming by PCR that recombination did not occur in the sRRVe-F4-TK vector with TK introduced and the sRRVgp-F4-hCD19t vector with hCD19t introduced.

To facilitate cloning, primers were prepared by inserting NotI at the 5' side and MluI at the 3' side. Then, in order to clone hCD19t into the hopt-yCD site of the sRRVgp-F4-hopt-yCD vector, the vector was digested with NotI-MluI, and the amplified hCD19t was digested with NotI-MluI and recovered, and introduced into the vector to construct a sRRVgp-F4-hCD19t vector (SEQ. ID. NO: 54) (FIG. 22). Thereafter, viruses were synthesized with the combination of sRRVe-F4-TK (SEQ. ID. NO: 37) and sRRVgp-F4-hCD19t, and the titer of the virus vector was quantified. A recombination type analysis experiment was performed using the primers shown in Table 6 by taking 0.1 MOI of the virus. As a result, as shown in FIG. 23, it was confirmed that 2,946 bp of the amplification product of the sRRVe-F4-TK vector by the AmEnv961F/MFGSacIR primer and 2,591 bp of the amplification product of the sRRVgp-F4-hCD19t vector by the pol7130R/MFGSacIR primer were continuously amplified until passage 12 during virus replication and reinfection. These results indicate that virus replication and reinfection continued until passage 12. The above results suggest that both the sRRVe-F4-TK vector into which TK was introduced as well as the sRRVe-F4-hCD19t vector into which hCD19t was introduced showed excellent genome stability during virus replication.

<10-2> Construction of sRRVe-F4-hCD19t Vector and Confirmation of Recombination Occurrence The sRRVe-F4-hCD19t vector was constructed as follows. To secure hCD19t, hCD19t was amplified using the hCD19 variant 2 as a template with the primers shown in Table 8 below.

TABLE 8

| Primer | Sequence (5'→3') | SEQ. ID. NO: |
|---|---|---|
| hCD19t-NotI-F | cggcggccgcATGCCACCTC CTCGCCTCCTCTTC | 51 |
| hCD19t-SalI-R | tggtcgacTCATCTTTTCCT CCTCAGGACCAGG | 55 |

Figure 24:
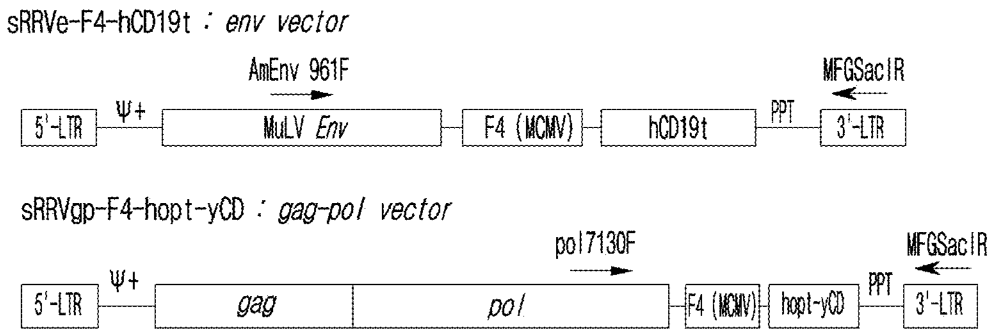
FIG. 24 is a schematic diagram of the sRRVgp-F4-hopt-yCD and sRRVe-F4-hCD19t vectors.
Figure 25:
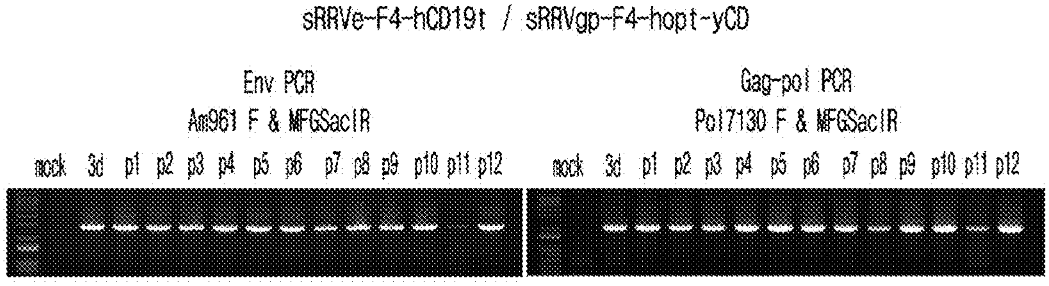
FIG. 25 is a diagram confirming by PCR that recombination did not occur in the sRRVgp-F4-hopt-yCD vector with hopt-yCD introduced and the sRRVe-F4-hCD19t vector with hCD19t introduced.

To facilitate cloning, primers were prepared by inserting NotI at the 5' side and SalI at the 3' side. Then, in order to clone hCD19t into the hCD19 site of the sRRVe-F4-hCD19 vector, the vector was digested with NotI-SalI, and the amplified hCD19t was digested with NotI-SalI and recovered, and introduced into the vector to construct a sRRVe-F4-hCD19t vector (SEQ. ID. NO: 56) (FIG. 24). Thereafter, viruses were synthesized with the combination of sRRVgp-F4-hopt-yCD (SEQ. ID. NO: 46) and sRRVe-F4-hCD19t, and the titer of the virus vector was quantified. A recombination type analysis experiment was performed using the primers shown in Table 6 by taking 0.1 MOI of the virus. As a result, as shown in FIG. 25, it was confirmed that 2,760 bp of the amplification product of the sRRVe-F4-hCD19t vector by the AmEnv961F/MFGSacIR primer and 2,089 bp of the amplification product of the sRRVgp-F4-hopt-yCD vector by the pol7130R/MFGSacIR primer were continuously amplified until passage 12. These results indicate that virus replication and reinfection continued until passage 12. The above results suggest that both the sRRVgp-F4-hopt-yCD vector into which hopt-yCD was introduced as well as the sRRVe-F4-hCD19t vector into which hCD19t was introduced showed excellent genome stability during virus replication.

<Example 11> Construction of Self-Replicating Retrovirus Vector with Minimized Recombination Occurrence into which Granulocyte-Macrophage Colony-Stimulating Factor (GM-CSF) is Introduced <11-1> Construction of sRRVgp-F4-mGM-CSF Vector and Confirmation of Recombination Occurrence Mouse GM-CSF and human GM-CSF were introduced into a self-replicating retrovirus vector as follows to promote immunity enhancement of a patient when applying the self-replicating retrovirus vector loaded with therapeutic genes and truncated hCD19 to cancer patients.

First, the sRRVgp-F4-mGM-CSF vector was constructed. To secure mouse GM-CSF (mGM-CSF), mGM-CSF was amplified using the constructed spRRVe-mGM-CSF (SEQ. ID. NO: 57) as a template with the primers shown in Table 9 below.

TABLE 9

| Primer | Sequence (5'→3') | SEQ. ID. NO: |
|---|---|---|
| mGM-CSF-F-NotI | cggcggccgcAGGATGTGG CTGCAGAATTT | 58 |
| mGM-CSF-R-MluI | tggtcgacTCATTTTTGGA CTGGTTTTT | 59 |

Figure 26:
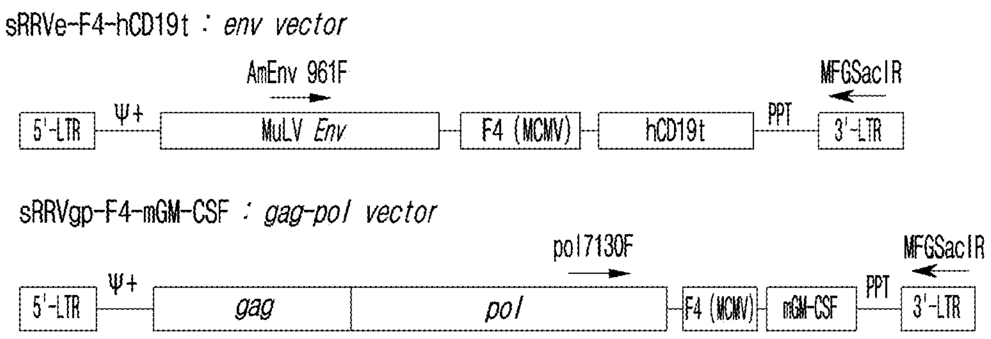
FIG. 26 is a schematic diagram of the sRRVgp-F4-mGM-CSF and sRRVe-F4-hCD19t vectors.
Figure 27:
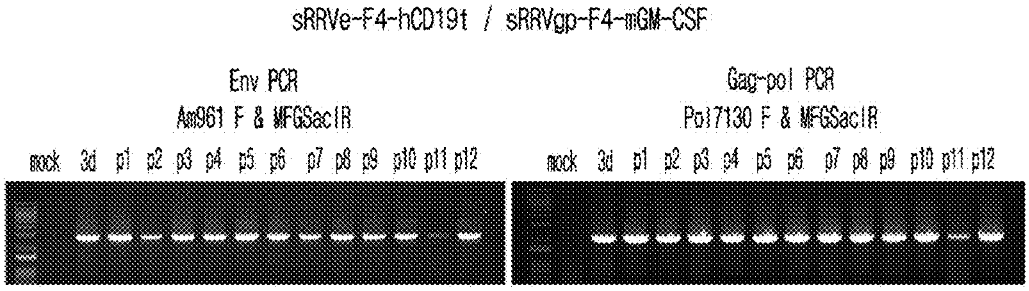
FIG. 27 is a diagram confirming by PCR that recombination did not occur in the sRRVgp-F4-mGM-CSF vector with mGM-CSF introduced and the sRRVe-F4-hCD19t vector with hCD19t introduced.

At this time, to facilitate cloning, primers were prepared by inserting NotI at the 5' side and MluI at the 3' side. Then, in order to clone mGM-CSF into the hopt-yCD site of the sRRVe-F4-hopt-yCD vector, the vector was digested with NotI-MluI, and the amplified mGM-CSF was digested with NotI-MluI and recovered, and introduced into the vector to construct a sRRVgp-F4-mGM-CSF vector (SEQ. ID. NO: 60) (FIG. 26). Thereafter, viruses were synthesized with the combination of sRRVgp-F4-mGM-CSF and sRRVe-F4-hCD19t (SEQ. ID. NO: 56), and the titer of the virus vector was quantified. A recombination type analysis experiment was performed using the primers shown in Table 6 by taking 0.1 MOI of the virus. As a result, as shown in FIG. 27, it was confirmed that 2,760 bp of the amplification product of the sRRVe-F4-hCD19t vector by the AmEnv961F/MFGSacIR primer and 2,041 bp of the amplification product of the sRRVgp-F4-mGM-CSF vector by the pol7130R/MFGSacIR primer were continuously amplified until passage 12 during virus replication and reinfection. The above results suggest that both the sRRVe-F4-hCD19t vector into which hCD19t was introduced as well as the sRRVgp-F4-mGM-CSF vector into which mGM-CSF was introduced showed excellent genome stability during virus replication.

<11-2> Construction of sRRVgp-F4-hGM-CSF Vector and Confirmation of Recombination Occurrence The sRRVgp-F4-hGM-CSF vector was constructed as follows. To secure hGM-CSF, hGM-CSF was amplified using the constructed spRRVe-hGM-CSF (SEQ. ID. NO: 61) as a template with the primers shown in Table 10 below.

TABLE 10

| Primer | Sequence (5'→3') | SEQ. ID. NO: |
|---|---|---|
| hGM-CSF-F-NotI | cggcggccgcAGGATGTGGC TGCAGAGC | 62 |
| hGM-CSF-R-MluI | tggtcgacTCACTCCTGGAC TGGCTCCC | 63 |

Figure 28:
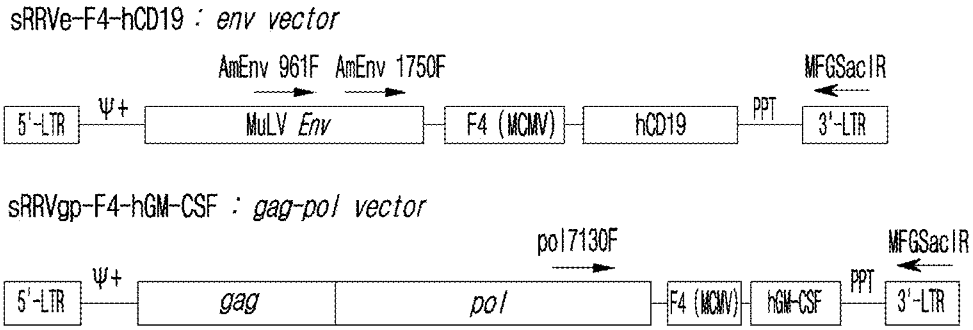
FIG. 28 is a schematic diagram of the sRRVgp-F4-hGM-CSF and sRRVe-F4-hCD19 vectors.
Figure 29:
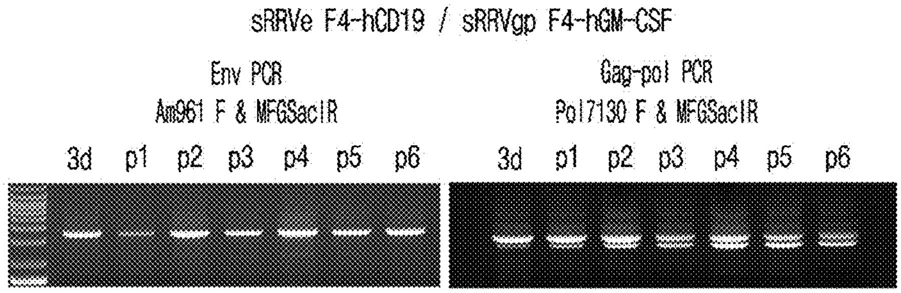
FIG. 29 is a diagram confirming by PCR that replication of the sRRVgp-F4-hGM-CSF vector did not occur completely due to the structural instability.

To facilitate cloning, primers were prepared by inserting NotI at the 5' side and MluI at the 3' side. Then, in order to clone hGM-CSF into the hopt-yCD site of the sRRVe-F4-hopt-yCD vector, the vector was digested with NotI-MluI, and the amplified hGM-CSF was digested with NotI-MluI and recovered, and cloned to construct a sRRVgp-F4-hGM-CSF vector (SEQ. ID. NO: 64) (FIG. 28). Thereafter, viruses were synthesized with the combination of sRRVgp-F4-hGM-CSF and sRRVe-F4-hCD19t (SEQ. ID. NO: 56), and the titer of the virus vector was quantified. A recombination type analysis experiment was performed using the primers shown in Table 6 by taking 0.1 MOI of the virus. As a result, as shown in FIG. 29, 3,460 bp of the amplification product of the sRRVe-F4-hCD19 vector by the AmEnv961F/MFGSacIR primer was continuously amplified until passage 6, but the amplification product of sRRVgp-F4-hGM-CSF by the pol7130R/MFGSacIR primer was observed as two types of amplification products from the initial infection to passage 6. Therefore, it was confirmed that the replication did not occur completely due to the instability of the genome structure from the initial infection.

<11-3> Securing Human Codon-Optimized Nucleotide Sequence of hGM-CSF

In order to solve the problem that replication did not occur completely due to recombination mutation in Example <11-2>, the hGM-CSF nucleotide sequence was converted into a human codon-optimized nucleotide sequence.

Securing and synthesizing the human codon nucleotide sequence was performed by requesting Cosmogentech Co., Ltd., Korea. At this time, in order to facilitate cloning into the self-replicating retroviral vector, the sequence was synthesized by inserting NotI at the 5' side and MluI at the 3' side (SEQ. ID. NO: 65).

Figure 30:
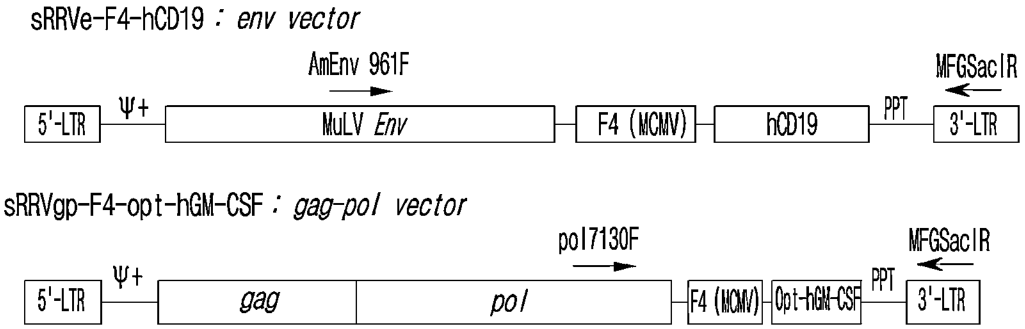
FIG. 30 is a schematic diagram of the sRRVgp-F4-hopt-GM-CSF and sRRVe-F4-hCD19 vectors.
Figure 31:
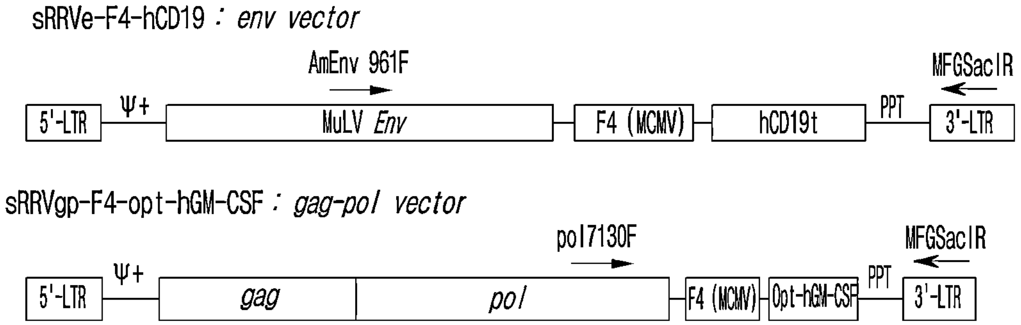
FIG. 31 is a schematic diagram of the sRRVgp-F4-hopt-GM-CSF and sRRVe-F4-hCD19t vectors.

<11-4> Construction of sRRVgp-F4-Hopt-GM-CSF Vector and Confirmation of Recombination Occurrence A sRRVgp-F4-hopt-GM-CSF vector (SEQ. ID. NO: 66) was constructed by cloning the hopt-GM-CSF synthesized in Example <11-3> into the hopt-yCD site of the sRRVe-F4-hopt-yCD vector digested with NotI and MluI (FIG. 30). Thereafter, viruses were synthesized with the combination of sRRVgp-F4-hopt-GM-CSF and sRRVe-F4-hCD19 (SEQ. ID. NO: 45) (FIG. 30), or sRRVgp-F4-hopt-GM-CSF and sRRVe-F4-hCD19t (SEQ. ID. NO: 56) (FIG. 31), and the titer of the virus vector was quantified. A recombination type analysis experiment was performed using the primers shown in Table 6 by taking 0.1 MOI of the virus.

Figure 32:
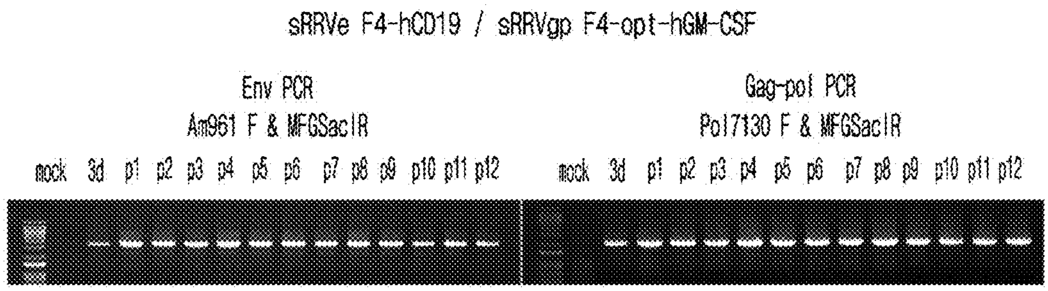
FIG. 32 is a diagram confirming by PCR that recombination did not occur in the sRRVgp-F4-hopt-GM-CSF vector with hopt-GM-CSF introduced and the sRRVe-F4-hCD19 vector with hCD19 introduced during virus replication.

As a result, as shown in FIG. 32, it was confirmed that 3,460 bp of the amplification product of the sRRVe-F4-hCD19 vector by the AmEnv961F/MFGSacIR primer and 2,047 bp of the amplification product of the sRRVgp-F4-hopt-GM-CSF vector by the pol7130R/MFGSacIR primer were continuously amplified until passage 12 during virus replication and reinfection. The above results suggest that both the sRRVe-F4-hCD19 vector into which hCD19 was introduced as well as the sRRVgp-F4-hopt-GM-CSF vector into which hopt-GM-CSF was introduced showed excellent genome stability during virus replication.

Figure 33:
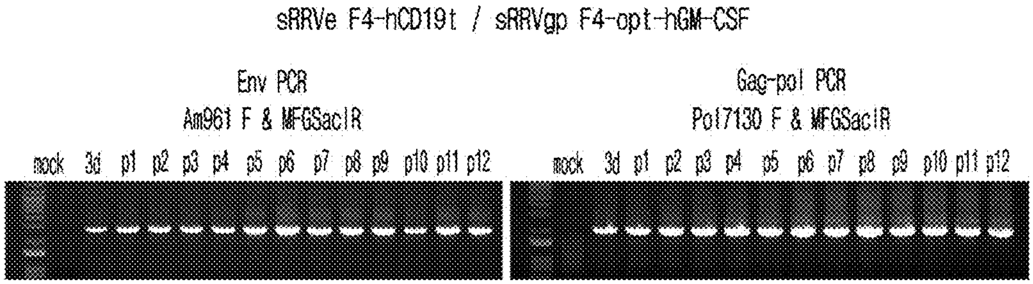
FIG. 33 is a diagram confirming by PCR that recombination did not occur in the sRRVgp-F4-hopt-GM-CSF vector with hopt-GM-CSF introduced and the sRRVe-F4-hCD19t vector with hCD19t introduced during virus replication.

In addition, as shown in FIG. 33, it was confirmed that 2,760 bp of the amplification product of the sRRVe-F4-hCD19t vector by the AmEnv961F/MFGSacIR primer and 2,047 bp of the amplification product of the sRRVgp-F4-hopt-GM-CSF vector by the pol7130R/MFGSacIR primer were continuously amplified until passage 12 during virus replication and reinfection. The above results suggest that both the sRRVe-F4-hCD19t vector into which hCD19t was introduced as well as the sRRVgp-F4-hopt-GM-CSF vector into which hopt-GM-CSF was introduced showed excellent genome stability during virus replication.

<Example 12> Confirmation of Expression Level of hCD19 or hCD19t in Cells Transfected with CD19-Expressing sRRV System <12-1> Confirmation of Expression Level of hCD19 or hCD19t by Flow Cytometry To confirm the expression of hCD19 and hCD19t (truncated hCD19) at the cellular level, U87MG cells were transfected with CD19-expressing sRRV, followed by flow cytometry.

First, sRRVgp-F4-DsRed/sRRVe-F4-hCD19, sRRVgp-F4-hCD19t/sRRVe-F4-TK, and sRRVgp-F4-yCD/sRRVe-F4-hCD19t vectors were prepared, respectively, and then U87MG cells were transfected with each of the gag-pol vector and the env vector by 0.3 MOI, respectively. The transfected cells were cultured under the same experimental conditions as before, harvested every 3 days, reacted with anti-hCD19 antibody for 1 hour, and then FITC fluorescence was observed by flow cytometry.

Figure 34:
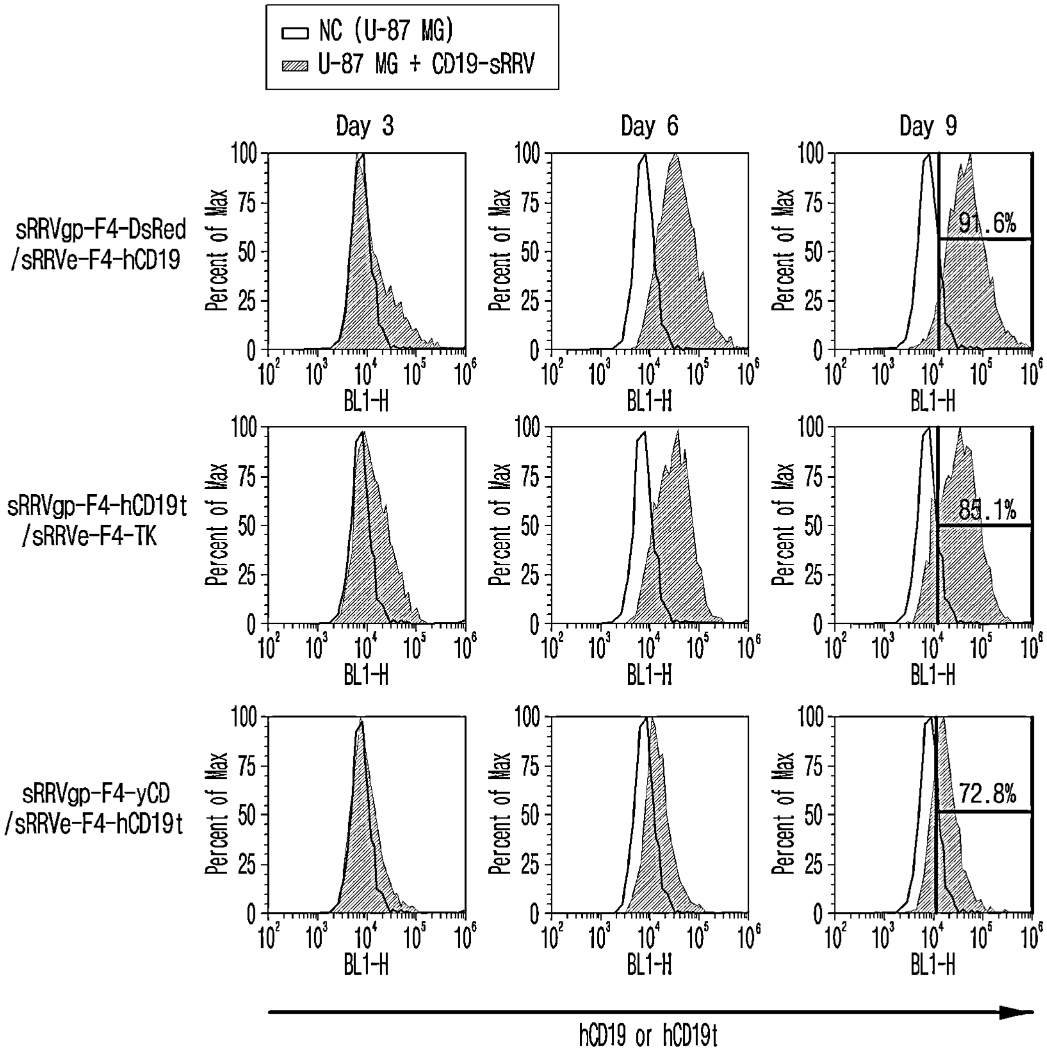
FIG. 34 is a set of graphs confirming that the expression of hCD19 or hCD19t increases over time in cells treated with the CD19-sRRV combination (sRRVgp-F4-DsRed/sRRVe-F4-hCD19, sRRVgp-F4-hCD19t/sRRVe-F4-TK, and sRRVgp-F4-yCD/sRRVe-F4-hCD19t) at the cellular level.

As a result, as shown in FIG. 34, the expression levels of hCD19 and hCD19t were increased over time. In the case of treatment with the sRRVgp-F4-DsRed/sRRVe-F4-hCD19 virus combination, fluorescence was observed from day 3, and FITC fluorescence was observed in most cells on day 9. A similar pattern was observed when the sRRVgp-F4-hCD19t/sRRVe-F4-TK virus combination was treated. In the case of treatment with the sRRVgp-F4-yCD/sRRVe-F4-hCD19t virus combination, fluorescence was partially observed from day 6, and fluorescence signals were observed weaker than other combinations on day 9, but the fluorescence signals were increased compared to the non-transfected U-87 MG.

From the above results, it was confirmed that all three virus combinations induced the expression of hCD19 and hCD19t by transfection.

<12-2> Confirmation of Expression Level of hCD19 or hCD19t by Western Blotting

Western blotting was performed to confirm the expression of hCD19 and hCD19t at the protein level. Specifically, U87MG cells were transfected with each CD19-sRRV combination by 0.3 MOI (total 0.6 MOI) and the cells were harvested every 3 days. The experiment was conducted with two types of antibodies, one that reacts to hCD19t and hCD19 (66298-1-1g) and the other that reacts only to hCD19 (ab134114).

Figure 35:
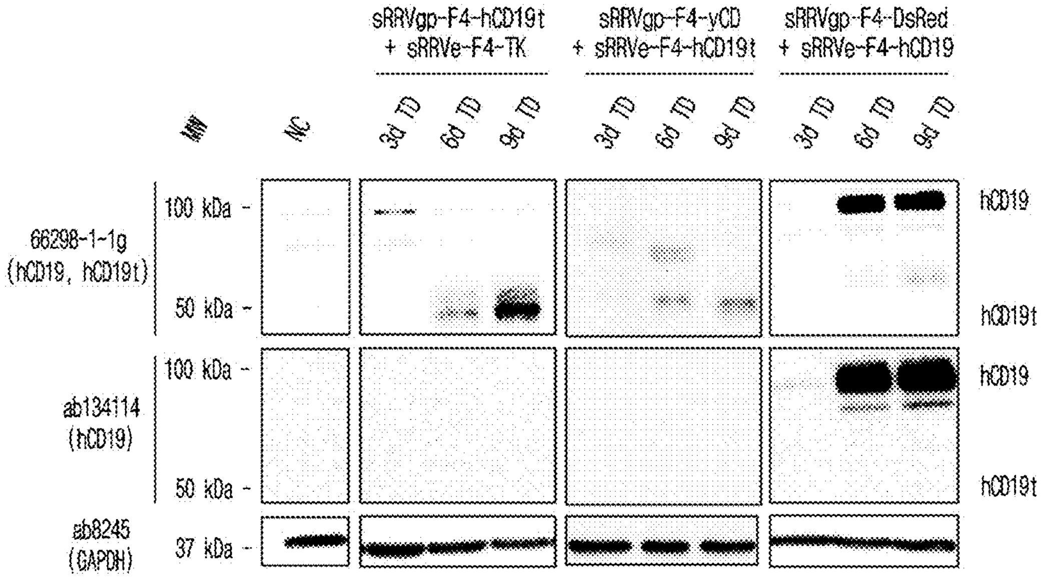
FIG. 35 is a diagram confirming that the expression of hCD19 or hCD19t increases over time in cells treated with the CD19-sRRV combination (sRRVgp-F4-DsRed/sRRVe-F4-hCD19, sRRVgp-F4-hCD19t/sRRVe-F4-TK, and sRRVgp-F4-yCD/sRRVe-F4-hCD19t) at the protein level using Western blotting.

As a result, as shown in FIG. 35, the expression of hCD19 and hCD19t was confirmed from day 6 in all cells transfected with each CD19-sRRV combination. The experimental group treated with the sRRVgp-F4-DsRed/sRRVe-F4-hCD19 virus combination showed high hCD19 expression from the $6^{th}$ day of transfection, and the expression level was similar on the $9^{th}$ day. In the experimental groups treated with the combinations of sRRVgp-F4-hCD19t/sRRVe-F4-TK and sRRVgp-F4-yCD/sRRVe-F4-hCD19t, the hCD19t expression was observed from the $6^{th}$ day and increased on the $9^{th}$ day. It was confirmed that the hCD19t expression was higher in the experimental group treated with the sRRVgp-F4-hCD19t/sRRVe-F4-TK combination.

<Example 13> Confirmation of Cancer Cell Death by Anti-CD19 CAR-T Treatment

<13-1> Confirmation of Cell Viability Using WST-1 Assay

WST-1 assay was performed to confirm whether the hCD19 and hCD19t expressed by CD19-sRRV actually induce apoptosis by anti-CD19 CAR-T.

Specifically, U87MG cells were transfected with each CD19-sRRV combination by 0.3 MOI (total 0.6 MOI) and after 9 days, the cells were harvested and seeded in a 96-well plate. On the next day, the cells were treated with anti-CD19 CAR-T at the E:T ratio of 0.05:1, 0.1:1, 0.5:1, and 1:1, and cultured together, and cell viability was measured by performing WST-1 assay every 24 hours.

Figure 36:
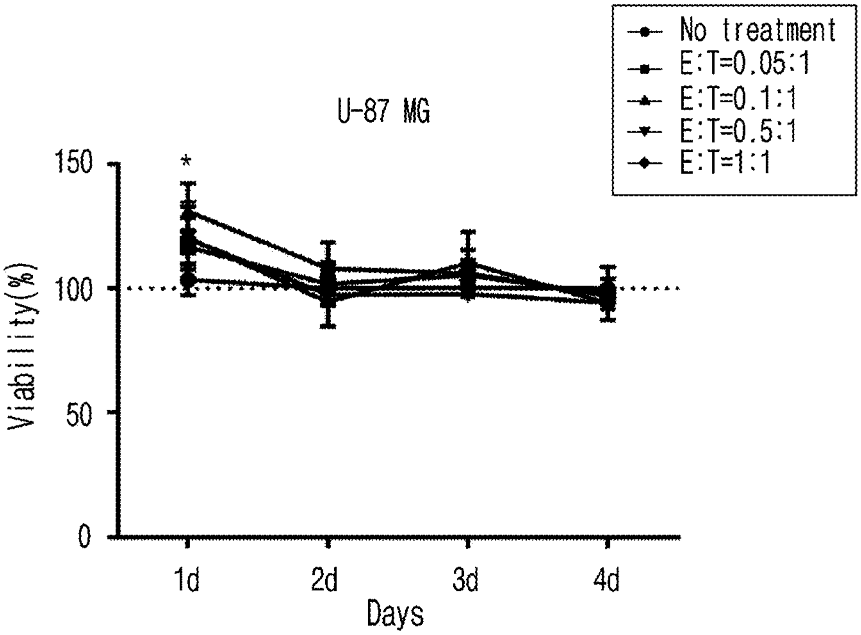
FIG. 36 is a graph confirming the cell death by anti-CD19 CAR-T in U-87 MG cells not treated with virus.
Figure 37:
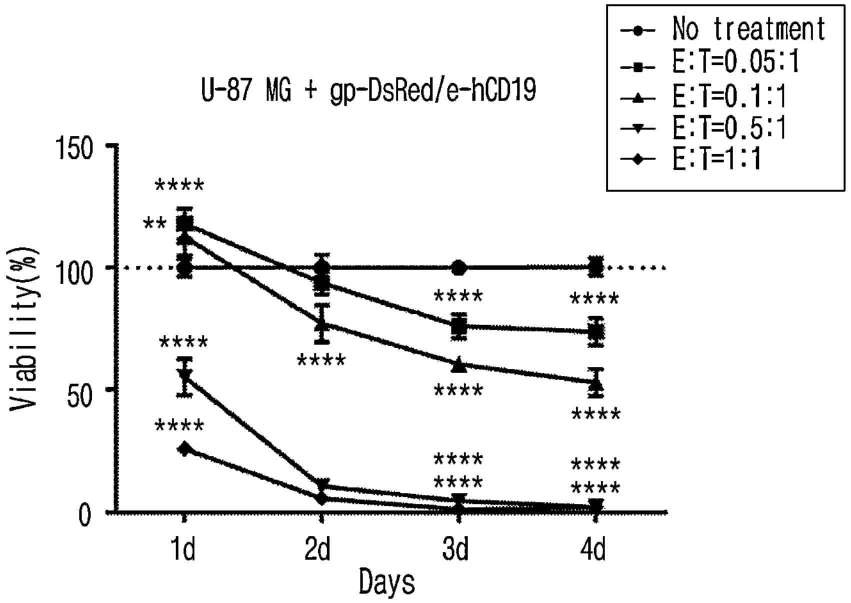
FIG. 37 is a graph confirming the cell death by anti-CD19 CAR-T in U-87 MG cells treated with sRRVgp-F4-DsRed/sRRVe-F4-hCD19.
Figure 38:
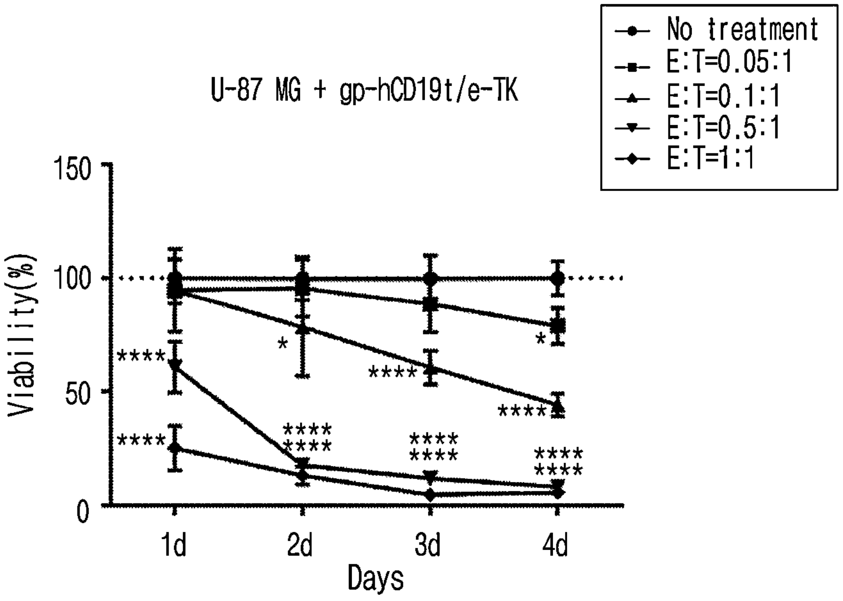
FIG. 38 is a graph confirming the cell death by anti-CD19 CAR-T in U-87 MG cells treated with sRRVgp-F4-hCD19t/sRRVe-F4-TK.
Figure 39:
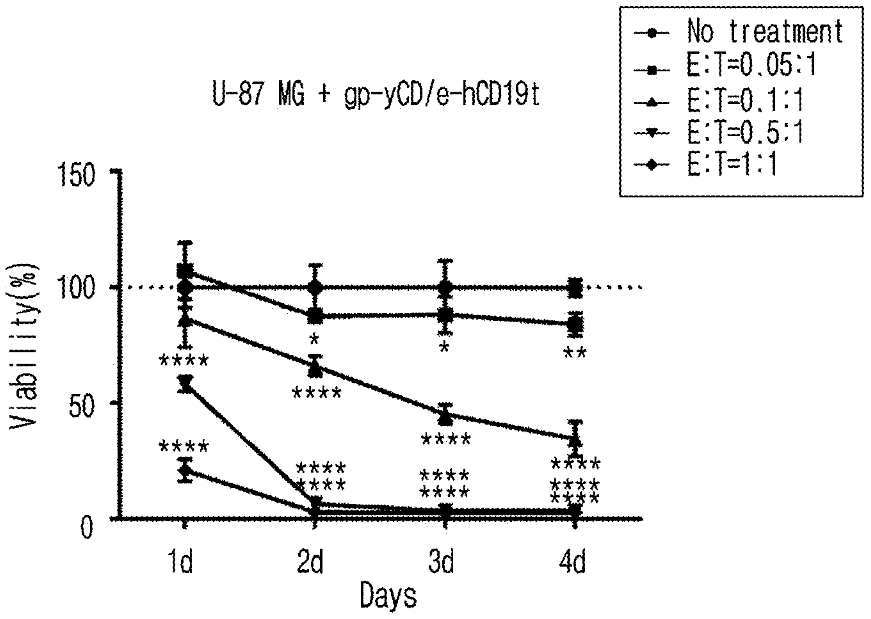
FIG. 39 is a graph confirming the cell death by anti-CD19 CAR-T in U-87 MG cells treated with sRRVgp-F4-yCD/sRRVe-F4-hCD19t.

As a result, as shown in FIG. 36, in U-87 MG cells not treated with virus, no decrease in viability was observed after the anti-CD19 CAR-T treatment. However, as shown in FIGS. 37 to 39, in cells transfected with hCD19 and hCD19t, the viability was decreased in proportion to the amount and time of the anti-CD19 CAR-T treatment. In the case of treatment with the E:T ratio of 1:1, all cells transfected with the three CD19-sRRV virus combinations (sRRVgp-F4-DsRed/sRRVe-F4-hCD19, sRRVgp-F4-hCD19t/sRRVe-F4-TK, sRRVgp-F4-yCD/sRRVe-F4-hCD19t) showed high cell death within 1 day of the treatment, and the viability was decreased by 25.8%, 24.8%, and 20%, respectively, and most of the cells died after 2 days. In the case of treatment with the E:T ratio of 0.5:1, the viability decreased by 54.9%, 54.3%, and 58.2% on the first day, respectively in all three groups, and most of the cells died after the second day. In the case of treatment with the E:T ratio of 0.1:1, the viability was gradually decreased over time. It was observed that the cell death effect by anti-CD19CAR-T was the highest in the experimental group transfected with sRRVgp-F4-yCD/sRRVe-F4-hCD19t.

<13-2> Confirmation of Cell Viability Using Crystal Violet Staining

Crystal violet staining was performed to visually observe cell death by anti-CD19 CAR-T.

Specifically, U87 MG cells were transfected with each CD19-sRRV combination by 0.3 MOI (total 0.6 MOI), and after 9 days, the cells were harvested and seeded in a 12-well plate. On the next day, the cells were treated with anti-CD19 CAR-T at the E:T ratio of 0.1:1, 0.5:1, and 1:1, respectively, and cultured together, and observed under a microscope at 24-hour intervals. After 4 days of CAR-T treatment, crystal violet staining was performed and observed as photographs.

Figure 40:
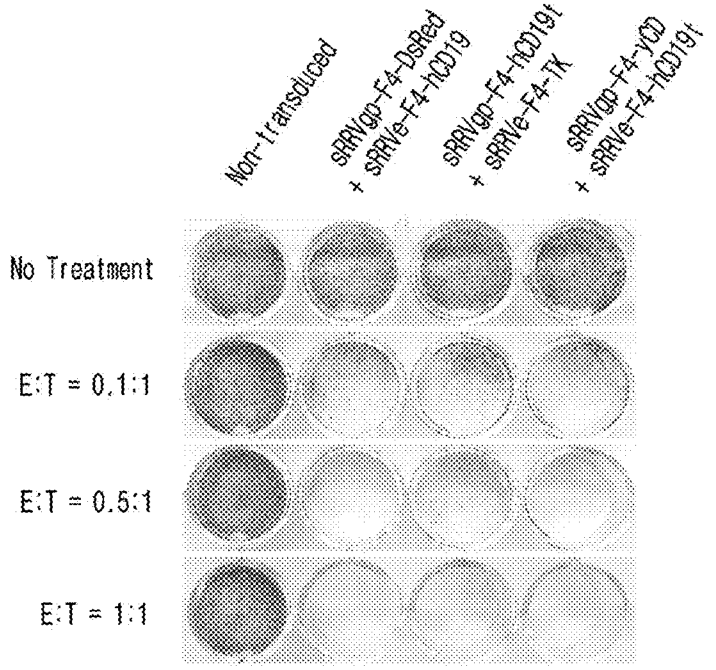
FIG. 40 is a set of photographs visually confirming the cell death by anti-CD19 CAR-T in U-87 MG cells treated with the CD19-sRRV combinations (sRRVgp-F4-DsRed/sRRVe-F4-hCD19, sRRVgp-F4-hCD19t/sRRVe-F4-TK, and sRRVgp-F4-yCD/sRRVe-F4-hCD19t).

As a result, as shown in FIG. 40, no cell death or morphological change was observed even after treatment with anti-CD19 CAR-T in U87 MG cells not treated with virus. However, in the cells transfected with the three CD19-sRRV virus combinations (sRRVgp-F4-DsRed/sRRVe-F4-hCD19, sRRVgp-F4-hCD19t/sRRVe-F4-TK, and sRRVgp-F4-yCD/sRRVe-F4-hCD19t), cell death was observed after 24 hours of anti-CD19 CAR-T treatment when the E:T ratio was 0.5:1 or higher, and most of the cells died after 72 hours of the treatment. Among them, the experimental group transfected with sRRVgp-F4-yCD/sRRVe-F4-hCD19t was similar to the experimental group transfected with sRRVgp-F4-DsRed/sRRVe-F4-hCD19, but it was observed that cell death by anti-CD19 CAR-T occurred more than the experimental group transfected with sRRVgp-F4-hCD19t/sRRVe-F4-TK.

---

What is claimed is:

1. A split-dual replicating-retrovirus vector system with minimized recombination occurrence, comprising:

1) a first recombinant retroviral expression vector containing a Gag-Pol gene, a sEF1α (short elongation factor 1α) promoter or a first MCMV (murine cytomegalovirus) promoter, and operably linked to a first therapeutic gene, wherein the first MCMV promoter is a minimized promoter consisting of a sequence selected from SEQ ID NO: 4, NO: 5, NO: 6 and NO: 7; and 2) a second recombinant retroviral expression vector containing an Env gene of a virus, and a second MCMV promoter, and operably linked to a second therapeutic gene, wherein the second MCMV promoter is a minimized promoter consisting of a sequence selected from SEQ ID NO: 4, NO: 5, NO: 6 and NO: 7.

2. The split-dual replicating-retrovirus vector system with minimized recombination occurrence according to claim 1, wherein the Gag-Pol gene is a Gag-Pol gene of Gibbon ape Leukemia virus (GaLV) or amphotropic murine leukemia virus (MuLV).

3. The split-dual replicating-retrovirus vector system with minimized recombination occurrence according to claim 1, wherein the sEF1α promoter is a polynucleotide consisting of a nucleotide sequence of SEQ ID NO: 18.

4. The split-dual replicating-retrovirus vector system with minimized recombination occurrence according to claim 1, wherein the virus Env gene is any one derived from the group consisting of Gibbon ape Leukemia virus (GaLV), amphotropic murine leukemia virus (MuLV), xenotropic murine leukemia virus (xenotropic MuLV), feline endogenous retrovirus (RD114), vesicular stomatitis virus (VSV) and measles virus (MV) Env genes.

5. The split-dual replicating-retrovirus vector system with minimized recombination occurrence according to claim 1, wherein the first therapeutic gene or the second therapeutic gene is any one selected from the group consisting of a suicide gene, a cytokine gene, and a cancer antigen gene.

6. The split-dual replicating-retrovirus vector mtawith minimized recombination occurrence according to claim 5, wherein the suicide gene is a thymidine kinase (TK) gene or a yeast cytosine deaminase (yCD) gene.

7. The split-dual replicating-retrovirus vector system with minimized recombination occurrence according to claim 5, wherein the cytokine gene is a granulocyte macrophage colony-stimulating factor (GM-CSF).

8. The split-dual replicating-retrovirus vector system with minimized recombination occurrence according to claim 5, wherein the cancer antigen gene is human CD19 (Cluster of Differentiation 19), CEA (Carcinoembryonic Antigen), or HER2 (human epidermal growth factor receptor 2).

9. The split-dual replicating-retrovirus vector system with minimized recombination occurrence according to claim 8, wherein the human CD19 gene is a polynucleotide having the nucleotide sequence represented by SEQ ID NO: 43.

10. The split-dual replicating-retrovirus vector system with minimized recombination occurrence according to claim 8, wherein the truncated human CD19 gene is a polynucleotide consisting of a nucleotide sequence of SEQ ID NO: 53.

11. A pharmaceutical composition for preventing or treating cancer comprising recombinant retroviruses comprising the split-dual replicating-retrovirus vector system of claim 1 as an active ingredient.

12. A pharmaceutical composition for preventing or treating cancer comprising a cell transfected or transduced with the split-dual replicating-retrovirus vector system of claim 1.

13. A method for preparing a split-dual replicating-retrovirus vector system with minimized recombination occurrence comprising the following steps:

1) a step of preparing a first recombinant retroviral expression vector containing a Gag-Pol gene of MuLV (Murine Leukemia virus), a sEF1α promoter or a first MCMV promoter, and operably linked to a first therapeutic gene, wherein the first MCMV promoter is a minimized promoter consisting of a sequence selected from SEQ ID NO: 4, NO: 5, NO: 6 and NO: 7; and 2) a step of preparing a second recombinant retroviral expression vector containing an Env gene of a virus, and a second MCMV promoter, and operably linked to a second therapeutic gene, wherein the second MCMV promoter is a minimized promoter consisting of a sequence selected from SEQ ID NO: 4, NO: 5, NO: 6 and NO: 7.

* * * * *